US007608451B2

(12) United States Patent
Cooper et al.

(10) Patent No.: US 7,608,451 B2
(45) **Date of Patent: *Oct. 27, 2009**

(54) GENE REGULATION IN TRANSGENIC ANIMALS USING A TRANSPOSON-BASED VECTOR

(75) Inventors: Richard K. Cooper, Baton Rouge, LA (US); Gary G. Cadd, North Attleboro, MA (US); William C. Fioretti, Addison, TX (US); Kenneth F. De Boer, Rygate, MT (US)

(73) Assignees: Transgen Rx, Inc., Baton Rouge, LA (US); The Board of Supervisors of Louisiana State University and Mechanical College, Baton Rouge, LA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/981,574

(22) Filed: Oct. 31, 2007

(65) Prior Publication Data

US 2008/0235813 A1 Sep. 25, 2008

Related U.S. Application Data

(63) Continuation of application No. 10/609,019, filed on Jun. 26, 2003, now Pat. No. 7,527,966.

(60) Provisional application No. 60/392,415, filed on Jun. 26, 2002, provisional application No. 60/441,392, filed on Jan. 21, 2003, provisional application No. 60/441,377, filed on Jan. 21, 2003, provisional application No. 60/441,502, filed on Jan. 21, 2003, provisional application No. 60/441,405, filed on Jan. 21, 2003, provisional application No. 60/441,447, filed on Jan. 21, 2003, provisional application No. 60/441,381, filed on Jan. 21, 2003.

(51) Int. Cl.
*C12N 15/85* (2006.01)
*C07H 21/04* (2006.01)
*A01K 67/027* (2006.01)

(52) U.S. Cl. .................. 435/320.1; 536/23.1; 536/24.1; 800/19

(58) Field of Classification Search .............. 435/320.1, 435/455; 536/23.1, 24.1; 800/14
See application file for complete search history.

(56) References Cited

U.S. PATENT DOCUMENTS 4,670,388 A 6/1987 Rubin et al.
4,870,009 A 9/1989 Evans et al.
4,914,025 A 4/1990 Manoil et al.
5,102,797 A 4/1992 Tucker et al.
5,162,215 A 11/1992 Bosselman et al.
5,212,080 A 5/1993 Nag et al.
5,512,483 A 4/1996 Mader et al.
5,556,782 A 9/1996 Cooper et al.
5,565,362 A 10/1996 Rosen
5,645,991 A 7/1997 Berg et al.
5,648,244 A 7/1997 Kuliopulos et al.
5,703,055 A 12/1997 Felgner et al.
5,719,055 A * 2/1998 Cooper .................... 435/320.1
5,733,779 A 3/1998 Reff
5,753,502 A 5/1998 Kilgannon et al.
5,861,478 A 1/1999 Jaynes
5,869,296 A 2/1999 Nag et al.
5,925,545 A 7/1999 Reznikoff et al.
5,948,622 A 9/1999 Reznikoff et al.
5,958,775 A 9/1999 Wickstrom et al.
5,962,410 A 10/1999 Jaynes et al.
5,965,443 A 10/1999 Reznikoff et al.
5,998,698 A 12/1999 Cooper et al.
6,080,912 A 6/2000 Bremel et al.
6,107,477 A 8/2000 Whitney et al.
6,140,129 A 10/2000 Cox et al.
6,156,568 A 12/2000 Cooper et al.
6,159,730 A 12/2000 Reff
6,159,736 A 12/2000 Reznikoff et al.
6,171,861 B1 1/2001 Hartley et al.
6,218,185 B1 4/2001 Shirk et al.
6,255,282 B1 7/2001 Jaynes
6,258,571 B1 7/2001 Chumakov et al.
6,261,554 B1 7/2001 Valerio et al.
6,291,214 B1 9/2001 Richards et al.
6,291,243 B1 9/2001 Fogarty et al.
6,291,740 B1 9/2001 Bremel et al.

(Continued)

FOREIGN PATENT DOCUMENTS

EP 1375654 1/2004

(Continued)

OTHER PUBLICATIONS

Jeltsch et al Eur. Journal of Biochem. 1982, 122, 291-295.*
Schulz Journal of Mol. Biol. , 1991, 221, 65-80.*
Meiss et al Biotechniques, 2000, 29(3): 476, 478-480.*
Fisher et al., "Induction of Terminal Differentiation in Cancer Cells as a Therapeutic Modality for Suppressing Tumor Growth: Studies Employing Human Melanoma," *Anticancer Research*, 1988, vol. 8 (5B), 1057.
"Gene Therapy a Suspect in Leukemia-Like Disease," *Science*, News of the Week, Oct. 4, 2002, vol. 298, 34-35.

(Continued)

*Primary Examiner*—Deborah Crouch
*Assistant Examiner*—Anoop Singh
(74) *Attorney, Agent, or Firm*—Kilpatrick Stockton LLP

(57) ABSTRACT

Administration of modified transposon-based vectors has been used to achieve stable incorporation of exogenous genes into animals. These transgenic animals produce transgenic progeny. Further, these transgenic animals produce large quantities of desired molecules encoded by the transgene. Transgenic egg-laying animals produce large quantities of desired molecules encoded by the transgene and deposit these molecules in the egg.

14 Claims, 7 Drawing Sheets

U.S. PATENT DOCUMENTS

| | | | |
|---|---|---|---|
| 6,303,568 B1 | 10/2001 | Jaynes et al. | |
| 6,316,692 B1 | 11/2001 | Readhead et al. | |
| 6,358,710 B1 | 3/2002 | Graves et al. | |
| 6,376,743 B1 | 4/2002 | Yanagimachi | |
| 6,475,798 B2 | 11/2002 | Fogarty et al. | |
| 6,489,458 B2 * | 12/2002 | Hackett et al. | 536/23.2 |
| 6,492,510 B2 | 12/2002 | Hasebe et al. | |
| 6,503,729 B1 | 1/2003 | Bult et al. | |
| 6,514,728 B1 | 2/2003 | Kai et al. | |
| 6,515,199 B1 | 2/2003 | Petitte et al. | |
| 6,528,699 B1 | 3/2003 | Meade et al. | |
| 6,563,017 B2 | 5/2003 | Muramatsu et al. | |
| 6,602,686 B1 | 8/2003 | Harrington et al. | |
| 6,670,185 B1 | 12/2003 | Harrington et al. | |
| 6,716,823 B1 | 4/2004 | Tang et al. | |
| 6,730,822 B1 | 5/2004 | Ivarie et al. | |
| 6,759,573 B2 | 7/2004 | Olhoft et al. | |
| 6,825,396 B2 * | 11/2004 | MacArthur | 800/19 |
| 6,852,510 B2 | 2/2005 | Bremel et al. | |
| 6,939,959 B2 | 9/2005 | Hu | |
| 7,005,296 B1 | 2/2006 | Handler | |
| 7,019,193 B2 | 3/2006 | Ditullio et al. | |
| 7,034,115 B1 | 4/2006 | Kawakami | |
| 7,083,980 B2 | 8/2006 | Reznikoff et al. | |
| 7,105,343 B1 | 9/2006 | Fraser, Jr. et al. | |
| 7,129,390 B2 | 10/2006 | Ivarie et al. | |
| 7,160,682 B2 | 1/2007 | Hackett et al. | |
| 7,199,279 B2 | 4/2007 | Rapp | |
| 7,294,507 B2 | 11/2007 | Harvey et al. | |
| 7,335,761 B2 | 2/2008 | Harvey et al. | |
| 7,375,258 B2 | 5/2008 | Harvey et al. | |
| 7,381,712 B2 | 6/2008 | Christman et al. | |
| 2001/0044937 A1 | 11/2001 | Schatten et al. | |
| 2002/0007051 A1 | 1/2002 | Cheo et al. | |
| 2002/0013955 A1 | 1/2002 | Ogden et al. | |
| 2002/0016975 A1 | 2/2002 | Hackett et al. | |
| 2002/0028488 A1 | 3/2002 | Singh et al. | |
| 2002/0028513 A1 | 3/2002 | Fogarty et al. | |
| 2002/0042137 A1 | 4/2002 | Richards et al. | |
| 2002/0052047 A1 | 5/2002 | Hasebe et al. | |
| 2002/0053092 A1 | 5/2002 | Readhead et al. | |
| 2002/0055172 A1 | 5/2002 | Harrington | |
| 2002/0056148 A1 | 5/2002 | Readhead et al. | |
| 2002/0072097 A1 | 6/2002 | deCardayre et al. | |
| 2002/0076797 A1 | 6/2002 | Lin | |
| 2002/0083479 A1 | 6/2002 | Winston et al. | |
| 2002/0099015 A1 | 7/2002 | Barber | |
| 2002/0104109 A1 | 8/2002 | Bremel et al. | |
| 2002/0108132 A1 | 8/2002 | Rapp | |
| 2002/0119573 A1 | 8/2002 | Shaw et al. | |
| 2002/0129398 A1 | 9/2002 | Winston et al. | |
| 2002/0132349 A1 | 9/2002 | Goryshin et al. | |
| 2002/0133835 A1 | 9/2002 | Winston et al. | |
| 2002/0138865 A1 | 9/2002 | Readhead et al. | |
| 2002/0148000 A1 | 10/2002 | Shen | |
| 2002/0150577 A1 | 10/2002 | Lee et al. | |
| 2002/0151034 A1 | 10/2002 | Zhang et al. | |
| 2002/0157125 A1 | 10/2002 | Lee et al. | |
| 2002/0160507 A1 | 10/2002 | Novy et al. | |
| 2002/0188105 A1 | 12/2002 | Craig et al. | |
| 2002/0199214 A1 | 12/2002 | Rapp | |
| 2003/0009026 A1 | 1/2003 | Hasebe et al. | |
| 2003/0017534 A1 | 1/2003 | Buelow et al. | |
| 2003/0055017 A1 | 3/2003 | Schwarz et al. | |
| 2003/0056241 A1 | 3/2003 | Matsuda et al. | |
| 2003/0061629 A1 | 3/2003 | Sutrave | |
| 2003/0074680 A1 | 4/2003 | Lee et al. | |
| 2003/0074681 A1 | 4/2003 | Macarthur | |
| 2003/0101472 A1 | 5/2003 | Baltimore et al. | |
| 2003/0115622 A1 | 6/2003 | Ponce de Leon et al. | |
| 2003/0121062 A1 | 6/2003 | Radcliffe et al. | |
| 2003/0126628 A1 | 7/2003 | Harvey et al. | |
| 2003/0126629 A1 | 7/2003 | Rapp et al. | |
| 2003/0140363 A1 | 7/2003 | Rapp | |
| 2003/0143740 A1 * | 7/2003 | Wooddell et al. | 435/455 |
| 2003/0150006 A1 | 8/2003 | Petitte et al. | |
| 2003/0150007 A1 | 8/2003 | Savakis et al. | |
| 2003/0154502 A1 | 8/2003 | Wimmer et al. | |
| 2003/0167492 A1 | 9/2003 | Lee et al. | |
| 2003/0170888 A1 | 9/2003 | Van de Lavoir et al. | |
| 2003/0172387 A1 | 9/2003 | Zhu et al. | |
| 2003/0177516 A1 | 9/2003 | Horseman et al. | |
| 2003/0182672 A1 | 9/2003 | Graham et al. | |
| 2003/0182675 A1 | 9/2003 | Etches et al. | |
| 2003/0217375 A1 | 11/2003 | Zcharia et al. | |
| 2003/0221206 A1 | 11/2003 | Schatten et al. | |
| 2003/0224519 A1 | 12/2003 | Harrington et al. | |
| 2004/0006776 A1 | 1/2004 | Meade et al. | |
| 2004/0018624 A1 | 1/2004 | Harrington et al. | |
| 2004/0019922 A1 | 1/2004 | Ivarie et al. | |
| 2004/0040052 A1 | 2/2004 | Radcliffe et al. | |
| 2004/0142475 A1 | 7/2004 | Barman et al. | |
| 2004/0158882 A1 | 8/2004 | Ivarie et al. | |
| 2004/0172667 A1 | 9/2004 | Cooper et al. | |
| 2004/0197910 A1 | 10/2004 | Cooper et al. | |
| 2004/0203158 A1 | 10/2004 | Hackett et al. | |
| 2004/0210954 A1 | 10/2004 | Harvey et al. | |
| 2004/0226057 A1 | 11/2004 | Christmann et al. | |
| 2004/0235011 A1 | 11/2004 | Cooper et al. | |
| 2004/0255345 A1 | 12/2004 | Rapp et al. | |
| 2005/0003414 A1 | 1/2005 | Harvey et al. | |
| 2005/0004030 A1 | 1/2005 | Fishetti et al. | |
| 2005/0034186 A1 | 2/2005 | Harvey et al. | |
| 2005/0050581 A1 | 3/2005 | Harvey et al. | |
| 2005/0066383 A1 | 3/2005 | Harvey | |
| 2005/0176047 A1 | 8/2005 | Harvey et al. | |
| 2005/0198700 A1 | 9/2005 | Christmann et al. | |
| 2005/0208038 A1 | 9/2005 | Fischetti et al. | |
| 2005/0273872 A1 | 12/2005 | Sang et al. | |
| 2005/0273873 A1 | 12/2005 | Christmann et al. | |
| 2006/0046248 A1 | 3/2006 | Rapp et al. | |
| 2006/0121509 A1 | 6/2006 | Hermiston et al. | |
| 2006/0123488 A1 | 6/2006 | Ivarie et al. | |
| 2006/0123504 A1 | 6/2006 | Leavitt et al. | |
| 2006/0171921 A1 | 8/2006 | Ivarie et al. | |
| 2006/0185024 A1 | 8/2006 | Ivarie et al. | |
| 2006/0185029 A1 | 8/2006 | Ivarie et al. | |
| 2006/0188478 A1 | 8/2006 | Ivarie et al. | |
| 2006/0210977 A1 | 9/2006 | Kaminski | |
| 2006/0218652 A1 | 9/2006 | Horn et al. | |
| 2006/0236413 A1 | 10/2006 | Ivics et al. | |
| 2006/0258603 A1 | 11/2006 | Ivics et al. | |
| 2007/0009991 A1 | 1/2007 | Horseman et al. | |
| 2007/0022485 A1 | 1/2007 | Tadeda et al. | |
| 2007/0113299 A1 | 5/2007 | Harvey et al. | |
| 2008/0235815 A1 | 9/2008 | Cooper et al. | |

FOREIGN PATENT DOCUMENTS

| | | |
|---|---|---|
| EP | 1364205 B1 | 5/2007 |
| EP | 1700914 A1 | 9/2008 |
| WO | WO-92/20316 | 11/1992 |
| WO | WO-93/24626 | 12/1993 |
| WO | WO-94/20608 | 9/1994 |
| WO | WO-95/31566 | 11/1995 |
| WO | WO-97/47739 | 12/1997 |
| WO | WO-99/09817 | 3/1999 |
| WO | WO-99/19472 | 4/1999 |
| WO | WO-99/40213 | 8/1999 |
| WO | WO-99/42569 | 8/1999 |
| WO | WO-00/11151 | 3/2000 |
| WO | WO-00/30437 | 6/2000 |
| WO | WO-00/23579 A9 | 9/2000 |
| WO | WO-00/56932 | 9/2000 |

| | | |
|---|---|---|
| WO | WO-01/14537 | 3/2001 |
| WO | WO-01/17344 | 3/2001 |
| WO | WO-01/19846 | 3/2001 |
| WO | WO-01/23525 | 4/2001 |
| WO | WO-01/26455 | 4/2001 |
| WO | WO-01/43540 | 6/2001 |
| WO | WO-01/71019 | 9/2001 |
| WO | WO-01/73094 | 10/2001 |
| WO | WO-01/83786 | 11/2001 |
| WO | WO-01/85965 | 11/2001 |
| WO | WO-02/47475 | 6/2002 |
| WO | WO-02/063293 | 8/2002 |
| WO | WO-03/014344 | 2/2003 |
| WO | WO-03/024199 | 3/2003 |
| WO | WO-03/025146 | 3/2003 |
| WO | WO-03/048364 | 6/2003 |
| WO | WO-03/064627 | 8/2003 |
| WO | WO-2004/009792 A2 | 1/2004 |
| WO | WO-2004/047531 | 6/2004 |
| WO | WO-2004/065581 A2 | 8/2004 |
| WO | WO-2004/067707 A3 | 8/2004 |
| WO | WO-2004/067743 A1 | 8/2004 |
| WO | WO-2004/080162 A2 | 9/2004 |
| WO | WO-2004/092351 | 10/2004 |
| WO | WO-2004/110143 | 12/2004 |
| WO | WO-2005/040215 A2 | 5/2005 |
| WO | WO-2005/062881 | 7/2005 |
| WO | WO-2005/084430 A1 | 9/2005 |
| WO | WO-2006/024867 A2 | 3/2006 |
| WO | WO-2006/026238 A2 | 3/2006 |
| WO | WO-2006/053245 A2 | 5/2006 |
| WO | WO-2006/055040 A2 | 5/2006 |
| WO | WO-2006/055931 A2 | 5/2006 |
| WO | WO-2006/065821 A2 | 6/2006 |
| WO | WO-2006/093847 | 9/2006 |

OTHER PUBLICATIONS

Massoud et al., "The Deleterious Effects of Human Erythropoietin Gene Driven by the Rabbit Whey Acidic Protein Gene Promoter in Transgenic Rabbits," *Reprod Nutr Dev*, 1996, 36(5), 555-563.

Pieper et al., "Restoration of Vascular Endothelial Function in Diabetes," *Diabetes Res. Clin. Pract. Suppl.*, 1996, S157-S162.

Sang, "Prospects for Transgenesis in the Chick," *Mech. Dev.*, 2004, 121(9): 1179-86.

Williamson et al., "Expression of the Lysostaphin Gene of *Staphylococcus simulans* in a Eukaryotic System," *Appl. Environ. Microbiol.*, Mar. 1994, 60(3), 771-776.

Abdel-Salam, et al., "Expression of Mouse Anticreatine Kinase (MAK33) Monoclonal Antibody in the Yeast," *Appl. Microbiol. Biotechnol.*, 2001, vol. 56, 157-164.

Afanassieff, et al., "Intratesticular Inoculation of Avian Leukosis Virus (ALV) in Chickens—Production of," *Avian Diseases*, 1996, 841-852.

Alexeyev, M. et al., "Mini-TN10 Transposon Derivatives for Insertion Mutagenesis and Gene Delivery into the Chromosome of Gram-negative Bacteria," *Gene*, 1995, vol. 160, pp. 59-62.

Andra, et al., "Generation and Characterization of Transgenic Mice Expressing Cobra Venom," *Molecular Immunology*, 2002, vol. 39, 357-365.

Araki, et al., "Site-Specific Recombination of a Transgene in Fertilized Eggs by Transient," *Proc. Natl. Acad. Sci. USA*, 1995, vol. 92, 160-164.

Argaud, et al., "Regulation of Rat Liver Glucose-6-Phosphatase Gene Expression in Different," *Diabetes*, Nov. 1, 1996, 1563-1571.

AU 2003261096 Examiner's First Report dated Jun. 7, 2007.

Awade, et al., "Comparison of Three Liquid Chromatographic Methods for Egg-White Protein," *Journal of Chromatography B.*, 1999, vol. 723, 69-74.

Awade, A. C. "On Hen Egg Fractionation: Applications of Liquid Chromatography to the Isolation and," *Z Lebensm Unters Forsch*, 1996, vol. 202, 1-14.

Beardsley, T. "Gene Therapy Setback: A Tragic Death Clouds the Future of an Innovative Treatment," *Scientific American*, 2000, No. 2.

Bell, et al., "Nucleotide Sequence of a cDNA Clone Encoding Human Preproinsulin," *Nature*, Nov. 29, 1979, vol. 282, 525-527.

Bolli, et al., "Insulin Analogues and Their Potential in the Management of Diabetes Mellitus," *Diabetologia*, 1999, vol. 42, 1151-1167.

Brinster, R. L. "Germline Stem Cell Transplantation and Transgenesis," *Science*, Jun. 21, 2002, vol. 296, 2174-2176.

Chatterjee, et al., "Retrofitting High Molecular Weight DNA Cloned in P1: Introduction of Reporter," *Genetic Analysis: Biomolecular*, 1996, vol. 13, 33-42.

Ciampi, M. S. et al., "Transposon Tn10 Provides a Promoter for Transcription of Adjacent Sequences," *Proc Natl Acad Sci USA*, Aug 1982, vol. 79, No. 16, 5016-5020.

Ciftci, et al., "Applications of Genetic Engineering in Veterinary Medicine," *Advanced Drug Delivery Reviews*, 2000, vol. 43, 57-64.

Davis, C. G. "The Many Faces of Epidermal Growth Factor Repeats," *New Biologist*, May 1990, 2(5), 410-419.

Davis, M. A. et al., "Tn10 Protects Itself at Two Levels from Fortuitous Activation by External Promoters," *Cell*, Nov. 11, 1985, vol. 43, No. 1, 379-387.

Dematteo, et al., "Engineering Tissue-Specific Expression of a Recombinant Adenovirus: Selective," *Journal of Surgical Research*, 1997, vol. 72, 155-161.

Desert, C. et al., "Comparisons of Different Electrophoretic Separations of Hen Egg White Proteins," *J. Agric. Food Chem.*, 2001, vol. 49, 4553-4561.

Dierich, A. et al., "Cell-Specificity of the Chicken Ovalbumin and Conalbumin Promoters," *EMBO. Journal*, 1987, 6(8), 2305-2312.

Dobeli, H. et al., "Recombinant Fusion Proteins for the Industrial Production of Disulfide Bridge Containing Peptides: Purification, Oxidation without Concatamer Formation, and Selective Cleavage," *Protein Expression and Purification*, 1998, 12, 404-414.

Dong, et al., "Hepatic Insulin Production Type-1 Diabetes," *Trends in Endocrinology*, Dec. 2001, vol. 12, 441-446.

Dunham, Rex A. et al., "Enhanced Bacterial Disease Resistance of Transgenic Channel Catfish *Ictalurus punctatus* Possessing Cecropin Genes," *Marine Biotechnology*, 2002, Springer Verlag, New York, NY, US, vol. 4, No. 3, 338-344.

Dupuy, A. et al., "Mammalian Germ-like Transgenesis by Transposition," *PNAS*, Apr. 2, 2002, vol. 99, 4495-4499.

Ebara, et al., "In Vivo Gene Transfer into Chicken Embryos via Primordial Germ Cells Using Green," *Journal of Reproduction*, 2000, vol. 46, 79-83.

Ebara, et al., "Possible Abnormalities of Chimeric Chicken Caused by the Introduction of," *Asian-Aus. J. Anim. Sci.*, 2000, vol. 13, 1514-1517.

Eggleston, et al., "A Sensitive and Rapid Assay for Homologous Recombination in Mosquito Cells," *BMC Genetics*, Dec. 17, 2001, vol. 2, No. 21, 1-9.

EP 037621729 First Office Action dated Jun. 9, 2006.

EP 037621729 Response to First Office Action dated Oct. 18, 2006.

EP 037621729 Second Office Action dated Nov. 23, 2006.

EP 037621729 Response to Second Office Action dated Apr. 2, 2007.

EP 037621729 Third Office Action dated Apr. 24, 2007.

EP 037621729 Response to Third Office Action dated Aug. 31, 2007.

EP 038002259 Office Action dated Aug. 30, 2006.

EP 038002259 Response to Office Action.

EP 038085635 First Office Action dated Oct. 5, 2005.

EP 038085635 Response to First Office Action dated Oct. 18, 2005.

EP 038085635 Search Report dated Jan. 23, 2007.

EP 038085635 Search Report dated Apr. 12, 2007.

EP 038085635 Second Office Action dated May 2, 2007.

Etches, et al., "Gene Transfer: Overcoming the Avian Problems (Abstract Provided)," *Proceeding, 5th World Congress*, Aug. 1994, vol. 20, 97-101.

Etches, et al., "Manipulation of the Avian Genome," 1993, pp. 15-28, 81-101, 103-119, 121-133, 165-184, 205-222, 223-230.

Etches, R. J. et al., "Strategies for the Production of Transgenic Chicken," *Methods in Molecular Biology*, 1997, vol. 62, 433-450.

Falqui, et al., "Reversal of Diabetes in Mice by Implantation of Human Fibroblasts Genetically Engineered to release matures Human Insulin," *Human Gene Therapy*, Jul. 20, 1999, vol. 10, 1753-1762.
Fischer, R. et al., "Antibody Production by Molecular Farming in Plants," *Journal of Biological Regulators and Homeostatic Agents*, Apr. 2000, Wichtig Editore, Milan, IT, vol. 14, No. 2, 83-92.
Fischer, S. et al., "Regulated Transposition of a Fish Transposon in the Mouse Germ Line," *Proc. Natl. Acad. Sci. USA*, 2001, vol. 98, No. 12, 6759-6764.
Fong, K. P. et al., "The Genes for Benzene Catabolism in *Pseudomonas putida* ML2 are Flanked by Two," *Plasmid*, Mar. 2000, vol. 43, No. 2, 103-110.
Gaub, Marie-Pierre et al., "The Chicken Ovalbumin Promoter is Under Negative Control Which is Relieved by Steroid Hormones," *EMBO. Journal*, 1987, 6(8), 2313-2320.
Ghosh, et al., "Liver-Directed Gene Therapy: Promises, Problems and Prospects at the Turn of the," *Journal of Hepatology*, 2000, vol. 32, 238-252.
Gibbins, A. M. "Chickens as Bioreactors—Harvesting Commercially-Valuable Proteins from the Egg," *Agri-food Research in Ontario*, 1996, 39-41.
Gibbins, et al., "Exploring the Product Possibilities Arising from Transgenic Poultry Technology," *Kungl. Skogs-och* 1997, vol. 136, 57-68.
Gibbins, et al., "Genetically-Engineered Poultry," *Lohmann Information*, 1997, No. 21, 3-6.
Gibbins, A. M. V. "The Chicken, the Egg, and the Ancient Mariner," *Nat. Biotechnol.*, 1998, vol. 16, 1013-1014.
Gibbins, A. M. V. "Transgenic Poultry Technology and Food Production," *Animal Biotechnology*, 1998, vol. 9, No. 3, 173-179.
Giddings, Glynis "Transgenic Plants as Protein Factories," *Current Opinion in Biotechnology*, London, GB, Oct 2001, vol. 12, No. 5, 450-454.
Ginsberg, et al., "The Road Ahead for Biologics Manufacturing," *Equity Research*, 2002, 1-23.
Hackett, P. B. et al., "Development of Genetic Tools for Transgenic Animals," *Transgenic Animals in Agriculture*, 1999, 19-35.
Han, et al., "Gene Transfer by Manipulation of Primordial Germ Cells in the Chicken," *AJAS*, 1994, vol. 7, No. 3, 427-434.
Harvey, A. et al., "Expression of Exogenous Protein in the White Egg of Transgenic Chickens," *Nature Biotechnology*, Apr. 2002, vol. 19, 396-399.
Heilig, R. et al., "NCBI Accession No. V00437-Gallus Gallus Fragment of Ovalbumin Gene Coding for the First Leader Exon."
Heilig, R. et al., "The Ovalbumin Gene Family, The 5' End Region of the X and Y Genes," *J. Mol. Bio.*, 1982, vol. 156, No. 1, pp. 1-19.
Hermann, et al., "Lipoprotein Receptors in Extraembryonic Tissues of the Chicken," *J. Biol. Chem.*, Jun. 2, 2000, vol. 275, 16837-16844.
Herrero, M. et al., "Transposon Vectors containing Non-Antibiotic Resistance Selection Markers for Cloning and Stable Chromosomal Insertion of Foreign Genes in Gram-Negative Bacteria," *Journal of Bacteriology*, 1990, vol. 172, No. 11, pp. 6557-6567.
Hillel, et al., "Strategies for the Rapid Introgression of a Specific Gene Modification into a," *Poultry Science*, 1993, vol. 72, 1197-1211.
Hong, et al., "Improved Transfection Efficiency of Chicken Gonadal Primordial Germ Cells for the," *Transgenic Research*, 1998, vol. 7, 247-252.
Horn, "A Versatile Vector Set for Animal Transgenesis," *Development Genes and Evolution*, 2000, vol. 210, No. 12, 630-637.
Houdebine, L. M. "The Methods to Generate Transgenic Animals and to Control Transgene Expression," *J. Biotechnol.*, Sep. 25, 2002, vol. 98, 145-160.
Houdebine, L. M. "Transgenic Animal Bioreactors," *Transgenic Research*, Oct. 2000, vol. 9, No. 4-5, 305-320.
IN 99/KOL NP/2005 Official Action dated Jun. 17, 2006.
Ivarie, et al., "Avian Transgenesis: Progress Towards the Promise," *TRENDS in Biotech*, 2003, vol. 21, No. 1, 14-19.
Izsvak, et al., "Sleeping Beauty, A Wide Host-Range Transposon Vector for Genetic Transformation," *J. Mol. Biol.*, 2000, vol. 302, 93-102.
Jarvis, et al., "Influence of Different Signal Peptides and Prosequences on Expression and," *The Journal of Biological Chemistry*, Aug. 5, 1993, vol. 268, No. 22, 16754-16762.
Jeltsch, et al., "The Complete Nucleotide Sequence of the Chicken Ovotransferrin mRNA," *Eur.J. Biochem*, 1982, 122, 291-295.
Kaminski, et al., "Design of a Nonviral Vector for Site-Selective, Efficient Integration into the Human," *The FASEB Journal*, Aug. 2002, vol. 16, 1242-1247.
Kanda, et al., "Genetic Fusion of an a-Subunit Gene to the Follicle-Stimulating Hormone and," *Molecular Endocrinology*, Nov. 1999, vol. 13, No. 11, 1873-1881.
Kay, M. et al., "Viral Vectors for Gene Therapy: the Art of Turning Infectious Agents into Vehicles of Therapeutics," *Nature Medicine*, 2001, vol. 7, No. 1, 33-40.
Kleckner, N. et al., "Transposon Tn10: Genetic Organization, Regulation and Insertion Specificity," *Fed Proc*, Aug. 1982, vol. 41, No. 10, 2649-2652.
Kluin, PH. M. et al., "Proliferation of Spermatogonia and Sertoli Cells in Maturing Mice," *Anat. Embryol.*, 1984, vol. 169, 73-78.
Koga, et al., "The Medaka Fish Tol2 Transposable Element can Undergo Excision in Human and," *J Hum Genet*, Mar. 28, 2003, vol. 48, No. 5, 231-235.
Kousteni, S. et al., "Reversal of Bone Loss in Mice by Nongenotropic Signaling of Sex Steroids," *Science*, Oct. 25, 2002, vol. 298, 843-846.
Kozak, M. "At Least Six Nucleotides Preceding the AUG Initiator Codon Enhance Translation in," *J. Mol. Biol.*, 1987, vol. 196, 947-950.
Kozak, M. "Initiation of Translation in Prokaryotes and Eukaryotes," *Gene*, 1999, vol. 234, 187-208.
Kumaran, J. D. S. et al., "The Normal Development of the Testes in the White Plymouth Rock," *Testis Development in White*, 1948, 511-519.
Lampe, D. et al., "Hyperactive Transposase Mutants of the Himar1 Mariner Transposon," *Proc. Natl. Acad. Sci. USA*, Sep. 1999, vol. 96, 11428-11433.
Marshak, S. et al., "Purification of the Beta-Cell Glucose-sensitive Factor that Transactivates the Insulin," *Proc. Natl. Acad. Sci. USA*, Dec. 1996, vol. 93, 15057-15062.
Mather, et al., "The Mariner Transposable Element: A Potential Vector for Improved Integration of," *British Poultry Science*, Sep. 2000, vol. 41, S27-S28.
Meiss, et al., "Vectors for Dual Expression of Target Genes in Bacterial and Mammalian Cells", *BioTechniques* 2000 , vol. 29, No. 3, 476, 478, 480.
Mohammed, et al., "Deposition of Genetically Engineered Human Antibodies into the Egg Yolk of Hens," *Immunotechnology*, 1998, vol. 4, 115-125.
Monroe, D. et al., "The COUP-Adjacent Repressor (CAR) Element Participates in the Tissue-Specific," *Biochemica et Biophysica Acta*, 2000, vol. 1517, 27-32.
Muramatsu, T. et al., "Regulation of Ovalbumin Gene Expression," *Poultry and Avian Biology*, 1995, vol. 6, No. 2, 107-123.
Muzzin, et al., "Hepatic Insulin Gene Expressions as Treatment for Type 1 Diabetes Mellitus in Rats," *Mol Endo*, 1997, vol. 11, 833-837.
Nicklin, et al., "Analysis of Cell-Specific Promoters for Viral Gene Therapy Targeted at the Vascular," *Hypertension*, 2001, vol. 38, 65-70.
Oakberg, E. "Duration of Spermatogenesis in the Mouse and Timing of Stages of the Cycle of the," *Duration of Spermatogenesis*, 507-516.
Ochiai, H. et al., "Synthesis of Human Erythropoietin in Vivo in the Oviduct of Laying Hens by," *Poultry Science*, 1998, vol. 77, No. 2, 299-302.
Ono, T. et al., "Gene Transfer into Circulating Primorial Germ Cells of Quail Embryos," *Exp. Anim.*, 1995, vol. 4, No. 4, 275-278.
Osborne, et al., "A System for Insertional Mutagenesis and Chromosomal Rearrangement Using the," *Plant J.*, Apr. 1995, vol. 7, No. 4, 687-701.
Pain, B. et al. "Chicken Embryonic Stem Cells and Transgenic Strategies," *Cell Tissues Organs*, 1999, vol. 165, 212-219.
Park, H. "COUP-TF Plays a Dual Role in the Regulation of the Ovalbumin Gene," *Biochemistry*, 2000, vol. 39, 8537-8545.
PCT/US03/41269 International Search Report dated May 18, 2004.

PCT/US03/20389 Written Opinion dated Jun. 17, 2004.
PCT/US03/41261 International Search Report dated Nov. 3, 2004.
PCT/US03/41335 International Search Report dated Nov. 3, 2004.
PCT/US04/043092 International Search Report and Written Opinion dated May 11, 2006.
Phan, J. et al., "Structural Basis for the Substrate Specificity of Tobacco Etch Virus Protease," *Journal of Biological Chemistry*, Dec. 27, 2002, vol. 277, 50564-50572.
Platon, D. et al., "A Shortage of Monoclonal Antibody Manufacturing Capacity," *Pharmaceutical Fine Chemicals and BioMolecule Manufacturing Report*, Pharma Ventures Ltd. 2002.
Prudhomme, M. et al., "Diversity of Tn4001 Transposition Products: the Flanking IS256 Elements Can Form," *J Bacteriol*, 2002, vol. 184, No. 2, 433-443.
Qiu, Y. "Spatiotemporal Expression Patterns of Chicken Ovalbumin Upstream Promoter," *Proc. Natl. Acad. Sci.*, 1994, vol. 91, 4451-4455.
Richardson, P. D. "Gene Repair and Transposon-Mediated Gene Therapy," *Stem Cells*, 2002, vol. 20, 112-115.
Sakai, J. et al., "Two Classes of Tn10 Transposase Mutants that Suppress Mutations in the Tn10," *Genetics*, Nov. 1996, vol. 144, No. 3, 861-870.
Sarmasik, Aliye et al., "Transgenic Live-bearing Fish and Crustaceans Produced by Transforming Immature," *Marine Biotechnology*, 2001, vol. 3, No. 5, 470-477.
Sasakawa, C. et al., "Control of Transposon Tn5 Transposition in *Escherichia coli," Prod Natl Acad Sci USA*, Dec. 1982, vol. 79, No. 23, 7450-7454.
Schillberg, Stefan et al., "Apoplastic and Cytosolic Expression of Full-size Antibodies and Antibody Fragments in *Nicotiana tabacum," Transgenic Research*, Aug. 1999, vol. 8, No. 4, 255-263.
Schillberg, S. et al., "Molecular Farming of Recombinant Antibodies in Plants," *CMLS Cellular and Molecular Life Sciences*, Mar. 2003, Birkhauser Verlag, Heidelberg, DE, vol. 60, No. 3, 433-445.
Schlenstedt, et al., "Structural Requirements for Transport of PreprocecropinA and Related Presecretory," *The Journal of Biological Chemistry*, Dec. 5, 1992, vol. 236, No. 34, 24328-24332.
Schneider, et al., "An Epitope Tagged Mammalian / Prokaryotic Expression Vector with Positive," *Gene: An International Journal on*, 1997, vol. 197, 337-341.
Schultz, et al., "Translation Initiation of IS50R Read-through Transcripts," *J. Mol. Biol*, 1991, vol. 221, 65-80.
Seal, et al., "Mutational Studies Reveal a Complex Set of Positive and Negative Control Elements," *Mol. Cell Biol.*, May 1991, vol. 11, 2704-2717.
Sekine, Y. et al., "DNA Sequences Required for Translational Frameshifting in Production of the," *Mol Gen Genet*, Nov. 1992, vol. 235, No. 2-3, 325-332.
Sekine, Y. et al., "Identification of the Site of Translational Frameshifting Required for Production of the," *Mol Gen Genet*, Nov. 1992, vol. 235, No. 2-3, 317-324.
Sharma, S. et al., "Pancreatic Islet Expression of the Homeobox Factor STF-1 Relies on and E-box," *Journal of Biological Chemistry*, Jan. 26, 1996, vol. 271, 2294-2299.
Sherman, et al., "Transposition of the *Drosophila* Element Mariner into the Chicken Germ Line," *Nature Biotechnology*, Nov. 1998 , vol. 16, 1050-1053.
Sherratt, D. "Tn3 and Related Transposable Elements: Site-Specific Recombination and," *Mobile DNA*, 1989, 163-184.
Simons, R. W. et al., "Translational Control of IS10 Transposition," *Cell*, Sep. 1983, vol. 34, No. 2, 683-691.
Skolnick, et al., "From Genes to Protein Structure and Function: Novel Application of Computational Approaches in the Genomic Era," *Trends in Biotech*, 2000, vol. 18, pp. 34-39.
Skolnik, J. et al., "From Genes to Protein Structure and Function: Novel Applications of Computational Approaches in the Genomic Era," *Trends In Biotech*., 2000, 18:34-39.
Slowinski, et al., "Pattern of Prepo-Endothelin-1 Expression Revealed by Reporter-Gene Activity in," *Clinical Science*, vol. 103, No. 48, 445-475.
Vilen, et al., "Construction of Gene-Targeting Vectors: a Rapid Mu in vitro DNA Transposition," *Transgenic Research*, 2001, vol. 10, 69-80.
Von Specht, M. "English translation of Dissertation entitled Expression of a Recombinant Human Protein in vitro and in vivo in Oviduct Cells of Chickens, with Human Erythroprotein (hrEPO) as an Example," 2002, pp. 49-68.
Von Specht, M. "Expression eines rekombinanten humanen Proteins in vitro und in vivo in," *Dissertation*, 2002, 49-68.
Wallace, et al., *Biology the Science of Life*, 1986, vol. 2, 235.
Wang, A. et al., "Activation of Silent Genes by Transposons Tn5 and Tn10," *Genetics*, Dec. 1988, vol. 120, No. 4, 875-885.
Xanthopoulos, et al., "The Structure of the Gene for Cecropin B, an Antibacterial Immune Protein from," *European Journal of Biochemistry*, 1988, vol. 172, 371-376.
Zagoraiou, L. "In vivo Transposition of Minos, a *Drosophila* Mobile Element, in Mammalian Tissues," *Proc. Natl. Acad. Sci. USA*, 2001, vol. 98, No. 20, 11474-11478.
Zhukova, et al., "Expression of the Human Insulin Gene in the Gastric G Cells of Transgenic Mice," *Transgenic Research*, 2001, vol. 10, 329-338.
AU2003261096 Response to First Examination Report dated May 12, 2008.
AU2003261096 Second Examination Report dated Jun. 6, 2008.
AU2003261096 Response to Second Examination Report dated Sep. 8, 2008.
EP037621729 Supplementary Search Report dated Feb. 15, 2006.
EP037621729 Fourth Office Action dated Oct. 10, 2007.
EP037621729 Response to Fourth Office Action dated Feb. 11, 2008.
EP037621729 Fifth Office Action dated Feb. 26, 2008.
EP037621729 Response to Fifth Office Action dated Jul. 4, 2008.
EP037621729 Communication Under Rule 71(3) EPC dated Nov. 11, 2008.
EP038002259 Supplementary Partial Search Report dated May 26, 2006.
EP038002259 Second Office Action dated Jun. 14, 2007.
EP038002259 Response to Second Office Action dated Oct. 23, 2007.
EP038002259 Third Office Action dated Nov. 7, 2007.
EP038002259 Response to Third Office Action dated Mar. 17, 2008.
EP038002259 Fourth Office Action dated Mar. 31, 2008.
EP038002259 Response to Fourth Office Action dated May 30, 2008.
EP038002259 Communication Under Rule 71(3) EPC dated Aug. 19, 2008.
PCT/US03/20389 International Search Report dated Apr. 2, 2004.
Lillico, et al., "Transgenic Chickens as Bioreactors for Protein-Based Drugs," *Drug Discovery Today*, vol. 10, No. 3, Feb. 2005, pp. 191-196.
Mozdziak, et al., "Status of Transgenic Chicken Models for Developmental Biology," *Developmental Dynamics*, 2004, 229:414-421.

* cited by examiner

Pro | Transposase | Poly A — IS | Pro | Gene of Interest | IS

Pro

Transposase

Poly A

IS

Ov Pro

Ov Gene

TAG

ProInsulin Gene

PolyA

IS

Vit Pro
Transposase
Poly A
IS
Vit Pro
Vit Targ
ProInsulin
Poly A
IS

FIGURE 4

| IS | Oval Prom | prepro | Heavy chain | pro | Light chain | polyA | IS |
|---|---|---|---|---|---|---|---|

FIGURE 5

IS | Oval Prom | prepro | Light chain | ent | Heavy chain | polyA | IS

Figure 7:
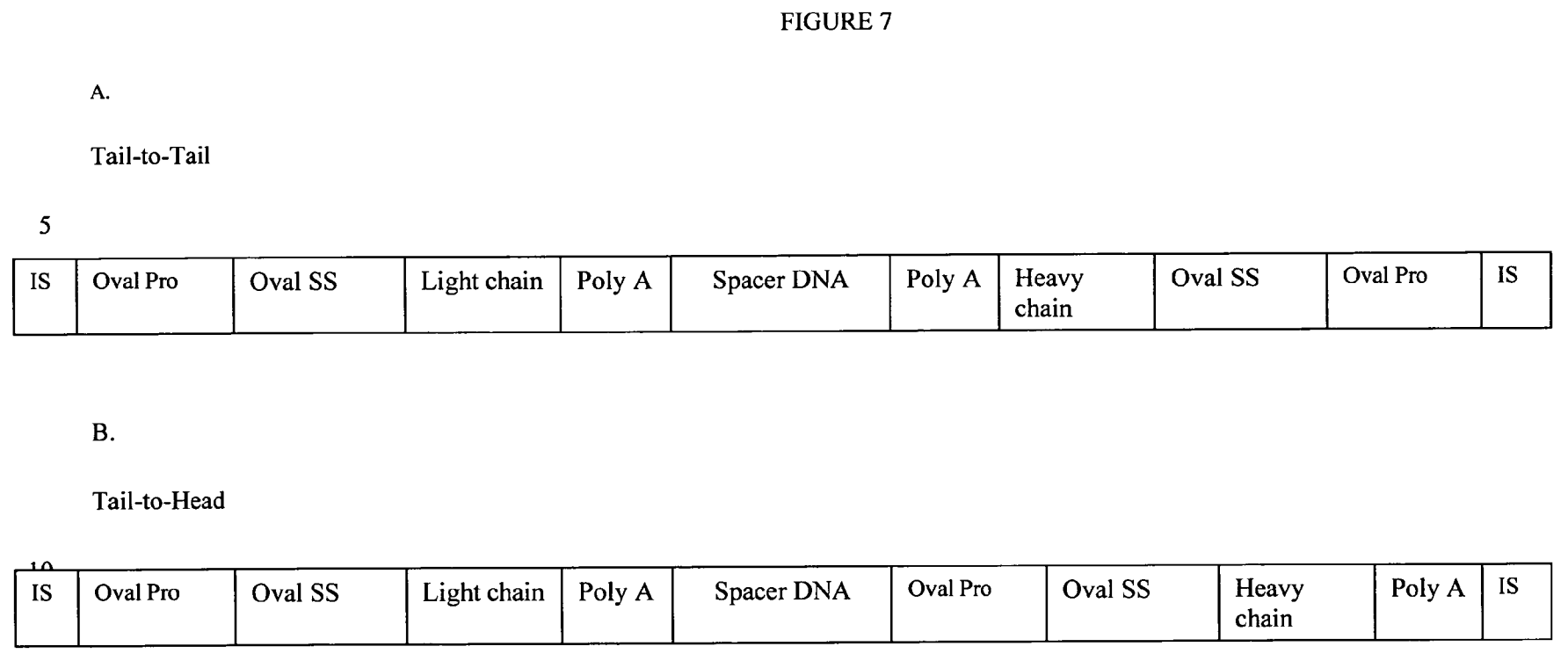

A. Tail-to-Tail

| IS | Oval Pro | Oval SS | Light chain | Poly A | Spacer DNA | Poly A | Heavy chain | Oval SS | Oval Pro | IS |
|---|---|---|---|---|---|---|---|---|---|---|

B. Tail-to-Head

| IS | Oval Pro | Oval SS | Light chain | Poly A | Spacer DNA | Oval Pro | Oval SS | Heavy chain | Poly A | IS |
|---|---|---|---|---|---|---|---|---|---|---|

GENE REGULATION IN TRANSGENIC ANIMALS USING A TRANSPOSON-BASED VECTOR

PRIORITY CLAIM TO RELATED APPLICATIONS

This application is a continuation application of U.S. patent application Ser. No. 10/609,019, filed Jun. 26, 2003, which claims benefit to Provisional Patent Application No. 60/392,415 filed Jun. 26, 2002, Provisional Patent Application No. 60/441,392 filed Jan. 21, 2003, Provisional Patent Application No. 60/441,377 filed Jan. 21, 2003, Provisional Patent Application No. 60/441,502 filed Jan. 21, 2003, Provisional Patent Application No. 60/441,405 filed Jan. 21, 2003, Provisional Patent Application No. 60/441,447 filed Jan. 21, 2003, and Provisional Patent Application No. 60/441,381 filed Jan. 21, 2003.

The U.S. Government has certain rights in this invention. The development of this invention was partially funded by the United States Government under a HATCH grant from the United States Department of Agriculture, partially funded by the United States Government with Formula 1433 funds from the United States Department of Agriculture and partially funded by the United States Government under contract DAAD 19-02016 awarded by the Army.

FIELD OF THE INVENTION

The present invention relates generally to cell-specific gene regulation in transgenic animals. Animals may be made transgenic through administration of a transposon-based vector through any method of administration including pronuclear injection, or intraembryonic, intratesticular, intraoviductal or intravenous administration. These transgenic animals contain the gene of interest in all cells, including germ cells. Animals may also be made transgenic by targeting specific cells for uptake and gene incorporation of the transposon-based vectors. Stable incorporation of a gene of interest into cells of the transgenic animals is demonstrated by expression of the gene of interest in a cell, wherein expression is regulated by a promoter sequence. The promoter sequence may be provided as a transgene along with the gene of interest or may be endogenous to the cell. The promoter sequence may be constitutive or inducible, wherein inducible promoters include tissue-specific promoters, developmentally regulated promoters and chemically inducible promoters.

BACKGROUND OF THE INVENTION

Transgenic animals are desirable for a variety of reasons, including their potential as biological factories to produce desired molecules for pharmaceutical, diagnostic and industrial uses. This potential is attractive to the industry due to the inadequate capacity in facilities used for recombinant production of desired molecules and the increasing demand by the pharmaceutical industry for use of these facilities. Numerous attempts to produce transgenic animals have met several problems, including low rates of gene incorporation and unstable gene incorporation. Accordingly, improved gene technologies are needed for the development of transgenic animals for the production of desired molecules.

Improved gene delivery technologies are also needed for the treatment of disease in animals and humans. Many diseases and conditions can be treated with gene-delivery technologies, which provide a gene of interest to a patient suffering from the disease or the condition. An example of such disease is Type 1 diabetes. Type 1 diabetes is an autoimmune disease that ultimately results in destruction of the insulin producing β-cells in the pancreas. Although patients with Type 1 diabetes may be treated adequately with insulin injections or insulin pumps, these therapies are only partially effective. Insulin replacement, such as via insulin injection or pump administration, cannot fully reverse the defect in the vascular endothelium found in the hyperglycemic state (Pieper et al., 1996. Diabetes Res. Clin. Pract. Suppl. S157-S162). In addition, hyper- and hypoglycemia occurs frequently despite intensive home blood glucose monitoring. Finally, careful dietary constraints are needed to maintain an adequate ratio of consumed calories consumed. This often causes major psychosocial stress for many diabetic patients. Development of gene therapies providing delivery of the insulin gene into the pancreas of diabetic patients could overcome many of these problems and result in improved life expectancy and quality of life.

Several of the prior art gene delivery technologies employed viruses that are associated with potentially undesirable side effects and safety concerns. The majority of current gene-delivery technologies useful for gene therapy rely on virus-based delivery vectors, such as adeno and adeno-associated viruses, retroviruses, and other viruses, which have been attenuated to no longer replicate. (Kay, M. A., et al. 2001. Nature Medicine 7:33-40).

There are multiple problems associated with the use or viral vectors. First, they are not tissue-specific. In fact, a gene therapy trial using adenovirus was recently halted because the vector was present in the patient's sperm (Gene trial to proceed despite fears that therapy could change child's genetic makeup. The New York Times, Dec. 23, 2001). Second, viral vectors are likely to be transiently incorporated, which necessitates re-treating a patient at specified time intervals. (Kay, M. A., et al. 2001. Nature Medicine 7:33-40). Third, there is a concern that a viral-based vector could revert to its virulent form and cause disease. Fourth, viral-based vectors require a dividing cell for stable integration. Fifth, viral-based vectors indiscriminately integrate into various cells and tissues, which can result in undesirable germline integration. Sixth, the required high titers needed to achieve the desired effect have resulted in the death of one patient and they are believed to be responsible for induction of cancer in a separate study. (Science, News of the Week, Oct. 4, 2002).

Accordingly, what is needed is a new vector to produce transgenic animals and humans with stably incorporated genes, which vector does not cause disease or other unwanted side effects. There is also a need for DNA constructs that would be stably incorporated into the tissues and cells of animals and humans, including cells in the resting state, which are not replicating. There is a further recognized need in the art for DNA constructs capable of delivering genes to specific tissues and cells of animals and humans.

When incorporating a gene of interest into an animal for the production of a desired protein or when incorporating a gene of interest in an animal or human for the treatment of a disease, it is often desirable to selectively activate incorporated genes using inducible promoters. These inducible promoters are regulated by substances either produced or recognized by the transcription control elements within the cell in which the gene is incorporated. In many instances, control of gene expression is desired in transgenic animals or humans so that incorporated genes are selectively activated at desired times and/or under the influence of specific substances. Accordingly, what is needed is a means to selectively activate genes introduced into the genome of cells of a transgenic animal or human. This can be taken a step further to cause incorporation to be tissue-specific, which prevents widespread gene incorporation throughout a patient's body (animal or human). This decreases the amount of DNA needed for a treatment, decreases the chance of incorporation in gametes, and targets gene delivery, incorporation, and expression to the desired tissue where the gene is needed to function.

SUMMARY OF THE INVENTION

The present invention addresses the problems described above by providing new, effective and efficient compositions for producing transgenic animals and for treating disease in animals or humans. Transgenic animals include all egg-laying animals and milk-producing animals. Transgenic animals further include but are not limited to avians, fish, amphibians, reptiles, insects, mammals and humans. In a preferred embodiment, the animal is an avian animal. In another preferred embodiment, the animal is a milk-producing animal, including but not limited to bovine, porcine, ovine and equine animals. Animals are made transgenic through administration of a composition comprising a transposon-based vector designed for stable incorporation of a gene of interest for production of a desired protein, together with an acceptable carrier. A transfection reagent is optionally added to the composition before administration.

The transposon-based vectors of the present invention include a transposase, operably-linked to a first promoter, and a coding sequence for a protein or peptide of interest operably-linked to a second promoter, wherein the coding sequence for the protein or peptide of interest and its operably-linked promoter are flanked by transposase insertion sequences recognized by the transposase. The transposon-based vector also includes the following characteristics: a) one or more modified Kozak sequences comprising ACCATG (SEQ ID NO:13) at the 3' end of the first promoter to enhance expression of the transposase; b) modifications of the codons for the first several N-terminal amino acids of the transposase, wherein the nucleotide at the third base position of each codon was changed to an A or a T without changing the corresponding amino acid; c) addition of one or more stop codons to enhance the termination of transposase synthesis; and/or, d) addition of an effective polyA sequence operably-linked to the transposase to further enhance expression of the transposase gene.

Use of the compositions of the present invention results in highly efficient and stable incorporation of a gene of interest into the genome of transfected animals. For example, transgenic avians have been mated and produce transgenic progeny in the G1 generation. The transgenic progeny have been mated and produce transgenic progeny in the G2 generation.

The present invention also provides for tissue-specific incorporation and/or expression of a gene of interest. Tissue-specific incorporation of a gene of interest may be achieved by placing the transposase gene under the control of a tissue-specific promoter, whereas tissue-specific expression of a gene of interest may be achieved by placing the gene of interest under the control of a tissue-specific promoter. In some embodiments, the gene of interest is transcribed under the influence of an ovalbumin, or other oviduct specific, promoter. Linking the gene of interest to an oviduct specific promoter in an egg-laying animal results in synthesis of a desired molecule and deposition of the desired molecule in a developing egg. The present invention further provides for stable incorporation and expression of genes in the epithelial cells of the mammary gland in milk-producing animals. Transcription of the gene of interest in the epithelial cells of the mammary gland results in synthesis of a desired molecule and deposition of the desired molecule in the milk. A preferred molecule is a protein. In some embodiments, the desired molecule deposited in the milk is an antiviral protein, an antibody, or a serum protein.

In other embodiments, specific incorporation of the proinsulin gene into liver cells of a diabetic animal results in the improvement of the animal's condition. Such improvement is achieved by placing a transposase gene under the control of a liver-specific promoter, which drives integration of the gene of interest in liver cells of the diabetic animal.

The present invention advantageously produces a high number of transgenic animals having a gene of interest stably incorporated. These transgenic animals successfully pass the desired gene to their progeny. The transgenic animals of the present invention also produce large amounts of a desired molecule encoded by the transgene. Transgenic egg-laying animals, particularly avians, produce large amounts of a desired protein that is deposited in the egg for rapid harvest and purification. Transgenic milk-producing animals produce large amounts of a desired protein that is deposited in the milk for rapid harvest and purification.

Any desired gene may be incorporated into the novel transposon-based vectors of the present invention in order to synthesize a desired molecule in the transgenic animals. Proteins, peptides and nucleic acids are preferred desired molecules to be produced by the transgenic animals of the present invention. Particularly preferred proteins are antibody proteins.

This invention provides a composition useful for the production of transgenic hens capable of producing substantially high amounts of a desired protein or peptide. Entire flocks of transgenic birds may be developed very quickly in order to produce industrial amounts of desired molecules. The present invention solves the problems inherent in the inadequate capacity of fermentation facilities used for bacterial production of molecules and provides a more efficient and economical way to produce desired molecules. Accordingly, the present invention provides a means to produce large amounts of therapeutic, diagnostic and reagent molecules.

Transgenic chickens are excellent in terms of convenience and efficiency of manufacturing molecules such as proteins and peptides. Starting with a single transgenic rooster, thousands of transgenic offspring can be produced within a year. (In principle, up to forty million offspring could be produced in just three generations). Each transgenic female is expected to lay at least 250 eggs/year, each potentially containing hundreds of milligrams of the selected protein. Flocks of chickens numbering in the hundreds of thousands are readily handled through established commercial systems. The technologies for obtaining eggs and fractionating them are also well known and widely accepted. Thus, for each therapeutic, diagnostic, or other protein of interest, large amounts of a substantially pure material can be produced at relatively low incremental cost.

A wide range of recombinant peptides and proteins can be produced in transgenic egg-laying animals and milk-producing animals. Enzymes, hormones, antibodies, growth factors, serum proteins, commodity proteins, biological response modifiers, peptides and designed proteins may all be made through practice of the present invention. For example, rough estimates suggest that it is possible to produce in bulk growth hormone, insulin, or Factor VIII, and deposit them in transgenic egg whites, for an incremental cost in the order of one dollar per gram. At such prices it is feasible to consider administering such medical agents by inhalation or even orally, instead of through injection. Even if bioavailability rates through these avenues were low, the cost of a much higher effective-dose would not be prohibitive.

In one embodiment, the egg-laying transgenic animal is an avian. The method of the present invention may be used in avians including Ratites, Psittaciformes, Falconiformes, Piciformes, Strigiformes, Passeriformes, Coraciformes, Ralliformes, Cuculiformes, Columbiformes, Galliformes, Anseriformes, and Herodiones. Preferably, the egg-laying transgenic animal is a poultry bird. More preferably, the bird is a chicken, turkey, duck, goose or quail. Another preferred bird is a ratite, such as, an emu, an ostrich, a rhea, or a cassowary. Other preferred birds are partridge, pheasant, kiwi, parrot, parakeet, macaw, falcon, eagle, hawk, pigeon, cockatoo, song birds, jay bird, blackbird, finch, warbler, canary, toucan, mynah, or sparrow.

In another embodiment, the transgenic animal is a milk-producing animal, including but not limited to bovine, ovine, porcine, equine, and primate animals.

Milk-producing animals include but are not limited to cows, goats, horses, pigs, buffalo, rabbits, non-human primates, and humans.

Accordingly, it is an object of the present invention to provide novel transposon-based vectors.

It is another object of the present invention to provide novel transposon-based vectors that encode for the production of desired proteins or peptides in cells.

It is an object of the present invention to produce transgenic animals through administration of a transposon-based vector.

Another object of the present invention is to produce transgenic animals through administration of a transposon-based vector, wherein the transgenic animals produce desired proteins or peptides.

Yet another object of the present invention is to produce transgenic animals through administration of a transposon-based vector, wherein the transgenic animals produce desired proteins or peptides and deposit the proteins or peptides in eggs or milk.

It is a further object of the present invention to produce transgenic animals through intraembryonic, intratesticular or intraoviductal administration of a transposon-based vector.

It is further an object of the present invention to provide a method to produce transgenic animals through administration of a transposon-based vector that are capable of producing transgenic progeny.

Yet another object of the present invention is to provide a method to produce transgenic animals through administration of a transposon-based vector that are capable of producing a desired molecule, such as a protein, peptide or nucleic acid.

Another object of the present invention is to provide a method to produce transgenic animals through administration of a transposon-based vector, wherein such administration results in modulation of endogenous gene expression.

It is another object of the present invention to provide transposon-vectors useful for cell- or tissue-specific expression of a gene of interest in an animal or human with the purpose of gene therapy.

It is yet another object of the present invention to provide a method to produce transgenic avians through administration of a transposon-based vector that are capable of producing proteins, peptides or nucleic acids.

It is another object of the present invention to produce transgenic animals through administration of a transposon-based vector encoding an antibody or a fragment thereof.

Still another object of the present invention is to provide a method to produce transgenic avians through administration of a transposon-based vector that are capable of producing proteins or peptides and depositing these proteins or peptides in the egg.

Another object of the present invention is to provide transgenic avians that contain a stably incorporated transgene.

Still another object of the present invention is to provide eggs containing desired proteins or peptides encoded by a transgene incorporated into the transgenic avian that produces the egg.

It is further an object of the present invention to provide a method to produce transgenic milk-producing animals through administration of a transposon-based vector that are capable of producing proteins, peptides or nucleic acids.

Still another object of the present invention is to provide a method to produce transgenic milk-producing animals through administration of a transposon-based vector that are capable of producing proteins or peptides and depositing these proteins or peptides in their milk.

Another object of the present invention is to provide transgenic milk-producing animals that contain a stably incorporated transgene.

Another object of the present invention is to provide transgenic milk-producing animals that are capable of producing proteins or peptides and depositing these proteins or peptides in their milk.

Yet another object of the present invention is to provide milk containing desired molecules encoded by a transgene incorporated into the transgenic milk-producing animals that produce the milk.

Still another object of the present invention is to provide milk containing desired proteins or peptides encoded by a transgene incorporated into the transgenic milk-producing animals that produce the milk.

A further object of the present invention to provide a method to produce transgenic sperm through administration of a transposon-based vector to an animal.

A further object of the present invention to provide transgenic sperm that contain a stably incorporated transgene.

An advantage of the present invention is that transgenic animals are produced with higher efficiencies than observed in the prior art.

Another advantage of the present invention is that these transgenic animals possess high copy numbers of the transgene.

Another advantage of the present invention is that the transgenic animals produce large amounts of desired molecules encoded by the transgene.

Still another advantage of the present invention is that desired molecules are produced by the transgenic animals much more efficiently and economically than prior art methods, thereby providing a means for large scale production of desired molecules, particularly proteins and peptides.

These and other objects, features and advantages of the present invention will become apparent after a review of the following detailed description of the disclosed embodiments and claims.

BRIEF DESCRIPTION OF THE FIGURES

FIG. 1 depicts schematically a transposon-based vector containing a transposase operably linked to a first promoter and a gene of interest operably-linked to a second promoter, wherein the gene of interest and its operably-linked promoter are flanked by insertion sequences (IS) recognized by the transposase. "Pro" designates a promoter. In this and subsequent figures, the size of the actual nucleotide sequence is not necessarily proportionate to the box representing that sequence.

FIG. 2 depicts schematically a transposon-based vector for targeting deposition of a polypeptide in an egg white wherein Ov pro is the ovalbumin promoter, Ov protein is the ovalbumin protein and PolyA is a polyadenylation sequence. The TAG sequence includes a spacer, the gp41 hairpin loop from HIV I and a protein cleavage site.

FIG. 4 depicts schematically a transposon-based vector for targeting deposition of a polypeptide in an egg yolk wherein Vit pro is the vitellogenin promoter and Vit targ is the vitellogenin targeting sequence.

FIG. 5 depicts schematically a transposon-based vector for expression of antibody heavy and light chains. Prepro indicates a prepro sequence from cecropin and pro indicates a pro sequence from cecropin.

FIG. 6 depicts schematically a transposon-based vector for expression of antibody heavy and light chains. Ent indicates an enterokinase cleavage sequence.

FIG. 7 depicts schematically egg white targeted expression of antibody heavy and light chains from one vector in either tail-to-tail (FIG. 7A) or tail-to-head (FIG. 7B) configuration. In the tail-to-tail configuration, the ovalbumin signal sequence adjacent to the gene for the light chain contains on its 3' end an enterokinase cleavage site (not shown) to allow cleavage of the signal sequence from the light chain, and the ovalbumin signal sequence adjacent to the gene for the heavy chain contains on its 5' end an enterokinase cleavage site (not shown) to allow cleavage of the signal sequence from the heavy chain. In the tail-to-head configuration, the ovalbumin signal sequence adjacent to the gene for the heavy chain and the light chain contains on its 3' end an enterokinase cleavage site (not shown) to allow cleavage of the signal sequence from the heavy or light chain.

DETAILED DESCRIPTION OF THE INVENTION

Figure 3:
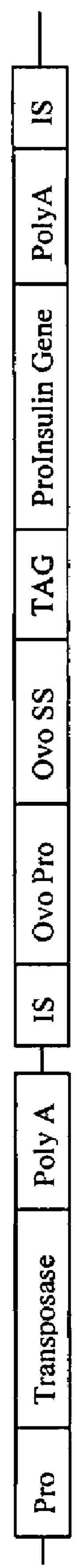
FIG. 3 depicts schematically a transposon-based vector for targeting deposition of a polypeptide in an egg white wherein Ovo pro is the ovomucoid promoter and Ovo SS is the ovomucoid signal sequence. The TAG sequence includes a spacer, the gp41 hairpin loop from HIV I and a protein cleavage site.

The present invention provides a new, effective and efficient method of producing transgenic animals, particularly egg-laying animals and milk-producing animals, through administration of a composition comprising a transposon-based vector designed for stable incorporation of a gene of interest for production of a desired molecule.

Definitions

It is to be understood that as used in the specification and in the claims, "a" or "an" can mean one or more, depending upon the context in which it is used. Thus, for example, reference to "a cell" can mean that at least one cell can be utilized.

The term "antibody" is used interchangeably with the term "immunoglobulin" and is defined herein as a protein synthesized by an animal or a cell of the immune system in response to the presence of a foreign substance commonly referred to as an "antigen" or an "immunogen". The term antibody includes fragments of antibodies. Antibodies are characterized by specific affinity to a site on the antigen, wherein the site is referred to an "antigenic determinant" or an "epitope". Antigens can be naturally occurring or artificially engineered. Artificially engineered antigens include but are not limited to small molecules, such as small peptides, attached to haptens such as macromolecules, for example proteins, nucleic acids, or polysaccharides. Artificially designed or engineered variants of naturally occurring antibodies and artificially designed or engineered antibodies not occurring in nature are all included in the current definition. Such variants include conservatively substituted amino acids and other forms of substitution as described in the section concerning proteins and polypeptides.

As used herein, the term "egg-laying animal" includes all amniotes such as birds, turtles, lizards and monotremes. Monotremes are egg-laying mammals and include the platypus and echidna. The term "bird" or "fowl," as used herein, is defined as a member of the Aves class of animals which are characterized as warm-blooded, egg-laying vertebrates primarily adapted for flying. Avians include, without limitation, Ratites, Psittaciformes, Falconiformes, Piciformes, Strigiformes, Passeriformes, Coraciformes, Ralliformes, Cuculiformes, Columbiformes, Galliformes, Anseriformes, and Herodiones. The term "Ratite," as used herein, is defined as a group of flightless, mostly large, running birds comprising several orders and including the emus, ostriches, kiwis, and cassowaries. The term "Psittaciformes", as used herein, includes parrots and refers to a monofamilial order of birds that exhibit zygodactylism and have a strong hooked bill. A "parrot" is defined as any member of the avian family Psittacidae (the single family of the Psittaciformes), distinguished by the short, stout, strongly hooked beak. The term "chicken" as used herein denotes chickens used for table egg production, such as egg-type chickens, chickens reared for public meat consumption, or broilers, and chickens reared for both egg and meat production ("dual-purpose" chickens). The term "chicken" also denotes chickens produced by primary breeder companies, or chickens that are the parents, grandparents, great-grandparents, etc. of those chickens reared for public table egg, meat, or table egg and meat consumption.

The term "egg" is defined herein as a large female sex cell enclosed in a porous, calcarous or leathery shell, produced by birds and reptiles. The term "ovum" is defined as a female gamete, and is also known as an egg. Therefore, egg production in all animals other than birds and reptiles, as used herein, is defined as the production and discharge of an ovum from an ovary, or "ovulation". Accordingly, it is to be understood that the term "egg" as used herein is defined as a large female sex cell enclosed in a porous, calcarous or leathery shell, when a bird or reptile produces it, or it is an ovum when it is produced by all other animals.

The term "milk-producing animal" refers herein to mammals including, but not limited to, bovine, ovine, porcine, equine, and primate animals. Milk-producing animals include but are not limited to cows, llamas, camels, goats, reindeer, zebu, water buffalo, yak, horses, pigs, rabbits, non-human primates, and humans.

The term "gene" is defined herein to include a coding region for a protein, peptide or polypeptide.

The term "vector" is used interchangeably with the terms "construct", "DNA construct" and "genetic construct" to denote synthetic nucleotide sequences used for manipulation of genetic material, including but not limited to cloning, subcloning, sequencing, or introduction of exogenous genetic material into cells, tissues or organisms, such as birds. It is understood by one skilled in the art that vectors may contain synthetic DNA sequences, naturally occurring DNA sequences, or both. The vectors of the present invention are transposon-based vectors as described herein.

When referring to two nucleotide sequences, one being a regulatory sequence, the term "operably-linked" is defined herein to mean that the two sequences are associated in a manner that allows the regulatory sequence to affect expression of the other nucleotide sequence. It is not required that the operably-linked sequences be directly adjacent to one another with no intervening sequence(s).

The term "regulatory sequence" is defined herein as including promoters, enhancers and other expression control elements such as polyadenylation sequences, matrix attachment sites, insulator regions for expression of multiple genes on a single construct, ribosome entry/attachment sites, introns that are able to enhance expression, and silencers.

Transposon-Based Vectors

While not wanting to be bound by the following statement, it is believed that the nature of the DNA construct is an important factor in successfully producing transgenic animals. The "standard" types of plasmid and viral vectors that have previously been almost universally used for transgenic work in all species, especially avians, have low efficiencies and may constitute a major reason for the low rates of transformation previously observed. The DNA (or RNA) constructs previously used often do not integrate into the host DNA, or integrate only at low frequencies. Other factors may have also played a part, such as poor entry of the vector into target cells. The present invention provides transposon-based vectors that can be administered to an animal that overcome the prior art problems relating to low transgene integration frequencies. Two preferred transposon-based vectors of the present invention in which a tranposase, gene of interest and other polynucleotide sequences may be introduced are termed pTnMCS (SEQ ID NO:36) and pTnMod (SEQ ID NO:1).

The transposon-based vectors of the present invention produce integration frequencies an order of magnitude greater than has been achieved with previous vectors. More specifically, intratesticular injections performed with a prior art transposon-based vector (described in U.S. Pat. No. 5,719,055) resulted in 41% sperm positive roosters whereas intratesticular injections performed with the novel transposon-based vectors of the present invention resulted in 77% sperm positive roosters. Actual frequencies of integration were estimated by either or both comparative strength of the PCR signal from the sperm and histological evaluation of the testes and sperm by quantitative PCR.

Figure 1:
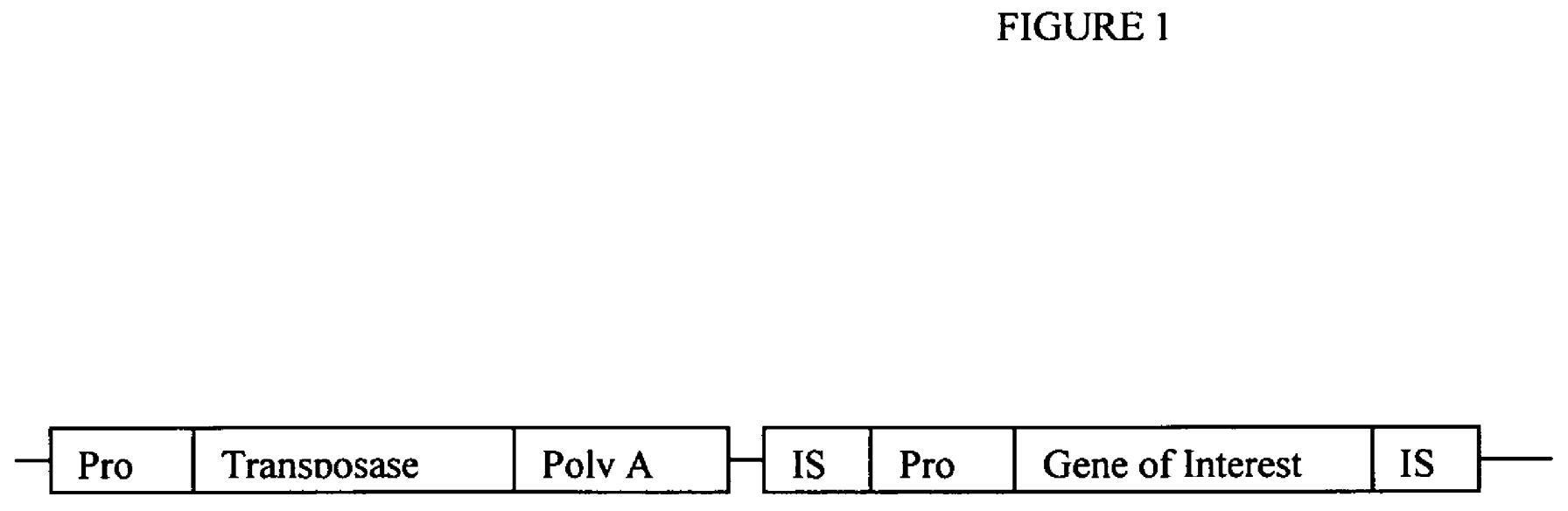

The transposon-based vectors of the present invention include a transposase gene operably-linked to a first promoter, and a coding sequence for a desired protein or peptide operably-linked to a second promoter, wherein the coding sequence for the desired protein or peptide and its operably-linked promoter are flanked by transposase insertion sequences recognized by the transposase. The transposon-based vector also includes one or more of the following characteristics: a) one or more modified Kozak sequences comprising ACCATG (SEQ ID NO:13) at the 3' end of the first promoter to enhance expression of the transposase; b) modifications of the codons for the first several N-terminal amino acids of the transposase, wherein the third base of each codon was changed to an A or a T without changing the corresponding amino acid; c) addition of one or more stop codons to enhance the termination of transposase synthesis; and, d) addition of an effective polyA sequence operably-linked to the transposase to further enhance expression of the transposase gene. FIG. 1 shows a schematic representation of several components of the transposon-based vector. The present invention further includes vectors containing more than one gene of interest, wherein a second or subsequent gene of interest is operably-linked to the second promoter or to a different promoter. It is also to be understood that the transposon-based vectors shown in the Figures are representational of the present invention and that the order of the vector elements may be different than that shown in the Figures, that the elements may be present in various orientations, and that the vectors may contain additional elements not shown in the Figures.

Transposases and Insertion Sequences

In a further embodiment of the present invention, the transposase found in the transposase-based vector is an altered target site (ATS) transposase and the insertion sequences are those recognized by the ATS transposase. However, the transposase located in the transposase-based vectors is not limited to a modified ATS transposase and can be derived from any transposase. Transposases known in the prior art include those found in AC7, Tn5SEQ1, Tn916, Tn951, Tn1721, Tn2410, Tn1681, Tn1, Tn2, Tn3, Tn4, Tn5, Tn6, Tn9, Tn10, Tn30, Tn101, Tn903, Tn501, Tn1000 (γδ), Tn1681, Tn2901, AC transposons, Mp transposons, Spm transposons, En transposons, Dotted transposons, Mu transposons, Ds transposons, dSpm transposons and I transposons. According to the present invention, these transposases and their regulatory sequences are modified for improved functioning as follows: a) the addition one or more modified Kozak sequences comprising ACCATG (SEQ ID NO:13) at the 3' end of the promoter operably-linked to the transposase; b) a change of the codons for the first several amino acids of the transposase, wherein the third base of each codon was changed to an A or a T without changing the corresponding amino acid; c) the addition of one or more stop codons to enhance the termination of transposase synthesis; and/or, d) the addition of an effective polyA sequence operably-linked to the transposase to further enhance expression of the transposase gene.

Although not wanting to be bound by the following statement, it is believed that the modifications of the first several N-terminal codons of the transposase gene increase transcription of the transposase gene, in part, by increasing strand dissociation. It is preferable that between approximately 1 and 20, more preferably 3 and 15, and most preferably between 4 and 12 of the first N-terminal codons of the transposase are modified such that the third base of each codon is changed to an A or a T without changing the encoded amino acid. In one embodiment, the first ten N-terminal codons of the transposase gene are modified in this manner. It is also preferred that the transposase contain mutations that make it less specific for preferred insertion sites and thus increases the rate of transgene insertion as discussed in U.S. Pat. No. 5,719,055.

In some embodiments, the transposon-based vectors are optimized for expression in a particular host by changing the methylation patterns of the vector DNA. For example, prokaryotic methylation may be reduced by using a methylation deficient organism for production of the transposon-based vector. The transposon-based vectors may also be methylated to resemble eukaryotic DNA for expression in a eukaryotic host.

Transposases and insertion sequences from other analogous eukaryotic transposon-based vectors that can also be modified and used are, for example, the *Drosophila* P element derived vectors disclosed in U.S. Pat. No. 6,291,243; the *Drosophila* mariner element described in Sherman et al. (1998); or the sleeping beauty transposon. See also Hackett et al. (1999); D. Lampe et al., 1999. Proc. Natl. Acad. Sci. USA, 96:11428-11433; S. Fischer et al., 2001. Proc. Natl. Acad. Sci. USA, 98:6759-6764; L. Zagoraiou et al., 2001. Proc. Natl. Acad. Sci. USA, 98:11474-11478; and D. Berg et al. (Eds.), Mobile DNA, Amer. Soc. Microbiol. (Washington, D.C., 1989). However, it should be noted that bacterial transposon-based elements are preferred, as there is less likelihood that a eukaryotic transposase in the recipient species will recognize prokaryotic insertion sequences bracketing the transgene.

Many transposases recognize different insertion sequences, and therefore, it is to be understood that a transposase-based vector will contain insertion sequences recognized by the particular transposase also found in the transposase-based vector.

In a preferred embodiment of the invention, the insertion sequences have been shortened to about 70 base pairs in length as compared to those found in wild-type transposons that typically contain insertion sequences of well over 100 base pairs.

While the examples provided below incorporate a "cut and insert" Tn10 based vector that is destroyed following the insertion event, the present invention also encompasses the use of a "rolling replication" type transposon-based vector. Use of a rolling replication type transposon allows multiple copies of the transposon/transgene to be made from a single transgene construct and the copies inserted. This type of transposon-based system thereby provides for insertion of multiple copies of a transgene into a single genome. A rolling replication type transposon-based vector may be preferred when the promoter operably-linked to gene of interest is endogenous to the host cell and present in a high copy number or highly expressed. However, use of a rolling replication system may require tight control to limit the insertion events to non-lethal levels. Tn1, Tn2, Tn3, Tn4, Tn5, Tn9, Tn21, Tn501, Tn551, Tn951, Tn1721, Tn2410 and Tn2603 are examples of a rolling replication type transposon, although Tn5 could be both a rolling replication and a cut and insert type transposon.

Stop Codons and PolyA Sequences

In one embodiment, the transposon-based vector contains two stop codons operably-linked to the transposase and/or to the gene of interest. In an alternate embodiment, one stop codon of UAA or UGA is operably linked to the transposase and/or to the gene of interest. As used herein an "effective polyA sequence" refers to either a synthetic or non-synthetic sequence that contains multiple and sequential nucleotides containing an adenine base (an A polynucleotide string) and that increases expression of the gene to which it is operably-linked. A polyA sequence may be operably-linked to any gene in the transposon-based vector including, but not limited to, a transposase gene and a gene of interest. In one embodiment, a polyA sequence comprises the polynucleotide sequence provided in SEQ ID NO:28. A preferred polyA sequence is optimized for use in the host animal or human. In one embodiment, the polyA sequence is optimized for use in a bird, and more specifically, a chicken. The chicken optimized polyA sequence generally contains a minimum of 60 base pairs, and more preferably between approximately 60 and several hundred base pairs, that precede the A polynucleotide string and thereby separate the stop codon from the A polynucleotide string. A chicken optimized polyA sequence may also have a reduced amount of CT repeats as compared to a synthetic polyA sequence. In one embodiment of the present invention, the polyA sequence comprises a conalbumin polyA sequence as provided in SEQ ID NO:33 and as taken from GenBank accession # Y00407, base pairs 10651-11058.

Promoters and Enhancers

The first promoter operably-linked to the transposase gene and the second promoter operably-linked to the gene of interest can be a constitutive promoter or an inducible promoter. Constitutive promoters include, but are not limited to, immediate early cytomegalovirus (CMV) promoter, herpes simplex virus 1 (HSV1) immediate early promoter, SV40 promoter, lysozyme promoter, early and late CMV promoters, early and late HSV promoters, β-actin promoter, tubulin promoter, Rous-Sarcoma virus (RSV) promoter, and heat-shock protein (HSP) promoter. Inducible promoters include tissue-specific promoters, developmentally-regulated promoters and chemically inducible promoters. Examples of tissue-specific promoters include the glucose 6 phosphate (G6P) promoter, vitellogenin promoter, ovalbumin promoter, ovomucoid promoter, conalbumin promoter, ovotransferrin promoter, prolactin promoter, kidney uromodulin promoter, and placental lactogen promoter. In one embodiment, the vitellogenin promoter includes a polynucleotide sequence of SEQ ID NO:17. The G6P promoter sequence may be deduced from a rat G6P gene untranslated upstream region provided in GenBank accession number U57552.1. Examples of developmentally-regulated promoters include the homeobox promoters and several hormone induced promoters. Examples of chemically inducible promoters include reproductive hormone induced promoters and antibiotic inducible promoters such as the tetracycline inducible promoter and the zinc-inducible metallothionine promoter.

Other inducible promoter systems include the Lac operator repressor system inducible by IPTG (isopropyl beta-D-thiogalactoside) (Cronin, A. et al. 2001. Genes and Development, v. 15), ecdysone-based inducible systems (Hoppe, U. C. et al. 2000. Mol. Ther. 1:159-164); estrogen-based inducible systems (Braselmann, S. et al. 1993. Proc. Natl. Acad. Sci. 90:1657-1661); progesterone-based inducible systems using a chimeric regulator, GLVP, which is a hybrid protein consisting of the GAL4 binding domain and the herpes simplex virus transcriptional activation domain, VP16, and a truncated form of the human progesterone receptor that retains the ability to bind ligand and can be turned on by RU486 (Wang, et al. 1994. Proc. Natl. Acad. Sci. 91:8180-8184); CID-based inducible systems using chemical inducers of dimerization (CIDs) to regulate gene expression, such as a system wherein rapamycin induces dimerization of the cellular proteins FKBP12 and FRAP (Belshaw, P. J. et al. 1996. J. Chem. Biol. 3:731-738; Fan, L. et al. 1999. Hum. Gene Ther. 10:2273-2285; Shariat, S. F. et al. 2001. Cancer Res. 61:2562-2571; Spencer, D. M. 1996. Curr. Biol. 6:839-847). Chemical substances that activate the chemically inducible promoters can be administered to the animal containing the transgene of interest via any method known to those of skill in the art.

Other examples of cell or tissue-specific and constitutive promoters include but are not limited to smooth-muscle SM22 promoter, including chimeric SM22alpha/telokin promoters (Hoggatt A. M. et al., 2002. Circ Res. 91(12):1151-9); ubiquitin C promoter (Biochim Biophys Acta, 2003. Jan. 3; 1625(1):52-63); Hsf2 promoter; murine COMP (cartilage oligomeric matrix protein) promoter; early B cell-specific mb-1 promoter (Sigvardsson M., et al., 2002. Mol. Cell. Biol. 22(24):8539-51); prostate specific antigen (PSA) promoter (Yoshimura I. et al., 2002, J. Urol. 168(6):2659-64); exorh promoter and pineal expression-promoting element (Asaoka Y., et al., 2002. Proc. Natl. Acad. Sci. 99(24):15456-61); neural and liver ceramidase gene promoters (Okino N. et al., 2002. Biochem. Biophys. Res. Commun. 299(1):160-6); PSP94 gene promoter/enhancer (Gabril M. Y. et al., 2002. Gene Ther. 9(23):1589-99); promoter of the human FAT/CD36 gene (Kuriki C., et al., 2002. Biol. Pharm. Bull. 25(11): 1476-8); VL30 promoter (Staplin W. R. et al., 2002. Blood Oct. 24, 2002); IL-10 promoter (Brenner S., et al., 2002. J. Biol. Chem. Dec. 18, 2002).

Examples of avian promoters include, but are not limited to, promoters controlling expression of egg white proteins, such as ovalbumin, ovotransferrin (conalbumin), ovomucoid, lysozyme, ovomucin, g2 ovoglobulin, g3 ovoglobulin, ovoflavoprotein, ovostatin (ovomacroglobin), cystatin, avidin, thiamine-binding protein, glutamyl aminopeptidase minor glycoprotein 1, minor glycoprotein 2; and promoters controlling expression of egg-yolk proteins, such as vitellogenin, very low-density lipoproteins, low density lipoprotein, cobalamin-binding protein, riboflavin-binding protein, biotin-binding protein (Awade, 1996. Z. Lebensm. Unters. Forsch. 202:1-14). An advantage of using the vitellogenin promoter is that it is active during the egg-laying stage of an animal's life-cycle, which allows for the production of the protein of interest to be temporally connected to the import of the protein of interest into the egg yolk when the protein of interest is equipped with an appropriate targeting sequence.

Liver-specific promoters of the present invention include, but are not limited to, the following promoters, vitellogenin promoter, G6P promoter, cholesterol-7-alpha-hydroxylase (CYP7A) promoter, phenylalanine hydroxylase (PAH) promoter, protein C gene promoter, insulin-like growth factor I (IGF-I) promoter, bilirubin UDP-glucuronosyltransferase promoter, aldolase B promoter, furin promoter, metallothioneine promoter, albumin promoter, and insulin promoter.

Also included in the present invention are promoters that can be used to target expression of a protein of interest into the milk of a milk-producing animal including, but not limited to, β lactoglobin promoter, whey acidic protein promoter, lactalbumin promoter and casein promoter.

Promoters associated with cells of the immune system may also be used. Acute phase promoters such as interleukin (IL)-1 and IL-2 may be employed. Promoters for heavy and light chain Ig may also be employed. The promoters of the T cell receptor components CD4 and CD8, B cell promoters and the promoters of CR2 (complement receptor type 2) may also be employed. Immune system promoters are preferably used when the desired protein is an antibody protein.

Also included in this invention are modified promoters/enhancers wherein elements of a single promoter are duplicated, modified, or otherwise changed. In one embodiment, steroid hormone-binding domains of the ovalbumin promoter are moved from about −6.5 kb to within approximately the first 1000 base pairs of the gene of interest. Modifying an existing promoter with promoter/enhancer elements not found naturally in the promoter, as well as building an entirely synthetic promoter, or drawing promoter/enhancer elements from various genes together on a non-natural backbone, are all encompassed by the current invention.

Accordingly, it is to be understood that the promoters contained within the transposon-based vectors of the present invention may be entire promoter sequences or fragments of promoter sequences. For example, in one embodiment, the promoter operably linked to a gene of interest is an approximately 900 base pair fragment of a chicken ovalbumin promoter (SEQ ID NO:40). The constitutive and inducible promoters contained within the transposon-based vectors may also be modified by the addition of one or more modified Kozak sequences of ACCATG (SEQ ID NO:13).

As indicated above, the present invention includes transposon-based vectors containing one or more enhancers. These enhancers may or may not be operably-linked to their native promoter and may be located at any distance from their operably-linked promoter. A promoter operably-linked to an enhancer is referred to herein as an "enhanced promoter." The enhancers contained within the transposon-based vectors are preferably enhancers found in birds, and more preferably, an ovalbumin enhancer, but are not limited to these types of enhancers. In one embodiment, an approximately 675 base pair enhancer element of an ovalbumin promoter is cloned upstream of an ovalbumin promoter with 300 base pairs of spacer DNA separating the enhancer and promoter. In one embodiment, the enhancer used as a part of the present invention comprises base pairs 1-675 of a Chicken Ovalbumin enhancer from GenBank accession #S82527.1. The polynucleotide sequence of this enhancer is provided in SEQ ID NO:37.

Also included in some of the transposon-based vectors of the present invention are cap sites and fragments of cap sites. In one embodiment, approximately 50 base pairs of a 5' untranslated region wherein the capsite resides are added on the 3' end of an enhanced promoter or promoter. An exemplary 5' untranslated region is provided in SEQ ID NO:38. A putative cap-site residing in this 5' untranslated region preferably comprises the polynucleotide sequence provided in SEQ ID NO:39.

In one embodiment of the present invention, the first promoter operably-linked to the transposase gene is a constitutive promoter and the second promoter operably-linked to the gene of interest is a tissue-specific promoter. In this embodiment, use of the first constitutive promoter allows for constitutive activation of the transposase gene and incorporation of the gene of interest into virtually all cell types, including the germline of the recipient animal. Although the gene of interest is incorporated into the germline generally, the gene of interest is only expressed in a tissue-specific manner. It should be noted that cell- or tissue-specific expression as described herein does not require a complete absence of expression in cells or tissues other than the preferred cell or tissue. Instead, "cell-specific" or "tissue-specific" expression refers to a majority of the expression of a particular gene of interest in the preferred cell or tissue, respectively.

When incorporation of the gene of interest into the germline is not preferred, the first promoter operably-linked to the transposase gene can be a tissue-specific promoter. For example, transfection of a transposon-based vector containing a transposase gene operably-linked to a liver-specific promoter such as the G6P promoter or vitellogenin promoter provides for activation of the transposase gene and incorporation of the gene of interest in the cells of the liver but not into the germline and other cells generally. In this second embodiment, the second promoter operably-linked to the gene of interest can be a constitutive promoter or an inducible promoter. In a preferred embodiment, both the first promoter and the second promoter are a G6P promoter. In embodiments wherein tissue-specific expression or incorporation is desired, it is preferred that the transposon-based vector is administered directly to the tissue of interest or to an artery leading to the tissue of interest.

Accordingly, cell specific promoters may be used to enhance transcription in selected tissues. In birds, for example, promoters that are found in cells of the fallopian tube, such as ovalbumin, conalbumin, ovomucoid and/or lysozyme, are used in the vectors to ensure transcription of the gene of interest in the epithelial cells and tubular gland cells of the fallopian tube, leading to synthesis of the desired protein encoded by the gene and deposition into the egg white. In mammals, promoters specific for the epithelial cells of the alveoli of the mammary gland, such as prolactin, insulin, beta lactoglobin, whey acidic protein, lactalbumin, casein, and/or placental lactogen, are used in the design of vectors used for transfection of these cells for the production of desired proteins for deposition into the milk. In liver cells, the G6P promoter may be employed to drive transcription of the gene of interest for protein production. Proteins made in the liver of birds may be delivered to the egg yolk.

In order to achieve higher or more efficient expression of the transposase gene, the promoter and other regulatory sequences operably-linked to the transposase gene may be those derived from the host. These host specific regulatory sequences can be tissue specific as described above or can be of a constitutive nature. For example, an avian actin promoter and its associated polyA sequence can be operably-linked to a transposase in a transposase-based vector for transfection into an avian. Examples of other host specific promoters that could be operably-linked to the transposase include the myosin and DNA or RNA polymerase promoters.

Directing Sequences

In some embodiments of the present invention, the gene of interest is operably-linked to a directing sequence or a sequence that provides proper conformation to the desired protein encoded by the gene of interest. As used herein, the term "directing sequence" refers to both signal sequences and targeting sequences. An egg directing sequence includes, but is not limited to, an ovomucoid signal sequence, an ovalbumin signal sequence and a vitellogenin targeting sequence. The term "signal sequence" refers to an amino acid sequence, or the polynucleotide sequence that encodes the amino acid sequence, that directs the protein to which it is linked to the endoplasmic reticulum in a eukaryote, and more preferably the translocational pores in the endoplasmic reticulum, or the plasma membrane in a prokaryote, or mitochondria, such us for the purpose of gene therapy of mitochondrial diseases. Signal and targeting sequences can be used to direct a desired protein into, for example, the milk, when the transposon-based vectors are administered to a milk-producing animal.

Figure 2:
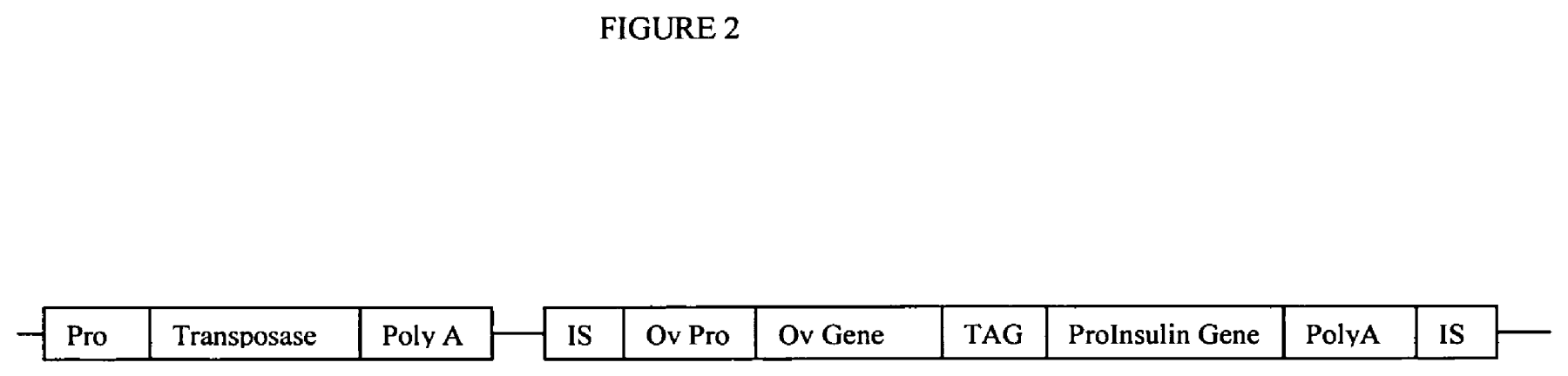

Signal sequences can also be used to direct a desired protein into, for example, a secretory pathway for incorporation into the egg yolk or the egg white, when the transposon-based vectors are administered to a bird or other egg-laying animal. One example of such a transposon-based vector is provided in FIG. 3 wherein the gene of interest is operably linked to the ovomucoid signal sequence. The present invention also includes a gene of interest operably-linked to a second gene containing a signal sequence. An example of such an embodiment is shown in FIG. 2 wherein the gene of interest is operably-linked to the ovalbumin gene that contains an ovalbumin signal sequence. Other signal sequences that can be included in the transposon-based vectors include, but are not limited to the ovotransferrin and lysozyme signal sequences.

As also used herein, the term "targeting sequence" refers to an amino acid sequence, or the polynucleotide sequence encoding the amino acid sequence, which amino acid sequence is recognized by a receptor located on the exterior of a cell. Binding of the receptor to the targeting sequence results in uptake of the protein or peptide operably-linked to the targeting sequence by the cell. One example of a targeting sequence is a vitellogenin targeting sequence that is recognized by a vitellogenin receptor (or the low density lipoprotein receptor) on the exterior of an oocyte. In one embodiment, the vitellogenin targeting sequence includes the polynucleotide sequence of SEQ ID NO:18. In another embodiment, the vitellogenin targeting sequence includes all or part of the vitellogenin gene. Other targeting sequences include VLDL and Apo E, which are also capable of binding the vitellogenin receptor. Since the ApoE protein is not endogenously expressed in birds, its presence may be used advantageously to identify birds carrying the transposon-based vectors of the present invention.

Genes of Interest Encoding Desired Proteins

A gene of interest selected for stable incorporation is designed to encode any desired protein or peptide or to regulate any cellular response. In some embodiments, the desired proteins or peptides are deposited in an egg or in milk. It is to be understood that the present invention encompasses transposon-based vectors containing multiple genes of interest. The multiple genes of interest may each be operably-linked to a separate promoter and other regulatory sequence(s) or may all be operably-linked to the same promoter and other regulatory sequences(s). In one embodiment, multiple gene of interest are linked to a single promoter and other regulatory sequence(s) and each gene of interest is separated by a cleavage site or a pro portion of a signal sequence.

Protein and peptide hormones are a preferred class of proteins in the present invention. Such protein and peptide hormones are synthesized throughout the endocrine system and include, but are not limited to, hypothalamic hormones and hypophysiotropic hormones, anterior, intermediate and posterior pituitary hormones, pancreatic islet hormones, hormones made in the gastrointestinal system, renal hormones, thymic hormones, parathyroid hormones, adrenal cortical and medullary hormones. Specifically, hormones that can be produced using the present invention include, but are not limited to, chorionic gonadotropin, corticotropin, erythropoietin, glucagons, IGF-1, oxytocin, platelet-derived growth factor, calcitonin, follicle-stimulating hormone, leutinizing hormone, thyroid-stimulating hormone, insulin, gonadotropin-releasing hormone and its analogs, vasopressin, octreotide, somatostatin, prolactin, adrenocorticotropic hormone, antidiuretic hormone, thyrotropin-releasing hormone (TRH), growth hormone-releasing hormone (GHRH), dopamine, melatonin, thyroxin ($T_4$), parathyroid hormone (PTH), glucocorticoids such as cortisol, mineralocorticoids such as aldosterone, androgens such as testosterone, adrenaline (epinephrine), noradrenaline (norepinephrine), estrogens such as estradiol, progesterone, glucagons, calcitrol, calciferol, atrial-natriuretic peptide, gastrin, secretin, cholecystokinin (CCK), neuropeptide Y, ghrelin, $PYY_{3-36}$, angiotensinogen, thrombopoietin, and leptin. By using appropriate polynucleotide sequences, species-specific hormones may be made by transgenic animals.

In one embodiment of the present invention, the gene of interest is a proinsulin gene and the desired molecule is insulin. Proinsulin consists of three parts: a C-peptide and two long strands of amino acids (called the alpha and beta chains) that later become linked together to form the insulin molecule. FIGS. 2 and 3 are schematics of transposon-based vector constructs containing a proinsulin gene operably-linked to an ovalbumin promoter and ovalbumin protein or an ovomucoid promoter and ovomucoid signal sequence, respectively. In these embodiments, proinsulin is expressed in the oviduct tubular gland cells and then deposited in the egg white. One example of a proinsulin polynucleotide sequence is shown in SEQ ID NO:21, wherein the C-peptide cleavage site spans from Arg at position 31 to Arg at position 65.

Serum proteins including lipoproteins such as high density lipoprotein (HDL), HDL-Milano and low density lipoprotein, albumin, clotting cascade factors, factor VIII, factor IX, fibrinogen, and globulins are also included in the group of desired proteins of the present invention. Immunoglobulins are one class of desired globulin molecules and include but are not limited to IgG, IgM, IgA, IgD, IgE, IgY, lambda chains, kappa chains and fragments thereof; Fc fragments, and Fab fragments. Desired antibodies include, but are not limited to, naturally occurring antibodies, human antibodies, humanized antibodies, and hybrid antibodies. Genes encoding modified versions of naturally occurring antibodies or fragments thereof and genes encoding artificially designed antibodies or fragments thereof may be incorporated into the transposon-based vectors of the present invention. Desired antibodies also include antibodies with the ability to bind specific ligands, for example, antibodies against proteins associated with cancer-related molecules, such as anti-her 2, or anti-CA125. Accordingly, the present invention encompasses a transposon-based vector containing one or more genes encoding a heavy immunoglobulin (Ig) chain and a light Ig chain. Further, more than one gene encoding for more than one antibody may be administered in one or more transposon-based vectors of the present invention. In this manner, an egg may contain more than one type of antibody in the egg white, the egg yolk or both.

Figure 5:
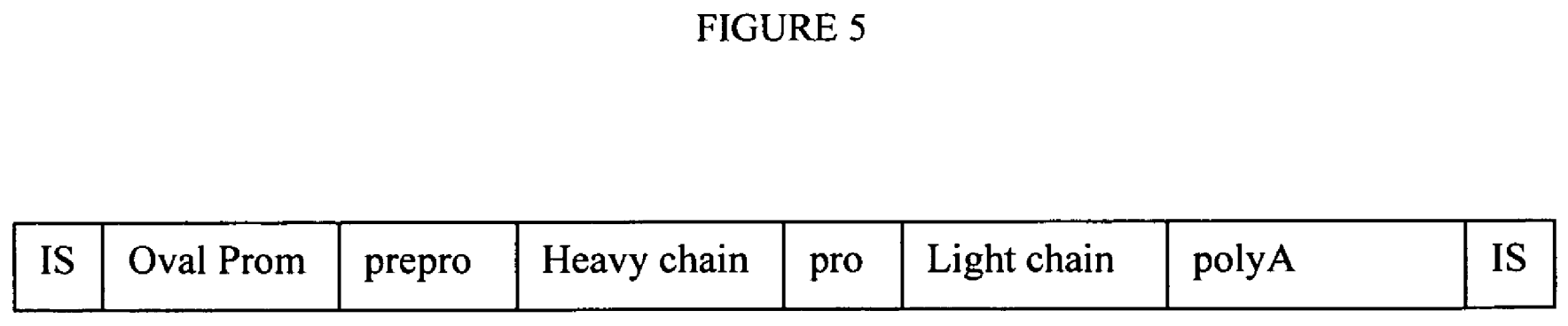
Figure 6:
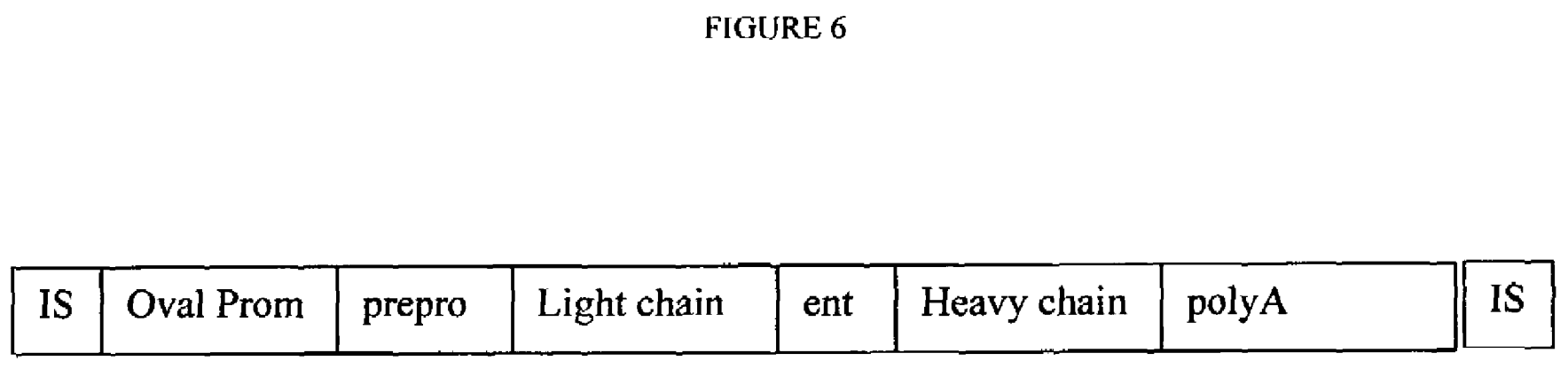

In one embodiment, a transposon-based vector contains a heavy Ig chain and a light Ig chain, both operably linked to a promoter. FIGS. 5 and 6 schematically depict exemplary constructs of this embodiment. More specifically, FIG. 5 shows a construct containing a cecropin pre-pro sequence and a cecropin pro sequence, wherein the pre sequence functions to direct the resultant protein into the endoplasmic reticulum and the pro sequences and the pro sequences are cleaved upon secretion of the protein from a cell into which the construct has been transfected. FIG. 6 shows a construct containing an enterokinase cleavage site. In this embodiment, it may be required to further remove several additional amino acids from the light chain following cleavage by enterokinase. In another embodiment, the transposon-based vector comprises a heavy Ig chain operably-linked to one promoter and a light Ig chain operably-linked to another promoter. FIG. 7 schematically depicts an exemplary construct of this embodiment. The present invention also encompasses a transposon-based vector containing genes encoding portions of a heavy Ig chain and/or portions of a light Ig chain. The present invention further includes a transposon-based vector containing a gene that encodes a fusion protein comprising a heavy and/or light Ig chain, or portions thereof.

Antibodies used as therapeutic reagents include but are not limited to antibodies for use in cancer immunotherapy against specific antigens, or for providing passive immunity to an animal or a human against an infectious disease or a toxic agent. Antibodies used as diagnostic reagents include, but are not limited to antibodies that may be labeled and detected with a detector, for example antibodies with a fluorescent label attached that may be detected following exposure to specific wavelengths. Such labeled antibodies may be primary antibodies directed to a specific antigen, for example, rhodamine-labeled rabbit anti-growth hormone, or may be labeled secondary antibodies, such as fluorescein-labeled goat-anti chicken IgG. Such labeled antibodies are known to one of ordinary skill in the art. Labels useful for attachment to antibodies are also known to one of ordinary skill in the art. Some of these labels are described in the "Handbook of Fluorescent Probes and Research Products", ninth edition, Richard P. Haugland (ed) Molecular Probes, Inc. Eugene, Oreg.), which is incorporated herein in its entirety.

Antibodies produced with using the present invention may be used as laboratory reagents for numerous applications including radioimmunoassay, western blots, dot blots, ELISA, immunoaffinity columns and other procedures requiring antibodies as known to one of ordinary skill in the art. Such antibodies include primary antibodies, secondary antibodies and tertiary antibodies, which may be labeled or unlabeled.

Antibodies that may be made with the practice of the present invention include, but are not limited to primary antibodies, secondary antibodies, designer antibodies, anti-protein antibodies, anti-peptide antibodies, anti-DNA antibodies, anti-RNA antibodies, anti-hormone antibodies, anti-hypophysiotropic peptides, antibodies against non-natural antigens, anti-anterior pituitary hormone antibodies, anti-posterior pituitary hormone antibodies, anti-venom antibodies, anti-tumor marker antibodies, antibodies directed against epitopes associated with infectious disease, including, anti-viral, anti-bacterial, anti-protozoal, anti-fungal, anti-parasitic, anti-receptor, anti-lipid, anti-phospholipid, anti-growth factor, anti-cytokine, anti-monokine, anti-idiotype, and anti-accessory (presentation) protein antibodies. Antibodies made with the present invention, as well as light chains or heavy chains, may also be used to inhibit enzyme activity.

Antibodies that may be produced using the present invention include, but are not limited to, antibodies made against the following proteins: Bovine γ-Globulin, Serum; Bovine IgG, Plasma; Chicken γ-Globulin, Serum; Human γ-Globulin, Serum; Human IgA, Plasma; Human $IgA_1$, Myeloma; Human $IgA_2$, Myeloma; Human $IgA_2$, Plasma; Human IgD, Plasma; Human IgE, Myeloma; Human IgG, Plasma; Human IgG, Fab Fragment, Plasma; Human IgG, $F(ab')_2$ Fragment, Plasma; Human IgG, Fc Fragment, Plasma; Human $IgG_1$, Myeloma; Human $IgG_2$, Myeloma; Human $IgG_3$, Myeloma; Human $IgG_4$, Myeloma; Human IgM, Myeloma; Human IgM, Plasma; Human Immunoglobulin, Light Chain κ, Urine; Human Immunoglobulin, Light Chains κ and λ, Plasma; Mouse γ-Globulin, Serum; Mouse IgG, Serum; Mouse IgM, Myeloma; Rabbit γ-Globulin, Serum; Rabbit IgG, Plasma; and Rat γ-Globulin, Serum. In one embodiment, the transposon-based vector comprises the coding sequence of light and heavy chains of a murine monoclonal antibody that shows specificity for human seminoprotein (GenBank Accession numbers AY129006 and AY129304 for the light and heavy chains, respectively).

A further non-limiting list of antibodies that recognize other antibodies is as follows: Anti-Chicken IgG, heavy (H) & light (L) Chain Specific (Sheep); Anti-Goat γ-Globulin (Donkey); Anti-Goat IgG, Fc Fragment Specific (Rabbit); Anti-Guinea Pig γ-Globulin (Goat); Anti-Human Ig, Light Chain, Type κ Specific; Anti-Human Ig, Light Chain, Type λ Specific; Anti-Human IgA, α-Chain Specific (Goat); Anti-Human IgA, Fab Fragment Specific; Anti-Human IgA, Fc Fragment Specific; Anti-Human IgA, Secretory; Anti-Human IgE, ϵChain Specific (Goat); Anti-Human IgE, Fc Fragment Specific; Anti-Human IgG, Fc Fragment Specific (Goat); Anti-Human IgG, γ-Chain Specific (Goat); Anti-Human IgG, Fc Fragment Specific; Anti-Human IgG, Fd Fragment Specific; Anti-Human IgG, H & L Chain Specific (Goat); Anti-Human $IgG_1$, Fc Fragment Specific; Anti-Human $IgG_2$, Fc Fragment Specific; Anti-Human $IgG_2$, Fd Fragment Specific; Anti-Human $IgG_3$, Hinge Specific; Anti-Human $IgG_4$, Fc Fragment Specific; Anti-Human IgM, Fc Fragment Specific; Anti-Human IgM, μ-Chain Specific; Anti-Mouse IgE, ϵ-Chain Specific; Anti-Mouse γ-Globulin (Goat); Anti-Mouse IgG, γ-Chain Specific (Goat); Anti-Mouse IgG, γ-Chain Specific (Goat) $F(ab')_2$ Fragment; Anti-Mouse IgG, H & L Chain Specific (Goat); Anti-Mouse IgM, μ-Chain Specific (Goat); Anti-Mouse IgM, H & L Chain Specific (Goat); Anti-Rabbit γ-Globulin (Goat); Anti-Rabbit IgG, Fc Fragment Specific (Goat); Anti-Rabbit IgG, H & L Chain Specific (Goat); Anti-Rat γ-Globulin (Goat); Anti-Rat IgG, H & L Chain Specific; Anti-Rhesus Monkey γ-Globulin (Goat); and, Anti-Sheep IgG, H & L Chain Specific.

Another non-limiting list of the antibodies that may be produced using the present invention is provided in product catalogs of companies such as Phoenix Pharmaceuticals, Inc. (530 Harbor Boulevard, Belmont, Calif.), Peninsula Labs (San Carlos Calif.), SIGMA (St. Louis, Mo.), Cappel ICN (Irvine, Calif.), and Calbiochem (La Jolla, Calif.), which are all available electronically via the internet and which are incorporated herein by reference in their entirety. The polynucleotide sequences encoding these antibodies may be obtained from the scientific literature, from patents, and from databases such as GenBank. Alternatively, one of ordinary skill in the art may design the polynucleotide sequence to be incorporated into the genome by choosing the codons that encode for each amino acid in the desired antibody. Antibodies made by the transgenic animals of the present invention include antibodies that may be used as therapeutic reagents, for example in cancer immunotherapy against specific antigens, as diagnostic reagents and as laboratory reagents for numerous applications including immunoneutralization, radioimmunoassay, western blots, dot blots, ELISA, immunoprecipitation and immunoaffinity columns. Some of these antibodies include, but are not limited to, antibodies which bind the following ligands: adrenomedulin, amylin, calcitonin, amyloid, calcitonin gene-related peptide, cholecystokinin, gastrin, gastric inhibitory peptide, gastrin releasing peptide, interleukin, interferon, cortistatin, somatostatin, endothelin, sarafotoxin, glucagon, glucagon-like peptide, insulin, atrial natriuretic peptide, BNP, CNP, neurokinin, substance P, leptin, neuropeptide Y, melanin concentrating hormone, melanocyte stimulating hormone, orphanin, endorphin, dynorphin, enkephalin, enkephalin, leumorphin, peptide F, PACAP, PACAP-related peptide, parathyroid hormone, urocortin, corticotrophin releasing hormone, PHM, PHI, vasoactive intestinal polypeptide, secretin, ACTH, angiotensin, angiostatin, bombesin, endostatin, bradykinin, FMRF amide, galanin, gonadotropin releasing hormone (GnRH) associated peptide, GnRH, growth hormone releasing hormone, inhibin, granulocyte-macrophage colony stimulating factor (GM-CSF), motilin, neurotensin, oxytocin, vasopressin, osteocalcin, pancreastatin, pancreatic polypeptide, peptide YY, proopiomelanocortin, transforming growth factor, vascular endothelial growth factor, vesicular monoamine transporter, vesicular acetylcholine transporter, ghrelin, NPW, NPB, C3d, prokinetican, thyroid stimulating hormone, luteinizing hormone, follicle stimulating hormone, prolactin, growth hormone, beta-lipotropin, melatonin, kallikriens, kinins, prostaglandins, erythropoietin, p146 (SEQ ID NO:18 amino acid sequence, SEQ ID NO:19, nucleotide sequence), estrogen, testosterone, corticosteroids, mineralocorticoids, thyroid hormone, thymic hormones, connective tissue proteins, nuclear proteins, actin, avidin, activin, agrin, albumin, and prohormones, propeptides, splice variants, fragments and analogs thereof.

The following is yet another non-limiting of antibodies that can be produced by the methods of present invention: abciximab (ReoPro), abciximab anti-platelet aggregation monoclonal antibody, anti-CD11a (hu1124), anti-CD18 antibody, anti-CD20 antibody, anti-cytomegalovirus (CMV) antibody, anti-digoxin antibody, anti-hepatitis B antibody, anti-HER-2 antibody, anti-idiotype antibody to GD3 glycolipid, anti-IgE antibody, anti-IL-2R antibody, antimetastatic cancer antibody (mAb 17-1A), anti-rabies antibody, anti-respiratory syncytial virus (RSV) antibody, anti-Rh antibody, anti-TCR, anti-TNF antibody, anti-VEGF antibody and fab fragment thereof, rattlesnake venom antibody, black widow spider venom antibody, coral snake venom antibody, antibody against very late antigen-4 (VLA-4), C225 humanized antibody to EGF receptor, chimeric (human & mouse) antibody against TNFα, antibody directed against GPIIb/IIIa receptor on human platelets, gamma globulin, anti-hepatitis B immunoglobulin, human anti-D immunoglobulin, human antibodies against *S aureus*, human tetanus immunoglobulin, humanized antibody against the epidermal growth receptor-2, humanized antibody against the α subunit of the interleukin-2 receptor, humanized antibody CTLA4IG, humanized antibody to the IL-2 R α-chain, humanized anti-CD40-ligand monoclonal antibody (5c8), humanized mAb against the epidermal growth receptor-2, humanized mAb to rous sarcoma virus, humanized recombinant antibody (IgG1k) against respiratory syncytial virus (RSV), lymphocyte immunoglobulin (anti-thymocyte antibody), lymphocyte immunoglobulin, mAb against factor VII, MDX-210 bi-specific antibody against HER-2, MDX-22, MDX-220 bi-specific antibody against TAG-72 on tumors, MDX-33 antibody to FcγR1 receptor, MDX-447 bi-specific antibody against EGF receptor, MDX-447 bispecific humanized antibody to EGF receptor, MDX-RA immunotoxin (ricin A linked) antibody, Medi-507 antibody (humanized form of BTI-322) against CD2 receptor on T-cells, monoclonal antibody LDP-02, muromonab-CD3(OKT3) antibody, OKT3 ("muromomab-CD3") antibody, PRO 542 antibody, ReoPro ("abciximab") antibody, and TNF-IgG fusion protein.

The antibodies prepared using the methods of the present invention may also be designed to possess specific labels that may be detected through means known to one of ordinary skill in the art. The antibodies may also be designed to possess specific sequences useful for purification through means known to one of ordinary skill in the art. Specialty antibodies designed for binding specific antigens may also be made in transgenic animals using the transposon-based vectors of the present invention.

Production of a monoclonal antibody using the transposon-based vectors of the present invention can be accomplished in a variety of ways. In one embodiment, two vectors may be constructed: one that encodes the light chain, and a second vector that encodes the heavy chain of the monoclonal antibody. These vectors may then be incorporated into the genome of the target animal by methods disclosed herein. In an alternative embodiment, the sequences encoding light and heavy chains of a monoclonal antibody may be included on a single DNA construct. For example, the coding sequence of light and heavy chains of a murine monoclonal antibody that show specificity for human seminoprotein can be expressed using transposon-based constructs of the present invention (GenBank Accession numbers AY129006 and AY129304 for the light and heavy chains, respectively).

Further included in the present invention are proteins and peptides synthesized by the immune system including those synthesized by the thymus, lymph nodes, spleen, and the gastrointestinal associated lymph tissues (GALT) system. The immune system proteins and peptides proteins that can be made in transgenic animals using the transposon-based vectors of the present invention include, but are not limited to, alpha-interferon, beta-interferon, gamma-interferon, alpha-interferon A, alpha-interferon 1, G-CSF, GM-CSF, interlukin-1 (IL-1), IL-2, IL-3, IL-4, IL-5, IL-6, IL-7, IL-8, IL-9, IL-10, IL-11, IL-12, IL-13, TNF-α, and TNF-β. Other cytokines included in the present invention include cardiotrophin, stromal cell derived factor, macrophage derived chemokine (MDC), melanoma growth stimulatory activity (MGSA), macrophage inflammatory proteins 1 alpha (MIP-1 alpha), 2, 3 alpha, 3 beta, 4 and 5.

Lytic peptides such as p146 are also included in the desired molecules of the present invention. In one embodiment, the p146 peptide comprises an amino acid sequence of SEQ ID NO:19. The present invention also encompasses a transposon-based vector comprising a p146 nucleic acid comprising a polynucleotide sequence of SEQ ID NO:20.

Enzymes are another class of proteins that may be made through the use of the transposon-based vectors of the present invention. Such enzymes include but are not limited to adenosine deaminase, alpha-galactosidase, cellulase, collagenase, dnasel, hyaluronidase, lactase, L-asparaginase, pancreatin, papain, streptokinase B, subtilisin, superoxide dismutase, thrombin, trypsin, urokinase, fibrinolysin, glucocerebrosidase and plasminogen activator. In some embodiments wherein the enzyme could have deleterious effects, additional amino acids and a protease cleavage site are added to the carboxy end of the enzyme of interest in order to prevent expression of a functional enzyme. Subsequent digestion of the enzyme with a protease results in activation of the enzyme.

Extracellular matrix proteins are one class of desired proteins that may be made through the use of the present invention. Examples include but are not limited to collagen, fibrin, elastin, laminin, and fibronectin and subtypes thereof. Intracellular proteins and structural proteins are other classes of desired proteins in the present invention.

Growth factors are another desired class of proteins that may be made through the use of the present invention and include, but are not limited to, transforming growth factor-α ("TGF-α"), transforming growth factor-β (TGF-β), platelet-derived growth factors (PDGF), fibroblast growth factors (FGF), including FGF acidic isoforms 1 and 2, FGF basic form 2 and FGF 4, 8, 9 and 10, nerve growth factors (NGF) including NGF 2.5 s, NGF 7.0 s and beta NGF and neurotrophins, brain derived neurotrophic factor, cartilage derived factor, growth factors for stimulation of the production of red blood cells, growth factors for stimulation of the production of white blood cells, bone growth factors (BGF), basic fibroblast growth factor, vascular endothelial growth factor (VEGF), granulocyte colony stimulating factor (G-CSF), insulin like growth factor (IGF) I and II, hepatocyte growth factor, glial neurotrophic growth factor (GDNF), stem cell factor (SCF), keratinocyte growth factor (KGF), transforming growth factors (TGF), including TGFs alpha, beta, beta1, beta2, beta3, skeletal growth factor, bone matrix derived growth factors, bone derived growth factors, erythropoietin (EPO) and mixtures thereof.

Another desired class of proteins that may be made may be made through the use of the present invention include but are not limited to leptin, leukemia inhibitory factor (LIF), tumor necrosis factor alpha and beta, ENBREL, angiostatin, endostatin, thrombospondin, osteogenic protein-1, bone morphogenetic proteins 2 and 7, osteonectin, somatomedin-like peptide, and osteocalcin.

A non-limiting list of the peptides and proteins that may be made may be made through the use of the present invention is provided in product catalogs (electronically available over the internet) of companies such as Phoenix Pharmaceuticals, Inc. (530 Harbor Boulevard, Belmont, Calif.), Peninsula Labs (San Carlos, Calif.), SIGMA (St. Louis, Mo.), Cappel ICN, (Irvine, Calif.), and Calbiochem (La Jolla, Calif.). The polynucleotide sequences encoding these proteins and peptides of interest may be obtained from the scientific literature, from patents, and from databases such as GenBank. Alternatively, one of ordinary skill in the art may design the polynucleotide sequence to be incorporated into the genome by choosing the codons that encode for each amino acid in the desired protein or peptide.

Some of these desired proteins or peptides that may be made through the use of the present invention include but are not limited to the following: adrenomedulin, amylin, calcitonin, amyloid, calcitonin gene-related peptide, cholecystokinin, gastrin, gastric inhibitory peptide, gastrin releasing peptide, interleukin, interferon, cortistatin, somatostatin, endothelin, sarafotoxin, glucagon, glucagon-like peptide, insulin, atrial natriuretic peptide, BNP, CNP, neurokinin, substance P, leptin, neuropeptide Y, melanin concentrating hormone, melanocyte stimulating hormone, orphanin, endorphin, dynorphin, enkephalin, leumorphin, peptide F, PACAP, PACAP-related peptide, parathyroid hormone, urocortin, corticotrophin releasing hormone, PHM, PHI, vasoactive intestinal polypeptide, secretin, ACTH, angiotensin, angiostatin, bombesin, endostatin, bradykinin, FMRF amide, galanin, gonadotropin releasing hormone (GnRH) associated peptide, GnRH, growth hormone releasing hormone, inhibin, granulocyte-macrophage colony stimulating factor (GM-CSF), motilin, neurotensin, oxytocin, vasopressin, osteocalcin, pancreastatin, pancreatic polypeptide, peptide YY, proopiomelanocortin, transforming growth factor, vascular endothelial growth factor, vesicular monoamine transporter, vesicular acetylcholine transporter, ghrelin, NPW, NPB, C3d, prokinetican, thyroid stimulating hormone, luteinizing hormone, follicle stimulating hormone, prolactin, growth hormone, beta-lipotropin, melatonin, kallikriens, kinins, prostaglandins, erythropoietin, p146 (SEQ ID NO:19, amino acid sequence, SEQ ID NO:20, nucleotide sequence), thymic hormones, connective tissue proteins, nuclear proteins, actin, avidin, activin, agrin, albumin, and prohormones, propeptides, splice variants, fragments and analogs thereof.

Other desired proteins that may be made by the transgenic animals of the present invention include bacitracin, polymixin b, vancomycin, cyclosporine, anti-RSV antibody, alpha-1 antitrypsin (AAT), anti-cytomegalovirus antibody, anti-hepatitis antibody, anti-inhibitor coagulant complex, anti-rabies antibody, anti-Rh(D) antibody, adenosine deaminase, anti-digoxin antibody, antivenin crotalidae (rattlesnake venom antibody), antivenin latrodectus (black widow spider venom antibody), antivenin micrurus (coral snake venom antibody), aprotinin, corticotropin (ACTH), diphtheria antitoxin, lymphocyte immune globulin (anti-thymocyte antibody), protamine, thyrotropin, capreomycin, α-galactosidase, gramicidin, streptokinase, tetanus toxoid, tyrothricin, IGF-1, proteins of varicella vaccine, anti-TNF antibody, anti-IL-2r antibody, anti-HER-2 antibody, OKT3 ("muromonab-CD3") antibody, TNF-IgG fusion protein, ReoPro ("abciximab") antibody, ACTH fragment 1-24, desmopressin, gonadotropin-releasing hormone, histrelin, leuprolide, lypressin, nafarelin, peptide that binds GPIIb/GPIIIa on platelets (integrilin), goserelin, capreomycin, colistin, anti-respiratory syncytial virus, lymphocyte immune globulin (Thymoglovin, Atgam), panorex, alpha-antitrypsin, botulinin, lung surfactant protein, tumor necrosis receptor-IgG fusion protein (enbrel), gonadorelin, proteins of influenza vaccine, proteins of rotavirus vaccine, proteins of *haemophilus* b conjugate vaccine, proteins of poliovirus vaccine, proteins of pneumococcal conjugate vaccine, proteins of meningococcal C vaccine, proteins of influenza vaccine, megakaryocyte growth and development factor (MGDF), neuroimmunophilin ligand-A (NIL-A), brain-derived neurotrophic factor (BDNF), glial cell line-derived neurotrophic factor (GDNF), leptin (native), leptin B, leptin C, IL-IRA (interleukin-1RA), R-568, novel erythropoiesis-stimulating protein (NESP), humanized mAb to rous sarcoma virus (MEDI-493), glutamyl-tryptophan dipeptide IM862, LFA-3TIP immunosuppressive, humanized anti-CD40-ligand monoclonal antibody (5c8), gelsonin enzyme, tissue factor pathway inhibitor (TFPI), proteins of meningitis B vaccine, antimetastatic cancer antibody (mAb 17-1A), chimeric (human & mouse) mAb against TNFα, mAb against factor VII, relaxin, capreomycin, glycopeptide (LY333328), recombinant human activated protein C (rhAPC), humanized mAb against the epidermal growth receptor-2, altepase, anti-CD20 antigen, C2B8 antibody, insulin-like growth factor-1, atrial natriuretic peptide (anaritide), tenectaplase, anti-CD11a antibody (hu 1124), anti-CD18 antibody, mAb LDP-02, anti-VEGF antibody, fab fragment of anti-VEGF Ab, APO2 ligand (tumor necrosis factor-related apoptosis-inducing ligand), rTGF-β (transforming growth factor-β), alpha-antitrypsin, ananain (a pineapple enzyme), humanized mAb CTLA4IG, PRO542 (mAb), D2E7 (mAb), calf intestine alkaline phosphatase, α-L-iduronidase, α-L-galactosidase (humanglutamic acid decarboxylase, acid sphingomyelinase, bone morphogenetic protein-2 (rhBMP-2), proteins of HIV vaccine, T cell receptor (TCR) peptide vaccine, TCR peptides, V beta 3 and V beta 13.1. (IR502), (IR501), BI 1050/1272 mAb against very late antigen-4 (VLA-4), C225 humanized mAb to EGF receptor, anti-idiotype antibody to GD3 glycolipid, antibacterial peptide against *H. pylori*, MDX-447 bispecific humanized mAb to EGF receptor, anti-cytomegalovirus (CMV), Medi-491 B19 parvovirus vaccine, humanized recombinant mAb (IgG1k) against respiratory syncytial virus (RSV), urinary tract infection vaccine (against "pili" on *Escherichia coli* strains), proteins of Lyme disease vaccine against *B. burgdorferi* protein (DbpA), proteins of Medi-501 human papilloma virus-11 vaccine (HPV), *Streptococcus pneumoniae* vaccine, Medi-507 mAb (humanized form of BTI-322) against CD2 receptor on T-cells, MDX-33 mAb to FcγR1 receptor, MDX-RA immunotoxin (ricin A linked) mAb, MDX-210 bi-specific mAb against HER-2, MDX-447 bi-specific mAb against EGF receptor, MDX-22, MDX-220 bi-specific mAb against TAG-72 on tumors, colony-stimulating factor (CSF) (molgramostim), humanized mAb to the IL-2 R α-chain (basiliximab), mAb to IgE (IGE 025A), myelin basic protein-altered peptide (MSP771A), humanized mAb against the epidermal growth receptor-2, humanized mAb against the α subunit of the interleukin-2 receptor, low molecular weight heparin, anti-hemophillic factor, and bactericidal/permeability-increasing protein (r-BPI).

The peptides and proteins made using the present invention may be labeled using labels and techniques known to one of ordinary skill in the art. Some of these labels are described in the "Handbook of Fluorescent Probes and Research Products", ninth edition, Richard P. Haugland (ed) Molecular Probes, Inc. Eugene, Oreg.), which is incorporated herein in its entirety. Some of these labels may be genetically engineered into the polynucleotide sequence for the expression of the selected protein or peptide. The peptides and proteins may also have label-incorporation "handles" incorporated to allow labeling of an otherwise difficult or impossible to label protein.

It is to be understood that the various classes of desired peptides and proteins, as well as specific peptides and proteins described in this section may be modified as described below by inserting selected codons for desired amino acid substitutions into the gene incorporated into the transgenic animal.

The present invention may also be used to produce desired molecules other than proteins and peptides including, but not limited to, lipoproteins such as high density lipoprotein (HDL), HDL-Milano, and low density lipoprotein, lipids, carbohydrates, siRNA and ribozymes. In these embodiments, a gene of interest encodes a nucleic acid molecule or a protein that directs production of the desired molecule.

The present invention further encompasses the use of inhibitory molecules to inhibit endogenous (i.e., non-vector) protein production. These inhibitory molecules include antisense nucleic acids, siRNA and inhibitory proteins. In one embodiment, a transposon-based vector containing an ovalbumin DNA sequence, that upon transcription forms a double stranded RNA molecule, is transfected into an animal such as a bird and the bird's production of endogenous ovalbumin protein is reduced by the interference RNA mechanism (RNAi). Additionally, inducible knockouts or knockdowns of the endogenous protein may be created to achieve a reduction or inhibition of endogenous protein production.

Modified Desired Proteins and Peptides

"Proteins", "peptides," "polypeptides" and "oligopeptides" are chains of amino acids (typically L-amino acids) whose alpha carbons are linked through peptide bonds formed by a condensation reaction between the carboxyl group of the alpha carbon of one amino acid and the amino group of the alpha carbon of another amino acid. The terminal amino acid at one end of the chain (i.e., the amino terminal) has a free amino group, while the terminal amino acid at the other end of the chain (i.e., the carboxy terminal) has a free carboxyl group. As such, the term "amino terminus" (abbreviated N-terminus) refers to the free alpha-amino group on the amino acid at the amino terminal of the protein, or to the alpha-amino group (imino group when participating in a peptide bond) of an amino acid at any other location within the protein. Similarly, the term "carboxy terminus" (abbreviated C-terminus) refers to the free carboxyl group on the amino acid at the carboxy terminus of a protein, or to the carboxyl group of an amino acid at any other location within the protein.

Typically, the amino acids making up a protein are numbered in order, starting at the amino terminal and increasing in the direction toward the carboxy terminal of the protein. Thus, when one amino acid is said to "follow" another, that amino acid is positioned closer to the carboxy terminal of the protein than the preceding amino acid.

The term "residue" is used herein to refer to an amino acid (D or L) or an amino acid mimetic that is incorporated into a protein by an amide bond. As such, the amino acid may be a naturally occurring amino acid or, unless otherwise limited, may encompass known analogs of natural amino acids that function in a manner similar to the naturally occurring amino acids (i.e., amino acid mimetics). Moreover, an amide bond mimetic includes peptide backbone modifications well known to those skilled in the art.

Furthermore, one of skill will recognize that, as mentioned above, individual substitutions, deletions or additions which alter, add or delete a single amino acid or a small percentage of amino acids (typically less than about 5%, more typically less than about 1%) in an encoded sequence are conservatively modified variations where the alterations result in the substitution of an amino acid with a chemically similar amino acid. Conservative substitution tables providing functionally similar amino acids are well known in the art. The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

A conservative substitution is a substitution in which the substituting amino acid (naturally occurring or modified) is structurally related to the amino acid being substituted, i.e., has about the same size and electronic properties as the amino acid being substituted. Thus, the substituting amino acid would have the same or a similar functional group in the side chain as the original amino acid. A "conservative substitution" also refers to utilizing a substituting amino acid which is identical to the amino acid being substituted except that a functional group in the side chain is protected with a suitable protecting group.

Suitable protecting groups are described in Green and Wuts, "Protecting Groups in Organic Synthesis", John Wiley and Sons, Chapters 5 and 7, 1991, the teachings of which are incorporated herein by reference. Preferred protecting groups are those which facilitate transport of the peptide through membranes, for example, by reducing the hydrophilicity and increasing the lipophilicity of the peptide, and which can be cleaved, either by hydrolysis or enzymatically (Ditter et al., 1968. J. Pharm. Sci. 57:783; Ditter et al., 1968. J. Pharm. Sci. 57:828; Ditter et al., 1969. J. Pharm. Sci. 58:557; King et al., 1987. Biochemistry 26:2294; Lindberg et al., 1989. Drug Metabolism and Disposition 17:311; Tunek et al., 1988. Biochem. Pharm. 37:3867; Anderson et al., 1985 Arch. Biochem. Biophys. 239:538; and Singhal et al., 1987. FASEB J. 1:220). Suitable hydroxyl protecting groups include ester, carbonate and carbamate protecting groups. Suitable amine protecting groups include acyl groups and alkoxy or aryloxy carbonyl groups, as described above for N-terminal protecting groups. Suitable carboxylic acid protecting groups include aliphatic, benzyl and aryl esters, as described below for C-terminal protecting groups. In one embodiment, the carboxylic acid group in the side chain of one or more glutamic acid or aspartic acid residues in a peptide of the present invention is protected, preferably as a methyl, ethyl, benzyl or substituted benzyl ester, more preferably as a benzyl ester.

Provided below are groups of naturally occurring and modified amino acids in which each amino acid in a group has similar electronic and steric properties. Thus, a conservative substitution can be made by substituting an amino acid with another amino acid from the same group. It is to be understood that these groups are non-limiting, i.e. that there are additional modified amino acids which could be included in each group.

Group I includes leucine, isoleucine, valine, methionine and modified amino acids having the following side chains: ethyl, n-propyl n-butyl. Preferably, Group I includes leucine, isoleucine, valine and methionine.

Group II includes glycine, alanine, valine and a modified amino acid having an ethyl side chain. Preferably, Group II includes glycine and alanine.

Group III includes phenylalanine, phenylglycine, tyrosine, tryptophan, cyclohexylmethyl glycine, and modified amino residues having substituted benzyl or phenyl side chains. Preferred substituents include one or more of the following: halogen, methyl, ethyl, nitro, $—NH_2$, methoxy, ethoxy and —CN. Preferably, Group III includes phenylalanine, tyrosine and tryptophan.

Group IV includes glutamic acid, aspartic acid, a substituted or unsubstituted aliphatic, aromatic or benzylic ester of glutamic or aspartic acid (e.g., methyl, ethyl, n-propyl isopropyl, cyclohexyl, benzyl or substituted benzyl), glutamine, asparagine, —CO—NH— alkylated glutamine or asparagines (e.g., methyl, ethyl, n-propyl and iso-propyl) and modified amino acids having the side chain $—(CH_2)_3—COOH$, an ester thereof (substituted or unsubstituted aliphatic, aromatic or benzylic ester), an amide thereof and a substituted or unsubstituted N-alkylated amide thereof. Preferably, Group IV includes glutamic acid, aspartic acid, methyl aspartate, ethyl aspartate, benzyl aspartate and methyl glutamate, ethyl glutamate and benzyl glutamate, glutamine and asparagine.

Group V includes histidine, lysine, ornithine, arginine, N-nitroarginine, β-cycloarginine, γ-hydroxyarginine, N-amidinocitruline and 2-amino-4-guanidinobutanoic acid, homologs of lysine, homologs of arginine and homologs of ornithine. Preferably, Group V includes histidine, lysine, arginine and ornithine. A homolog of an amino acid includes from 1 to about 3 additional or subtracted methylene units in the side chain.

Group VI includes serine, threonine, cysteine and modified amino acids having C1-C5 straight or branched alkyl side chains substituted with —OH or —SH, for example, $—CH_2CH_2OH$, $—CH_2CH_2CH_2OH$ or $—CH_2CH_2OHCH_3$. Preferably, Group VI includes serine, cysteine or threonine.

In another aspect, suitable substitutions for amino acid residues include "severe" substitutions. A "severe substitution" is a substitution in which the substituting amino acid (naturally occurring or modified) has significantly different size and/or electronic properties compared with the amino acid being substituted. Thus, the side chain of the substituting amino acid can be significantly larger (or smaller) than the side chain of the amino acid being substituted and/or can have functional groups with significantly different electronic properties than the amino acid being substituted. Examples of severe substitutions of this type include the substitution of phenylalanine or cyclohexylmethyl glycine for alanine, isoleucine for glycine, a D amino acid for the corresponding L amino acid, or $—NH—CH[(—CH_2)_5—COOH]—CO—$ for aspartic acid. Alternatively, a functional group may be added to the side chain, deleted from the side chain or exchanged with another functional group. Examples of severe substitutions of this type include adding of valine, leucine or isoleucine, exchanging the carboxylic acid in the side chain of aspartic acid or glutamic acid with an amine, or deleting the amine group in the side chain of lysine or ornithine. In yet another alternative, the side chain of the substituting amino acid can have significantly different steric and electronic properties that the functional group of the amino acid being substituted. Examples of such modifications include tryptophan for glycine, lysine for aspartic acid and $—(CH_2)_4COOH$ for the side chain of serine. These examples are not meant to be limiting.

In another embodiment, for example in the synthesis of a peptide 26 amino acids in length, the individual amino acids may be substituted according in the following manner:

$AA_1$, is serine, glycine, alanine, cysteine or threonine;

$AA_2$ is alanine, threonine, glycine, cysteine or serine;

$AA_3$ is valine, arginine, leucine, isoleucine, methionine, ornithine, lysine, N-nitroarginine, β-cycloarginine, γ-hydroxyarginine, N-amidinocitruline or 2-amino-4-guanidinobutanoic acid;

$AA_4$ is proline, leucine, valine, isoleucine or methionine;

$AA_5$ is tryptophan, alanine, phenylalanine, tyrosine or glycine;

$AA_6$ is serine, glycine, alanine, cysteine or threonine;

$AA_7$ is proline, leucine, valine, isoleucine or methionine;

$AA_8$ is alanine, threonine, glycine, cysteine or serine;

$AA_9$ is alanine, threonine, glycine, cysteine or serine;

$AA_{10}$ is leucine, isoleucine, methionine or valine;

$AA_{11}$ is serine, glycine, alanine, cysteine or threonine;

$AA_{12}$ is leucine, isoleucine, methionine or valine;

$AA_{13}$ is leucine, isoleucine, methionine or valine;

$AA_{14}$ is glutamine, glutamic acid, aspartic acid, asparagine, or a substituted or unsubstituted aliphatic or aryl ester of glutamic acid or aspartic acid;

$AA_{15}$ is arginine, N-nitroarginine, β-cycloarginine, γ-hydroxy-arginine, N-amidinocitruline or 2-amino-4-guanidino-butanoic acid $AA_{16}$ is proline, leucine, valine, isoleucine or methionine;

$AA_{17}$ is serine, glycine, alanine, cysteine or threonine;

$AA_{18}$ is glutamic acid, aspartic acid, asparagine, glutamine or a substituted or unsubstituted aliphatic or aryl ester of glutamic acid or aspartic acid;

$AA_{19}$ is aspartic acid, asparagine, glutamic acid, glutamine, leucine, valine, isoleucine, methionine or a substituted or unsubstituted aliphatic or aryl ester of glutamic acid or aspartic acid;

$AA_{20}$ is valine, arginine, leucine, isoleucine, methionine, ornithine, lysine, N-nitroarginine, β-cycloarginine, γ-hydroxyarginine, N-amidinocitruline or 2-amino-4-guanidinobutanoic acid;

$AA_{21}$ is alanine, threonine, glycine, cysteine or serine;

$AA_{22}$ is alanine, threonine, glycine, cysteine or serine;

$AA_{23}$ is histidine, serine, threonine, cysteine, lysine or ornithine;

$AA_{24}$ is threonine, aspartic acid, serine, glutamic acid or a substituted or unsubstituted aliphatic or aryl ester of glutamic acid or aspartic acid;

$AA_{25}$ is asparagine, aspartic acid, glutamic acid, glutamine, leucine, valine, isoleucine, methionine or a substituted or unsubstituted aliphatic or aryl ester of glutamic acid or aspartic acid; and $AA_{26}$ is cysteine, histidine, serine, threonine, lysine or ornithine.

It is to be understood that these amino acid substitutions may be made for longer or shorter peptides than the 26 mer in the preceding example above, and for proteins.

In one embodiment of the present invention, codons for the first several N-terminal amino acids of the transposase are modified such that the third base of each codon is changed to an A or a T without changing the corresponding amino acid. It is preferable that between approximately 1 and 20, more preferably 3 and 15, and most preferably between 4 and 12 of the first N-terminal codons of the gene of interest are modified such that the third base of each codon is changed to an A or a T without changing the corresponding amino acid. In one embodiment, the first ten N-terminal codons of the gene of interest are modified in this manner.

When several desired proteins, protein fragments or peptides are encoded in the gene of interest to be incorporated into the genome, one of skill in the art will appreciate that the proteins, protein fragments or peptides may be separated by a spacer molecule such as, for example, a peptide, consisting of one or more amino acids. Generally, the spacer will have no specific biological activity other than to join the desired proteins, protein fragments or peptides together, or to preserve some minimum distance or other spatial relationship between them. However, the constituent amino acids of the spacer may be selected to influence some property of the molecule such as the folding, net charge, or hydrophobicity. The spacer may also be contained within a nucleotide sequence with a purification handle or be flanked by proteolytic cleavage sites.

Such polypeptide spacers may have from about 5 to about 40 amino acid residues. The spacers in a polypeptide are independently chosen, but are preferably all the same. The spacers should allow for flexibility of movement in space and are therefore typically rich in small amino acids, for example, glycine, serine, proline or alanine. Preferably, peptide spacers contain at least 60%, more preferably at least 80% glycine or alanine. In addition, peptide spacers generally have little or no biological and antigenic activity. Preferred spacers are (Gly-Pro-Gly-Gly), (SEQ ID NO:5) and ($Gly_4$-Ser)$_y$, wherein x is an integer from about 3 to about 9 and y is an integer from about 1 to about 8. Specific examples of suitable spacers include

```
(Gly-Pro-Gly-Gly)3

                                              SEQ ID NO:6
Gly Pro Gly Gly Gly Pro Gly Gly Gly Pro Gly Gly

(Gly4-Ser)3

                                              SEQ ID NO:7
Gly Gly Gly Gly Ser Gly Gly Gly Gly Ser Gly Gly

Gly Gly Ser
or

(Gly4-Ser)4

                                              SEQ ID NO:8
Gly Gly Gly Gly Ser Gly Gly Gly Gly Ser Gly Gly

Gly Gly Ser Gly Gly Gly Gly Ser.
```

Nucleotide sequences encoding for the production of residues which may be useful in purification of the expressed recombinant protein may also be built into the vector. Such sequences are known in the art and include the glutathione binding domain from glutathione S-transferase, polylysine, hexa-histidine or other cationic amino acids, thioredoxin, hemagglutinin antigen and maltose binding protein.

Additionally, nucleotide sequences may be inserted into the gene of interest to be incorporated so that the protein or peptide can also include from one to about six amino acids that create signals for proteolytic cleavage. In this manner, if a gene is designed to make one or more peptides or proteins of interest in the transgenic animal, specific nucleotide sequences encoding for amino acids recognized by enzymes may be incorporated into the gene to facilitate cleavage of the large protein or peptide sequence into desired peptides or proteins or both. For example, nucleotides encoding a proteolytic cleavage site can be introduced into the gene of interest so that a signal sequence can be cleaved from a protein or peptide encoded by the gene of interest. Nucleotide sequences encoding other amino acid sequences which display pH sensitivity or chemical sensitivity may also be added to the vector to facilitate separation of the signal sequence from the peptide or protein of interest.

In one embodiment of the present invention, a TAG sequence is linked to the gene of interest. The TAG sequence serves three purposes: 1) it allows free rotation of the peptide or protein to be isolated so there is no interference from the native protein or signal sequence, i.e. vitellogenin, 2) it provides a "purification handle" to isolate the protein using column purification, and 3) it includes a cleavage site to remove the desired protein from the signal and purification sequences. Accordingly, as used herein, a TAG sequence includes a spacer sequence, a purification handle and a cleavage site. The spacer sequences in the TAG proteins contain one or more repeats shown in SEQ ID NO:25. A preferred spacer sequence comprises the sequence provided in SEQ ID NO:26. One example of a purification handle is the gp41 hairpin loop from HIV I. Exemplary gp41 polynucleotide and polypeptide sequences are provided in SEQ ID NO:24 and SEQ ID NO:23, respectively. However, it should be understood that any antigenic region may be used as a purification handle, including any antigenic region of gp41. Preferred purification handles are those that elicit highly specific antibodies. Additionally, the cleavage site can be any protein cleavage site known to one of ordinary skill in the art and includes an enterokinase cleavage site comprising the Asp Asp Asp Asp Lys sequence (SEQ ID NO:9) and a furin cleavage site. Constructs containing a TAG sequence are shown in FIGS. 2 and 3. In one embodiment of the present invention, the TAG sequence comprises a polynucleotide sequence of SEQ ID NO:22.

Methods of Administering Transposon-Based Vectors

In addition to the transposon-based vectors described above, the present invention also includes methods of administering the transposon-based vectors to an animal, methods of producing a transgenic animal wherein a gene of interest is incorporated into the germline of the animal and methods of producing a transgenic animal wherein a gene of interest is incorporated into cells other than the germline cells of the animal. The transposon-based vectors of the present invention may be administered to an animal via any method known to those of skill in the art, including, but not limited to, intraembryonic, intratesticular, intraoviduct, intraperitoneal, intraarterial, intravenous, topical, oral, nasal, and pronuclear injection methods of administration, or any combination thereof. The transposon-based vectors may also be administered within the lumen of an organ, into an organ, into a body cavity, into the cerebrospinal fluid, through the urinary system or through any route to reach the desired cells.

The transposon-based vectors may be delivered through the vascular system to be distributed to the cells supplied by that vessel. For example, the compositions may be placed in the artery supplying the ovary or supplying the fallopian tube to transfect cells in those tissues. In this manner, follicles could be transfected to create a germline transgenic animal. Alternatively, supplying the compositions through the artery leading to the oviduct would preferably transfect the tubular gland and epithelial cells. Such transfected cells could manufacture a desired protein or peptide for deposition in the egg white. Administration of the compositions through the portal vein would target uptake and transformation of hepatic cells. Administration through the urethra and into the bladder would target the transitional epithelium of the bladder. Administration through the vagina and cervix would target the lining of the uterus. Administration through the internal mammary artery would transfect secretory cells of the lactating mammary gland to perform a desired function, such as to synthesize and secrete a desired protein or peptide into the milk.

In a preferred embodiment, the animal is an egg-laying animal, and more preferably, an avian. In one embodiment, between approximately 1 and 50 μg, preferably between 1 and 20 μg, and more preferably between 5 and 10 μg of transposon-based vector DNA is administered to the oviduct of a bird. Optimal ranges depending upon the type of bird and the bird's stage of sexual maturity. Intraoviduct administration of the transposon-based vectors of the present invention result in a PCR positive signal in the oviduct tissue, whereas intravascular administration results in a PCR positive signal in the liver. In other embodiments, the transposon-based vector is administered to an artery that supplies the oviduct or the liver. These methods of administration may also be combined with any methods for facilitating transfection, including without limitation, electroporation, gene guns, injection of naked DNA, and use of dimethyl sulfoxide (DMSO).

The present invention includes a method of intraembryonic administration of a transposon-based vector to an avian embryo comprising the following steps: 1) incubating an egg on its side at room temperature for two hours to allow the embryo contained therein to move to top dead center (TDC); 2) drilling a hole through the shell without penetrating the underlying shell membrane; 3) injecting the embryo with the transposon-based vector in solution; 4) sealing the hole in the egg; and 5) placing the egg in an incubator for hatching. Administration of the transposon-based vector can occur anytime between immediately after egg lay (when the embryo is at Stage X) and hatching. Preferably, the transposon-based vector is administered between 1 and 7 days after egg lay, more preferably between 1 and 2 days after egg lay. The transposon-based vectors may be introduced into the embryo in amounts ranging from about 5.0 μg to 10 pg, preferably 1.0 μg to 100 pg. Additionally, the transposon-based vector solution volume may be between approximately 1 μl to 75 μl in quail and between approximately 1 μl to 500 μl in chicken.

The present invention also includes a method of intratesticular administration of a transposon-based vector including injecting a bird with a composition comprising the transposon-based vector, an appropriate carrier and an appropriate transfection reagent. In one embodiment, the bird is injected before sexual maturity, preferably between approximately 4-14 weeks, more preferably between approximately 6-14 weeks and most preferably between 8-12 weeks old. In another embodiment, a mature bird is injected with a transposon-based vector an appropriate carrier and an appropriate transfection reagent. The mature bird may be any type of bird, but in one example the mature bird is a quail.

A bird is preferably injected prior to the development of the blood-testis barrier, which thereby facilitates entry of the transposon-based vector into the seminiferous tubules and transfection of the spermatogonia or other germline cells. At and between the ages of 4, 6, 8, 10, 12, and 14 weeks, it is believed that the testes of chickens are likely to be most receptive to transfection. In this age range, the blood/testis barrier has not yet formed, and there is a relatively high number of spermatogonia relative to the numbers of other cell types, e.g., spermatids, etc. See J. Kumaran et al., 1949. Poultry Sci., 29:511-520. See also E. Oakberg, 1956. Am. J. Anatomy, 99:507-515; and P. Kluin et al., 1984. Anat. Embryol., 169:73-78.

The transposon-based vectors may be introduced into a testis in an amount ranging from about 0.1 μg to 10 μg, preferably 1 μg to 10 μg, more preferably 3 μg to 10 μg. In a quail, about 5 μg is a preferred amount. In a chicken, about 5 μg to 10 μg per testis is preferred. These amounts of vector DNA may be injected in one dose or multiple doses and at one site or multiple sites in the testis. In a preferred embodiment, the vector DNA is administered at multiple sites in a single testis, both testes being injected in this manner. In one embodiment, injection is spread over three injection sites: one at each end of the testis, and one in the middle. Additionally, the transposon-based vector solution volume may be between approximately 1 μl to 75 μl in quail and between approximately 1 μl to 500 μl in chicken. In a preferred embodiment, the transposon-based vector solution volume may be between approximately 20 μl to 60 μl in quail and between approximately 50 μl to 250 μl in chicken. Both the amount of vector DNA and the total volume injected into each testis may be determined based upon the age and size of the bird.

According to the present invention, the transposon-based vector is administered in conjunction with an acceptable carrier and/or transfection reagent. Acceptable carriers include, but are not limited to, water, saline, Hanks Balanced Salt Solution (HBSS), Tris-EDTA (TE) and lyotropic liquid crystals. Transfection reagents commonly known to one of ordinary skill in the art that may be employed include, but are not limited to, the following: cationic lipid transfection reagents, cationic lipid mixtures, polyamine reagents, liposomes and combinations thereof; SUPERFECT®, Cytofectene, BioPORTER®, GenePORTER®, NeuroPORTER®, and perfectin from Gene Therapy Systems; lipofectamine, cellfectin, DMRIE-C oligofectamine, and PLUS reagent from Invitrogen; Xtreme gene, fugene, DOSPER and DOTAP from Roche; Lipotaxi and Genejammer from Strategene; and Escort from SIGMA. In one embodiment, the transfection reagent is SUPERFECT®. The ratio of DNA to transfection reagent may vary based upon the method of administration. In one embodiment, the transposon-based vector is administered intratesticularly and the ratio of DNA to transfection reagent can be from 1:1.5 to 1:15, preferably 1:2 to 1:10, all expressed as wt/vol. Transfection may also be accomplished using other means known to one of ordinary skill in the art, including without limitation electroporation, gene guns, injection of naked DNA, and use of dimethyl sulfoxide (DMSO).

Depending upon the cell or tissue type targeted for transfection, the form of the transposon-based vector may be important. Plasmids harvested from bacteria are generally closed circular supercoiled molecules, and this is the preferred state of a vector for gene delivery because of the ease of preparation. In some instances, transposase expression and insertion may be more efficient in a relaxed, closed circular configuration or in a linear configuration. In still other instances, a purified transposase protein may be co-injected with a transposon-based vector containing the gene of interest for more immediate insertion. This could be accomplished by using a transfection reagent complexed with both the purified transposase protein and the transposon-based vector.

Testing for and Breeding Animals Carrying the Transgene

Following administration of a transposon-based vector to an animal, DNA is extracted from the animal to confirm integration of the gene of interest. Actual frequencies of integration are estimated both by comparative strength of the PCR signal, and by histological evaluation of the tissues by quantitative PCR. Another method for estimating the rate of transgene insertion is the so-called primed in situ hybridization technique (PRINS). This method determines not only which cells carry a transgene of interest, but also into which chromosome the gene has inserted, and even what portion of the chromosome. Briefly, labeled primers are annealed to chromosome spreads (affixed to glass slides) through one round of PCR, and the slides are then developed through normal in situ hybridization procedures. This technique combines the best features of in situ PCR and fluorescence in situ hybridization (FISH) to provide distinct chromosome location and copy number of the gene in question. The 28s rRNA gene will be used as a positive control for spermatogonia to confirm that the technique is functioning properly. Using different fluorescent labels for the transgene and the 28s gene causes cells containing a transgene to fluoresce with two different colored tags.

Breeding experiments are also conducted to determine if germline transmission of the transgene has occurred. In a general bird breeding experiment performed according to the present invention, each male bird was exposed to 2-3 different adult female birds for 3-4 days each. This procedure was continued with different females for a total period of 6-12 weeks. Eggs were collected daily for up to 14 days after the last exposure to the transgenic male, and each egg was incubated in a standard incubator. In the first series of experiments the resulting embryos were examined for transgene presence at day 3 or 4 using PCR.

Any male producing a transgenic embryo was bred to additional females. Eggs from these females were incubated, hatched, and the chicks tested for the exogenous DNA. Any embryos that died were necropsied and examined directly for the transgene or protein encoded by the transgene, either by fluorescence or PCR. The offspring that hatched and were found to be positive for the exogenous DNA were raised to maturity. These birds were bred to produce further generations of transgenic birds, to verify efficiency of the transgenic procedure and the stable incorporation of the transgene into the germ line. The resulting embryos were examined for transgene presence at day 3 or 4 using PCR.

It is to be understood that the above procedure can be modified to suit animals other than birds and that selective breeding techniques may be performed to amplify gene copy numbers and protein output.

Production of Desired Proteins or Peptides in Egg White

In one embodiment, the transposon-based vectors of the present invention may be administered to a bird for production of desired proteins or peptides in the egg white. These transposon-based vectors preferably contain one or more of an ovalbumin promoter, an ovomucoid promoter, an ovalbumin signal sequence and an ovomucoid signal sequence. Oviduct-specific ovalbumin promoters are described in B. O'Malley et al., 1987. EMBO J., vol. 6, pp. 2305-12; A. Qiu et al., 1994. Proc. Nat. Acad. Sci. (USA), vol. 91, pp. 4451-4455; D. Monroe et al., 2000. Biochim. Biophys. Acta, 1517 (1):27-32; H. Park et al., 2000. Biochem., 39:8537-8545; and T. Muramatsu et al., 1996. Poult. Avian Biol. Rev., 6:107-123. Examples of transposon-based vectors designed for production of a desired protein in an egg white are shown in FIGS. 2 and 3.

Production of Desired Proteins or Peptides in Egg Yolk

The present invention is particularly advantageous for production of recombinant peptides and proteins of low solubility in the egg yolk. Such proteins include, but are not limited to, membrane-associated or membrane-bound proteins, lipophilic compounds; attachment factors, receptors, and components of second messenger transduction machinery. Low solubility peptides and proteins are particularly challenging to produce using conventional recombinant protein production techniques (cell and tissue cultures) because they aggregate in water-based, hydrophilic environments. Such aggregation necessitates denaturation and re-folding of the recombinantly-produced proteins, which may deleteriously affect their structure and function. Moreover, even highly soluble recombinant peptides and proteins may precipitate and require denaturation and renaturation when produced in sufficiently high amounts in recombinant protein production systems. The present invention provides an advantageous resolution of the problem of protein and peptide solubility during production of large amounts of recombinant proteins.

In one embodiment of the present invention, deposition of a desired protein into the egg yolk is accomplished by attaching a sequence encoding a protein capable of binding to the yolk vitellogenin receptor to a gene of interest that encodes a desired protein. This transposon-based vector can be used for the receptor-mediated uptake of the desired protein by the oocytes. In a preferred embodiment, the sequence ensuring the binding to the vitellogenin receptor is a targeting sequence of a vitellogenin protein. The invention encompasses various vitellogenin proteins and their targeting sequences. In a preferred embodiment, a chicken vitellogenin protein targeting sequence is used, however, due to the high degree of conservation among vitellogenin protein sequences and known cross-species reactivity of vitellogenin targeting sequences with their egg-yolk receptors, other vitellogenin targeting sequences can be substituted. One example of a construct for use in the transposon-based vectors of the present invention and for deposition of an insulin protein in an egg yolk is provided in SEQ ID NO:27. In this embodiment, the transposon-based vector contains a vitellogenin promoter, a vitellogenin targeting sequence, a TAG sequence, a pro-insulin sequence and a synthetic polyA sequence. The present invention includes, but is not limited to, vitellogenin targeting sequences residing in the N-terminal domain of vitellogenin, particularly in lipovitellin I. In one embodiment, the vitellogenin targeting sequence contains the polynucleotide sequence of SEQ ID NO:18.

Figure 4:
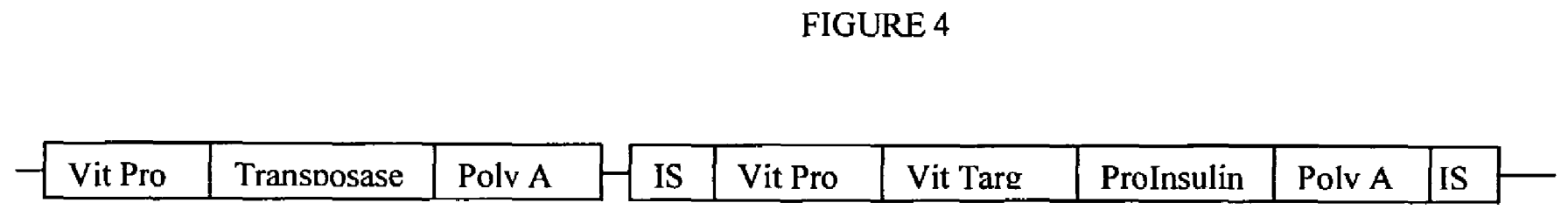

In a preferred embodiment, the transposon-based vector contains a transposase gene operably-linked to a liver-specific promoter and a gene of interest operably-linked to a liver-specific promoter and a vitellogenin targeting sequence. FIG. 4 shows an example of such a construct. In another preferred embodiment, the transposon-based vector contains a transposase gene operably-linked to a constitutive promoter and a gene of interest operably-linked to a liver-specific promoter and a vitellogenin targeting sequence.

Isolation and Purification of Desired Protein or Peptide

For large-scale production of protein, an animal breeding stock that is homozygous for the transgene is preferred. Such homozygous individuals are obtained and identified through, for example, standard animal breeding procedures or PCR protocols.

Once expressed, peptides, polypeptides and proteins can be purified according to standard procedures known to one of ordinary skill in the art, including ammonium sulfate precipitation, affinity columns, column chromatography, gel electrophoresis, high performance liquid chromatography, immunoprecipitation and the like. Substantially pure compositions of about 50 to 99% homogeneity are preferred, and 80 to 95% or greater homogeneity are most preferred for use as therapeutic agents.

In one embodiment of the present invention, the animal in which the desired protein is produced is an egg-laying animal. In a preferred embodiment of the present invention, the animal is an avian and a desired peptide, polypeptide or protein is isolated from an egg white. Egg white containing the exogenous protein or peptide is separated from the yolk and other egg constituents on an industrial scale by any of a variety of methods known in the egg industry. See, e.g., W. Stadelman et al. (Eds.), Egg Science & Technology, Haworth Press, Binghamton, N.Y. (1995). Isolation of the exogenous peptide or protein from the other egg white constituents is accomplished by any of a number of polypeptide isolation and purification methods well known to one of ordinary skill in the art. These techniques include, for example, chromatographic methods such as gel permeation, ion exchange, affinity separation, metal chelation, HPLC, and the like, either alone or in combination. Another means that may be used for isolation or purification, either in lieu of or in addition to chromatographic separation methods, includes electrophoresis. Successful isolation and purification is confirmed by standard analytic techniques, including HPLC, mass spectroscopy, and spectrophotometry. These separation methods are often facilitated if the first step in the separation is the removal of the endogenous ovalbumin fraction of egg white, as doing so will reduce the total protein content to be further purified by about 50%.

To facilitate or enable purification of a desired protein or peptide, transposon-based vectors may include one or more additional epitopes or domains. Such epitopes or domains include DNA sequences encoding enzymatic or chemical cleavage sites including, but not limited to, an enterokinase cleavage site; the glutathione binding domain from glutathione S-transferase; polylysine; hexa-histidine or other cationic amino acids; thioredoxin; hemagglutinin antigen; maltose binding protein; a fragment of gp41 from HIV; and other purification epitopes or domains commonly known to one of skill in the art.

In one representative embodiment, purification of desired proteins from egg white utilizes the antigenicity of the ovalbumin carrier protein and particular attributes of a TAG linker sequence that spans ovalbumin and the desired protein. The TAG sequence is particularly useful in this process because it contains 1) a highly antigenic epitope, a fragment of gp41 from HIV, allowing for stringent affinity purification, and, 2) a recognition site for the protease enterokinase immediately juxtaposed to the desired protein. In a preferred embodiment, the TAG sequence comprises approximately 50 amino acids. A representative TAG sequence is provided below.

(SEQ ID NO:22)

Pro Ala Asp Asp Ala Pro Ala Asp Asp Ala Pro Ala

Asp Asp Ala Pro Ala Asp Asp Ala Pro Ala Asp Asp

Ala Pro Ala Asp Asp Ala Thr Thr Cys Ile Leu Lys

Gly Ser Cys Gly Trp Ile Gly Leu Leu *Asp Asp Asp*

*Asp Lys*

The underlined sequences were taken from the hairpin loop domain of HIV gp-41 (SEQ ID NO:23). Sequences in italics represent the cleavage site for enterokinase (SEQ ID NO:9). The spacer sequence upstream of the loop domain was made from repeats of (Pro Ala Asp Asp Ala) (SEQ ID NO:25) to provide free rotation and promote surface availability of the hairpin loop from the ovalbumin carrier protein.

Isolation and purification of a desired protein is performed as follows:

1. Enrichment of the egg white protein fraction containing ovalbumin and the transgenic ovalbumin-TAG-desired protein.
2. Size exclusion chromatography to isolate only those proteins within a narrow range of molecular weights (a further enrichment of step 1).
3. Ovalbumin affinity chromatography. Highly specific antibodies to ovalbumin will eliminate virtually all extraneous egg white proteins except ovalbumin and the transgenic ovalbumin-TAG-desired protein.
4. gp41 affinity chromatography using anti-gp41 antibodies. Stringent application of this step will result in virtually pure transgenic ovalbumin-TAG-desired protein.
5. Cleavage of the transgene product can be accomplished in at least one of two ways:
   - a. The transgenic ovalbumin-TAG-desired protein is left attached to the gp41 affinity resin (beads) from step 4 and the protease enterokinase is added. This liberates the transgene target protein from the gp41 affinity resin while the ovalbumin-TAG sequence is retained. Separation by centrifugation (in a batch process) or flow through (in a column purification), leaves the desired protein together with enterokinase in solution. Enterokinase is recovered and reused.
   - b. Alternatively, enterokinase is immobilized on resin (beads) by the addition of poly-lysine moieties to a non-catalytic area of the protease. The transgenic ovalbumin-TAG-desired protein eluted from the affinity column of step 4 is then applied to the protease resin. Protease action cleaves the ovalbumin-TAG sequence from the desired protein and leaves both entities in solution. The immobilized enterokinase resin is recharged and reused.

c. The choice of these alternatives is made depending upon the size and chemical composition of the transgene target protein.

6. A final separation of either of these two (5a or 5b) protein mixtures is made using size exclusion, or enterokinase affinity chromatography. This step allows for desalting, buffer exchange and/or polishing, as needed.

Cleavage of the transgene product (ovalbumin-TAG-desired protein) by enterokinase, then, results in two products: ovalbumin-TAG and the desired protein. More specific methods for isolation using the TAG label is provided in the Examples. Some desired proteins may require additions or modifications of the above-described approach as known to one of ordinary skill in the art. The method is scaleable from the laboratory bench to pilot and production facility largely because the techniques applied are well documented in each of these settings.

It is believed that a typical chicken egg produced by a transgenic animal of the present invention will contain at least 0.001 mg, from about 0.001 to 1.0 mg, or from about 0.001 to 100.0 mg of exogenous protein, peptide or polypeptide, in addition to the normal constituents of egg white (or possibly replacing a small fraction of the latter).

One of skill in the art will recognize that after biological expression or purification, the desired proteins, fragments thereof and peptides may possess a conformation substantially different than the native conformations of the proteins, fragments thereof and peptides. In this case, it is often necessary to denature and reduce protein and then to cause the protein to re-fold into the preferred conformation. Methods of reducing and denaturing proteins and inducing re-folding are well known to those of skill in the art.

Production of Protein or Peptide in Milk

In addition to methods of producing eggs containing transgenic proteins or peptides, the present invention encompasses methods for the production of milk containing transgenic proteins or peptides. These methods include the administration of a transposon-based vector described above to a mammal. In one embodiment, the transposon-based vector contains a transposase operably-linked to a constitutive promoter and a gene of interest operably-linked to mammary specific promoter. Genes of interest can include, but are not limited to antiviral and antibacterial proteins and immunoglobulins.

Treatment of Disease and Animal Improvement

In addition to production and isolation of desired molecules, the transposon-based vectors of the present invention can be used for the treatment of various genetic disorders. For example, one or more transposon-based vectors can be administered to a human or animal for the treatment of a single gene disorder including, but not limited to, Huntington's disease, alpha-1-antitrypsin deficiency Alzheimer's disease, various forms or breast cancer, cystic fibrosis, galactosemia, congenital hypothyroidism, maple syrup urine disease, neurofibromatosis 1, phenylketonuria, sickle cell disease, and Smith-Lemli-Opitz (SLO/RSH) Syndrome. Other diseases caused by single gene disorders that may be treated with the present invention include, autoimmune diseases, shipping fever in cattle, mastitis, bacterial or viral diseases, alteration of skin pigment in animals. In these embodiments, the transposon-based vector contains a non-mutated, or non-disease causing form of the gene known to cause such disorder. Preferably, the transposase contained within the transposase-based vector is operably linked to an inducible promoter such as a tissue-specific promoter such that the non-mutated gene of interest is inserted into a specific tissue wherein the mutated gene is expressed in vivo.

In one embodiment of the present invention, a transposon-based vector comprising a gene encoding proinsulin is administered to diabetic animals or humans for incorporation into liver cells in order to treat or cure diabetes. The specific incorporation of the proinsulin gene into the liver is accomplished by placing the transposase gene under the control of liver-specific promoter, such as G6P. This approach is useful for treatment of both Type I and Type II diabetes. The G6P promoter has been shown to be glucose responsive (Arguad, D., et al. 1996. Diabetes 45:1563-1571), and thus, glucose-regulated insulin production is achieved using DNA constructs of the present invention. Integrating a proinsulin gene into liver cells circumvents the problem of destruction of pancreatic islet cells in the course of Type I diabetes.

In another embodiment, shortly after diagnosis of Type I diabetes, the cells of the immune system destroying pancreatic β-cells are selectively removed using the transposon-based vectors of the present invention, thus allowing normal β-cells to repopulate the pancreas.

For treatment of Type II diabetes, a transposon-based vector containing a proinsulin gene is specifically incorporated into the pancreas by placing the transposase gene under the control of a pancreas-specific promoter, such as an insulin promoter. In this embodiment, the vector is delivered to a diabetic animal or human via injection into an artery feeding the pancreas. For delivery, the vector is complexed with a transfection agent. The artery distributes the complex throughout the pancreas, where individual cells receive the vector DNA. Following uptake into the target cell, the insulin promoter is recognized by transcriptional machinery of the cell, the transposase encoded by the vector is expressed, and stable integration of the proinsulin gene occurs. It is expected that a small percentage of the transposon-based vector is transported to other tissues, and that these tissues are transfected. However, these tissues are not stably transfected and the proinsulin gene is not incorporated into the cells' DNA due to failure of these cells to activate the insulin promoter. The vector DNA is likely lost when the cell dies or degraded over time.

In other embodiments, one or more transposon-based vectors are administered to an avian for the treatment of a viral or bacterial infection/disease including, but not limited to, Colibacillosis (Coliform infections), Mycoplasmosis (CRD, Air sac, Sinusitis), Fowl Cholera, Necrotic Enteritis, Ulcerative Enteritis (Quail disease), Pullorum Disease, Fowl Typhoid, Botulism, Infectious Coryza, Erysipelas, Avian Pox, Newcastle Disease, Infectious Bronchitis, Quail Bronchitis, Lymphoid Leukosis, Marek's Disease (Visceral Leukosis), Infectious Bursal Disease (Gumboro). In these embodiments, the transposon-based vectors may be used in a manner similar to traditional vaccines.

In still other embodiments, one or more transposon-based vectors are administered to an animal for the production of an animal with enhanced growth characteristics and nutrient utilization.

The transposon-based vectors of the present invention can be used to transform any animal cell, including but not limited to: cells producing hormones, cytokines, growth factors, or any other biologically active substance; cells of the immune system; cells of the nervous system; muscle (striatal, cardiac, smooth) cells; vascular system cells; endothelial cells; skin cells; mammary cells; and lung cells, including bronchial and alveolar cells. Transformation of any endocrine cell by a transposon-based vector is contemplated as a part of a present invention. In one aspect of the present invention, cells of the immune system may be the target for incorporation of a desired gene or genes encoding for production of antibodies. Accordingly, the thymus, bone marrow, beta lymphocytes (or B cells), gastrointestinal associated lymphatic tissue (GALT), Peyer's patches, bursa Fabricius, lymph nodes, spleen, and tonsil, and any other lymphatic tissue, may all be targets for administration of the compositions of the present invention.

The transposon-based vectors of the present invention can be used to modulate (stimulate or inhibit) production of any substance, including but not limited to a hormone, a cytokine, or a growth factor, by an animal or a human cell. Modulation of a regulated signal within a cell or a tissue, such as production of a second messenger, is also contemplated as a part of the present invention. Use of the transposon-based vectors of the present invention is contemplated for treatment of any animal or human disease or condition that results from underproduction (such as diabetes) or overproduction (such as hyperthyroidism) of a hormone or other endogenous biologically active substance. Use of the transposon-based vectors of the present invention to integrate nucleotide sequences encoding RNA molecules, such as anti-sense RNA or short interfering RNA, is also contemplated as a part of the present invention.

Additionally, the transposon-based vectors of the present invention may be used to provide cells or tissues with "beacons", such as receptor molecules, for binding of therapeutic agents in order to provide tissue and cell specificity for the therapeutic agents. Several promoters and exogenous genes can be combined in one vector to produce progressive, controlled treatments from a single vector delivery.

The following examples will serve to further illustrate the present invention without, at the same time, however, constituting any limitation thereof. On the contrary, it is to be clearly understood that resort may be had to various embodiments, modifications and equivalents thereof which, after reading the description herein, may suggest themselves to those skilled in the art without departing from the spirit of the invention.

EXAMPLE 1

Preparation of Transposon-Based Vector PTnMod

A vector was designed for inserting a desired coding sequence into the genome of eukaryotic cells, given below as SEQ ID NO:1. The vector of SEQ ID NO:1, termed pTnMod, was constructed and its sequence verified.

This vector employed a cytomegalovirus (CMV) promoter. A modified Kozak sequence (ACCATG) (SEQ ID NO:13) was added to the promoter. The nucleotide in the wobble position in nucleotide triplet codons encoding the first 10 amino acids of transposase was changed to an adenine (A) or thymine (T), which did not alter the amino acid encoded by this codon. Two stop codons were added and a synthetic polyA was used to provide a strong termination sequence. This vector uses a promoter designed to be active soon after entering the cell (without any induction) to increase the likelihood of stable integration. The additional stop codons and synthetic polyA insures proper termination without read through to potential genes downstream.

The first step in constructing this vector was to modify the transposase to have the desired changes. Modifications to the transposase were accomplished with the primers High Efficiency forward primer (Hef) Altered transposase (ATS)-Hef 5' ATCTCGAGACCATGTGTGAACTTGATATTTACATGATTCTCTTTACC 3' (SEQ ID NO:10) and Altered transposase-High efficiency reverse primer (Her) 5' GATTGATCATTATCATAATTTCCCCAAAGCGTAACC 3' (SEQ ID NO:11, a reverse complement primer). In the 5' forward primer ATS-Hef, the sequence CTCGAG (SEQ ID NO:12) is the recognition site for the restriction enzyme Xho I, which permits directional cloning of the amplified gene. The sequence ACCATG (SEQ ID NO:13) contains the Kozak sequence and start codon for the transposase and the underlined bases represent changes in the wobble position to an A or T of codons for the first 10 amino acids (without changing the amino acid coded by the codon). Primer ATS-Her (SEQ ID NO:11) contains an additional stop codon TAA in addition to native stop codon TGA and adds a Bcl I restriction site, TGATCA (SEQ ID NO:14), to allow directional cloning. These primers were used in a PCR reaction with pTnLac (p defines plasmid, tn defines transposon, and lac defines the beta fragment of the lactose gene, which contains a multiple cloning site) as the template for the transposase and a FailSafe™ PCR System (which includes enzyme, buffers, dNTP's, $MgCl_2$ and PCR Enhancer; Epicentre Technologies, Madison, Wis.). Amplified PCR product was electrophoresed on a 1% agarose gel, stained with ethidium bromide, and visualized on an ultraviolet transilluminator. A band corresponding to the expected size was excised from the gel and purified from the agarose using a Zymo Clean Gel Recovery Kit (Zymo Research, Orange, Calif.). Purified DNA was digested with restriction enzymes Xho I (5') and Bcl I (3') (New England Biolabs, Beverly, Mass.) according to the manufacturer's protocol. Digested DNA was purified from restriction enzymes using a Zymo DNA Clean and Concentrator kit (Zymo Research).

Plasmid gWiz (Gene Therapy Systems, San Diego, Calif.) was digested with restriction enzymes Sal I and BamH I (New England Biolabs), which are compatible with Xho I and Bcl I, but destroy the restriction sites. Digested gWhiz was separated on an agarose gel, the desired band excised and purified as described above. Cutting the vector in this manner facilitated directional cloning of the modified transposase (mATS) between the CMV promoter and synthetic polyA.

To insert the mATS between the CMV promoter and synthetic polyA in gWhiz, a Stratagene T4 Ligase Kit (Stratagene, Inc. La Jolla, Calif.) was used and the ligation set up according to the manufacturer's protocol. Ligated product was transformed into *E. coli* Top10 competent cells (Invitrogen Life Technologies, Carlsbad, Calif.) using chemical transformation according to Invitrogen's protocol. Transformed bacteria were incubated in 1 ml of SOC (GIBCO BRL, CAT# 15544-042) medium for 1 hour at 37° C. before being spread to LB (Luria-Bertani media (broth or agar)) plates supplemented with 100 μg/ml ampicillin (LB/amp plates). These plates were incubated overnight at 37° C. and resulting colonies picked to LB/amp broth for overnight growth at 37° C. Plasmid DNA was isolated using a modified alkaline lysis protocol (Sambrook et al., 1989), electrophoresed on a 1% agarose gel, and visualized on a U.V. transilluminator after ethidium bromide staining. Colonies producing a plasmid of the expected size (approximately 6.4 kbp) were cultured in at least 250 ml of LB/amp broth and plasmid DNA harvested using a Qiagen Maxi-Prep Kit (column purification) according to the manufacturer's protocol (Qiagen, Inc., Chatsworth, Calif.). Column purified DNA was used as template for sequencing to verify the changes made in the transposase were the desired changes and no further changes or mutations occurred due to PCR amplification. For sequencing, Perkin-Elmer's Big Dye Sequencing Kit was used. All samples were sent to the Gene Probes and Expression Laboratory (LSU School of Veterinary Medicine) for sequencing on a Perkin-Elmer Model 377 Automated Sequencer.

Once a clone was identified that contained the desired mATS in the correct orientation, primers CMVf-NgoM IV (5' TTGCCGGCATCAGATTGGCTAT (SEQ ID NO:15); underlined bases denote NgoM IV recognition site) and Syn-polyA-BstE II (5' AGAGGTCACCGGGTCAATTCT-TCAGCACCTGGTA (SEQ ID NO:16); underlined bases denote BstE II recognition site) were used to PCR amplify the entire CMV promoter, mATS, and synthetic polyA for cloning upstream of the transposon in pTnLac. The PCR was conducted with FailSafe™ as described above, purified using the Zymo Clean and Concentrator kit, the ends digested with NgoM IV and BstE II (New England Biolabs), purified with the Zymo kit again and cloned upstream of the transposon in pTnLac as described below.

Plasmid pTnLac was digested with NgoM IV and BstE II to remove the ptac promoter and transposase and the fragments separated on an agarose gel. The band corresponding to the vector and transposon was excised, purified from the agarose, and dephosphorylated with calf intestinal alkaline phosphatase (New England Biolabs) to prevent self-annealing. The enzyme was removed from the vector using a Zymo DNA Clean and Concentrator-5. The purified vector and CMVp/mATS/polyA were ligated together using a Stratagene T4 Ligase Kit and transformed into *E. coli* as described above.

Colonies resulting from this transformation were screened (mini-preps) as describe above and clones that were the correct size were verified by DNA sequence analysis as described above. The vector was given the name pTnMod (SEQ ID NO:1) and includes the following components:

Base pairs 1-130 are a remainder of F1(−) on from pBluescriptII sk(−) (Stratagene), corresponding to base pairs 1-130 of pBluescriptII sk(−).

Base pairs 131-132 are a residue from ligation of restriction enzyme sites used in constructing the vector.

Base pairs 133-1777 are the CMV promoter/enhancer taken from vector pGWiz (Gene Therapy Systems), corresponding to bp 229-1873 of pGWiz. The CMV promoter was modified by the addition of an ACC sequence upstream of ATG.

Base pairs 1778-1779 are a residue from ligation of restriction enzyme sites used in constructing the vector. A3

Base pairs 1780-1785 are the Kozak sequence of SEQ ID NO:13, and base pairs 1783-2987 are the coding sequence for the transposase, modified from Tn10 (GenBank accession J01829) by optimizing codons for stability of the transposase mRNA and for the expression of protein. More specifically, in each of the codons for the first ten amino acids of the transposase, G or C was changed to A or T when such a substitution would not alter the amino acid that was encoded.

Base pairs 2988-2993 are two engineered stop codons.

Base pair 2994 is a residue from ligation of restriction enzyme sites used in constructing the vector.

Base pairs 2995-3410 are a synthetic polyA sequence taken from the pGWiz vector (Gene Therapy Systems), corresponding to bp 1922-2337 of 10 pGWiz.

Base pairs 3415-3718 are non-coding DNA that is residual from vector pNK2859.

Base pairs 3719-3761 are non-coding λ DNA that is residual from pNK2859.

Base pairs 3762-3831 are the 70 bp of the left insertion sequence recognized by the transposon Tn10.

Base pairs 3832-3837 are a residue from ligation of restriction enzyme sites used in constructing the vector.

Base pairs 3838-4527 are the multiple cloning site from pBluescriptII sk(20), corresponding to bp 924-235 of pBluescriptII sk(−). This multiple cloning site may be used to insert any coding sequence of interest into the vector.

Base pairs 4528-4532 are a residue from ligation of restriction enzyme sites used in constructing the vector.

Base pairs 4533-4602 are the 70 bp of the right insertion sequence recognized by the transposon Tn10.

Base pairs 4603-4644 are non-coding λ DNA that is residual from pNK2859.

Base pairs 4645-5488 are non-coding DNA that is residual from pNK2859.

Base pairs 5489-7689 are from the pBluescriptII sk(−) base vector—(Stratagene, Inc.), corresponding to bp 761-2961 of pBluescriptII sk(−).

Completing pTnMod is a pBluescript backbone that contains a colE I origin of replication and an antibiotic resistance marker (ampicillin).

It should be noted that all non-coding DNA sequences described above can be replaced with any other non-coding DNA sequence(s). Missing nucleotide sequences in the above construct represent restriction site remnants.

All plasmid DNA was isolated by standard procedures. Briefly, *Escherichia coli* containing the plasmid was grown in 500 mL aliquots of LB broth (supplemented with an appropriate antibiotic) at 37° C. overnight with shaking. Plasmid DNA was recovered from the bacteria using a Qiagen Maxi-Prep kit (Qiagen, Inc., Chatsworth, Calif.) according to the manufacturer's protocol. Plasmid DNA was resuspended in 500 μL of PCR-grade water and stored at −20° C. until used.

EXAMPLE 2

Preparation of Transposon-Based Vector pTnMod (CMV/Red)

A vector was designed for inserting a reporter gene (DsRed) under the control of the CMV promoter into the genome of vertebrate cells given below as SEQ ID NO:2. The reporter gene chosen was the DsRed gene, driven by the immediate early cytomegalovirus promoter, to produce a plasmid called pTnCMV/DsRed. The DsRed gene product is a red fluorescent protein from an IndoPacific sea anemone, *Discosoma* sp., which fluoresces bright red at 558 nm. It is to be understood that the reporter gene, i.e., the DsRed gene, is only one embodiment of the present invention and that any gene of interest may be inserted into the plasmid in place of the DsRed reporter gene in any Experiment described herein.

The vector of SEQ ID NO:2, named pTnMod (CMV/Red), was constructed, and its sequence verified by re-sequencing. SEQ ID NO:2, pTnMod (CMV/Red), includes the following components:

Base pairs 1-130 are a remainder of F1(−) on from pBluescriptII sk(−) (Stratagene), corresponding to bp 1-130 of pBluescriptII sk(−).

Base pairs 131-132 are a residue from ligation of restriction enzyme sites used in constructing the vector.

Base pairs 133-1777 are the CMV promoter/enhancer taken from vector pGWiz (Gene Therapy Systems, corresponding to bp 229-1873 of pGWiz.

Base pairs 1778-1779 are a residue from ligation of restriction enzyme sites used in constructing the vector.

Base pairs 1780-1785 are the Kozak sequence of SEQ ID NO:13, and base pairs 1783-2987 are the coding sequence for the transposase, modified from Tn10 (GenBank accession J01829) by optimizing codons as discussed above.

Base pairs 2988-2993 are two engineered stop codons.

Base pair 2994 is a residue from ligation of restriction enzyme sites used in constructing the vector.

Base pairs 2995-3410 are a synthetic polyA sequence taken from the pGWiz vector (Gene Therapy Systems), corresponding to bp 1922-2337 of pGWiz.

Base pairs 3415-3718 are non-coding DNA that is residual from vector pNK2859.

Base pairs 3719-3761 are non-coding λ DNA that is residual from pNK2859.

Base pairs 3762-3831 are the 70 bp of the left insertion sequence recognized by the transposon Tn10.

Base pairs 3832-3837 are a residue from ligation of restriction enzyme sites used in constructing the vector.

Base pairs 3838-4044 are part of the multiple cloning site from pBluescriptII sk(−), corresponding to bp 924-718 of pBluescriptII sk(−).

Base pairs 4045-4048 are a residue from ligation of restriction enzyme sites used in constructing the vector.

Base pairs 4049-5693 are the CMV promoter/enhancer, taken from vector pGWiz (Gene Therapy Systems), corresponding to bp 229-1873 of pGWiz.

Base pairs 5694-5701 are a residue from ligation of restriction enzyme sites used in constructing the vector.

Base pairs 5702-6617 are the DsRed reporter coding sequence, including polyA sequence, from pDsRed1.1 (Clontech), corresponding to bp 77-992 of pDsRed1.1.

Base pairs 6618-7101 are part of the multiple cloning site from pBluescriptII sk(−), corresponding to bp 718-235 of pBluescriptII sk(−).

Base pairs 7102-7106 are a residue from ligation of restriction enzyme sites used in constructing the vector.

Base pairs 7107-7176 are the 70 bp of the right insertion sequence recognized by the transposon Tn10.

Base pairs 7177-7218 are non-coding λ DNA that is residual from pNK2859.

Base pairs 7219-8062 are non-coding DNA that is residual from pNK2859.

Base pairs 8063-10263 are from the pBluescriptII sk(−) base vector (Stratagene, Inc.), corresponding to bp 761-2961 of pBluescriptII sk(−).

It should be noted that all non-coding DNA sequences described above can be replaced with any other non-coding DNA sequence(s).

EXAMPLE 3

Preparation of Transposon-Based Vector pTnMod (Oval/Red)—Chicken

A vector was designed for inserting a reporter gene (DsRed) under the control of the ovalbumin promoter, and including the ovalbumin signal sequence, into the genome of a bird. One version of this vector is given below as SEQ ID NO:3. The vector of SEQ ID NO:3, named pTnMod (Oval/Red)—Chicken, includes chicken ovalbumin promoter and signal sequences.

SEQ ID NO:3, pTnMod (Oval/Red)—Chicken, includes the following components:

Base pairs 1-130 are a remainder of F1(−) on from pBluescriptII sk(−) (Stratagene), corresponding to bp 1-130 of pBluescriptII sk(−).

Base pairs 131-132 are a residue from ligation of restriction enzyme sites used in constructing the vector.

Base pairs 133-1777 are the CMV promoter/enhancer taken from vector pGWiz (Gene Therapy Systems, corresponding to bp 229-1873 of pGWiz.

Base pairs 1778-1779 are a residue from ligation of restriction enzyme sites used in constructing the vector.

Base pairs 1780-1785 are the Kozak sequence of SEQ ID NO:13, and base pairs 1783-2987 are the coding sequence for the transposase, modified from Tn10 (GenBank accession J01829) by optimizing codons as discussed above.

Base pairs 2988-2993 are two engineered stop codons.

Base pair 2994 is a residue from ligation of restriction enzyme sites used in constructing the vector.

Base pairs 2995-3410 are a synthetic polyA sequence taken from the pGWiz vector (Gene Therapy Systems), corresponding to bp 1922-2337 of pGWiz.

Base pairs 3415-3718 are non-coding DNA that is residual from vector pNK2859.

Base pairs 3719-3761 are non-coding λ DNA that is residual from 10 pNK2859.

Base pairs 3762-3831 are the 70 bp of the left insertion sequence recognized by the transposon Tn 10.

Base pairs 3832-3837 are a residue from ligation of restriction enzyme sites used in constructing the vector.

Base pairs 3838-4044 are part of the multiple cloning site from pBluescriptII sk(−), corresponding to bp 924-718 of pBluescriptII sk(−).

Base pairs 4045-4049 are a residue from ligation of restriction enzyme sites used in constructing the vector.

Base pairs 4050-4951 contain upstream elements of the (including SDRE, steroid-dependent response element). See GenBank accession number J00895 M24999, bp 431-1332. Base pairs 4952-4959 are a residue from ligation of restriction enzyme sites used in constructing the vector.

Base pairs 4960-5112 are the chicken ovalbumin signal sequence (GenBank accession number J00895 M24999, bp 2996-3148).

Base pairs 5113-5118 are a residue from ligation of restriction enzyme sites used in constructing the vector.

Base pairs 5119-6011 are the DsRed reporter coding sequence, including polyA sequence, from pDsRed1.1 (Clontech), corresponding to bp 100-992 of pDsRed1.1.

Base pairs 6012-6017 are a residue from ligation of restriction enzyme sites used in constructing the vector.

Base pairs 6018-6056 are part of the multiple cloning site of the ZeroBlunt Topo cloning vector (Invitrogen), corresponding to bp 337-377 of ZeroBlunt.

Base pairs 6057-6062 are a residue from ligation of restriction enzyme sites used in constructing the vector.

Base pairs 6063-6495 are part of the multiple cloning site from pBluescriptll sk(−), corresponding to bp 667-235 of pBluescriptII sk(−).

Base pairs 6496-6500 are a residue from ligation of restriction enzyme sites used in constructing the vector.

Base pairs 6501-6570 are the 70 bp of the right insertion sequence recognized by the transposon Tn10.

Base pairs 6571-6612 are non-coding λ DNA that is residual from pNK2859.

Base pairs 6613-7477 are non-coding DNA that is residual from pNK2859.

Base pairs 7478-9678 are from the pBluescriptII sk(−) base vector (Stratagene, Inc.), corresponding to bp 761-2961 of pBluescriptII sk(−).

It should be noted that all non-coding DNA sequences described above can be replaced with any other non-coding DNA sequence(s).

EXAMPLE 4

Preparation of Transposon-Based Vector pTnMod(Oval/Red)—Quail

A vector was designed for inserting a reporter gene (DsRed) under the control of the ovalbumin promoter, and including the ovalbumin signal sequence, into the genome of a bird given below as SEQ ID NO:4. The vector of SEQ ID NO:4, named pTnMod (Oval/Red)—Quail, has been constructed, and selected portions of the sequence have been verified by re-sequencing.

SEQ ID NO:4, pTnMod (Oval/Red)—Quail, includes the following components:

Base pairs 1-130 are a remainder of F1(−) on from pBluescriptII sk(−) (Stratagene), corresponding to bp 1-130 of pBluescriptII sk(−).

Base pairs 131-132 are a residue from ligation of restriction enzyme sites used in constructing the vector.

Base pairs 133-1777 are the CMV promoter/enhancer taken from vector pGWiz (Gene Therapy Systems), corresponding to bp 229-1873 of pGWiz.

Base pairs 1778-1779 are a residue from ligation of restriction enzyme sites used in constructing the vector.

Base pairs 1780-1785 are the Kozak sequence of SEQ ID NO:13, and base pairs 1783-2987 are the coding sequence for the transposase, modified from Tn10 (GenBank accession J01829) by optimizing codons as discussed above.

Base pairs 2988-2993 are two engineered stop codons. Base pair 2994 is a residue from ligation of restriction enzyme sites used in constructing the vector.

Base pairs 2995-3410 are a synthetic polyA sequence taken from the pGWiz vector (Gene Therapy Systems), corresponding to bp 1922-2337 of pGWiz.

Base pairs 3415-3718 are non-coding DNA that is residual from vector pNK2859.

Base pairs 3719-3761 are non-coding λ DNA that is residual from pNK2859.

Base pairs 3762-3831 are the 70 base pairs of the left insertion sequence recognized by the transposon Tn10.

Base pairs 3832-3837 are a residue from ligation of restriction enzyme sites used in constructing the vector.

Base pairs 3838-4044 are part of the multiple cloning site from pBluescriptII sk(−), corresponding to bp 924-718 of pBluescriptII sk(−).

Base pairs 4045-4049 are a residue from ligation of restriction enzyme sites used in constructing the vector.

Base pairs 4050-4934 are the Japanese quail ovalbumin promoter (including SDRE, steroid-dependent response element). The Japanese quail ovalbumin promoter was isolated by its high degree of homology to the chicken ovalbumin promoter (GenBank accession number J00895 M24999, base pairs 431-1332). Some deletions were noted in the quail sequence, as compared to the chicken sequence.

Base pairs 4935-4942 are a residue from ligation of restriction enzyme sites used in constructing the vector.

Base pairs 4943-5092 are the Japanese quail ovalbumin signal sequence. The quail signal sequence was isolated by its high degree of homology to the chicken signal sequence (GenBank accession number J00895 M24999, base pairs 2996-3148). Some deletions were noted in the quail sequence, as compared to the chicken sequence.

Base pairs 5093-5098 are a residue from ligation of restriction enzyme sites used in constructing the vector.

Base pairs 5099-5991 are the DsRed reporter coding sequence, including polyA sequence, from pDsRed1.1 (Clontech), corresponding to bp 100-992 of pDsRed 1.1.

Base pairs 5992-5997 are a residue from ligation of restriction enzyme sites used in constructing the vector.

Base pairs 5998-6036 are part of the multiple cloning site of the ZeroBlunt Topo cloning vector (Invitrogen), corresponding to base pairs 337-377 of ZeroBlunt.

Base pairs 6037-6042 are a residue from ligation of restriction enzyme sites used in constructing the vector.

Base pairs 6043-6475 are part of the multiple cloning site from pBluescriptII sk(−), corresponding to bp 667-235 of pBluescriptII sk(−).

Base pairs 6476-6480 are a residue from ligation of restriction enzyme sites used in constructing the vector.

Base pairs 6481-6550 are the 70 bp of the right insertion sequence recognized by the transposon Tn10.

Base pairs 6551-6592 are non-coding λ DNA that is residual from pNK2859.

Base pairs 6593-7457 are non-coding DNA that is residual from pNK2859.

Base pairs 7458-9658 are from the pBluescriptII sk(−) base vector (Stratagene, Inc.), corresponding to base pairs 761-2961 of pBluescriptII sk(−).

It should be noted that all non-coding DNA sequences described above can be replaced with any other non-coding DNA sequence(s).

EXAMPLE 5

Transfection of Stage X Japanese Quail Eggs with pTnMod(Oval/Red)—Quail via Embryo Injection Transgenic Japanese quail were produced by transfecting Stage X embryos and the heritability of the transgene delivered by embryo transfection was established. More specifically, fertile eggs were collected in the morning and placed at 15° C. until enough were collected for injection, but were held no longer than 7 days. Stage X embryos (eggs) were assigned to one of two treatment groups. Before treatment, each egg was incubated on its side at room temperature for about 2 hours to allow the embryo to move to "top dead center" (TDC). Each egg was transfected by drilling a 1 mm hole (directly above the embryo) through the shell without penetrating the underlying shell membrane. A 0.5 ml syringe fitted with a 28 gauge needle was used to deliver DNA complexed to a transfecting reagent, i.e. SUPERFECT®, in a 50 μl volume. An adhesive disc was used to seal the hole and provide a label for treatment identification. After all eggs were transfected, they were set in an incubator with the adhesive disc pointing upward for hatching.

Each bird that hatched was bled at one week of age, DNA was extracted from blood cells, and PCR was conducted using 28s primers as a positive control and primers specific to DsRed. Any bird that was negative was terminated, while positive birds were monitored to determine maintenance of the transgene. Birds consistently positive were maintained until sexual maturity and bred. Positive male and female birds were mated. The eggs of mated hens were hatched and the resulting chicks, the G1 generation, were evaluated to determine if they were transgenic. All G1s resulting from this mating were bled and PCR conducted as described above.

Egg injection: Two treatment groups and one control group were used for this experiment. Vector pTnMod (Oval/Red) in supercoiled form (Treatment 1) and in linear form (Treatment 2) were used to transfect 15 eggs per treatment. To obtain linear DNA for this experiment, pTnMod (Oval/Red) was digested with NgoM IV, column purified, and resuspended in TE buffer.

Each egg was injected with 0.75 μg of DNA complexed with SUPERFECT® in a 1:3 ratio in a total injection volume of 50 μl Hank's Balanced Salt solution (HBSS) was used to bring the volume to 50 μl. The DNA Superfect mixture must be allowed to incubate (for complex formation) at room temperature for 10 minutes prior to injection and must be used within 40 minutes post initial mixing. Eggs were incubated as described above after injection.

Results: In the supercoiled injection group, 2 females and 1 male were identified as PCR positive using primers specific to the DsRed coding sequence. These birds were mated as described above. Blood was taken from the G1 chicks and PCR was conducted. The results showed that the transgene was incorporated into the gametes of these birds. The G1 chicks from these birds were examined on a weekly basis until it was verified that the gene was not present or enough transgenic GIs were obtained to initiate a breeding flock of fully transgenic birds. Eggs from these G1 chicks expressed DsRed protein in the albumin portion of their eggs.

EXAMPLE 6

Intratesticular Injection of Chickens with pTnMod(CMV/Red) (SEQ ID NO:2)

Immature birds of different ages (4, 6, 8, 10, 12, and 14 weeks) were placed under anesthesia and injected in the testes with the construct pTnMod(CMV/Red). A saline solution containing 1-5 μg of purified DNA vector, mixed with SUPERFECT® transfecting reagent (Qiagen, Valencia, Calif.) in a 1:6 (wt:vol) ratio. The volume of saline was adjusted so that the total volume injected into each testis was 150-200 μl, depending on the age and size of the bird. For the 4- and 6-week-old chickens, 1 μg DNA in 150 μl was injected in each testis, divided into three doses of 50 μl each. For the older birds, 200 μl total volume was injected, containing either 3 μg DNA (for 8-week-old birds) or 5 μg DNA (for older birds) per testis. First, one testis was surgically exposed prior to injection. After injection, the incision was sutured, and the sequence was repeated for the alternate testis.

From six to nine months post-surgery, weekly sperm samples were taken from each injected bird, as well as from control birds. Each sperm sample was evaluated for uptake and expression of the injected gene. Samples were evaluated by PCR on whole sperm, within one week after collection.

Approximately 100 male white leghorn chickens, in groups of 5-26, at ages 4, 6, 8, 10, 12, and 14 weeks, were used as this is the age range in which it is expected that the testes are likely to be most "receptive." In this age range, the blood/testis barrier has not yet formed, and there is a relatively high number of spermatogonia relative to the numbers of other cell types, e.g., spermatids, etc. See J. Kumaran et al., 1949. Poultry Sci., vol. 29, pp. 511-520. See also E. Oakberg, 1956. Am. J. Anatomy, vol. 99, pp. 507-515; and P. Kluin et al., 1984. Anat. Embryol., vol. 169, pp. 73-78.

The experimental and control males were obtained from commercial sources at one day of age, and maintained in brooders until used. The male birds were housed in temperature-controlled spaces in individual standard caging as they approached maturity. They were given water and standard commercial feed ad lib. They were kept initially in a 23:1 hour light/dark cycle, stepped down at approximately weekly intervals to a 15:8 hour light/dark cycle, as this regimen has been reported to optimize sexual maturity and fertility.

Surgical and DNA Injection Procedures

At the appropriate ages, groups of individual males were starved overnight and then subjected to transgene delivery by direct intratesticular injection of DNA by experienced animal surgeons. Each male was anesthetized with isoflurane via a simplified gas machine.

Various devices and anesthesia machines have previously been described for administering isoflurane (and other gaseous anesthetics) to birds. See Alsage et al., Poultry Sci., 50:1876-1878 (1971); Greenlees et al., Am. J. Vet. Res., vol. 51, pp. 757-758 (1990). However, these prior techniques are somewhat cumbersome and complex to implement. A novel and much simpler system to administer isoflurane (or other gaseous) anesthesia was developed due to the deficiencies in the prior art, a system that we found worked well on all ages of chicks. A standard nose cone was placed over the chick's head, similar to the system that has been used for decades to administer ether to mice. A plastic tube approximately 3.5 cm in diameter and 12 cm long was filled with cotton, into which was poured approximately 2 mL isoflurane (Abbott Laboratories, Chicago). The chick's head was placed partially into the cylinder, and was held in place there intermittently throughout the surgery as required to maintain the proper plane of anesthesia, without overdosing.

Each anesthetized bird was positioned on its side on an animal board with cords tractioning the wings and feet to allow access to the testes area. The area was swabbed with 0.5% chlorhexidine, and a 2 cm dorsolateral incision was made in the skin over the testis (similar to the procedure commonly used for caponization). A small-animal retractor was used to spread the last two ribs, exposing the testis. The DNA solution was then mixed with SUPERFECT® (Qiagen) according to the manufacturer's protocol, approximately a 1:6 wt/vol ratio, to a final concentration of 0.01-0.05 μg/μl. This resulted in 1-5 μg total DNA (in a 150-200 μl volume) being injected into each testis, spread over three injection sites: one at each end of the testis, and one in the middle.

The injection device was a standard 25 gauge, ½ inch (1.27 cm) hypodermic needle, attached to a 50, 100, or 200 μl syringe. Approximately 5 mm of the needle tip was bent at a 90 degree angle, to facilitate insertion into the testes. Approximately 50-70 μl of the DNA-SUPERFECT® solution was injected into each of three sites per testis. The multiple injections were calculated to suffuse the DNA throughout the whole testis, the idea being to promote contact between DNA and spermatogonia as much as feasible. We estimated that our procedure resulted in the injection of about 100,000 DNA molecules per spermatogonium. The construct used in these tests was a highly potent constitutive modified CMV promoter, operatively linked to the DsRed gene as shown in SEQ ID NO:2.

Following injection, the incision was closed in two layers with 4-0 absorbable suture, and then the contralateral testis was similarly exposed and injected. Following surgery, each bird was returned to its cage to recover. One hundred thirteen males were ultimately used in the experimental regimen to increase the overall likelihood of success, along with 4 control birds (16 weeks 20 old) subjected to sham surgery (with injections containing only the transfection reagent.

Evaluation of Birds

Thus, a total of 113 white leghorn chickens were injected with the DNA vector in groups of 5-26 at varying ages. Fourteen birds were transformed at 4 weeks, 23 birds at 6 weeks; 26 birds at 8 weeks; 23 birds at 10 weeks; 5 birds at 12 weeks; and 22 birds at 14 weeks. Sixteen birds died before they could be sampled, so to date, 97 roosters have been sampled, plus the four controls. Birds were evaluated at 18-24 weeks of age for (a) potential transformation in the sperm, and (b) successful testis transfection. Sperm samples were obtained from each rooster by manual manipulation using standard techniques. The sperm were washed, and their DNA was extracted following the techniques of G. Mann et al., 1993. J. Reprod. Fert., 99:505-12. The samples were then frozen until analyzed. Evaluation was conducted by PCR analysis to detect DNA integration into the sperm, or into any of the testicular cells. Additionally, selected testes were harvested at the end of the sperm sampling period.

Of 97 birds tested, at least 22 showed probable positive results. Positive results were observed at all transformation ages, except for 4 weeks, which was not tested. At least two birds were confirmed positive by PCR of sperm, conducted four months after the initial injection. These results were transient in many cases, however since it was believed that the DsRed gene product used in these initial proof of concept experiments was toxic. Nevertheless, the positive PCR results presumptively demonstrated that the transgene was incorporated into spermatogonia (before puberty), and that it was carried in transgenic sperm. Such sperm could then transmit the gene to subsequent generations, resulting in the production of true, germ-line transgenic "founder" birds.

To further confirm that the DNA had been incorporated into the sperm, and that contaminating vector was not being detected from other sources, it was confirmed through PCR on sperm of experimental birds, and on positive and negative controls that the sperm of the experimental birds lacked DNA encoding the transposase. The design of the preferred transposon-based vector is such that the sequence encoding the transposase is contained in the vector, but is not incorporated into the transformed chromosome. Thus, presence of the exogenous coding sequence, coupled with absence of the transposase gene, is strong evidence for incorporation of the exogenous coding sequence, or transgene.

These results demonstrated proof of concept, as positive PCR results were obtained from the sperm of treated birds. Interpretation of these preliminary results was made more difficult by the fact that the modified CMV promoter used in the experiment was probably too "hot." As the DsRed product is not secreted from the cells, the product built up intracellularly to levels that were toxic, frequently killing the cells. Even this result, of course, means that the transformation was successful. The transgene could not have killed the cells otherwise.

In order to resolve to the problem with toxicity of the DsRed gene product, experiments were conducted using a different reporter gene operably linked to the ovalbumin promoter, so that the transgene was expressed in the egg white. These experiments are provided in Examples 12-15 below.

EXAMPLE 7

Transfection of Male White Leghorn Chickens Using the Vector pTnMod(Oval/Red)—Quail (SEQ ID NO:4) via Testicular Injections In further experiments conducted on leghorn chickens, it was demonstrated that chickens injected intratesticularly at 8, 10, 12, or 14 weeks of age, had, on average, approximately 40% positive sperm between 6 and 8 months after injection. In other experiments, successful transfection was achieved with chickens injected at 13 weeks of age.

Forty-nine white leghorn roosters approximately 8, 10, 12, or 14 weeks of age were obtained and housed. Birds were identified, wing banded, and assigned to a treatment group. If appropriate (based on testes size and vascularization), one testis was caponized and the entire DNA injection volume was delivered to the remaining testis. Thirty-two males received DNA injections of 5 μg DNA/testis at a 1:3 ratio of DNA to SUPERFECT®. The remaining birds were used as controls. After injection, all birds were mated with at least 5 females and observed until sexual maturity and egg-laying began. All eggs collected prior to peak egg production (approximately 24 weeks of age for the hens) were incubated and candled to determine embryo presence. Any embryos identified were incubated to hatch to extract DNA, PCR was conducted, and transgene presence was determined.

Roosters positive for the pTnMod(Oval/Red)—Quail construct were kept to produce F1 offspring (eggs collected at peak production). Offspring from this hatch were bled, DNA extracted from the blood, and PCR conducted using primers specific for the DsRed gene. It was determined that 77% of the offspring were transgenic.

EXAMPLE 8

Transfection of Mature Male Japanese Quail Using the Vector pTnMod(Oval/Red)—Quail (SEQ ID NO:4) via Testicular Injections Twelve sexually mature males (at approximately 13 weeks of age) underwent surgery for testicular injection as described above for chickens. At 21-28 days of age, the birds were identified, leg banded, debeaked, and separated based on sex. Injections comprised 5 μg/testes of the vector in concentrations 1:3 or 1:10 for SUPERFECT® or a 1:1 ratio with Mirrus. The study consisted of 3 treatment groups with 5 males in the 1:3 DNA:SUPERFECT® group, 3 males in the 1:10 DNA:SUPERFECT® group, and 4 males in the 1:1 Mirrus group. All surgeries were conducted in one day.

Any unincorporated DNA was allowed to clear from the testes by holding the birds for 19 days before mating with females. At 15 weeks of age, 2 age-matched females were housed with each treated male. The presence of the transfected DNA was determined in the fertilized eggs during the second week of egg lay. The subsequent eggs collected from parents producing positively identified transgenic eggs were collected and stored until taken to hatch.

PCR performed on the sperm of quail injected at three months of age indicated successful incorporation of the DsRed transgene into the quail sperm.

EXAMPLE 9

Transfection of Immature Male Japanese Quail Using the Vector pTnMod(Oval/Red)—Quail (SEQ ID NO:4) via Testicular Injections Approximately 450 quail eggs were set and hatched. At 21-28 days of age, the birds were identified, wingbanded, debeaked, and separated based on sex. At 4 weeks of age, 65 male birds underwent surgery and testicular injections as described above. Injections comprised a control and 2 μg/testes of the vector in varying concentrations (0, 1/3, 1/5, and 1/10) of three different transfection reagents: 1) SUPERFECT®, 2) Mirus/Panvera and 3) Dosper. The study comprised 13 treatment groups with 5 males per group. One transfection reagent was administered per day.

At 7 weeks of age, 2 age-matched females were housed with each treated male. The presence of the transfected DNA was determined in the fertilized eggs during the second week of egg lay. The subsequent eggs collected from parents producing positively identified transgenic eggs were collected and stored until taken to hatch. PCR performed on the sperm of quail injected at four and five weeks of age indicated successful incorporation of the DsRed transgene into the quail sperm.

EXAMPLE 10

Preparation of Transposon-Based Vector pTnMod(Oval/ENT TAG/p146/PA)—Chicken

A vector is designed for inserting a p146 gene under the control of a chicken ovalbumin promoter, and a ovalbumin gene including an ovalbumin signal sequence, into the genome of a bird given below as SEQ ID NO:29.

Base pairs 1-130 are a remainder of F1(−) ori of pBluescriptII sk(−) (Stratagene) corresponding to base pairs 1-130 of pBluescriptII sk(−).

Base pairs 133-1777 are a CMV promoter/enhancer taken from vector pGWiz (Gene Therapy Systems) corresponding to base pairs 229-1873 of pGWiz.

Base pairs 1780-1785 are the Kozak sequence of SEQ ID NO:13, and base pairs 1783-2987 are the coding sequence for the transposase, modified from Tn10 (GenBank accession J01829).

Base pairs 2988-2993 are an engineered stop codon.

Base pairs 2995-3410 are a synthetic polyA from pGWiz (Gene Therapy Systems) corresponding to base pairs 1922-2337 of pGWiz.

Base pairs 3415-3718 are non coding DNA that is residual from vector pNK2859.

Base pairs 3719-3761 are λ DNA that is residual from pNK2859.

Base pairs 3762-3831 are the 70 base pairs of the left insertion sequence (IS10) recognized by the transposon Tn10.

Base pairs 3838-4044 are a multiple cloning site from pBluescriptll sk(−) corresponding to base pairs 924-718 of pBluescriptII sk(−).

Base pairs 4050-4951 are a chicken ovalbumin promoter (including SDRE) that corresponds to base pairs 431-1332 of the chicken ovalbumin promoter in GenBank Accession Number J00895 M24999.

Base pairs 4958-6115 are a chicken ovalbumin signal sequence and Ovalbumin gene that correspond to base pairs 66-1223 of GenBank Accession Number V00383.1 (The STOP codon being omitted).

Base pairs 6122-6271 are a TAG sequence containing a gp41 hairpin loop from HIV I, an enterokinase cleavage site and a spacer (synthetic).

Base pairs 6272-6316 are a p146 sequence (synthetic) with 2 added stop codons.

Base pairs 6324-6676 are a synthetic polyadenylation sequence from pGWiz (Gene Therapy Systems) corresponding to base pairs 1920-2272 of pGWiz.

Base pairs 6682-7114 are a multiple cloning site from pBluescriptII sk(−) corresponding to base pairs 667-235 of pBluescriptII sk(−).

Base pairs 7120-7189 are the 70 base pairs of the right insertion sequence (IS10) recognized by the transposon Tn10.

Base pairs 7190-7231 are λ DNA that is residual from pNK2859.

Base pairs 7232-8096 are non coding DNA that is residual from pNK2859.

Base pairs 8097-10297 are pBluescript sk(−) base vector (Stratagene, Inc.) corresponding to base pairs 761-2961 of pBluescriptII sk(−).

It should be noted that all non-coding DNA sequences described above can be replaced with any other non-coding DNA sequence(s). Missing nucleotide sequences in the above construct represent restriction site remnants.

EXAMPLE 11

Preparation of Transposon-Based Vector pTnMod(Oval/ENT TAG/p146/PA)—Quail

A vector is designed for inserting a p146 gene under the control of a quail ovalbumin promoter, and a ovalbumin gene including an ovalbumin signal sequence, into the genome of a bird given below as SEQ ID NO:30.

Base pairs 1-130 are a remainder of F1(−) ori of pBluescriptII sk(−) (Stratagene) corresponding to base pairs 1-130 of pBluescriptII sk(−).

Base pairs 133-1777 are a CMV promoter/enhancer taken from vector pGWiz (Gene Therapy Systems) corresponding to base pairs 229-1873 of pGWiz.

Base pairs 1780-1785 are the Kozak sequence of SEQ ID NO:13, and base pairs 1783-2987 are the coding sequence for the transposase, modified from Tn10 (GenBank accession J01829).

Base pairs 2988-2993 are an engineered stop codon.

Base pairs 2995-3410 are a synthetic polyA from pGWiz (Gene Therapy Systems) corresponding to base pairs 1922-2337 of pGWiz.

Base pairs 3415-3718 are non coding DNA that is residual from vector pNK2859.

Base pairs 3719-3761 are λ DNA that is residual from pNK2859.

Base pairs 3762-3831 are the 70 base pairs of the left insertion sequence (IS10) recognized by the transposon Tn10.

Base pairs 3838-4044 are a multiple cloning site from pBluescriptII sk(−) corresponding to base pairs 924-718 of pBluescriptII sk(−).

Base pairs 4050-4938 are the Japanese quail ovalbumin promoter (including SDRE, steroid-dependent response element). The Japanese quail ovalbumin promoter was isolated by its high degree of homology to the chicken ovalbumin promoter (GenBank accession number J00895 M24999, base pairs 431-1332).

Bp 4945-6092 are a quail ovalbumin signal sequence and ovalbumin gene that corresponds to base pairs 54-1201 of GenBank accession number X53964.1. (The STOP codon being omitted).

Base pairs 6097-6246 are a TAG sequence containing a gp41 hairpin loop from HIV I, an enterokinase cleavage site and a spacer (synthetic).

Base pairs 6247-6291 are a p146 sequence (synthetic) with 2 added stop codons.

Base pairs 6299-6651 are a synthetic polyadenylation sequence from pGWiz (Gene Therapy Systems) corresponding to base pairs 1920-2272 of pGWiz.

Base pairs 6657-7089 are a multiple cloning site from pBluescriptII sk(−) corresponding to base pairs 667-235 of pBluescriptII sk(−).

Base pairs 7095-7164 are the 70 base pairs of the right insertion sequence (IS10) recognized by the transposon Tn 10.

Base pairs 7165-7206 are λ DNA that is residual from pNK2859.

Base pairs 7207-8071 are non coding DNA that is residual from pNK2859.

Base pairs 8072-10272 are pBluescript sk(−) base vector (Stratagene, Inc.) corresponding to base pairs 761-2961 of pBluescriptII sk(−).

It should be noted that all non-coding DNA sequences described above can be replaced with any other non-coding DNA sequence(s). Missing nucleotide sequences in the above construct represent restriction site remnants.

EXAMPLE 12

Preparation of Transposon-Based Vector pTnMod(Oval/Ent Tag/ProIns/PA)—Chicken A vector is designed for inserting a proinsulin gene under the control of a chicken ovalbumin promoter, and a ovalbumin gene including an ovalbumin signal sequence, into the genome of a bird given below as SEQ ID NO:31.

Base pairs 1-130 are a remainder of F1(−) ori of pBluescriptII sk(−) (Stratagene) corresponding to base pairs 1-130 of pBluescriptII sk(−).

Base pairs 133-1777 are a CMV promoter/enhancer taken from vector pGWiz (Gene Therapy Systems) corresponding to base pairs 229-1873 of pGWiz.

Base pairs 1780-1785 are the Kozak sequence of SEQ ID NO:13, and base pairs 1783-2987 are the coding sequence for the transposase, modified from Tn10 (GenBank accession J01829).

Base pairs 2988-2993 are an engineered stop codon.

Base pairs 2995-3410 are a synthetic polyA from pGWiz (Gene Therapy Systems) corresponding to base pairs 1922-2337 of pGWiz.

Base pairs 3415-3718 are non coding DNA that is residual from vector pNK2859.

Base pairs 3719-3761 are λ DNA that is residual from pNK2859.

Base pairs 3762-3831 are the 70 base pairs of the left insertion sequence (IS10) recognized by the transposon Tn10.

Base pairs 3838-4044 are a multiple cloning site from pBluescriptII sk(−) corresponding to base pairs 924-718 of pBluescriptII sk(−).

Base pairs 4050-4951 are a chicken ovalbumin promoter (including SDRE) that corresponds to base pairs 431-1332 of the chicken ovalbumin promoter in GenBank Accession Number J00895 M24999.

Base pairs 4958-6115 are a chicken ovalbumin signal sequence and ovalbumin gene that correspond to base pairs 66-1223 of GenBank Accession Number V00383.1. (The STOP codon being omitted).

Base pairs 6122-6271 are a TAG sequence containing a gp41 hairpin loop from HIV I, an enterokinase cleavage site and a spacer (synthetic).

Base pairs 6272-6531 are a proinsulin gene.

Base pairs 6539-6891 are a synthetic polyadenylation sequence from pGWiz (Gene Therapy Systems) corresponding to base pairs 1920-2272 of pGWiz.

Base pairs 6897-7329 are a multiple cloning site from pBluescriptII sk(−) corresponding to base pairs 667-235 of pBluescriptII sk(−).

Base pairs 7335-7404 are the 70 base pairs of the right insertion sequence (IS10) recognized by the transposon Tn10.

Base pairs 7405-7446 are λ DNA that is residual from pNK2859.

Base pairs 7447-8311 are non coding DNA that is residual from pNK2859.

Base pairs 8312-10512 are pBluescript sk(−) base vector (Stratagene, Inc.) corresponding to base pairs 761-2961 of pBluescriptII sk(−).

It should be noted that all non-coding DNA sequences described above can be replaced with any other non-coding DNA sequence(s). Missing nucleotide sequences in the above construct represent restriction site remnants.

EXAMPLE 13

Preparation of Transposon-Based Vector pTnMod(Oval/Ent Tag/ProIns/PA)—Quail

A vector is designed for inserting a proinsulin gene under the control of a chicken ovalbumin promoter, and a ovalbumin gene including an ovalbumin signal sequence, into the genome of a bird given below as SEQ ID NO:32.

Base pairs 1-130 are a remainder of F1(−) ori of pBluescriptII sk(−) (Stratagene) corresponding to base pairs 1-130 of pBluescriptII sk(−).

Base pairs 133-1777 are a CMV promoter/enhancer taken from vector pGWiz (Gene Therapy Systems) corresponding to base pairs 229-1873 of pGWiz.

Base pairs 1780-1785 are the Kozak sequence of SEQ ID NO:13, and base pairs 1783-2987 are the coding sequence for the transposase, modified from Tn10 (GenBank accession J01829).

Base pairs 2988-2993 are an engineered stop codon.

Base pairs 2995-3410 are a synthetic polyA from pGWiz (Gene Therapy Systems) corresponding to base pairs 1922-2337 of pGWiz.

Base pairs 3415-3718 are non coding DNA that is residual from vector pNK2859.

Base pairs 3719-3761 are λ DNA that is residual from pNK2859.

Base pairs 3762-3831 are the 70 base pairs of the left insertion sequence (IS10) recognized by the transposon Tn10.

Base pairs 3838-4044 are a multiple cloning site from pBluescriptII sk(−) corresponding to base pairs 924-718 of pBluescriptII sk(−).

Base pairs 4050-4938 are the Japanese quail ovalbumin promoter (including SDRE, steroid-dependent response element). The Japanese quail ovalbumin promoter was isolated by its high degree of homology to the chicken ovalbumin promoter (GenBank accession number J00895 M24999, base pairs 431-1332). Some deletions were noted in the quail sequence, as compared to the chicken sequence.

Base pairs 4945-6092 are a quail ovalbumin signal sequence and ovalbumin gene that corresponds to base pairs 54-1201 of GenBank accession number X53964.1. (The STOP codon being omitted).

Base pairs 6093-6246 are a TAG sequence containing a gp41 hairpin loop from HIV I an enterokinase cleavage site and a spacer (synthetic).

Base pairs 6247-6507 are a proinsulin gene.

Base pairs 6514-6866 are a synthetic polyadenylation sequence from pGWiz (Gene Therapy Systems) corresponding to base pairs 1920-2272 of pGWiz.

Base pairs 6867-7303 are a multiple cloning site from pBluescriptII sk(−) corresponding to base pairs 667-235 of pBluescriptII sk(−).

Base pairs 7304-7379 are the 70 base pairs of the right insertion sequence (IS10) recognized by the transposon Tn10.

Base pairs 7380-7421 are λ DNA that is residual from pNK2859.

Base pairs 7422-8286 are non coding DNA that is residual from pNK2859.

Base pairs 8287-10487 are pBluescript sk(−) base vector (Stratagene, Inc.) corresponding to base pairs 761-2961 of pBluescriptII sk(−).

It should be noted that all non-coding DNA sequences described above can be replaced with any other non-coding DNA sequence(s). Missing nucleotide sequences in the above construct represent restriction site remnants.

EXAMPLE 14

Transfection of Immature Leghorn Roosters Using a Transposon-Based Vector Containing a Proinsulin Gene via Testicular Injections Vectors containing the elements Oval promoter/Oval gene/GP41 Enterokinase TAG/Proinsulin/Poly A (SEQ ID NO:31 or 43) and CMV promoter/Oval gene/GP41 Enterokinase TAG/Proinsulin/Poly A (SEQ ID NO:41 or 42) were each injected into the tests of 11 week old white leghorn roosters. These birds were held under normal conditions until sexual maturity was reached.

At the time of sexual maturity, each bird was handled and manipulated to obtain sperm. Sperm samples were collected in Hank's Buffered Salt Solution (HBSS) and stored at either −20° C. or 4° C. until needed. DNA was extracted from sperm using a MoBio Ultra Clean DNA Bloodspin Kit (MoBio laboratories, Solana Beach Calif.). Fifty microliters of sperm was used in the DNA extraction protocol and the purified genomic DNA eluted in 100 μl of water. In each PCR reaction, approximately 0.5-0.75 μg of genomic DNA was used with primers anchored in the entag-1 (5') and the synthetic polyA-2 (3'), which amplify a 685 bp fragment. Five of nine birds gave positive reactions for the presence of the appropriate vector construct. These birds were then mated with normal females.

Birds that did not yield positive results with PCR on the sperm were sacrificed, their testes removed, and DNA extracted using an approximately 25 mg piece of tissue in a Qiagen DNEasy Tissue Kit; purified DNA was eluted in 200 μl water and PCR conducted as described above. Two of these birds gave a very strong, positive PCR reaction.

EXAMPLE 15

Transfection of Japanese Quail Using a Transposon-Based Vector Containing a Proinsulin Gene via Oviduct Injections Two experiments were conducted in Japanese quail using transpose-based vectors containing either Oval Promoter/Oval Gene/GP41 Enterokinase TAG/Proinsulin/Poly A (SEQ ID NO:31 or 43) or CMV promoter/Oval gene/GP41 Enterokinase TAG/Proinsulin/Poly A (SEQ ID NO:41 or 42).

In the first experiment, the Oval promoter/Oval gene/GP41 Enterokinase TAG/Proinsulin/Poly A containing construct was injected into the oviduct of sexually mature quail; three hens received 5 μg at a 1:3 Superfect ratio and three received 10 μg at a 1:3 Superfect ratio. As of the writing of the present application, at least one bird that received 10 μg of DNA was producing human proinsulin in egg white (other birds remain to be tested). This experiment indicates that 1) the DNA has been stable for at least 3 months; 2) protein levels are comparable to those observed with a constitutive promoter such as the CMV promoter; and 3) sexually mature birds can be injected and results obtained without the need for cell culture.

In the second experiment, the transposon-based vector containing CMV promoter/Oval gene/GP41 Enterokinase TAG/Proinsulin/Poly A was injected into the oviduct of sexually immature Japanese quail. A total of 9 birds were injected. Of the 8 survivors, 3 produced human proinsulin in the white of their eggs for over 6 weeks. An ELISA assay described in detail below was developed to detect GP41 in the fusion peptide (Oval gene/GP41 Enterokinase TAG/Proinsulin) since the GP41 peptide sequence is unique and not found as part of normal egg white protein. In all ELISA assays, the same birds produced positive results and all controls worked as expected.

ELISA Procedure: Individual egg white samples were diluted in sodium carbonate buffer, pH 9.6, and added to individual wells of 96 well microtiter ELISA plates at a total volume of 0.1 ml. These plates were then allowed to coat overnight at 4° C. Prior to ELISA development, the plates were allowed warm to room temperature. Upon decanting the coating solutions and blotting away any excess, non-specific binding of antibodies was blocked by adding a solution of phosphate buffered saline (PBS), 1% (w/v) BSA, and 0.05% (v/v) Tween 20 and allowing it to incubate with shaking for a minimum of 45 minutes. This blocking solution was subsequently decanted and replaced with a solution of the primary antibody (Goat Anti-GP41 TAG) diluted in fresh PBS/BSA/Tween 20. After a two hour period of incubation with the primary antibody, each plate was washed with a solution of PBS and 0.05% Tween 20 in an automated plate washer to remove unbound antibody. Next, the secondary antibody, Rabbit anti-Goat Alkaline Phosphatase-conjugated, was diluted in PBS/BSA/Tween 20 and allowed to incubate 1 hour. The plates were then subjected to a second wash with PBS/Tween 20. Antigen was detected using a solution of p-Nitrophenyl Phosphate in Diethanolamine Substrate Buffer for Alkaline Phosphatase and measuring the absorbance at 30 minutes and 1 hour.

EXAMPLE 16

Optimization of Intra-Oviduct and Intra-Ovarian Arterial Injections

Overall transfection rates of oviduct cells in a flock of chicken or quail hens are enhanced by synchronizing the development of the oviduct and ovary within the flock. When the development of the oviducts and ovaries are uniform across a group of hens and when the stage of oviduct and ovarian development can be determined or predicted, timing of injections is optimized to transfect the greatest number of cells. Accordingly, oviduct development is synchronized as described below to ensure that a large and uniform proportion of oviduct secretory cells are transfected with the gene of interest.

Hens are treated with estradiol to stimulate oviduct maturation as described in Oka and Schimke (T. Oka and R T Schimke, J. Cell Biol., 41, 816 (1969)), Palmiter, Christensen and Schimke (J. Biol. Chem. 245(4):833-845, 1970). Specifically, repeated daily injections of 1 mg estradiol benzoate are performed sometime before the onset of sexual maturation, a period ranging from 1-14 weeks of age. After a stimulation period sufficient to maximize development of the oviduct, hormone treatment is withdrawn thereby causing regression in oviduct secretory cell size but not cell number. At an optimum time after hormone withdrawal, the oviducts of treated hens are injected with the transposon-based vector. Hens are subjected to additional estrogen stimulation after an optimized time during which the transposon-based vector is taken up into oviduct secretory cells. Re-stimulation by estrogen activates the transposon mechanism of the transposon-based vector, causing the integration of the gene of interest into the host genome. Estrogen stimulation is then withdrawn and hens continue normal sexual development. If a developmentally regulated promoter such as the ovalbumin promoter is used, expression of the transposon-based vector initiates in the oviduct at the time of sexual maturation. Intra-ovarian artery injection during this window allows for high and uniform transfection efficiencies of ovarian follicles to produce germ-line transfections and possibly oviduct expression.

Other means are also used to synchronize the development, or regression, of the oviduct and ovary to allow high and uniform transfection efficiencies. Alterations of lighting and/or feed regimens, for example, cause hens to 'molt' during which time the oviduct and ovary regress. Molting is used to synchronize hens for transfection, and may be used in conjunction with other hormonal methods to control regression and/or development of the oviduct and ovary.

EXAMPLE 17

Isolation of Human Proinsulin Using Anti-TAG Column Chromotography

A HiTrap NHS-activated 1 mL column (Amersham) was charged with a 30 amino acid peptide that contained the gp-41 epitope containing gp-41's native disulfide bond that stabilizes the formation of the gp-41 hairpin loop. The 30 amino acid gp41 peptide is provided as SEQ ID NO:23. Approximately 10 mg of the peptide was dissolved in coupling buffer (0.2 M $NaHCO_3$, 0.5 M NaCl, pH 8.3 and the ligand was circulated on the column for 2 hours at room temperature at 0.5 mL/minute. Excess active groups were then deactivated using 6 column volumes of 0.5 M ethanolamine, 0.5 M NaCl, pH 8.3 and the column was washed alternately with 6 column volumes of acetate buffer (0.1 M acetate, 0.5 M NaCl, pH 4.0) and ethanolamine (above). The column was neutralized using 1×PBS. The column was then washed with buffers to be used in affinity purification: 75 mM Tris, pH 8.0 and elution buffer, 100 mM glycine-HCl, 0.5 M NaCl, pH 2.7. Finally, the column was equilibrated in 75 mM Tris buffer, pH 8.0.

Antibodies to gp-41 were raised in goats by inoculation with the gp-41 peptide described above. More specifically, goats were inoculated, given a booster injection of the gp-41 peptide and then bled. Serum was harvested by centrifugation. Approximately 30 mL of goat serum was filtered to 0.45 uM and passed over a TAG column at a rate of 0.5 mL/min. The column was washed with 75 mM Tris, pH 8.0 until absorbance at 280 nm reached a baseline. Three column volumes (3 mL) of elution buffer (100 mM glycine, 0.5 M NaCl, pH 2.7) was applied, followed by 75 mM Tris buffer, pH 8.0, all at a rate of 0.5 mL/min. One milliliter fractions were collected. Fractions were collected into 200 uL 1 M Tris, pH 9.0 to neutralize acidic factions as rapidly as possible. A large peak eluted from the column, coincident with the application the elution buffer. Fractions were pooled. Analysis by SDS-PAGE showed a high molecular weight species that separated into two fragments under reducing condition, in keeping with the heavy and light chain structure of IgG.

Pooled antibody fractions were used to charge two 1 mL HiTrap NHS-activated columns, attached in series. Coupling was carried out in the same manner as that used for charging the TAG column.

Isolation of Ovalbumin-TAG-Proinsulin from Egg White

Egg white from quail and chickens treated by intra-oviduct injection of the CMV-ovalbumin-TAG-proinsulin construct were pooled. Viscosity was lowered by subjecting the allantoid fluid to successively finer pore sizes using negative pressure filtration, finishing with a 0.22 μM pore size. Through the process, egg white was diluted approximately 1:16. The clarified sample was loaded on the Anti-TAG column and eluted in the same manner as described for the purification of the anti-TAG antibodies. A peak of absorbance at 280 nm, coincident with the application of the elution buffer, indicated that protein had been specifically eluted from the Anti-TAG column. Fractions containing the eluted peak were pooled for analysis.

The pooled fractions from the Anti-TAG affinity column were characterized by SDS-PAGE and western blot analysis. SDS-PAGE of the pooled fractions revealed a 60 kDal molecular weight band not present in control egg white fluid, consistent with the predicted molecular weight of the transgenic protein. Although some contaminating bands were observed, the 60 kDal species was greatly enriched compared to the other proteins. An aliquot of the pooled fractions was cleaved overnight at room temperature with the protease, enterokinase. SDS-PAGE analysis of the cleavage product, revealed a band not present in the uncut material that co-migrated with a commercial human proinsulin positive control. Western blot analysis showed specific binding to the 60 kDal species under non-reducing condition (which preserve the hairpin epitope of gp-41 by retaining the disulfide bond). Western analysis of the low molecular weight species that appeared upon cleavage with an anti-human proinsulin antibody, conclusively identified the cleaved fragment as human proinsulin.

EXAMPLE 18

Construction of a Transposon-Based Transgene for the Expression of a Monoclonal Antibody Production of a monoclonal antibody using transposon-based transgenic methodology is accomplished in a variety of ways.

1) two vectors are constructed: one that encodes the light chain and a second vector that encodes the heavy chain of the monoclonal antibody. These vectors are then incorporated into the genome of the target animal by at least one of two methods: a) direct transfection of a single animal with both vectors (simultaneously or as separate events); or, b) a male and a female of the species carry in their germline one of the vectors and then they are mated to produce progeny that inherit a copy of each.
2) the light and heavy chains are included on a single DNA construct, either separated by insulators and expression is governed by the same (or different) promoters, or by using a single promoter governing expression of both transgenes with the inclusion of elements that permit separate transcription of both transgenes, such as an internal ribosome entry site.

The following example describes the production of a transposon-based DNA construct that contains both the coding region for a monoclonal light chain and a heavy chain on a single construct. Beginning with the vector pTnMod, the coding sequences for the heavy and light chains are added, each preceded by an appropriate promoter and signal sequence. Using methods known to one skilled in the art, approximately 1 Kb of the proximal elements of the ovalbumin promoter are linked to the signal sequence of ovalbumin or some other protein secreted from the target tissue. Two copies of the promoter and signal sequence are added to the multiple cloning site of pTnMod, leaving space and key restriction sites between them to allow the subsequent addition of the coding sequences of the light and heavy chains of the monoclonal antibody. Methods known to one skilled in the art allow the coding sequences of the light and heavy chains to be inserted in-frame for appropriate expression. For example, the coding sequence of light and heavy chains of a murine monoclonal antibody that show specificity for human seminoprotein have recently been disclosed (GenBank Accession numbers AY129006 and AY129304 for the light and heavy chains, respectively). The light chain cDNA sequence is provided in SEQ ID NO:34, whereas the cDNA of the heavy chain is reported as provided in SEQ ID NO:35.

Thus one skilled in the art can produce both the heavy and light chains of a monoclonal antibody in a single cell within a target tissue and species. If the modified cell contained normal posttranslational modification capabilities, the two chains would form their native configuration and disulfide attachments and be substrates for glycosylation. Upon secretion, then, the monoclonal antibody is accumulated, for example, in the egg white of a chicken egg, if the transgenes are expressed in the magnum of the oviduct.

It should also be noted that, although this example details production of a full-length murine monoclonal antibody, the method is quite capable of producing hybrid antibodies (e.g. a combination of human and murine sequences; 'humanized' monoclonal antibodies), as well as useful antibody fragments, known to one skilled in the art, such as Fab, Fc, F(ab) and Fv fragments. This method can be used to produce molecules containing the specific areas thought to be the antigen recognition sequences of antibodies (complementarity determining regions), linked, modified or incorporated into other proteins as desired.

EXAMPLE 19

Treatment of Rats with a Transposon-Based Vector for Tissue-Specific Insulin Gene Incorporation Rats are made diabetic by administering the drug streptozotocin (Zanosar; Upjohn, Kalamazoo, Mich.) at approximately 200 mg/kg. The rats are bred and maintained according to standard procedures. A transposon-based vector containing a proinsulin gene, an appropriate carrier, and, optionally, a transfection agent, are injected into rats' singhepatic (if using G6P) artery with the purpose of stable transformation. Incorporation of the insulin gene into the rat genome and levels of insulin expression are ascertained by a variety of methods known in the art. Blood and tissue samples from live or sacrificed animals are tested. A combination of PCR, Southern and Northern blots, in-situ hybridization and related nucleic acid analysis methods are used to determine incorporation of the vector-derived proinsulin DNA and levels of transcription of the corresponding mRNA in various organs and tissues of the rats. A combination of SDS-PAGE gels, Western Blot analysis, radioimmunoassay, and ELISA and other methods known to one of ordinary skill in the art are used to determine the presence of insulin and the amount produced. Additional transfections of the vector are used to increase protein expression if the initial amounts of the expressed insulin are not satisfactory, or if the level of expression tapers off. The physiological condition of the rats is closely examined post-transfection to register positive or any negative effects of the gene therapy. Animals are examined over extended periods of time post-transfection in order to monitor the stability of gene incorporation and protein expression.

EXAMPLE 20

Exemplary Transposon-Based Vectors

The following example provides a description of various transposon-based vectors of the present invention and several constructs for insertion into the transposon-based vectors of the present invention. These examples are not meant to be limiting in any way. The constructs for insertion into a transposon-based vector are provided in a cloning vector labeled pTnMCS.

pTnMCS (Base Vector)

Bp 1-130 Remainder of F1 (−) ori of pBluescriptII sk(−) (Stratagene) bp1-130

Bp 133-1777 CMV promoter/enhancer taken from vector pGWiz (Gene Therapy Systems) bp229-1873

Bp 1783-2991 Transposase, from Tn10 (GenBank accession #J01829) bp 108-1316

Bp 2992-3344 Non coding DNA from vector pNK2859

Bp 3345-3387 Lambda DNA from pNK2859

Bp 3388-3457 70 bp of IS10 left from Tn10

Bp 3464-3670 Multiple cloning site from pBluescriptII sk(−), thru the XmaI site bp924-718

Bp 3671-3715 Multiple cloning site from pBluescriptII sk(−), from the XmaI site thru the XhoI site. These base pairs are usually lost when cloning into pTnMCS, bp 717-673

Bp 3716-4153 Multiple cloning site from pBluescriptII sk(−), from the XhoI site bp672-235

Bp 4159-4228 70 bp of IS10 left from Tn10

Bp 4229-4270 Lambda DNA from pNK2859

Bp 4271-5114 Non-coding DNA from pNK2859

Bp 5115-7315 pBluescript sk (−) base vector (Stratagene, Inc.) bp 761-2961 pTnMCS (CMV-prepro-ent-hGH-CPA)

Bp 1-3670 from vector PTnMCS, bp 1-3670

Bp 3676-5320 CMV promoter/enhancer taken from vector pGWiz (Gene Therapy Systems), bp 230-1864

Bp 5326-5496 Capsite/Prepro taken from GenBank accession # X07404, bp 563-733

Bp 5504-5652 Synthetic spacer sequence and hairpin loop of HIV gp41 with an added enterokinase cleavage site Bp 5653-6306 Human growth hormone taken from GenBank accession # V00519, bp 1-654

Bp 6313-6720 Conalbumin polyA taken from GenBank accession # Y00407, bp 10651-11058

Bp 6722-10321 from cloning vector pTnMCS, bp 3716-7315 pTnMCS (CMV-CHOVg-ent-ProInsulin-synPA) (SEQ ID NO:41)

Bp 1-3670 from vector PTnMCS, bp 1-3670

Bp 3676-5320 CMV promoter/enhancer taken from vector pGWiz (Gene Therapy Systems), bp 230-1864

Bp 5327-6480 Chicken ovalbumin gene taken from GenBank accession # V00383, bp 66-1219

Bp 6487-6636 Synthetic spacer sequence and hairpin loop of HIV gp41 with an added enterokinase cleavage site Bp 6637-6897 Human Proinsulin taken from GenBank accession # NM000207, bp 117-377

Bp 6898-6942 Spacer DNA, derived as an artifact from the cloning vectors pTOPO Blunt II (Invitrogen) and pGWiz (Gene Therapy Systems)

Bp 6943-7295 Synthetic polyA from the cloning vector pGWiz (Gene Therapy Systems), bp 1920-2271

Bp 7296-10895 from cloning vector pTnMCS, bp 3716-7315 pTnMCS (CMV-prepro-ent-ProInsulin-synPA)

Bp 1-3670 from vector PTnMCS, bp 1-3670

Bp 3676-5320 CMV promoter/enhancer taken from vector pGWiz (Gene Therapy Systems), bp 230-1864

Bp 5326-5496 Capsite/Prepro taken from GenBank accession # X07404, bp 563-733

Bp 5504-5652 Synthetic spacer sequence and hairpin loop of HIV gp41 with an added enterokinase cleavage site Bp 5653-5913 Human Proinsulin taken from GenBank accession # NM000207, bp 117-377

Bp 5914-5958 Spacer DNA, derived as an artifact from the cloning vectors pTOPO Blunt II (Invitrogen) and pGWiz (Gene Therapy Systems)

Bp 5959-6310 Synthetic polyA from the cloning vector pGWiz (Gene Therapy Systems), bp 1920-2271

Bp 6313-9912 from cloning vector pTnMCS, bp 3716-7315 pTnMCS(Chicken OVep+OVg'+ENT+proins+syn polyA)

Bp 1-3670 from vector pTnMCS, bp 1-3670

Bp 3676-4350 Chicken Ovalbumin enhancer taken from GenBank accession #S82527.1 bp 1-675

Bp 4357-5692 Chicken Ovalbumin promoter taken from GenBank accession # J00895M24999 bp 1-1336

Bp 5699-6917 Chicken Ovalbumin gene from GenBank Accession # V00383.1 bp 2-1220. (This sequence includes the 5'UTR, containing putative cap site, bp 5699-5762.)

Bp 6924-7073 Synthetic spacer sequence and hairpin loop of HIV gp41 with an added enterokinase cleavage site Bp 7074-7334 Human proinsulin GenBank Accession # NM000207 bp 117-377

Bp 7335-7379 Spacer DNA, derived as an artifact from the cloning vectors pTOPO Blunt II (Invitrogen) and gWiz (Gene Therapy Systems)

Bp 7380-7731 Synthetic polyA from the cloning vector gWiz (Gene Therapy Systems) bp 1920-2271

Bp 7733-11332 from vector pTnMCS, bp 3716-7315 pTnMCS(Chicken OVep+prepro+ENT+proins+syn polyA)

Bp 1-3670 from cloning vector pTnMCS, bp 1-3670

Bp 3676-4350 Chicken Ovalbumin enhancer taken from GenBank accession # S82527.1 bp 1-675

Bp 4357-5692 Chicken Ovalbumin promoter taken from GenBank accession # J00895-M24999 bp 1-1336

Bp 5699-5869 Cecropin cap site and Prepro, Genbank accession # X07404 bp 563-733

Bp 5876-6025 Synthetic spacer sequence and hairpin loop of HIV gp41 with an added enterokinase cleavage site Bp 6026-6286 Human proinsulin GenBank Accession # NM000207 bp 117-377

Bp 6287-6331 Spacer DNA, derived as an artifact from the cloning vectors pTOPO Blunt II (Invitrogen) and gWiz (Gene Therapy Systems)

Bp 6332-6683 Synthetic polyA from the cloning vector gWiz (Gene Therapy Systems) bp 1920-2271

Bp 6685-10284 from cloning vector pTnMCS, bp 3716-7315 pTnMCS(Quail OVep+OVg'+ENT+proins+syn polyA)

Bp 1-3670 from cloning vector pTnMCS, bp 1-3670

Bp 3676-4333 Quail Ovalbumin enhancer: 658 bp sequence, amplified in-house from quail genomic DNA, roughly equivalent to the far-upstream chicken ovalbumin enhancer, GenBank accession # S82527.1, bp 1-675. (There are multiple base pair substitutions and deletions in the quail sequence, relative to chicken, so the number of bases does not correspond exactly.)

Bp 4340-5705 Quail Ovalbumin promoter: 1366 bp sequence, amplified in-house from quail genomic DNA, roughly corresponding to chicken ovalbumin promoter, GenBank accession # J00895-M24999 bp 1-1336. (There are multiple base pair substitutions and deletions between the quail and chicken sequences, so the number of bases does not correspond exactly.)

Bp 5712-6910 Quail Ovalbumin gene, EMBL accession # X53964, bp 1-1199. (This sequence includes the 5'UTR, containing putative cap site bp 5712-5764.)

Bp 6917-7066 Synthetic spacer sequence and hairpin loop of HIV gp41 with an added enterokinase cleavage site Bp 7067-7327 Human proinsulin GenBank Accession # NM000207 bp 117-377

Bp 7328-7372 Spacer DNA, derived as an artifact from the cloning vectors pTOPO Blunt II (Invitrogen) and gWiz (Gene Therapy Systems)

Bp 7373-7724 Synthetic polyA from the cloning vector gWiz (Gene Therapy Systems) bp 1920-2271

Bp 7726-11325 from cloning vector pTnMCS, bp 3716-7315 pTnMCS(CHOVep-prepro-ent-hGH-CPA)

Bp 1-3670 from vector PTnMCS, bp 1-3670

Bp 3676-4350 Chicken Ovalbumin enhancer taken from GenBank accession # S82527.1, bp 1-675

Bp 4357-5692 Chicken Ovalbumin promoter taken from GenBank accession # J00899-M24999, bp 1-1336

Bp 5699-5869 Capsite/Prepro taken from GenBank accession # X07404, bp 563-733

Bp 5877-6025 Synthetic spacer sequence and hairpin loop of HIV gp41 with an added enterokinase cleavage site Bp 6026-6679 Human growth hormone taken from GenBank accession # V00519, bp 1-654

Bp 6686-7093 Conalbumin polyA taken from GenBank accession # Y00407, bp 10651-11058

Bp 7095-10694 from cloning vector pTnMCS, bp 3716-7315 pTnMCS(Quail OVep+prepro+ENT+proins+syn polyA)

Bp 1-3670 from cloning vector pTnMCS, bp 1-3670

Bp 3676-4333 Quail Ovalbumin enhancer: 658 bp sequence, amplified in-house from quail genomic DNA, roughly equivalent to the far-upstream chicken ovalbumin enhancer, GenBank accession #S82527.1, bp 1-675. (There are multiple base pair substitutions and deletions in the quail sequence, relative to chicken, so the number of bases does not correspond exactly.)

Bp 4340-5705 Quail Ovalbumin promoter: 1366 bp sequence, amplified in-house from quail genomic DNA, roughly corresponding to chicken ovalbumin promoter, GenBank accession # J00895-M24999 bp 1-1336. (There are multiple base pair substitutions and deletions between the quail and chicken sequences, so the number of bases does not correspond exactly.)

Bp 5712-5882 Cecropin cap site and Prepro, Genbank accession # X07404 bp 563-733

Bp 5889-6038 Synthetic spacer sequence and hairpin loop of HIV gp41 with an added enterokinase cleavage site Bp 6039-6299 Human proinsulin GenBank Accession # NM000207 bp 117-377

Bp 6300-6344 Spacer DNA, derived as an artifact from the cloning vectors pTOPO Blunt II (Invitrogen) and gWiz (Gene Therapy Systems)

Bp 6345-6696 Synthetic polyA from the cloning vector gWiz (Gene Therapy Systems) bp 1920-2271

Bp 6698-10297 from cloning vector pTnMCS, bp 3716-7315 pTnMOD

Bp 1-130 remainder of F1 (–) ori of pBluescriptII sk(–) (Stratagene) bp1-130

Bp 133-1777 CMV promoter/enhancer taken from vector pGWiz (Gene Therapy Systems) bp229-1873

Bp 1783-2991 Transposase, modified from Tn10 (GenBank accession #J01829) bp 108-1316

Bp 2992-2994 Engineered stop codon

Bp 2996-3411 Synthetic polyA from gWiz (Gene Therapy Systems) bp 1922-2337

Bp 3412-3719 Non-coding DNA from vector pNK2859

Bp 3720-3762 Lambda DNA from pNK2859

Bp 3763-3832 70 bp of IS10 left from Tn10

Bp 3839-4045 Multiple cloning site from pBluescriptII sk(–), thru the XmaI site bp 924-718

Bp 4046-4090 Multiple cloning site from pBluescriptII sk(–), from the XmaI site thru the XhoI site. These base pairs are usually lost when cloning into pTnMCS. bp 717-673

Bp 4091-4528 Multiple cloning site from pBluescriptII sk(–), from the XhoI site bp 672-235

Bp 4534-4603 70 bp of IS10 left from Tn10

Bp 4604-4645 Lambda DNA from pNK2859

Bp 4646-5489 Non-coding DNA from pNK2859

Bp 5490-7690 pBluescript sk (–) base vector (Stratagene, INC) bp 761-2961 pTnMOD (CHOVep-prepro-ent-hGH-CPA)

Bp 1-4045 from vector pTnMOD, bp 1-4045

Bp 4051-4725 Chicken Ovalbumin enhancer taken from GenBank accession # S82527.1, bp 1-675

Bp 4732-6067 Chicken Ovalbumin promoter taken from GenBank accession # J00899-M24999, bp 1-1336

Bp 6074-6245 Capsite/Prepro taken from GenBank accession # X07404, bp 563-733

Bp 6252-6400 Synthetic spacer sequence and hairpin loop of HIV gp41 with an added enterokinase cleavage site Bp 6401-7054 Human growth hormone taken from GenBank accession # V00519, bp 1-654

Bp 7061-7468 Conalbumin polyA taken from GenBank accession # Y00407, bp 10651-11058

Bp 7470-11069 from cloning vector pTnMOD, bp 3716-7315 pTnMOD (CMV-CHOVg-ent-ProInsulin-synPA) (SEQ ID NO:42)

Bp 1-4045 from vector pTnMOD, bp 1-4045

Bp 4051-5695 CMV promoter/enhancer taken from vector pGWiz (Gene therapy systems), bp 230-1864

Bp 5702-6855 Chicken ovalbumin gene taken from GenBank accession # V00383, bp 66-1219

Bp 6862-7011 Synthetic spacer sequence and hairpin loop of HIV gp41 with an added enterokinase cleavage site Bp 7012-7272 Human Proinsulin taken from GenBank accession # NM000207, bp 117-377

Bp 7273-7317 Spacer DNA, derived as an artifact from the cloning vectors pTOPO Blunt II (Invitrogen) and pGWiz (Gene Therapy Systems)

Bp 7318-7670 Synthetic polyA from the cloning vector pGWiz (Gene Therapy Systems), bp 1920-2271

Bp 7672-11271 from cloning vector pTnMOD, bp 3716-7315 pTnMOD (CMV-prepro-ent-hGH-CPA)

Bp 1-4045 from vector pTnMOD, bp 1-4045

Bp 4051-5695 CMV promoter/enhancer taken from vector pGWiz (Gene therapy systems), bp 230-1864

Bp 5701-5871 Capsite/Prepro taken from GenBank accession # X07404, bp 563-733

Bp 5879-6027 Synthetic spacer sequence and hairpin loop of HIV gp41 with an added enterokinase cleavage site Bp 6028-6681 Human growth hormone taken from GenBank accession # V00519, bp 1-654

Bp 6688-7095 Conalbumin polyA taken from GenBank accession # Y00407, bp 10651-11058

Bp 7097-10696 from cloning vector pTnMOD, bp 3716-7315 pTnMOD (CMV-prepro-ent-ProInsulin-synPA)

Bp 1-4045 from vector pTnMOD, bp 1-4045

Bp 4051-5695 CMV promoter/enhancer taken from vector pGWiz (Gene therapy systems), bp 230-1864

Bp 5701-5871 Capsite/Prepro taken from GenBank accession # X07404, bp 563-733

Bp 5879-6027 Synthetic spacer sequence and hairpin loop of HIV gp41 with an added enterokinase cleavage site Bp 6028-6288 Human Proinsulin taken from GenBank accession # NM000207, bp 117-377

Bp 6289-6333 Spacer DNA, derived as an artifact from the cloning vectors pTOPO Blunt II (Invitrogen) and pGWiz (Gene Therapy Systems)

Bp 6334-6685 Synthetic polyA from the cloning vector pGWiz (Gene Therapy Systems), bp 1920-2271

Bp 6687-10286 from cloning vector pTnMOD, bp 3716-7315 pTnMOD(Chicken OVep+OVg'+ENT+proins+syn polyA) (SEQ ID NO:43)

Bp 1-4045 from cloning vector pTnMOD, bp 1-4045

Bp 4051-4725 Chicken Ovalbumin enhancer taken from GenBank accession # S82527.1 bp 1-675

Bp 4732-6067 Chicken Ovalbumin promoter taken from GenBank accession # J00895-M24999 bp 1-1336

Bp 6074-7292 Chicken Ovalbumin gene from GenBank Accession # V00383.1 bp 2-1220. (This sequence includes the 5'UTR, containing putative cap site bp 6074-6137.)

Bp 7299-7448 Synthetic spacer sequence and hairpin loop of HIV gp41 with an added enterokinase cleavage site Bp 7449-7709 Human proinsulin GenBank Accession # NM000207 bp 117-377

Bp 7710-7754 Spacer DNA, derived as an artifact from the cloning vectors pTOPO Blunt II (Invitrogen) and gWiz (Gene Therapy Systems)

Bp 7755-8106 Synthetic polyA from the cloning vector gWiz (Gene Therapy Systems) bp 1920-2271

Bp 8108-11707 from cloning vector pTnMCS, bp 3716-7315 pTnMOD(Chicken OVep+prepro+ENT+proins+syn polyA)

Bp 1-4045 from cloning vector pTnMOD, bp 1-4045

Bp 4051-4725 Chicken Ovalbumin enhancer taken from GenBank accession # S82527.1 bp 1-675

Bp 4732-6067 Chicken Ovalbumin promoter taken from GenBank accession # J00895-M24999 bp 1-1336

Bp 6074-6244 Cecropin cap site and Prepro, Genbank accession # X07404 bp 563-733

Bp 6251-6400 Synthetic spacer sequence and hairpin loop of HIV gp41 with an added enterokinase cleavage site Bp 6401-6661 Human proinsulin GenBank Accession # NM000207 bp 117-377

Bp 6662-6706 Spacer DNA, derived as an artifact from the cloning vectors pTOPO Blunt II (Invitrogen) and gWiz (Gene Therapy Systems)

Bp 6707-7058 Synthetic polyA from the cloning vector gWiz (Gene Therapy Systems) bp 1920-2271

Bp 7060-10659 from cloning vector pTnMOD, bp 3716-7315 pTnMOD(Quail OVep+OVg'+ENT+proins+syn polyA

Bp 1-4045 from cloning vector pTnMOD, bp 1-4045

Bp 4051-4708 Quail Ovalbumin enhancer: 658 bp sequence, amplified in-house from quail genomic DNA, roughly equivalent to the far-upstream chicken ovalbumin enhancer, GenBank accession # S82527.1, bp 1-675. (There are multiple base pair substitutions and deletions in the quail sequence, relative to chicken, so the number of bases does not correspond exactly.)

Bp 4715-6080 Quail Ovalbumin promoter: 1366 bp sequence, amplified in-house from quail genomic DNA, roughly corresponding to chicken ovalbumin promoter, GenBank accession # J00895-M24999 bp 1-1336. (There are multiple base pair substitutions and deletions between the quail and chicken sequences, so the number of bases does not correspond exactly.)

Bp 6087-7285 Quail Ovalbumin gene, EMBL accession # X53964, bp 1-1199. (This sequence includes the 5'UTR, containing putative cap site bp 6087-6139.)

Bp 7292-7441 Synthetic spacer sequence and hairpin loop of HIV gp41 with an added enterokinase cleavage site Bp 7442-7702 Human proinsulin GenBank Accession # NM000207 bp 117-377

Bp 7703-7747 Spacer DNA, derived as an artifact from the cloning vectors pTOPO Blunt II (Invitrogen) and gWiz (Gene Therapy Systems)

Bp 7748-8099 Synthetic polyA from the cloning vector gWiz (Gene Therapy Systems) bp 1920-2271

Bp 8101-11700 from cloning vector pTnMOD, bp 3716-7315 pTnMOD(Quail OVep+prepro+ENT+proins+syn polyA)

Bp 1-4045 from cloning vector pTnMOD, bp 1-4045

Bp 4051-4708 Quail Ovalbumin enhancer: 658 bp sequence, amplified in-house from quail genomic DNA, roughly equivalent to the far-upstream chicken ovalbumin enhancer, GenBank accession #S82527.1, bp 1-675. (There are multiple base pair substitutions and deletions in the quail sequence, relative to chicken, so the number of bases does not correspond exactly.)

Bp 4715-6080 Quail Ovalbumin promoter: 1366 bp sequence, amplified in-house from quail genomic DNA, roughly corresponding to chicken ovalbumin promoter, GenBank accession # J00895-M24999 bp 1-1336. (There are multiple base pair substitutions and deletions between the quail and chicken sequences, so the number of bases does not correspond exactly.)

Bp 6087-6257 Cecropin cap site and Prepro, Genbank accession # X07404 bp 563-733

Bp 6264-6413 Synthetic spacer sequence and hairpin loop of HIV gp41 with an added enterokinase cleavage site Bp 6414-6674 Human proinsulin GenBank Accession # NM000207 bp 117-377

Bp 6675-6719 Spacer DNA, derived as an artifact from the cloning vectors pTOPO Blunt II (Invitrogen) and gWiz (Gene Therapy Systems)

Bp 6720-7071 Synthetic polyA from the cloning vector gWiz (Gene Therapy Systems) bp 1920-2271

Bp 7073-10672 from cloning vector pTnMOD, bp 3716-7315

PTnMod(CMV/Transposase/ChickOvep/prepro/ProteinA/ConpolyA)

BP 1-130 remainder of F1 (−) ori of pBluescriptII sk(−) (Stragagene) bp 1-130.

BP 133-1777 CMV promoter/enhancer taken from vector pGWiz (Gene Therapy Systems) bp 229-1873.

BP 1780-2987 Transposase, modified from Tn10 (GenBank #J0 1829).

BP 2988-2990 Engineered stop codon.

BP 2991-3343 non coding DNA from vector pNK2859.

BP 3344-3386 Lambda DNA from pNK2859.

BP 3387-3456 70 bp of IS10 left from Tn10.

BP 3457-3674 multiple cloning site from pBluescriptII sk(−) bp 924-707.

BP 3675-5691 Chicken Ovalbumin enhancer plus promoter from a Topo Clone 10 maxi 040303 (5' XmaI, 3' BamHI)

BP 5698-5865 prepro with Cap site amplified from cecropin of pMON200 GenBank # X07404 (5'BamHI, 3'KpnI)

BP 5872-7338 Protein A gene from GenBank# J01786, mature peptide bp 292-1755 (5'KpnI, 3'SacII)

BP 7345-7752 ConPolyA from Chicken conalbumin polyA from GenBank # Y00407 bp 10651-11058. (5'SacII, 3'XhoI)

BP 7753-8195 multiple cloning site from pBluescriptII sk(−) bp 677-235.

BP 8196-8265 70 bp of IS10 left from Tn10.

BP 8266-8307 Lamda DNA from pNK2859

BP 8308-9151 noncoding DNA from pNK2859

BP 9152-11352 pBluescriptII sk(−) base vector (Stratagene, INC.) bp 761-2961

All patents, publications and abstracts cited above are incorporated herein by reference in their entirety. It should be understood that the foregoing relates only to preferred embodiments of the present invention and that numerous modifications or alterations may be made therein without departing from the spirit and the scope of the present invention as defined in the following claims.

We claim:

1. A vector comprising:

a modified transposase gene operably linked to a first promoter, wherein the nucleotide sequence 3' to the first promoter comprises a modified Kozak sequence as set forth in SEQ ID NO: 13, and wherein a plurality of the first twenty codons of the transposase gene are modified from the wild-type sequence by changing the nucleotide at the third base position of the codon to an adenine or thymine without modifying the amino acid encoded by the codon; and one or more genes of interest operably-linked to one or more additional promoters, wherein the one or more genes of interest and their operably-linked promoters are flanked by transposase insertion sequences recognized by a transposase encoded by the modified transposase gene wherein the vector comprises the sequence as set forth in SEQ ID NO:1.

2. The vector of claim 1, wherein the modified transposase gene comprises an adenine or thymine at the third position in each of codons 2-10 of the modified transposase gene.

3. The vector of claim 1, wherein one gene of interest is operably-linked to a second promoter.

4. The vector of claim 3, wherein the second promoter is a constitutive promoter.

5. The vector of claim 3, wherein the second promoter is an inducible promoter.

6. The vector of claim 5, wherein the inducible promoter is an ovalbumin promoter, a conalbumin promoter, an ovomucoid promoter, or a vitellogenin promoter.

7. The vector of claim 1, further comprising a polyA sequence operably linked to the transposase gene, wherein the polyA sequence is a conalbumin polyA sequence.

8. The vector of claim 1, wherein a first gene of interest is operably-linked to a second promoter and a second gene of interest is operably-linked to a third promoter.

9. The vector of claim 1, wherein a first and a second gene of interest are operably-linked to a second promoter.

10. The vector of claim 1, further comprising an enhancer operably-linked to the one or more genes of interest.

11. The vector of claim 10, wherein the enhancer comprises at least a portion of an ovalbumin enhancer.

12. The vector of claim 1, further comprising an egg directing sequence operably-linked to the one or more genes of interest.

13. The vector of claim 12, wherein the egg directing sequence is an ovalbumin signal sequence or an ovomucoid signal sequence.

14. The vector of claim 12, wherein the egg directing sequence is a vitellogenin targeting sequence.

* * * * *

UNITED STATES PATENT AND TRADEMARK OFFICE

CERTIFICATE OF CORRECTION

PATENT NO. : 7,608,451 B2
APPLICATION NO. : 11/981574
DATED : October 27, 2009
INVENTOR(S) : Richard K. Cooper et al.

It is certified that error appears in the above-identified patent and that said Letters Patent is hereby corrected as shown below:

Title page, item [73] in the Assignees:

Please change the spelling of the first Assignee to --TransGenRx, Inc.--

Please change the second Assignee to read:

--The Board of Supervisors of Louisiana State University and Agricultural and Mechanical College--n Signed and Sealed this Seventh Day of September, 2010

David J. Kappos
*Director of the United States Patent and Trademark Office*

UNITED STATES PATENT AND TRADEMARK OFFICE

CERTIFICATE OF CORRECTION

PATENT NO. : 7,608,451 B2
APPLICATION NO. : 11/981574
DATED : October 27, 2009
INVENTOR(S) : Richard K. Cooper et al.

It is certified that error appears in the above-identified patent and that said Letters Patent is hereby corrected as shown below:

Title page, item [73] in the Assignees:

Please change the spelling of the first Assignee to --TransGenRx, Inc.--

Please change the second Assignee to read:

--The Board of Supervisors of Louisiana State University and Agricultural and Mechanical College-- Delete “n”

This certificate supersedes the Certificate of Correction issued September 7, 2010.

Signed and Sealed this

Twenty-third Day of November, 2010

David J. Kappos
*Director of the United States Patent and Trademark Office*

SEQUENCE LISTING

```
<160> NUMBER OF SEQ ID NOS: 43

<210> SEQ ID NO 1
<211> LENGTH: 7689
<212> TYPE: DNA
<213> ORGANISM: Artificial Sequence
<220> FEATURE:
<223> OTHER INFORMATION: Synthetic

<400> SEQUENCE: 1

ctgacgcgcc ctgtagcggc gcattaagcg cggcgggtgt ggtggttacg cgcagcgtga     60
```

-continued

```
ccgctacact tgccagcgcc ctagcgcccg ctcctttcgc tttcttccct tcctttctcg    120
ccacgttcgc cggcatcaga ttggctattg gccattgcat acgttgtatc catatcataa    180
tatgtacatt tatattggct catgtccaac attaccgcca tgttgacatt gattattgac    240
tagttattaa tagtaatcaa ttacggggtc attagttcat agcccatata tggagttccg    300
cgttacataa cttacggtaa atggcccgcc tggctgaccg cccaacgacc cccgcccatt    360
gacgtcaata atgacgtatg ttcccatagt aacgccaata gggactttcc attgacgtca    420
atgggtggag tatttacggt aaactgccca cttggcagta catcaagtgt atcatatgcc    480
aagtacgccc cctattgacg tcaatgacgg taaatggccc gcctggcatt atgcccagta    540
catgacctta tgggactttc ctacttggca gtacatctac gtattagtca tcgctattac    600
catggtgatg cggttttggc agtacatcaa tgggcgtgga tagcggtttg actcacgggg    660
atttccaagt ctccacccca ttgacgtcaa tgggagtttg ttttggcacc aaaatcaacg    720
ggactttcca aaatgtcgta acaactccgc cccattgacg caaatgggcg gtaggcgtgt    780
acggtgggag gtctatataa gcagagctcg tttagtgaac cgtcagatcg cctggagacg    840
ccatccacgc tgttttgacc tccatagaag acaccgggac cgatccagcc tccgcggccg    900
ggaacggtgc attggaacgc ggattccccg tgccaagagt gacgtaagta ccgcctatag    960
actctatagg cacacccctt tggctcttat gcatgctata ctgtttttgg cttggggcct   1020
atacaccccc gcttccttat gctataggtg atggtatagc ttagcctata ggtgtgggtt   1080
attgaccatt attgaccact cccctattgg tgacgatact ttccattact aatccataac   1140
atggctcttt gccacaacta tctctattgg ctatatgcca atactctgtc cttcagagac   1200
tgacacggac tctgtatttt tacaggatgg ggtcccattt attatttaca aattcacata   1260
tacaacaacg ccgtcccccg tgcccgcagt ttttattaaa catagcgtgg gatctccacg   1320
cgaatctcgg gtacgtgttc cggacatggg ctcttctccg gtagcggcgg agcttccaca   1380
tccgagccct ggtcccatgc ctccagcggc tcatggtcgc tcggcagctc cttgctccta   1440
acagtggagg ccagacttag gcacagcaca atgcccacca ccaccagtgt gccgcacaag   1500
gccgtggcgg tagggtatgt gtctgaaaat gagcgtggag attgggctcg cacggctgac   1560
gcagatggaa gacttaaggc agcggcagaa gaagatgcag gcagctgagt tgttgtattc   1620
tgataagagt cagaggtaac tcccgttgcg gtgctgttaa cggtggaggg cagtgtagtc   1680
tgagcagtac tcgttgctgc cgcgcgcgcc accagacata atagctgaca gactaacaga   1740
ctgttccttt ccatgggtct tttctgcagt caccgtcgga ccatgtgtga acttgatatt   1800
ttacatgatt ctctttacca attctgcccc gaattacact taaaacgact caacagctta   1860
acgttggctt gccacgcatt acttgactgt aaaactctca ctcttaccga acttggccgt   1920
aacctgccaa ccaaagcgag aacaaaacat aacatcaaac gaatcgaccg attgttaggt   1980
aatcgtcacc tccacaaaga gcgactcgct gtataccgtt ggcatgctag ctttatctgt   2040
tcgggaatac gatgcccatt gtacttgttg actggtctga tattcgtgag caaaaacgac   2100
ttatggtatt gcgagcttca gtcgcactac acggtcgttc tgttactctt tatgagaaag   2160
cgttcccgct ttcagagcaa tgttcaaaga aagctcatga ccaatttcta gccgaccttg   2220
cgagcattct accgagtaac accacaccgc tcattgtcag tgatgctggc tttaaagtgc   2280
catggtataa atccgttgag aagctgggtt ggtactggtt aagtcgagta agaggaaaag   2340
tacaatatgc agacctagga gcggaaaact ggaaacctat cagcaactta catgatatgt   2400
```

-continued

```
catctagtca ctcaaagact ttaggctata agaggctgac taaaagcaat ccaatctcat   2460

gccaaattct attgtataaa tctcgctcta aaggccgaaa aaatcagcgc tcgacacgga   2520

ctcattgtca ccacccgtca cctaaaatct actcagcgtc ggcaaaggag ccatgggttc   2580

tagcaactaa cttacctgtt gaaattcgaa cacccaaaca acttgttaat atctattcga   2640

agcgaatgca gattgaagaa accttccgag acttgaaaag tcctgcctac ggactaggcc   2700

tacgccatag ccgaacgagc agctcagagc gttttgatat catgctgcta atcgccctga   2760

tgcttcaact aacatgttgg cttgcgggcg ttcatgctca gaaacaaggt tgggacaagc   2820

acttccaggc taacacagtc agaaatcgaa acgtactctc aacagttcgc ttaggcatgg   2880

aagtttgcg gcattctggc tacacaataa caagggaaga cttactcgtg gctgcaaccc   2940

tactagctca aaatttattc acacatggtt acgctttggg gaaattatga taatgatcca   3000

gatcacttct ggctaataaa agatcagagc tctagagatc tgtgtgttgg tttttgtgg   3060

atctgctgtg ccttctagtt gccagccatc tgttgtttgc cctcccccg tgccttcctt   3120

gaccctggaa ggtgccactc ccactgtcct ttcctaataa aatgaggaaa ttgcatcgca   3180

ttgtctgagt aggtgtcatt ctattctggg gggtggggtg gggcagcaca gcaaggggga   3240

ggattgggaa gacaatagca ggcatgctgg ggatgcggtg ggctctatgg gtacctctct   3300

ctctctctct ctctctctct ctctctctct ctctcggtac ctctctctct ctctctctct   3360

ctctctctct ctctctctct cggtaccagg tgctgaagaa ttgacccggt gaccaaaggt   3420

gccttttatc atcactttaa aaataaaaaa caattactca gtgcctgtta taagcagcaa   3480

ttaattatga ttgatgccta catcacaaca aaaactgatt taacaaatgg ttggtctgcc   3540

ttagaaagta tatttgaaca ttatcttgat tatattattg ataataataa aaaccttatc   3600

cctatccaag aagtgatgcc tatcattggt tggaatgaac ttgaaaaaaa ttagccttga   3660

atacattact ggtaaggtaa acgccattgt cagcaaattg atccaagaga accaacttaa   3720

agctttcctg acggaatgtt aattctcgtt gaccctgagc actgatgaat cccctaatga   3780

ttttggtaaa aatcattaag ttaaggtgga tacacatctt gtcatatgat cccggtaatg   3840

tgagttagct cactcattag gcaccccagg ctttacactt tatgcttccg gctcgtatgt   3900

tgtgtggaat tgtgagcgga taacaatttc acacaggaaa cagctatgac catgattacg   3960

ccaagcgcgc aattaaccct cactaaaggg aacaaaagct ggagctccac cgcggtggcg   4020

gccgctctag aactagtgga tcccccgggc tgcaggaatt cgatatcaag cttatcgata   4080

ccgctgacct cgaggggggg cccggtaccc aattcgccct atagtgagtc gtattacgcg   4140

cgctcactgg ccgtcgtttt acaacgtcgt gactgggaaa accctggcgt tacccaactt   4200

aatcgccttg cagcacatcc ccctttcgcc agctggcgta atagcgaaga ggcccgcacc   4260

gatcgccctt cccaacagtt gcgcagcctg aatggcgaat ggaaattgta agcgttaata   4320

ttttgttaaa attcgcgtta aatttttgtt aaatcagctc attttttaac caataggccg   4380

aaatcggcaa aatcccttat aaatcaaaag aatagaccga gatagggttg agtgttgttc   4440

cagtttggaa caagagtcca ctattaaaga acgtggactc caacgtcaaa gggcgaaaaa   4500

ccgtctatca gggcgatggc ccactactcc gggatcatat gacaagatgt gtatccacct   4560

taacttaatg atttttacca aaatcattag gggattcatc agtgctcagg gtcaacgaga   4620

attaacattc cgtcaggaaa gcttatgatg atgatgtgct taaaaactta ctcaatggct   4680

ggttatgcat atcgcaatac atgcgaaaaa cctaaaagag cttgccgata aaaaaggcca   4740

atttattgct atttaccgcg gctttttatt gagcttgaaa gataaataaa atagataggt   4800
```

-continued

```
tttatttgaa gctaaatctt ctttatcgta aaaaatgccc tcttgggtta tcaagagggt   4860
cattatattt cgcggaataa catcatttgg tgacgaaata actaagcact tgtctcctgt   4920
ttactcccct gagcttgagg ggttaacatg aaggtcatcg atagcaggat aataatacag   4980
taaaacgcta aaccaataat ccaaatccag ccatcccaaa ttggtagtga atgattataa   5040
ataacagcaa acagtaatgg gccaataaca ccggttgcat tggtaaggct caccaataat   5100
ccctgtaaag caccttgctg atgactcttt gtttggatag acatcactcc ctgtaatgca   5160
ggtaaagcga tcccaccacc agccaataaa attaaaacag ggaaaactaa ccaaccttca   5220
gatataaacg ctaaaaaggc aaatgcacta ctatctgcaa taaatccgag cagtactgcc   5280
gtttttttcgc ccatttagtg gctattcttc ctgccacaaa ggcttggaat actgagtgta   5340
aaagaccaag acccgtaatg aaaagccaac catcatgcta ttcatcatca cgatttctgt   5400
aatagcacca caccgtgctg gattggctat caatgcgctg aaataataat caacaaatgg   5460
catcgttaaa taagtgatgt ataccgatca gcttttgttc cctttagtga gggttaattg   5520
cgcgcttggc gtaatcatgg tcatagctgt ttcctgtgtg aaattgttat ccgctcacaa   5580
ttccacacaa catacgagcc ggaagcataa agtgtaaagc ctggggtgcc taatgagtga   5640
gctaactcac attaattgcg ttgcgctcac tgcccgcttt ccagtcggga aacctgtcgt   5700
gccagctgca ttaatgaatc ggccaacgcg cggggagagg cggtttgcgt attgggcgct   5760
cttccgcttc ctcgctcact gactcgctgc gctcggtcgt tcggctgcgg cgagcggtat   5820
cagctcactc aaaggcggta atacggttat ccacagaatc aggggataac gcaggaaaga   5880
acatgtgagc aaaaggccag caaaaggcca ggaaccgtaa aaaggccgcg ttgctggcgt   5940
ttttccatag gctccgcccc cctgacgagc atcacaaaaa tcgacgctca agtcagaggt   6000
ggcgaaaccc gacaggacta taaagatacc aggcgtttcc ccctggaagc tccctcgtgc   6060
gctctcctgt tccgaccctg ccgcttaccg gatacctgtc cgcctttctc ccttcgggaa   6120
gcgtggcgct ttctcatagc tcacgctgta ggtatctcag ttcggtgtag gtcgttcgct   6180
ccaagctggg ctgtgtgcac gaaccccccg ttcagcccga ccgctgcgcc ttatccggta   6240
actatcgtct tgagtccaac ccggtaagac acgacttatc gccactggca gcagccactg   6300
gtaacaggat tagcagagcg aggtatgtag gcggtgctac agagttcttg aagtggtggc   6360
ctaactacgg ctacactaga aggacagtat ttggtatctg cgctctgctg aagccagtta   6420
ccttcggaaa aagagttggt agctcttgat ccggcaaaca aaccaccgct ggtagcggtg   6480
gtttttttgt ttgcaagcag cagattacgc gcagaaaaaa aggatctcaa gaagatcctt   6540
tgatcttttc tacggggtct gacgctcagt ggaacgaaaa ctcacgttaa gggattttgg   6600
tcatgagatt atcaaaaagg atcttcacct agatcctttt aaattaaaaa tgaagtttta   6660
aatcaatcta aagtatatat gagtaaactt ggtctgacag ttaccaatgc ttaatcagtg   6720
aggcacctat ctcagcgatc tgtctatttc gttcatccat agttgcctga ctccccgtcg   6780
tgtagataac tacgatacgg gagggcttac catctggccc cagtgctgca atgataccgc   6840
gagacccacg ctcaccggct ccagatttat cagcaataaa ccagccagcc ggaagggccg   6900
agcgcagaag tggtcctgca actttatccg cctccatcca gtctattaat tgttgccggg   6960
aagctagagt aagtagttcg ccagttaata gtttgcgcaa cgttgttgcc attgctacag   7020
gcatcgtggt gtcacgctcg tcgtttggta tggcttcatt cagctccggt tcccaacgat   7080
caaggcgagt tacatgatcc cccatgttgt gcaaaaaagc ggttagctcc ttcggtcctc   7140
```

-continued

```
cgatcgttgt cagaagtaag ttggccgcag tgttatcact catggttatg gcagcactgc   7200

ataattctct tactgtcatg ccatccgtaa gatgcttttc tgtgactggt gagtactcaa   7260

ccaagtcatt ctgagaatag tgtatgcggc gaccgagttg ctcttgcccg gcgtcaatac   7320

gggataatac cgcgccacat agcagaactt taaaagtgct catcattgga aaacgttctt   7380

cggggcgaaa actctcaagg atcttaccgc tgttgagatc cagttcgatg taacccactc   7440

gtgcacccaa ctgatcttca gcatctttta ctttcaccag cgtttctggg tgagcaaaaa   7500

caggaaggca aaatgccgca aaaaagggaa taagggcgac acggaaatgt tgaatactca   7560

tactcttcct ttttcaatat tattgaagca tttatcaggg ttattgtctc atgagcggat   7620

acatatttga atgtatttag aaaaataaac aaataggggt tccgcgcaca tttccccgaa   7680

aagtgccac                                                           7689
```

<210> SEQ ID NO 2
<211> LENGTH: 10263
<212> TYPE: DNA
<213> ORGANISM: Artificial Sequence
<220> FEATURE:
<223> OTHER INFORMATION: Synthetic

<400> SEQUENCE: 2

```
ctgacgcgcc ctgtagcggc gcattaagcg cggcgggtgt ggtggttacg cgcagcgtga     60

ccgctacact tgccagcgcc ctagcgcccg ctcctttcgc tttcttccct tcctttctcg    120

ccacgttcgc cggcatcaga ttggctattg gccattgcat acgttgtatc catatcataa    180

tatgtacatt tatattggct catgtccaac attaccgcca tgttgacatt gattattgac    240

tagttattaa tagtaatcaa ttacggggtc attagttcat agcccatata tggagttccg    300

cgttacataa cttacggtaa atggcccgcc tggctgaccg cccaacgacc cccgcccatt    360

gacgtcaata atgacgtatg ttcccatagt aacgccaata gggactttcc attgacgtca    420

atgggtggag tatttacggt aaactgccca cttggcagta catcaagtgt atcatatgcc    480

aagtacgccc cctattgacg tcaatgacgg taaatggccc gcctggcatt atgcccagta    540

catgacctta tgggactttc ctacttggca gtacatctac gtattagtca tcgctattac    600

catggtgatg cggttttggc agtacatcaa tgggcgtgga tagcggtttg actcacgggg    660

atttccaagt ctccacccca ttgacgtcaa tgggagtttg ttttggcacc aaaatcaacg    720

ggactttcca aaatgtcgta acaactccgc cccattgacg caaatgggcg gtaggcgtgt    780

acggtgggag gtctatataa gcagagctcg tttagtgaac cgtcagatcg cctggagacg    840

ccatccacgc tgttttgacc tccatagaag acaccgggac cgatccagcc tccgcggccg    900

ggaacggtgc attggaacgc ggattccccg tgccaagagt gacgtaagta ccgcctatag    960

actctatagg cacacccctt tggctcttat gcatgctata ctgtttttgg cttggggcct   1020

atacaccccc gcttccttat gctataggtg atggtatagc ttagcctata ggtgtgggtt   1080

attgaccatt attgaccact cccctattgg tgacgatact ttccattact aatccataac   1140

atggctcttt gccacaacta tctctattgg ctatatgcca atactctgtc cttcagagac   1200

tgacacggac tctgtatttt tacaggatgg ggtcccattt attatttaca aattcacata   1260

tacaacaacg ccgtcccccg tgcccgcagt ttttattaaa catagcgtgg gatctccacg   1320

cgaatctcgg gtacgtgttc cggacatggg ctcttctccg gtagcggcgg agcttccaca   1380

tccgagccct ggtcccatgc ctccagcggc tcatggtcgc tcggcagctc cttgctccta   1440

acagtggagg ccagacttag gcacagcaca atgcccacca ccaccagtgt gccgcacaag   1500
```

-continued

```
gccgtggcgg tagggtatgt gtctgaaaat gagcgtggag attgggctcg cacggctgac   1560
gcagatggaa gacttaaggc agcggcagaa gaagatgcag gcagctgagt tgttgtattc   1620
tgataagagt cagaggtaac tcccgttgcg gtgctgttaa cggtggaggg cagtgtagtc   1680
tgagcagtac tcgttgctgc cgcgcgcgcc accagacata atagctgaca gactaacaga   1740
ctgttccttt ccatgggtct ttctgcagt caccgtcgga ccatgtgtga acttgatatt   1800
ttacatgatt ctctttacca attctgcccc gaattacact taaaacgact caacagctta   1860
acgttggctt gccacgcatt acttgactgt aaaactctca ctcttaccga acttggccgt   1920
aacctgccaa ccaaagcgag aacaaaacat aacatcaaac gaatcgaccg attgttaggt   1980
aatcgtcacc tccacaaaga gcgactcgct gtataccgtt ggcatgctag ctttatctgt   2040
tcgggaatac gatgcccatt gtacttgttg actggtctga tattcgtgag caaaaacgac   2100
ttatggtatt gcgagcttca gtcgcactac acggtcgttc tgttactctt tatgagaaag   2160
cgttcccgct ttcagagcaa tgttcaaaga aagctcatga ccaatttcta gccgaccttg   2220
cgagcattct accgagtaac accacaccgc tcattgtcag tgatgctggc tttaaagtgc   2280
catggtataa atccgttgag aagctgggtt ggtactggtt aagtcgagta agaggaaaag   2340
tacaatatgc agacctagga gcggaaaact ggaaacctat cagcaactta catgatatgt   2400
catctagtca ctcaaagact ttaggctata agaggctgac taaaagcaat ccaatctcat   2460
gccaaattct attgtataaa tctcgctcta aaggccgaaa aaatcagcgc tcgacacgga   2520
ctcattgtca ccacccgtca cctaaaatct actcagcgtc ggcaaaggag ccatgggttc   2580
tagcaactaa cttacctgtt gaaattcgaa cacccaaaca acttgttaat atctattcga   2640
agcgaatgca gattgaagaa accttccgag acttgaaaag tcctgcctac ggactaggcc   2700
tacgccatag ccgaacgagc agctcagagc gttttgatat catgctgcta atcgccctga   2760
tgcttcaact aacatgttgg cttgcgggcg ttcatgctca gaaacaaggt tgggacaagc   2820
acttccaggc taacacagtc agaaatcgaa acgtactctc aacagttcgc ttaggcatgg   2880
aagttttgcg gcattctggc tacacaataa caagggaaga cttactcgtg gctgcaaccc   2940
tactagctca aaatttattc acacatggtt acgctttggg gaaattatga taatgatcca   3000
gatcacttct ggctaataaa agatcagagc tctagagatc tgtgtgttgg ttttttgtgg   3060
atctgctgtg ccttctagtt gccagccatc tgttgtttgc ccctcccccg tgccttcctt   3120
gaccctggaa ggtgccactc ccactgtcct ttcctaataa aatgaggaaa ttgcatcgca   3180
ttgtctgagt aggtgtcatt ctattctggg gggtggggtg gggcagcaca gcaaggggga   3240
ggattgggaa gacaatagca ggcatgctgg ggatgcggtg ggctctatgg gtacctctct   3300
ctctctctct ctctctctct ctctctctct ctctcggtac ctctctctct ctctctctct   3360
ctctctctct ctctctctct cggtaccagg tgctgaagaa ttgacccggt gaccaaaggt   3420
gccttttatc atcactttaa aaataaaaaa caattactca gtgcctgtta taagcagcaa   3480
ttaattatga ttgatgccta catcacaaca aaaactgatt taacaaatgg ttggtctgcc   3540
ttagaaagta tatttgaaca ttatcttgat tatattattg ataataataa aaaccttatc   3600
cctatccaag aagtgatgcc tatcattggt tggaatgaac ttgaaaaaaa ttagccttga   3660
atacattact ggtaaggtaa acgccattgt cagcaaattg atccaagaga accaacttaa   3720
agctttcctg acggaatgtt aattctcgtt gaccctgagc actgatgaat cccctaatga   3780
ttttggtaaa aatcattaag ttaaggtgga tacacatctt gtcatatgat cccggtaatg   3840
```

-continued

```
tgagttagct cactcattag gcaccccagg ctttacactt tatgcttccg gctcgtatgt   3900
tgtgtggaat tgtgagcgga taacaatttc acacaggaaa cagctatgac catgattacg   3960
ccaagcgcgc aattaaccct cactaaaggg aacaaaagct ggagctccac cgcggtggcg   4020
gccgctctag aactagtgga tcccccgggc atcagattgg ctattggcca ttgcatacgt   4080
tgtatccata tcataatatg tacatttata ttggctcatg tccaacatta ccgccatgtt   4140
gacattgatt attgactagt tattaatagt aatcaattac ggggtcatta gttcatagcc   4200
catatatgga gttccgcgtt acataactta cggtaaatgg cccgcctggc tgaccgccca   4260
acgacccccg cccattgacg tcaataatga cgtatgttcc catagtaacg ccaataggga   4320
ctttccattg acgtcaatgg gtggagtatt tacggtaaac tgcccacttg gcagtacatc   4380
aagtgtatca tatgccaagt acgcccccta ttgacgtcaa tgacggtaaa tggcccgcct   4440
ggcattatgc ccagtacatg accttatggg actttcctac ttggcagtac atctacgtat   4500
tagtcatcgc tattaccatg gtgatgcggt tttggcagta catcaatggg cgtggatagc   4560
ggtttgactc acggggattt ccaagtctcc accccattga cgtcaatggg agtttgtttt   4620
ggcaccaaaa tcaacgggac tttccaaaat gtcgtaacaa ctccgcccca ttgacgcaaa   4680
tgggcggtag gcgtgtacgg tgggaggtct atataagcag agctcgttta gtgaaccgtc   4740
agatcgcctg gagacgccat ccacgctgtt ttgacctcca tagaagacac cgggaccgat   4800
ccagcctccg cggccgggaa cggtgcattg gaacgcggat tccccgtgcc aagagtgacg   4860
taagtaccgc ctatagactc tataggcaca cccctttggc tcttatgcat gctatactgt   4920
ttttggcttg gggcctatac acccccgctt ccttatgcta taggtgatgg tatagcttag   4980
cctataggtg tgggttattg accattattg accactcccc tattggtgac gatactttcc   5040
attactaatc cataacatgg ctctttgcca caactatctc tattggctat atgccaatac   5100
tctgtccttc agagactgac acggactctg tatttttaca ggatggggtc ccatttatta   5160
tttacaaatt cacatataca acaacgccgt cccccgtgcc cgcagttttt attaaacata   5220
gcgtgggatc tccacgcgaa tctcgggtac gtgttccgga catgggctct tctccggtag   5280
cggcggagct tccacatccg agccctggtc ccatgcctcc agcggctcat ggtcgctcgg   5340
cagctccttg ctcctaacag tggaggccag acttaggcac agcacaatgc ccaccaccac   5400
cagtgtgccg cacaaggccg tggcggtagg gtatgtgtct gaaaatgagc gtggagattg   5460
ggctcgcacg gctgacgcag atggaagact taaggcagcg gcagaagaag atgcaggcag   5520
ctgagttgtt gtattctgat aagagtcaga ggtaactccc gttgcggtgc tgttaacggt   5580
ggagggcagt gtagtctgag cagtactcgt tgctgccgcg cgcgccacca gacataatag   5640
ctgacagact aacagactgt tcctttccat gggtcttttc tgcagtcacc gtctcgcgac   5700
agggatccac cggtcgccac catggtgcgc tcctccaaga acgtcatcaa ggagttcatg   5760
cgcttcaagg tgcgcatgga gggcaccgtg aacggccacg agttcgagat cgagggcgag   5820
ggcgagggcc gcccctacga gggccacaac accgtgaagc tgaaggtgac caagggcggc   5880
cccctgccct tcgcctggga catcctgtcc ccccagttcc agtacggctc caaggtgtac   5940
gtgaagcacc ccgccgacat ccccgactac aagaagctgt ccttccccga gggcttcaag   6000
tgggagcgcg tgatgaactt cgaggacggc ggcgtggtga ccgtgaccca ggactcctcc   6060
ctgcaggacg gctgcttcat ctacaaggtg aagttcatcg gcgtgaactt cccctccgac   6120
ggccccgtaa tgcagaagaa gaccatgggc tgggaggcct ccaccgagcg cctgtacccc   6180
cgcgacggcg tgctgaaggg cgagatccac aaggccctga agctgaagga cggcggccac   6240
```

-continued

```
tacctggtgg agttcaagtc catctacatg gccaagaagc ccgtgcagct gcccggctac   6300
tactacgtgg actccaagct ggacatcacc tcccacaacg aggactacac catcgtggag   6360
cagtacgagc gcaccgaggg ccgccaccac ctgttcctgt agcggccgcg actctagatc   6420
ataatcagcc ataccacatt tgtagaggtt ttacttgctt taaaaaacct cccacacctc   6480
cccctgaacc tgaaacataa aatgaatgca attgttgttg ttaacttgtt tattgcagct   6540
tataatggtt acaaataaag caatagcatc acaaatttca caaataaagc atttttttca   6600
ctgcattcta gttgtggccc gggctgcagg aattcgatat caagcttatc gataccgctg   6660
acctcgaggg ggggcccggt acccaattcg ccctatagtg agtcgtatta cgcgcgctca   6720
ctggccgtcg ttttacaacg tcgtgactgg gaaaaccctg gcgttaccca acttaatcgc   6780
cttgcagcac atcccccttt cgccagctgg cgtaatagcg aagaggcccg caccgatcgc   6840
ccttcccaac agttgcgcag cctgaatggc gaatggaaat tgtaagcgtt aatattttgt   6900
taaaattcgc gttaaatttt tgttaaatca gctcattttt taaccaatag gccgaaatcg   6960
gcaaaatccc ttataaatca aaagaataga ccgagatagg gttgagtgtt gttccagttt   7020
ggaacaagag tccactatta aagaacgtgg actccaacgt caaagggcga aaaaccgtct   7080
atcagggcga tggcccacta ctccgggatc atatgacaag atgtgtatcc accttaactt   7140
aatgattttt accaaaatca ttaggggatt catcagtgct cagggtcaac gagaattaac   7200
attccgtcag gaaagcttat gatgatgatg tgcttaaaaa cttactcaat ggctggttat   7260
gcatatcgca atacatgcga aaaacctaaa agagcttgcc gataaaaaag gccaatttat   7320
tgctatttac cgcggctttt tattgagctt gaaagataaa taaaatagat aggttttatt   7380
tgaagctaaa tcttctttat cgtaaaaaat gccctcttgg gttatcaaga gggtcattat   7440
atttcgcgga ataacatcat ttggtgacga aataactaag cacttgtctc ctgtttactc   7500
ccctgagctt gaggggttaa catgaaggtc atcgatagca ggataataat acagtaaaac   7560
gctaaaccaa taatccaaat ccagccatcc caaattggta gtgaatgatt ataaataaca   7620
gcaaacagta atgggccaat aacaccggtt gcattggtaa ggctcaccaa taatccctgt   7680
aaagcacctt gctgatgact ctttgtttgg atagacatca ctccctgtaa tgcaggtaaa   7740
gcgatcccac caccagccaa taaaattaaa acagggaaaa ctaaccaacc ttcagatata   7800
aacgctaaaa aggcaaatgc actactatct gcaataaatc cgagcagtac tgccgttttt   7860
tcgcccattt agtggctatt cttcctgcca caaaggcttg gaatactgag tgtaaaagac   7920
caagacccgt aatgaaaagc caaccatcat gctattcatc atcacgattt ctgtaatagc   7980
accacaccgt gctggattgg ctatcaatgc gctgaaataa taatcaacaa atggcatcgt   8040
taaataagtg atgtataccg atcagctttt gttcccttta gtgagggtta attgcgcgct   8100
tggcgtaatc atggtcatag ctgtttcctg tgtgaaattg ttatccgctc acaattccac   8160
acaacatacg agccggaagc ataaagtgta aagcctgggg tgcctaatga gtgagctaac   8220
tcacattaat tgcgttgcgc tcactgcccg ctttccagtc gggaaacctg tcgtgccagc   8280
tgcattaatg aatcggccaa cgcgcgggga gaggcggttt gcgtattggg cgctcttccg   8340
cttcctcgct cactgactcg ctgcgctcgg tcgttcggct gcggcgagcg gtatcagctc   8400
actcaaaggc ggtaatacgg ttatccacag aatcagggga taacgcagga aagaacatgt   8460
gagcaaaagg ccagcaaaag gccaggaacc gtaaaaaggc cgcgttgctg gcgtttttcc   8520
ataggctccg cccccctgac gagcatcaca aaaatcgacg ctcaagtcag aggtggcgaa   8580
```

-continued

```
acccgacagg actataaaga taccaggcgt ttccccctgg aagctccctc gtgcgctctc   8640

ctgttccgac cctgccgctt accggatacc tgtccgcctt tctcccttcg ggaagcgtgg   8700

cgctttctca tagctcacgc tgtaggtatc tcagttcggt gtaggtcgtt cgctccaagc   8760

tgggctgtgt gcacgaaccc cccgttcagc ccgaccgctg cgccttatcc ggtaactatc   8820

gtcttgagtc caacccggta agacacgact tatcgccact ggcagcagcc actggtaaca   8880

ggattagcag agcgaggtat gtaggcggtg ctacagagtt cttgaagtgg tggcctaact   8940

acggctacac tagaaggaca gtatttggta tctgcgctct gctgaagcca gttaccttcg   9000

gaaaaagagt tggtagctct tgatccggca aacaaaccac cgctggtagc ggtggttttt   9060

ttgtttgcaa gcagcagatt acgcgcagaa aaaaaggatc tcaagaagat cctttgatct   9120

tttctacggg gtctgacgct cagtggaacg aaaactcacg ttaagggatt ttggtcatga   9180

gattatcaaa aaggatcttc acctagatcc ttttaaatta aaaatgaagt tttaaatcaa   9240

tctaaagtat atatgagtaa acttggtctg acagttacca atgcttaatc agtgaggcac   9300

ctatctcagc gatctgtcta tttcgttcat ccatagttgc ctgactcccc gtcgtgtaga   9360

taactacgat acgggagggc ttaccatctg gccccagtgc tgcaatgata ccgcgagacc   9420

cacgctcacc ggctccagat ttatcagcaa taaaccagcc agccggaagg gccgagcgca   9480

gaagtggtcc tgcaacttta tccgcctcca tccagtctat taattgttgc cgggaagcta   9540

gagtaagtag ttcgccagtt aatagtttgc gcaacgttgt tgccattgct acaggcatcg   9600

tggtgtcacg ctcgtcgttt ggtatggctt cattcagctc cggttcccaa cgatcaaggc   9660

gagttacatg atcccccatg ttgtgcaaaa aagcggttag ctccttcggt cctccgatcg   9720

ttgtcagaag taagttggcc gcagtgttat cactcatggt tatggcagca ctgcataatt   9780

ctcttactgt catgccatcc gtaagatgct tttctgtgac tggtgagtac tcaaccaagt   9840

cattctgaga atagtgtatg cggcgaccga gttgctcttg cccggcgtca atacgggata   9900

ataccgcgcc acatagcaga actttaaaag tgctcatcat tggaaaacgt tcttcggggc   9960

gaaaactctc aaggatctta ccgctgttga gatccagttc gatgtaaccc actcgtgcac  10020

ccaactgatc ttcagcatct tttactttca ccagcgtttc tgggtgagca aaaacaggaa  10080

ggcaaaatgc cgcaaaaaag ggaataaggg cgacacggaa atgttgaata ctcatactct  10140

tcctttttca atattattga agcatttatc agggttattg tctcatgagc ggatacatat  10200

ttgaatgtat ttagaaaaat aaacaaatag gggttccgcg cacatttccc cgaaaagtgc  10260

cac                                                                10263
```

<210> SEQ ID NO 3
<211> LENGTH: 9678
<212> TYPE: DNA
<213> ORGANISM: Artificial Sequence
<220> FEATURE:
<223> OTHER INFORMATION: Synthetic

<400> SEQUENCE: 3

```
ctgacgcgcc ctgtagcggc gcattaagcg cggcgggtgt ggtggttacg cgcagcgtga     60

ccgctacact tgccagcgcc ctagcgcccg ctcctttcgc tttcttccct tcctttctcg    120

ccacgttcgc cggcatcaga ttggctattg gccattgcat acgttgtatc catatcataa    180

tatgtacatt tatattggct catgtccaac attaccgcca tgttgacatt gattattgac    240

tagttattaa tagtaatcaa ttacggggtc attagttcat agcccatata tggagttccg    300

cgttacataa cttacggtaa atggcccgcc tggctgaccg cccaacgacc cccgcccatt    360
```

-continued

```
gacgtcaata atgacgtatg ttcccatagt aacgccaata gggactttcc attgacgtca    420
atgggtggag tatttacggt aaactgccca cttggcagta catcaagtgt atcatatgcc    480
aagtacgccc cctattgacg tcaatgacgg taaatggccc gcctggcatt atgcccagta    540
catgacctta tgggactttc ctacttggca gtacatctac gtattagtca tcgctattac    600
catggtgatg cggttttggc agtacatcaa tgggcgtgga tagcggtttg actcacgggg    660
atttccaagt ctccacccca ttgacgtcaa tgggagtttg ttttggcacc aaaatcaacg    720
ggactttcca aaatgtcgta acaactccgc cccattgacg caaatgggcg gtaggcgtgt    780
acggtgggag gtctatataa gcagagctcg tttagtgaac cgtcagatcg cctggagacg    840
ccatccacgc tgttttgacc tccatagaag acaccgggac cgatccagcc tccgcggccg    900
ggaacggtgc attggaacgc ggattccccg tgccaagagt gacgtaagta ccgcctatag    960
actctatagg cacacccctt tggctcttat gcatgctata ctgtttttgg cttggggcct   1020
atacaccccc gcttccttat gctataggtg atggtatagc ttagcctata ggtgtgggtt   1080
attgaccatt attgaccact cccctattgg tgacgatact ttccattact aatccataac   1140
atggctcttt gccacaacta tctctattgg ctatatgcca atactctgtc cttcagagac   1200
tgacacggac tctgtatttt tacaggatgg ggtcccattt attatttaca aattcacata   1260
tacaacaacg ccgtcccccg tgcccgcagt ttttattaaa catagcgtgg gatctccacg   1320
cgaatctcgg gtacgtgttc cggacatggg ctcttctccg gtagcggcgg agcttccaca   1380
tccgagccct ggtcccatgc ctccagcggc tcatggtcgc tcggcagctc cttgctccta   1440
acagtggagg ccagacttag gcacagcaca atgcccacca ccaccagtgt gccgcacaag   1500
gccgtggcgg tagggtatgt gtctgaaaat gagcgtggag attgggctcg cacggctgac   1560
gcagatggaa gacttaaggc agcggcagaa gaagatgcag gcagctgagt tgttgtattc   1620
tgataagagt cagaggtaac tcccgttgcg gtgctgttaa cggtggaggg cagtgtagtc   1680
tgagcagtac tcgttgctgc cgcgcgcgcc accagacata atagctgaca gactaacaga   1740
ctgttccttt ccatgggtct tttctgcagt caccgtcgga ccatgtgtga acttgatatt   1800
ttacatgatt ctctttacca attctgcccc gaattacact taaaacgact caacagctta   1860
acgttggctt gccacgcatt acttgactgt aaaactctca ctcttaccga acttggccgt   1920
aacctgccaa ccaaagcgag aacaaaacat aacatcaaac gaatcgaccg attgttaggt   1980
aatcgtcacc tccacaaaga gcgactcgct gtataccgtt ggcatgctag ctttatctgt   2040
tcgggaatac gatgcccatt gtacttgttg actggtctga tattcgtgag caaaaacgac   2100
ttatggtatt gcgagcttca gtcgcactac acggtcgttc tgttactctt tatgagaaag   2160
cgttcccgct ttcagagcaa tgttcaaaga aagctcatga ccaatttcta gccgaccttg   2220
cgagcattct accgagtaac accacaccgc tcattgtcag tgatgctggc tttaaagtgc   2280
catggtataa atccgttgag aagctgggtt ggtactggtt aagtcgagta agaggaaaag   2340
tacaatatgc agacctagga gcggaaaact ggaaacctat cagcaactta catgatatgt   2400
catctagtca ctcaaagact ttaggctata agaggctgac taaaagcaat ccaatctcat   2460
gccaaattct attgtataaa tctcgctcta aaggccgaaa aaatcagcgc tcgacacgga   2520
ctcattgtca ccacccgtca cctaaaatct actcagcgtc ggcaaaggag ccatgggttc   2580
tagcaactaa cttacctgtt gaaattcgaa cacccaaaca acttgttaat atctattcga   2640
agcgaatgca gattgaagaa accttccgag acttgaaaag tcctgcctac ggactaggcc   2700
```

-continued

```
tacgccatag ccgaacgagc agctcagagc gttttgatat catgctgcta atcgccctga   2760
tgcttcaact aacatgttgg cttgcgggcg ttcatgctca gaaacaaggt tgggacaagc   2820
acttccaggc taacacagtc agaaatcgaa acgtactctc aacagttcgc ttaggcatgg   2880
aagttttgcg gcattctggc tacacaataa caagggaaga cttactcgtg gctgcaaccc   2940
tactagctca aaatttattc acacatggtt acgctttggg gaaattatga taatgatcca   3000
gatcacttct ggctaataaa agatcagagc tctagagatc tgtgtgttgg tttttttgtgg   3060
atctgctgtg ccttctagtt gccagccatc tgttgtttgc ccctcccccg tgccttcctt   3120
gaccctggaa ggtgccactc ccactgtcct ttcctaataa aatgaggaaa ttgcatcgca   3180
ttgtctgagt aggtgtcatt ctattctggg gggtggggtg gggcagcaca gcaaggggga   3240
ggattgggaa gacaatagca ggcatgctgg ggatgcggtg ggctctatgg gtacctctct   3300
ctctctctct ctctctctct ctctctctct ctctcggtac ctctctctct ctctctctct   3360
ctctctctct ctctctctct cggtaccagg tgctgaagaa ttgacccggt gaccaaaggt   3420
gccttttatc atcactttaa aaataaaaaa caattactca gtgcctgtta taagcagcaa   3480
ttaattatga ttgatgccta catcacaaca aaaactgatt taacaaatgg ttggtctgcc   3540
ttagaaagta tatttgaaca ttatcttgat tatattattg ataataataa aaaccttatc   3600
cctatccaag aagtgatgcc tatcattggt tggaatgaac ttgaaaaaaa ttagccttga   3660
atacattact ggtaaggtaa acgccattgt cagcaaattg atccaagaga accaacttaa   3720
agctttcctg acggaatgtt aattctcgtt gaccctgagc actgatgaat cccctaatga   3780
ttttggtaaa aatcattaag ttaaggtgga tacacatctt gtcatatgat cccggtaatg   3840
tgagttagct cactcattag gcaccccagg ctttacactt tatgcttccg gctcgtatgt   3900
tgtgtggaat tgtgagcgga taacaatttc acacaggaaa cagctatgac catgattacg   3960
ccaagcgcgc aattaaccct cactaaaggg aacaaaagct ggagctccac cgcggtggcg   4020
gccgctctag aactagtgga tcccccgggg aggtcagaat ggtttcttta ctgtttgtca   4080
attctattat ttcaatacag aacaatagct tctataactg aaatatattt gctattgtat   4140
attatgattg tccctcgaac catgaacact cctccagctg aatttcacaa ttcctctgtc   4200
atctgccagg ccattaagtt attcatggaa gatctttgag gaacactgca agttcatatc   4260
ataaacacat ttgaaattga gtattgtttt gcattgtatg gagctatgtt ttgctgtatc   4320
ctcagaaaaa aagtttgtta taaagcattc acacccataa aaagatagat ttaaatattc   4380
cagctatagg aaagaaagtg cgtctgctct tcactctagt ctcagttggc tccttcacat   4440
gcatgcttct ttatttctcc tattttgtca agaaaataat aggtcacgtc ttgttctcac   4500
ttatgtcctg cctagcatgg ctcagatgca cgttgtagat acaagaagga tcaaatgaaa   4560
cagacttctg gtctgttact acaaccatag taataagcac actaactaat aattgctaat   4620
tatgttttcc atctctaagg ttcccacatt tttctgtttt cttaaagatc ccattatctg   4680
gttgtaactg aagctcaatg gaacatgagc aatatttccc agtcttctct cccatccaac   4740
agtcctgatg gattagcaga acaggcagaa aacacattgt tacccagaat taaaaactaa   4800
tatttgctct ccattcaatc caaaatggac ctattgaaac taaaatctaa cccaatccca   4860
ttaaatgatt tctatggcgt caaaggtcaa acttctgaag ggaacctgtg ggtgggtcac   4920
aattcaggct atatattccc cagggctcag cggatctcca tgggctccat cggtgcagca   4980
agcatggaat tttgttttga tgtattcaag gagctcaaag tccaccatgc caatgagaac   5040
atcttctact gccccattgc catcatgtca gctctagcca tggtatacct gggtgcaaaa   5100
```

-continued

```
gacagcacca gggaattcgt gcgctcctcc aagaacgtca tcaaggagtt catgcgcttc   5160
aaggtgcgca tggagggcac cgtgaacggc cacgagttcg agatcgaggg cgagggcgag   5220
ggccgcccct acgagggcca caacaccgtg aagctgaagg tgaccaaggg cggcccctg    5280
cccttcgcct gggacatcct gtccccccag ttccagtacg gctccaaggt gtacgtgaag   5340
caccccgccg acatccccga ctacaagaag ctgtccttcc ccgagggctt caagtgggag   5400
cgcgtgatga acttcgagga cggcggcgtg gtgaccgtga cccaggactc ctccctgcag   5460
gacggctgct tcatctacaa ggtgaagttc atcggcgtga acttcccctc cgacggcccc   5520
gtaatgcaga agaagaccat gggctgggag gcctccaccg agcgcctgta cccccgcgac   5580
ggcgtgctga agggcgagat ccacaaggcc ctgaagctga aggacggcgg ccactacctg   5640
gtggagttca agtccatcta catggccaag aagcccgtgc agctgcccgg ctactactac   5700
gtggactcca agctggacat cacctcccac aacgaggact acaccatcgt ggagcagtac   5760
gagcgcaccg agggccgcca ccacctgttc ctgtagcggc cgcgactcta gatcataatc   5820
agccatacca catttgtaga ggttttactt gctttaaaaa acctcccaca cctccccctg   5880
aacctgaaac ataaaatgaa tgcaattgtt gttgttaact tgtttattgc agcttataat   5940
ggttacaaat aaagcaatag catcacaaat ttcacaaata aagcattttt ttcactgcat   6000
tctagttgtg gctcgagaag ggcgaattct gcagatatcc atcacactgg cggccgctcg   6060
aggggggggcc cggtacccaa ttcgccctat agtgagtcgt attacgcgcg ctcactggcc   6120
gtcgttttac aacgtcgtga ctgggaaaac cctggcgtta cccaacttaa tcgccttgca   6180
gcacatcccc ctttcgccag ctggcgtaat agcgaagagg cccgcaccga tcgcccttcc   6240
caacagttgc gcagcctgaa tggcgaatgg aaattgtaag cgttaatatt ttgttaaaat   6300
tcgcgttaaa tttttgttaa atcagctcat tttttaacca ataggccgaa atcggcaaaa   6360
tcccttataa atcaaaagaa tagaccgaga tagggttgag tgttgttcca gtttggaaca   6420
agagtccact attaaagaac gtggactcca acgtcaaagg gcgaaaaacc gtctatcagg   6480
gcgatggccc actactccgg gatcatatga caagatgtgt atccacctta acttaatgat   6540
ttttaccaaa atcattaggg gattcatcag tgctcagggt caacgagaat taacattccg   6600
tcaggaaagc ttatgatgat gatgtgctta aaaacttact caatggctgg ttatgcatat   6660
cgcaatacat gcgaaaaacc taaaagagct tgccgataaa aaaggccaat ttattgctat   6720
ttaccgcggc tttttattga gcttgaaaga taaataaaat agataggttt tatttgaagc   6780
taaatcttct ttatcgtaaa aaatgccctc ttgggttatc aagagggtca ttatatttcg   6840
cggaataaca tcatttggtg acgaaataac taagcacttg tctcctgttt actcccctga   6900
gcttgagggg ttaacatgaa ggtcatcgat agcaggataa taatacagta aaacgctaaa   6960
ccaataatcc aaatccagcc atcccaaatt ggtagtgaat gattataaat aacagcaaac   7020
agtaatgggc caataacacc ggttgcattg gtaaggctca ccaataatcc ctgtaaagca   7080
ccttgctgat gactctttgt ttggatagac atcactccct gtaatgcagg taaagcgatc   7140
ccaccaccag ccaataaaat taaaacaggg aaaactaacc aaccttcaga tataaacgct   7200
aaaaaggcaa atgcactact atctgcaata aatccgagca gtactgccgt tttttcgccc   7260
catttagtgg ctattcttcc tgccacaaag gcttggaata ctgagtgtaa aagaccaaga   7320
cccgctaatg aaaagccaac catcatgcta ttccatccaa aacgattttc ggtaaatagc   7380
acccacaccg ttgcgggaat ttggcctatc aattgcgctg aaaaataaat aatcaacaaa   7440
```

-continued

```
atggcatcgt tttaaataaa gtgatgtata ccgaattcag cttttgttcc ctttagtgag   7500
ggttaattgc gcgcttggcg taatcatggt catagctgtt tcctgtgtga aattgttatc   7560
cgctcacaat tccacacaac atacgagccg gaagcataaa gtgtaaagcc tggggtgcct   7620
aatgagtgag ctaactcaca ttaattgcgt tgcgctcact gcccgctttc cagtcgggaa   7680
acctgtcgtg ccagctgcat taatgaatcg gccaacgcgc ggggagaggc ggtttgcgta   7740
ttgggcgctc ttccgcttcc tcgctcactg actcgctgcg ctcggtcgtt cggctgcggc   7800
gagcggtatc agctcactca aaggcggtaa tacggttatc cacagaatca ggggataacg   7860
caggaaagaa catgtgagca aaaggccagc aaaaggccag gaaccgtaaa aaggccgcgt   7920
tgctggcgtt tttccatagg ctccgccccc ctgacgagca tcacaaaaat cgacgctcaa   7980
gtcagaggtg gcgaaacccg acaggactat aaagatacca ggcgtttccc cctggaagct   8040
ccctcgtgcg ctctcctgtt ccgaccctgc cgcttaccgg atacctgtcc gcctttctcc   8100
cttcgggaag cgtggcgctt tctcatagct cacgctgtag gtatctcagt tcggtgtagg   8160
tcgttcgctc caagctgggc tgtgtgcacg aaccccccgt tcagcccgac cgctgcgcct   8220
tatccggtaa ctatcgtctt gagtccaacc cggtaagaca cgacttatcg ccactggcag   8280
cagccactgg taacaggatt agcagagcga ggtatgtagg cggtgctaca gagttcttga   8340
agtggtggcc taactacggc tacactagaa ggacagtatt tggtatctgc gctctgctga   8400
agccagttac cttcggaaaa agagttggta gctcttgatc cggcaaacaa accaccgctg   8460
gtagcggtgg tttttttgtt tgcaagcagc agattacgcg cagaaaaaaa ggatctcaag   8520
aagatccttt gatcttttct acggggtctg acgctcagtg gaacgaaaac tcacgttaag   8580
ggattttggt catgagatta tcaaaaagga tcttcaccta gatcctttta aattaaaaat   8640
gaagttttaa atcaatctaa agtatatatg agtaaacttg gtctgacagt taccaatgct   8700
taatcagtga ggcacctatc tcagcgatct gtctatttcg ttcatccata gttgcctgac   8760
tccccgtcgt gtagataact acgatacggg agggcttacc atctggcccc agtgctgcaa   8820
tgataccgcg agacccacgc tcaccggctc cagatttatc agcaataaac cagccagccg   8880
gaagggccga gcgcagaagt ggtcctgcaa ctttatccgc ctccatccag tctattaatt   8940
gttgccggga agctagagta agtagttcgc cagttaatag tttgcgcaac gttgttgcca   9000
ttgctacagg catcgtggtg tcacgctcgt cgtttggtat ggcttcattc agctccggtt   9060
cccaacgatc aaggcgagtt acatgatccc ccatgttgtg caaaaaagcg gttagctcct   9120
tcggtcctcc gatcgttgtc agaagtaagt tggccgcagt gttatcactc atggttatgg   9180
cagcactgca taattctctt actgtcatgc catccgtaag atgcttttct gtgactggtg   9240
agtactcaac caagtcattc tgagaatagt gtatgcggcg accgagttgc tcttgcccgg   9300
cgtcaatacg ggataatacc gcgccacata gcagaacttt aaaagtgctc atcattggaa   9360
aacgttcttc ggggcgaaaa ctctcaagga tcttaccgct gttgagatcc agttcgatgt   9420
aacccactcg tgcacccaac tgatcttcag catcttttac tttcaccagc gtttctgggt   9480
gagcaaaaac aggaaggcaa aatgccgcaa aaaagggaat aagggcgaca cggaaatgtt   9540
gaatactcat actcttcctt tttcaatatt attgaagcat ttatcagggt tattgtctca   9600
tgagcggata catatttgaa tgtatttaga aaaataaaca aataggggtt ccgcgcacat   9660
ttccccgaaa agtgccac                                                 9678
```

<210> SEQ ID NO 4
<211> LENGTH: 9658

-continued

<212> TYPE: DNA
<213> ORGANISM: Artificial Sequence
<220> FEATURE:
<223> OTHER INFORMATION: Synthetic

<400> SEQUENCE: 4

```
ctgacgcgcc ctgtagcggc gcattaagcg cggcgggtgt ggtggttacg cgcagcgtga      60
ccgctacact tgccagcgcc ctagcgcccg ctcctttcgc tttcttccct tcctttctcg     120
ccacgttcgc cggcatcaga ttggctattg gccattgcat acgttgtatc catatcataa     180
tatgtacatt tatattggct catgtccaac attaccgcca tgttgacatt gattattgac     240
tagttattaa tagtaatcaa ttacggggtc attagttcat agcccatata tggagttccg     300
cgttacataa cttacggtaa atggcccgcc tggctgaccg cccaacgacc cccgcccatt     360
gacgtcaata atgacgtatg ttcccatagt aacgccaata gggactttcc attgacgtca     420
atgggtggag tatttacggt aaactgccca cttggcagta catcaagtgt atcatatgcc     480
aagtacgccc cctattgacg tcaatgacgg taaatggccc gcctggcatt atgcccagta     540
catgacctta tgggactttc ctacttggca gtacatctac gtattagtca tcgctattac     600
catggtgatg cggttttggc agtacatcaa tgggcgtgga tagcggtttg actcacgggg     660
atttccaagt ctccacccca ttgacgtcaa tgggagtttg ttttggcacc aaaatcaacg     720
ggactttcca aaatgtcgta acaactccgc cccattgacg caaatgggcg gtaggcgtgt     780
acggtgggag gtctatataa gcagagctcg tttagtgaac cgtcagatcg cctggagacg     840
ccatccacgc tgttttgacc tccatagaag acaccgggac cgatccagcc tccgcggccg     900
ggaacggtgc attggaacgc ggattccccg tgccaagagt gacgtaagta ccgcctatag     960
actctatagg cacacccctt tggctcttat gcatgctata ctgtttttgg cttggggcct    1020
atacaccccc gcttccttat gctataggtg atggtatagc ttagcctata ggtgtgggtt    1080
attgaccatt attgaccact cccctattgg tgacgatact ttccattact aatccataac    1140
atggctcttt gccacaacta tctctattgg ctatatgcca atactctgtc cttcagagac    1200
tgacacggac tctgtatttt tacaggatgg ggtcccattt attatttaca aattcacata    1260
tacaacaacg ccgtcccccg tgcccgcagt ttttattaaa catagcgtgg gatctccacg    1320
cgaatctcgg gtacgtgttc cggacatggg ctcttctccg gtagcggcgg agcttccaca    1380
tccgagccct ggtcccatgc ctccagcggc tcatggtcgc tcggcagctc cttgctccta    1440
acagtggagg ccagacttag gcacagcaca atgcccacca ccaccagtgt gccgcacaag    1500
gccgtggcgg tagggtatgt gtctgaaaat gagcgtggag attgggctcg cacggctgac    1560
gcagatggaa gacttaaggc agcggcagaa gaagatgcag gcagctgagt tgttgtattc    1620
tgataagagt cagaggtaac tcccgttgcg gtgctgttaa cggtggaggg cagtgtagtc    1680
tgagcagtac tcgttgctgc cgcgcgcgcc accagacata atagctgaca gactaacaga    1740
ctgttccttt ccatgggtct tttctgcagt caccgtcgga ccatgtgtga acttgatatt    1800
ttacatgatt ctctttacca attctgcccc gaattacact taaaacgact caacagctta    1860
acgttggctt gccacgcatt acttgactgt aaaactctca ctcttaccga acttggccgt    1920
aacctgccaa ccaaagcgag aacaaaacat aacatcaaac gaatcgaccg attgttaggt    1980
aatcgtcacc tccacaaaga gcgactcgct gtataccgtt ggcatgctag ctttatctgt    2040
tcgggaatac gatgcccatt gtacttgttg actggtctga tattcgtgag caaaaacgac    2100
ttatggtatt gcgagcttca gtcgcactac acggtcgttc tgttactctt tatgagaaag    2160
```

-continued

```
cgttcccgct ttcagagcaa tgttcaaaga aagctcatga ccaatttcta gccgaccttg   2220

cgagcattct accgagtaac accacaccgc tcattgtcag tgatgctggc tttaaagtgc   2280

catggtataa atccgttgag aagctgggtt ggtactggtt aagtcgagta agaggaaaag   2340

tacaatatgc agacctagga gcggaaaact ggaaacctat cagcaactta catgatatgt   2400

catctagtca ctcaaagact ttaggctata agaggctgac taaaagcaat ccaatctcat   2460

gccaaattct attgtataaa tctcgctcta aaggccgaaa aaatcagcgc tcgacacgga   2520

ctcattgtca ccacccgtca cctaaaatct actcagcgtc ggcaaaggag ccatgggttc   2580

tagcaactaa cttacctgtt gaaattcgaa cacccaaaca acttgttaat atctattcga   2640

agcgaatgca gattgaagaa accttccgag acttgaaaag tcctgcctac ggactaggcc   2700

tacgccatag ccgaacgagc agctcagagc gttttgatat catgctgcta atcgccctga   2760

tgcttcaact aacatgttgg cttgcgggcg ttcatgctca gaaacaaggt tgggacaagc   2820

acttccaggc taacacagtc agaaatcgaa acgtactctc aacagttcgc ttaggcatgg   2880

aagttttgcg gcattctggc tacacaataa caagggaaga cttactcgtg gctgcaaccc   2940

tactagctca aaatttattc acacatggtt acgctttggg gaaattatga taatgatcca   3000

gatcacttct ggctaataaa agatcagagc tctagagatc tgtgtgttgg tttttttgtgg  3060

atctgctgtg ccttctagtt gccagccatc tgttgtttgc ccctcccccg tgccttcctt   3120

gaccctggaa ggtgccactc ccactgtcct ttcctaataa aatgaggaaa ttgcatcgca   3180

ttgtctgagt aggtgtcatt ctattctggg gggtggggtg gggcagcaca gcaaggggga   3240

ggattgggaa gacaatagca ggcatgctgg ggatgcggtg ggctctatgg gtacctctct   3300

ctctctctct ctctctctct ctctctctct ctctcggtac ctctctctct ctctctctct   3360

ctctctctct ctctctctct cggtaccagg tgctgaagaa ttgacccggt gaccaaaggt   3420

gccttttatc atcactttaa aaataaaaaa caattactca gtgcctgtta taagcagcaa   3480

ttaattatga ttgatgccta catcacaaca aaaactgatt taacaaatgg ttggtctgcc   3540

ttagaaagta tatttgaaca ttatcttgat tatattattg ataataataa aaaccttatc   3600

cctatccaag aagtgatgcc tatcattggt tggaatgaac ttgaaaaaaa ttagccttga   3660

atacattact ggtaaggtaa acgccattgt cagcaaattg atccaagaga accaacttaa   3720

agctttcctg acggaatgtt aattctcgtt gaccctgagc actgatgaat cccctaatga   3780

ttttggtaaa aatcattaag ttaaggtgga tacacatctt gtcatatgat cccggtaatg   3840

tgagttagct cactcattag gcaccccagg ctttacactt tatgcttccg gctcgtatgt   3900

tgtgtggaat tgtgagcgga taacaatttc acacaggaaa cagctatgac catgattacg   3960

ccaagcgcgc aattaaccct cactaaaggg aacaaaagct ggagctccac cgcggtggcg   4020

gccgctctag aactagtgga tcccccgggg aggtcagaat ggtttcttta ctgtttgtca   4080

attctattat ttcaatacag aacaaaagct tctataactg aaatatattt gctattgtat   4140

attatgattg tccctcgaac catgaacact cctccagctg aatttcacaa ttcctctgtc   4200

atctgccagg ctggaagatc atggaagatc tctgaggaac attgcaagtt cataccataa   4260

actcatttgg aattgagtat tattttgctt tgaatggagc tatgttttgc agttccctca   4320

gaagaaaagc ttgttataaa gcgtctacac ccatcaaaag atatatttaa atattccaac   4380

tacagaaaga ttttgtctgc tcttcactct gatctcagtt ggtttcttca cgtacatgct   4440

tctttatttg cctattttgt caagaaaata ataggtcaag tcctgttctc acttatctcc   4500

tgcctagcat ggcttagatg cacgttgtac attcaagaag gatcaaatga aacagacttc   4560
```

-continued

```
tggtctgtta caacaaccat agtaataaac agactaacta ataattgcta attatgtttt   4620
ccatctctaa ggttcccaca tttttctgtt ttaagatccc attatctggt tgtaactgaa   4680
gctcaatgga acatgaacag tatttctcag tcttttctcc agcaatcctg acggattaga   4740
agaactggca gaaaacactt tgttacccag aattaaaaac taatatttgc tctcccttca   4800
atccaaaatg gacctattga aactaaaatc tgacccaatc ccattaaatt atttctatgg   4860
cgtcaaaggt caaacttttg aagggaacct gtgggtgggt cccaattcag gctatatatt   4920
ccccagggct cagcggatct ccatgggctc ctcgtgcagc aagcatggaa ttttgccttg   4980
atgtattcaa ggagctcaaa gtccaccatg ccaatgacaa catgctctac tcccctttg    5040
ccatctgtca actctggcca tggtctccct gggtgcaaaa gacagcacca gggaattcgt   5100
gcgctcctcc aagaacgtca tcaaggagtt catgcgcttc aaggtgcgca tggagggcac   5160
cgtgaacggc cacgagttcg agatcgaggg cgagggcgag ggccgcccct acgagggcca   5220
caacaccgtg aagctgaagg tgaccaaggg cggccccctg cccttcgcct gggacatcct   5280
gtccccccag ttccagtacg gctccaaggt gtacgtgaag caccccgccg acatccccga   5340
ctacaagaag ctgtccttcc ccgagggctt caagtgggag cgcgtgatga acttcgagga   5400
cggcggcgtg gtgaccgtga cccaggactc ctccctgcag gacggctgct tcatctacaa   5460
ggtgaagttc atcggcgtga acttcccctc cgacggcccc gtaatgcaga agaagaccat   5520
gggctgggag gcctccaccg agcgcctgta cccccgcgac ggcgtgctga agggcgagat   5580
ccacaaggcc ctgaagctga aggacggcgg ccactacctg gtggagttca agtccatcta   5640
catggccaag aagcccgtgc agctgcccgg ctactactac gtggactcca agctggacat   5700
cacctcccac aacgaggact acaccatcgt ggagcagtac gagcgcaccg agggccgcca   5760
ccacctgttc ctgtagcggc cgcgactcta gatcataatc agccatacca catttgtaga   5820
ggttttactt gctttaaaaa acctcccaca cctccccctg aacctgaaac ataaaatgaa   5880
tgcaattgtt gttgttaact tgtttattgc agcttataat ggttacaaat aaagcaatag   5940
catcacaaat ttcacaaata aagcattttt ttcactgcat tctagttgtg gctcgagaag   6000
ggcgaattct gcagatatcc atcacactgg cggccgctcg aggggggggcc cggtacccaa  6060
ttcgccctat agtgagtcgt attacgcgcg ctcactggcc gtcgttttac aacgtcgtga   6120
ctgggaaaac cctggcgtta cccaacttaa tcgccttgca gcacatcccc ctttcgccag   6180
ctggcgtaat agcgaagagg cccgcaccga tcgcccttcc caacagttgc gcagcctgaa   6240
tggcgaatgg aaattgtaag cgttaatatt ttgttaaaat tcgcgttaaa tttttgttaa   6300
atcagctcat tttttaacca ataggccgaa atcggcaaaa tcccttataa atcaaaagaa   6360
tagaccgaga tagggttgag tgttgttcca gtttggaaca agagtccact attaaagaac   6420
gtggactcca acgtcaaagg gcgaaaaacc gtctatcagg gcgatggccc actactccgg   6480
gatcatatga caagatgtgt atccacctta acttaatgat tttaccaaa atcattaggg    6540
gattcatcag tgctcagggt caacgagaat taacattccg tcaggaaagc ttatgatgat   6600
gatgtgctta aaaacttact caatggctgg ttatgcatat cgcaatacat gcgaaaaacc   6660
taaaagagct tgccgataaa aaaggccaat ttattgctat ttaccgcggc tttttattga   6720
gcttgaaaga taaataaaat agataggttt tatttgaagc taaatcttct ttatcgtaaa   6780
aaatgccctc ttgggttatc aagagggtca ttatatttcg cggaataaca tcatttggtg   6840
acgaaataac taagcacttg tctcctgttt actcccctga gcttgagggg ttaacatgaa   6900
```

-continued

```
ggtcatcgat agcaggataa taatacagta aaacgctaaa ccaataatcc aaatccagcc   6960
atcccaaatt ggtagtgaat gattataaat aacagcaaac agtaatgggc caataacacc   7020
ggttgcattg gtaaggctca ccaataatcc ctgtaaagca ccttgctgat gactctttgt   7080
ttggatagac atcactccct gtaatgcagg taaagcgatc ccaccaccag ccaataaaat   7140
taaaacaggg aaaactaacc aaccttcaga tataaacgct aaaaaggcaa atgcactact   7200
atctgcaata aatccgagca gtactgccgt tttttcgccc catttagtgg ctattcttcc   7260
tgccacaaag gcttggaata ctgagtgtaa aagaccaaga cccgctaatg aaaagccaac   7320
catcatgcta ttccatccaa aacgattttc ggtaaatagc acccacaccg ttgcgggaat   7380
ttggcctatc aattgcgctg aaaaataaat aatcaacaaa atggcatcgt tttaaataaa   7440
gtgatgtata ccgaattcag cttttgttcc ctttagtgag ggttaattgc gcgcttggcg   7500
taatcatggt catagctgtt tcctgtgtga aattgttatc cgctcacaat tccacacaac   7560
atacgagccg gaagcataaa gtgtaaagcc tggggtgcct aatgagtgag ctaactcaca   7620
ttaattgcgt tgcgctcact gcccgctttc cagtcgggaa acctgtcgtg ccagctgcat   7680
taatgaatcg gccaacgcgc ggggagaggc ggtttgcgta ttgggcgctc ttccgcttcc   7740
tcgctcactg actcgctgcg ctcggtcgtt cggctgcggc gagcggtatc agctcactca   7800
aaggcggtaa tacggttatc cacagaatca ggggataacg caggaaagaa catgtgagca   7860
aaaggccagc aaaaggccag gaaccgtaaa aaggccgcgt tgctggcgtt tttccatagg   7920
ctccgccccc ctgacgagca tcacaaaaat cgacgctcaa gtcagaggtg gcgaaacccg   7980
acaggactat aaagatacca ggcgtttccc cctggaagct ccctcgtgcg ctctcctgtt   8040
ccgaccctgc cgcttaccgg atacctgtcc gcctttctcc cttcgggaag cgtggcgctt   8100
tctcatagct cacgctgtag gtatctcagt tcggtgtagg tcgttcgctc caagctgggc   8160
tgtgtgcacg aaccccccgt tcagcccgac cgctgcgcct tatccggtaa ctatcgtctt   8220
gagtccaacc cggtaagaca cgacttatcg ccactggcag cagccactgg taacaggatt   8280
agcagagcga ggtatgtagg cggtgctaca gagttcttga agtggtggcc taactacggc   8340
tacactagaa ggacagtatt tggtatctgc gctctgctga agccagttac cttcggaaaa   8400
agagttggta gctcttgatc cggcaaacaa accaccgctg gtagcggtgg tttttttgtt   8460
tgcaagcagc agattacgcg cagaaaaaaa ggatctcaag aagatccttt gatcttttct   8520
acggggtctg acgctcagtg gaacgaaaac tcacgttaag ggattttggt catgagatta   8580
tcaaaaagga tcttcaccta gatcctttta aattaaaaat gaagttttaa atcaatctaa   8640
agtatatatg agtaaacttg gtctgacagt taccaatgct taatcagtga ggcacctatc   8700
tcagcgatct gtctatttcg ttcatccata gttgcctgac tccccgtcgt gtagataact   8760
acgatacggg agggcttacc atctggcccc agtgctgcaa tgataccgcg agacccacgc   8820
tcaccggctc cagatttatc agcaataaac cagccagccg gaagggccga gcgcagaagt   8880
ggtcctgcaa ctttatccgc ctccatccag tctattaatt gttgccggga agctagagta   8940
agtagttcgc cagttaatag tttgcgcaac gttgttgcca ttgctacagg catcgtggtg   9000
tcacgctcgt cgtttggtat ggcttcattc agctccggtt cccaacgatc aaggcgagtt   9060
acatgatccc ccatgttgtg caaaaaagcg gttagctcct tcggtcctcc gatcgttgtc   9120
agaagtaagt tggccgcagt gttatcactc atggttatgg cagcactgca taattctctt   9180
actgtcatgc catccgtaag atgcttttct gtgactggtg agtactcaac caagtcattc   9240
tgagaatagt gtatgcggcg accgagttgc tcttgcccgg cgtcaatacg ggataatacc   9300
```

-continued

```
gcgccacata gcagaacttt aaaagtgctc atcattggaa aacgttcttc ggggcgaaaa   9360

ctctcaagga tcttaccgct gttgagatcc agttcgatgt aacccactcg tgcacccaac   9420

tgatcttcag catcttttac tttcaccagc gtttctgggt gagcaaaaac aggaaggcaa   9480

aatgccgcaa aaaagggaat aagggcgaca cggaaatgtt gaatactcat actcttcctt   9540

tttcaatatt attgaagcat ttatcagggt tattgtctca tgagcggata catatttgaa   9600

tgtatttaga aaaataaaca aatagggggtt ccgcgcacat ttccccgaaa agtgccac    9658


<210> SEQ ID NO 5
<211> LENGTH: 4
<212> TYPE: PRT
<213> ORGANISM: Artificial Sequence
<220> FEATURE:
<223> OTHER INFORMATION: Synthetic

<400> SEQUENCE: 5

Gly Pro Gly Gly
1


<210> SEQ ID NO 6
<211> LENGTH: 12
<212> TYPE: PRT
<213> ORGANISM: Artificial Sequence
<220> FEATURE:
<223> OTHER INFORMATION: Synthetic

<400> SEQUENCE: 6

Gly Pro Gly Gly Gly Pro Gly Gly Gly Pro Gly Gly
1               5                   10


<210> SEQ ID NO 7
<211> LENGTH: 15
<212> TYPE: PRT
<213> ORGANISM: Artificial Sequence
<220> FEATURE:
<223> OTHER INFORMATION: Synthetic

<400> SEQUENCE: 7

Gly Gly Gly Gly Ser Gly Gly Gly Gly Ser Gly Gly Gly Gly Ser
1               5                   10                  15


<210> SEQ ID NO 8
<211> LENGTH: 20
<212> TYPE: PRT
<213> ORGANISM: Artificial Sequence
<220> FEATURE:
<223> OTHER INFORMATION: Synthetic

<400> SEQUENCE: 8

Gly Gly Gly Gly Ser Gly Gly Gly Gly Ser Gly Gly Gly Gly Ser Gly
1               5                   10                  15

Gly Gly Gly Ser
20


<210> SEQ ID NO 9
<211> LENGTH: 5
<212> TYPE: PRT
<213> ORGANISM: Artificial Sequence
<220> FEATURE:
<223> OTHER INFORMATION: Synthetic

<400> SEQUENCE: 9

Asp Asp Asp Asp Lys
```

-continued 1 5

<210> SEQ ID NO 10
<211> LENGTH: 48
<212> TYPE: DNA
<213> ORGANISM: Artificial Sequence
<220> FEATURE:
<223> OTHER INFORMATION: Synthetic

<400> SEQUENCE: 10
atctcgagac catgtgtgaa cttgatattt tacatgattc tctttacc 48

<210> SEQ ID NO 11
<211> LENGTH: 36
<212> TYPE: DNA
<213> ORGANISM: Artificial Sequence
<220> FEATURE:
<223> OTHER INFORMATION: Synthetic

<400> SEQUENCE: 11
gattgatcat tatcataatt tccccaaagc gtaacc 36

<210> SEQ ID NO 12
<211> LENGTH: 6
<212> TYPE: DNA
<213> ORGANISM: Artificial Sequence
<220> FEATURE:
<223> OTHER INFORMATION: Synthetic

<400> SEQUENCE: 12 ctcgag 6

<210> SEQ ID NO 13
<211> LENGTH: 6
<212> TYPE: DNA
<213> ORGANISM: Artificial Sequence
<220> FEATURE:
<223> OTHER INFORMATION: Synthetic

<400> SEQUENCE: 13 accatg 6

<210> SEQ ID NO 14
<211> LENGTH: 6
<212> TYPE: DNA
<213> ORGANISM: Artificial Sequence
<220> FEATURE:
<223> OTHER INFORMATION: Synthetic

<400> SEQUENCE: 14 tgatca 6

<210> SEQ ID NO 15
<211> LENGTH: 22
<212> TYPE: DNA
<213> ORGANISM: Artificial Sequence
<220> FEATURE:
<223> OTHER INFORMATION: Synthetic

<400> SEQUENCE: 15
ttgccggcat cagattggct at 22

<210> SEQ ID NO 16
<211> LENGTH: 34
<212> TYPE: DNA
<213> ORGANISM: Artificial Sequence -continued
<220> FEATURE:
<223> OTHER INFORMATION: Synthetic

<400> SEQUENCE: 16
agaggtcacc gggtcaattc ttcagcacct ggta 34

<210> SEQ ID NO 17
<211> LENGTH: 908
<212> TYPE: DNA
<213> ORGANISM: Artificial Sequence
<220> FEATURE:
<223> OTHER INFORMATION: Synthetic

<400> SEQUENCE: 17
tgaatgtgtt cttgtgttat caatataaat cacagttagt gatgaagttg gctgcaagcc 60
tgcatcagtt cagctacttg gctgcatttt gtatttggtt ctgtaggaaa tgcaaaaggt 120
tctaggctga cctgcacttc tatccctctt gccttactgc tgagaatctc tgcaggtttt 180
aattgttcac attttgctcc catttacttt ggaagataaa atatttacag aatgcttatg 240
aaacctttgt tcatttaaaa atattcctgg tcagcgtgac cggagctgaa agaacacatt 300
gatcccgtga tttcaataaa tacatatgtt ccatatattg tttctcagta gcctcttaaa 360
tcatgtgcgt tggtgcacat atgaatacat gaatagcaaa ggtttatctg gattacgctc 420
tggcctgcag gaatggccat aaaccaaagc tgagggaaga gggagagtat agtcaatgta 480
gattatactg attgctgatt gggttattat cagctagata acaacttggg tcaggtgcca 540
ggtcaacata acctgggcaa aaccagtctc atctgtggca ggaccatgta ccagcagcca 600
gccgtgaccc aatctaggaa agcaagtagc acatcaattt taaatttatt gtaaatgccg 660
tagtagaagt gttttactgt gatacattga aacttctggt caatcagaaa aaggtttttt 720
atcagagatg ccaaggtatt atttgatttt ctttattcgc cgtgaagaga atttatgatt 780
gcaaaaagag gagtgtttac ataaactgat aaaaaacttg aggaattcag cagaaaacag 840
ccacgtgttc ctgaacattc ttccataaaa gtctcaccat gcctggcaga gccctattca 900
ccttcgct 908

<210> SEQ ID NO 18
<211> LENGTH: 63
<212> TYPE: DNA
<213> ORGANISM: Artificial Sequence
<220> FEATURE:
<223> OTHER INFORMATION: Synthetic

<400> SEQUENCE: 18
atgaggggga tcatactggc attagtgctc acccttgtag gcagccagaa gtttgacatt 60
ggt 63

<210> SEQ ID NO 19
<211> LENGTH: 13
<212> TYPE: PRT
<213> ORGANISM: Artificial Sequence
<220> FEATURE:
<223> OTHER INFORMATION: Synthetic

<400> SEQUENCE: 19

Lys Tyr Lys Lys Ala Leu Lys Lys Leu Ala Lys Leu Leu
1 5 10

<210> SEQ ID NO 20
<211> LENGTH: 39

<212> TYPE: DNA
<213> ORGANISM: Artificial Sequence
<220> FEATURE:
<223> OTHER INFORMATION: Synthetic

<400> SEQUENCE: 20
aaatacaaaa aagcactgaa aaaactggca aaactgctg 39

<210> SEQ ID NO 21
<211> LENGTH: 260
<212> TYPE: DNA
<213> ORGANISM: Artificial Sequence
<220> FEATURE:
<223> OTHER INFORMATION: Synthetic

<400> SEQUENCE: 21
tttgtgaacc aacacctgtg cggctcacac ctggtggaag ctctctacct agtgtgcggg 60
gaacgaggct tcttctacac acccaagacc cgccgggagg cagaggacct gcaggtgggg 120
caggtggagc tgggcggggg ccctggtgca ggcagcctgc agcccttggc cctggagggg 180
tccctgcaga agcgtggcat tgtggaacaa tgctgtacca gcatctgctc cctctaccag 240
ctggagaact ctgcaactag 260

<210> SEQ ID NO 22
<211> LENGTH: 50
<212> TYPE: PRT
<213> ORGANISM: Artificial Sequence
<220> FEATURE:
<223> OTHER INFORMATION: Synthetic

<400> SEQUENCE: 22

Pro Ala Asp Asp Ala Pro Ala Asp Asp Ala Pro Ala Asp Asp Ala Pro
1 5 10 15

Ala Asp Asp Ala Pro Ala Asp Asp Ala Pro Ala Asp Asp Ala Thr Thr
20 25 30

Cys Ile Leu Lys Gly Ser Cys Gly Trp Ile Gly Leu Leu Asp Asp Asp
35 40 45

Asp Lys
50

<210> SEQ ID NO 23
<211> LENGTH: 16
<212> TYPE: PRT
<213> ORGANISM: Artificial Sequence
<220> FEATURE:
<223> OTHER INFORMATION: Synthetic

<400> SEQUENCE: 23

Ala Thr Thr Cys Ile Leu Lys Gly Ser Cys Gly Trp Ile Gly Leu Leu
1 5 10 15

<210> SEQ ID NO 24
<211> LENGTH: 30
<212> TYPE: PRT
<213> ORGANISM: Artificial Sequence
<220> FEATURE:
<223> OTHER INFORMATION: Synthetic

<400> SEQUENCE: 24

Pro Ala Asp Asp Ala Pro Ala Asp Asp Ala Thr Thr Cys Ile Leu Lys
1 5 10 15

Gly Ser Cys Gly Trp Ile Gly Leu Leu Asp Asp Asp Asp Lys
20 25 30

<210> SEQ ID NO 25
<211> LENGTH: 5
<212> TYPE: PRT
<213> ORGANISM: Artificial Sequence
<220> FEATURE:
<223> OTHER INFORMATION: Synthetic

<400> SEQUENCE: 25

```
Pro Ala Asp Asp Ala
1               5
```

<210> SEQ ID NO 26
<211> LENGTH: 29
<212> TYPE: PRT
<213> ORGANISM: Artificial Sequence
<220> FEATURE:
<223> OTHER INFORMATION: Synthetic

<400> SEQUENCE: 26

```
Pro Ala Asp Asp Ala Pro Ala Asp Asp Ala Pro Ala Asp Asp Ala Pro
1               5                   10                  15

Ala Asp Asp Ala Pro Ala Asp Asp Ala Pro Ala Asp Asp
20                  25
```

<210> SEQ ID NO 27
<211> LENGTH: 1626
<212> TYPE: DNA
<213> ORGANISM: Artificial Sequence
<220> FEATURE:
<223> OTHER INFORMATION: Synthetic

<400> SEQUENCE: 27

```
tgaatgtgtt cttgtgttat caatataaat cacagttagt gatgaagttg gctgcaagcc     60

tgcatcagtt cagctacttg gctgcatttt gtatttggtt ctgtaggaaa tgcaaaaggt    120

tctaggctga cctgcacttc tatccctctt gccttactgc tgagaatctc tgcaggtttt    180

aattgttcac attttgctcc catttacttt ggaagataaa atatttacag aatgcttatg    240

aaacctttgt tcatttaaaa atattcctgg tcagcgtgac cggagctgaa agaacacatt    300

gatcccgtga tttcaataaa tacatatgtt ccatatattg tttctcagta gcctcttaaa    360

tcatgtgcgt tggtgcacat atgaatacat gaatagcaaa ggtttatctg gattacgctc    420

tggcctgcag gaatggccat aaaccaaagc tgagggaaga gggagagtat agtcaatgta    480

gattatactg attgctgatt gggttattat cagctagata acaacttggg tcaggtgcca    540

ggtcaacata acctgggcaa aaccagtctc atctgtggca ggaccatgta ccagcagcca    600

gccgtgaccc aatctaggaa agcaagtagc acatcaattt taaatttatt gtaaatgccg    660

tagtagaagt gttttactgt gatacattga aacttctggt caatcagaaa aaggtttttt    720

atcagagatg ccaaggtatt atttgatttt ctttattcgc cgtgaagaga atttatgatt    780

gcaaaaagag gagtgtttac ataaactgat aaaaaacttg aggaattcag cagaaaacag    840

ccacgtgttc ctgaacattc ttccataaaa gtctcaccat gcctggcaga gccctattca    900

ccttcgctat gagggggatc atactggcat tagtgctcac ccttgtaggc agccagaagt    960

ttgacattgg tagactgaga atggcaagaa gaatgagaag atggtttgtg aaccaacacc   1020

tgtgcggctc acacctggtg gaagctctct acctagtgtg cggggaacga ggcttcttct   1080

acacacccaa gacccgccgg gaggcagagg acctgcaggt ggggcaggtg gagctgggcg   1140

ggggccctgg tgcaggcagc ctgcagccct tggccctgga ggggtccctg cagaagcgtg   1200
```

-continued

```
gcattgtgga acaatgctgt accagcatct gctccctcta ccagctggag aactactgca   1260
actagggcgc ctggatccag atcacttctg gctaataaaa gatcagagct ctagagatct   1320
gtgtgttggt tttttgtgga tctgctgtgc cttctagttg ccagccatct gttgtttgcc   1380
cctcccccgt gccttccttg accctggaag gtgccactcc cactgtcctt tcctaataaa   1440
atgaggaaat tgcatcgcat tgtctgagta ggtgtcattc tattctgggg ggtggggtgg   1500
ggcagcacag caagggggag gattgggaag acaatagcag gcatgctggg gatgcggtgg   1560
gctctatggg tacctctctc tctctctctc tctctctctc tctctctctc tctcggtacc   1620
tctctc                                                              1626
```

<210> SEQ ID NO 28
<211> LENGTH: 361
<212> TYPE: DNA
<213> ORGANISM: Artificial Sequence
<220> FEATURE:
<223> OTHER INFORMATION: Synthetic

<400> SEQUENCE: 28

```
ggcgcctgga tccagatcac ttctggctaa taaaagatca gagctctaga gatctgtgtg     60
ttggtttttt gtggatctgc tgtgccttct agttgccagc catctgttgt ttgcccctcc    120
cccgtgcctt ccttgaccct ggaaggtgcc actcccactg tcctttccta ataaaatgag    180
gaaattgcat cgcattgtct gagtaggtgt cattctattc tggggggtgg ggtggggcag    240
cacagcaagg gggaggattg ggaagacaat agcaggcatg ctggggatgc ggtgggctct    300
atgggtacct ctctctctct ctctctctct ctctctctct ctctctctcg gtacctctct    360
c                                                                    361
```

<210> SEQ ID NO 29
<211> LENGTH: 10297
<212> TYPE: DNA
<213> ORGANISM: Artificial Sequence
<220> FEATURE:
<223> OTHER INFORMATION: Synthetic

<400> SEQUENCE: 29

```
ctgacgcgcc ctgtagcggc gcattaagcg cggcgggtgt ggtggttacg cgcagcgtga     60
ccgctacact tgccagcgcc ctagcgcccg ctcctttcgc tttcttccct tcctttctcg    120
ccacgttcgc cggcatcaga ttggctattg gccattgcat acgttgtatc catatcataa    180
tatgtacatt tatattggct catgtccaac attaccgcca tgttgacatt gattattgac    240
tagttattaa tagtaatcaa ttacggggtc attagttcat agcccatata tggagttccg    300
cgttacataa cttacggtaa atggcccgcc tggctgaccg cccaacgacc cccgcccatt    360
gacgtcaata atgacgtatg ttcccatagt aacgccaata gggactttcc attgacgtca    420
atgggtggag tatttacggt aaactgccca cttggcagta catcaagtgt atcatatgcc    480
aagtacgccc cctattgacg tcaatgacgg taaatggccc gcctggcatt atgcccagta    540
catgacctta tgggactttc ctacttggca gtacatctac gtattagtca tcgctattac    600
catggtgatg cggttttggc agtacatcaa tgggcgtgga tagcggtttg actcacgggg    660
atttccaagt ctccacccca ttgacgtcaa tgggagtttg ttttggcacc aaaatcaacg    720
ggactttcca aaatgtcgta acaactccgc cccattgacg caaatgggcg gtaggcgtgt    780
acggtgggag gtctatataa gcagagctcg tttagtgaac cgtcagatcg cctggagacg    840
```

-continued

```
ccatccacgc tgttttgacc tccatagaag acaccgggac cgatccagcc tccgcggccg    900

ggaacggtgc attggaacgc ggattccccg tgccaagagt gacgtaagta ccgcctatag    960

actctatagg cacacccctt tggctcttat gcatgctata ctgtttttgg cttggggcct   1020

atacaccccc gcttccttat gctataggtg atggtatagc ttagcctata ggtgtgggtt   1080

attgaccatt attgaccact cccctattgg tgacgatact ttccattact aatccataac   1140

atggctcttt gccacaacta tctctattgg ctatatgcca atactctgtc cttcagagac   1200

tgacacggac tctgtatttt tacaggatgg ggtcccattt attatttaca aattcacata   1260

tacaacaacg ccgtcccccg tgcccgcagt ttttattaaa catagcgtgg gatctccacg   1320

cgaatctcgg gtacgtgttc cggacatggg ctcttctccg gtagcggcgg agcttccaca   1380

tccgagccct ggtcccatgc ctccagcggc tcatggtcgc tcggcagctc cttgctccta   1440

acagtggagg ccagacttag gcacagcaca atgcccacca ccaccagtgt gccgcacaag   1500

gccgtggcgg tagggtatgt gtctgaaaat gagcgtggag attgggctcg cacggctgac   1560

gcagatggaa gacttaaggc agcggcagaa gaagatgcag gcagctgagt tgttgtattc   1620

tgataagagt cagaggtaac tcccgttgcg gtgctgttaa cggtggaggg cagtgtagtc   1680

tgagcagtac tcgttgctgc cgcgcgcgcc accagacata atagctgaca gactaacaga   1740

ctgttccttt ccatgggtct tttctgcagt caccgtcgga ccatgtgtga acttgatatt   1800

ttacatgatt ctctttacca attctgcccc gaattacact taaaacgact caacagctta   1860

acgttggctt gccacgcatt acttgactgt aaaactctca ctcttaccga acttggccgt   1920

aacctgccaa ccaaagcgag aacaaaacat aacatcaaac gaatcgaccg attgttaggt   1980

aatcgtcacc tccacaaaga gcgactcgct gtataccgtt ggcatgctag ctttatctgt   2040

tcgggaatac gatgcccatt gtacttgttg actggtctga tattcgtgag caaaaacgac   2100

ttatggtatt gcgagcttca gtcgcactac acggtcgttc tgttactctt tatgagaaag   2160

cgttcccgct ttcagagcaa tgttcaaaga aagctcatga ccaatttcta gccgaccttg   2220

cgagcattct accgagtaac accacaccgc tcattgtcag tgatgctggc tttaaagtgc   2280

catggtataa atccgttgag aagctgggtt ggtactggtt aagtcgagta agaggaaaag   2340

tacaatatgc agacctagga gcggaaaact ggaaacctat cagcaactta catgatatgt   2400

catctagtca ctcaaagact ttaggctata agaggctgac taaaagcaat ccaatctcat   2460

gccaaattct attgtataaa tctcgctcta aaggccgaaa aaatcagcgc tcgacacgga   2520

ctcattgtca ccacccgtca cctaaaatct actcagcgtc ggcaaaggag ccatgggttc   2580

tagcaactaa cttacctgtt gaaattcgaa cacccaaaca acttgttaat atctattcga   2640

agcgaatgca gattgaagaa accttccgag acttgaaaag tcctgcctac ggactaggcc   2700

tacgccatag ccgaacgagc agctcagagc gttttgatat catgctgcta atcgccctga   2760

tgcttcaact aacatgttgg cttgcgggcg ttcatgctca gaaacaaggt tgggacaagc   2820

acttccaggc taacacagtc agaaatcgaa acgtactctc aacagttcgc ttaggcatgg   2880

aagttttgcg gcattctggc tacacaataa caagggaaga cttactcgtg gctgcaaccc   2940

tactagctca aaatttattc acacatggtt acgctttggg gaaattatga taatgatcca   3000

gatcacttct ggctaataaa agatcagagc tctagagatc tgtgtgttgg tttttgtgg   3060

atctgctgtg ccttctagtt gccagccatc tgttgtttgc ccctcccccg tgccttcctt   3120

gaccctggaa ggtgccactc ccactgtcct ttcctaataa aatgaggaaa ttgcatcgca   3180

ttgtctgagt aggtgtcatt ctattctggg gggtggggtg gggcagcaca gcaaggggga   3240
```

-continued

```
ggattgggaa gacaatagca ggcatgctgg ggatgcggtg ggctctatgg gtacctctct   3300
ctctctctct ctctctctct ctctctctct ctctcggtac ctctctctct ctctctctct   3360
ctctctctct ctctctctct cggtaccagg tgctgaagaa ttgacccggt gaccaaaggt   3420
gccttttatc atcactttaa aaataaaaaa caattactca gtgcctgtta taagcagcaa   3480
ttaattatga ttgatgccta catcacaaca aaaactgatt taacaaatgg ttggtctgcc   3540
ttagaaagta tatttgaaca ttatcttgat tatattattg ataataataa aaaccttatc   3600
cctatccaag aagtgatgcc tatcattggt tggaatgaac ttgaaaaaaa ttagccttga   3660
atacattact ggtaaggtaa acgccattgt cagcaaattg atccaagaga accaacttaa   3720
agctttcctg acggaatgtt aattctcgtt gaccctgagc actgatgaat cccctaatga   3780
ttttggtaaa aatcattaag ttaaggtgga tacacatctt gtcatatgat cccggtaatg   3840
tgagttagct cactcattag gcaccccagg ctttacactt tatgcttccg gctcgtatgt   3900
tgtgtggaat tgtgagcgga taacaatttc acacaggaaa cagctatgac catgattacg   3960
ccaagcgcgc aattaaccct cactaaaggg aacaaaagct ggagctccac cgcggtggcg   4020
gccgctctag aactagtgga tcccccgggg aggtcagaat ggtttcttta ctgtttgtca   4080
attctattat ttcaatacag aacaatagct tctataactg aaatatattt gctattgtat   4140
attatgattg tccctcgaac catgaacact cctccagctg aatttcacaa ttcctctgtc   4200
atctgccagg ccattaagtt attcatggaa gatctttgag gaacactgca agttcatatc   4260
ataaacacat ttgaaattga gtattgtttt gcattgtatg gagctatgtt ttgctgtatc   4320
ctcagaaaaa aagtttgtta taaagcattc acacccataa aaagatagat ttaaatattc   4380
cagctatagg aaagaaagtg cgtctgctct tcactctagt ctcagttggc tccttcacat   4440
gcatgcttct ttatttctcc tattttgtca agaaaataat aggtcacgtc ttgttctcac   4500
ttatgtcctg cctagcatgg ctcagatgca cgttgtagat acaagaagga tcaaatgaaa   4560
cagacttctg gtctgttact acaaccatag taataagcac actaactaat aattgctaat   4620
tatgttttcc atctctaagg ttcccacatt tttctgtttt cttaaagatc ccattatctg   4680
gttgtaactg aagctcaatg gaacatgagc aatatttccc agtcttctct cccatccaac   4740
agtcctgatg gattagcaga acaggcagaa aacacattgt tacccagaat taaaaactaa   4800
tatttgctct ccattcaatc caaaatggac ctattgaaac taaaatctaa cccaatccca   4860
ttaaatgatt tctatggcgt caaaggtcaa acttctgaag ggaacctgtg ggtgggtcac   4920
aattcaggct atatattccc cagggctcag cggatccatg ggctccatcg gcgcagcaag   4980
catggaattt tgttttgatg tattcaagga gctcaaagtc caccatgcca atgagaacat   5040
cttctactgc cccattgcca tcatgtcagc tctagccatg gtatacctgg gtgcaaaaga   5100
cagcaccagg acacagataa ataaggttgt tcgctttgat aaacttccag gattcggaga   5160
cagtattgaa gctcagtgtg gcacatctgt aaacgttcac tcttcactta gagacatcct   5220
caaccaaatc accaaaccaa atgatgttta ttcgttcagc cttgccagta gactttatgc   5280
tgaagagaga tacccaatcc tgccagaata cttgcagtgt gtgaaggaac tgtatagagg   5340
aggcttggaa cctatcaact ttcaaacagc tgcagatcaa gccagagagc tcatcaattc   5400
ctgggtagaa agtcagacaa atggaattat cagaaatgtc cttcagccaa gctccgtgga   5460
ttctcaaact gcaatggttc tggttaatgc cattgtcttc aaaggactgt gggagaaaac   5520
atttaaggat gaagacacac aagcaatgcc tttcagagtg actgagcaag aaagcaaacc   5580
```

-continued

```
tgtgcagatg atgtaccaga ttggtttatt tagagtggca tcaatggctt ctgagaaaat   5640
gaagatcctg gagcttccat ttgccagtgg gacaatgagc atgttggtgc tgttgcctga   5700
tgaagtctca ggccttgagc agcttgagag tataatcaac tttgaaaaac tgactgaatg   5760
gaccagttct aatgttatgg aagagaggaa gatcaaagtg tacttacctc gcatgaagat   5820
ggaggaaaaa tacaacctca catctgtctt aatggctatg ggcattactg acgtgtttag   5880
ctcttcagcc aatctgtctg gcatctcctc agcagagagc ctgaagatat ctcaagctgt   5940
ccatgcagca catgcagaaa tcaatgaagc aggcagagag gtggtagggt cagcagaggc   6000
tggagtggat gctgcaagcg tctctgaaga atttagggct gaccatccat tcctcttctg   6060
tatcaagcac atcgcaacca acgccgttct cttctttggc agatgtgttt cccctccgcg   6120
gccagcagat gacgcaccag cagatgacgc accagcagat gacgcaccag cagatgacgc   6180
accagcagat gacgcaccag cagatgacgc aacaacatgt atcctgaaag gctcttgtgg   6240
ctggatcggc ctgctggatg acgatgacaa aaaatacaaa aaagcactga aaaaactggc   6300
aaaactgctg taatgagggc gcctggatcc agatcacttc tggctaataa aagatcagag   6360
ctctagagat ctgtgtgttg gttttttgtg gatctgctgt gccttctagt tgccagccat   6420
ctgttgtttg cccctccccc gtgccttcct tgaccctgga aggtgccact cccactgtcc   6480
tttcctaata aaatgaggaa attgcatcgc attgtctgag taggtgtcat tctattctgg   6540
ggggtggggt ggggcagcac agcaaggggg aggattggga agacaatagc aggcatgctg   6600
gggatgcggt gggctctatg ggtacctctc tctctctctc tctctctctc tctctctctc   6660
tctctcggta cctctctcga ggggggggcc cggtacccaat tcgccctata gtgagtcgta   6720
ttacgcgcgc tcactggccg tcgttttaca acgtcgtgac tgggaaaacc ctggcgttac   6780
ccaacttaat cgccttgcag cacatccccc tttcgccagc tggcgtaata gcgaagaggc   6840
ccgcaccgat cgcccttccc aacagttgcg cagcctgaat ggcgaatgga aattgtaagc   6900
gttaatattt tgttaaaatt cgcgttaaat ttttgttaaa tcagctcatt ttttaaccaa   6960
taggccgaaa tcggcaaaat cccttataaa tcaaaagaat agaccgagat agggttgagt   7020
gttgttccag tttggaacaa gagtccacta ttaaagaacg tggactccaa cgtcaaaggg   7080
cgaaaaaccg tctatcaggg cgatggccca ctactccggg atcatatgac aagatgtgta   7140
tccaccttaa cttaatgatt tttaccaaaa tcattagggg attcatcagt gctcagggtc   7200
aacgagaatt aacattccgt caggaaagct tatgatgatg atgtgcttaa aaacttactc   7260
aatggctggt tatgcatatc gcaatacatg cgaaaaacct aaaagagctt gccgataaaa   7320
aaggccaatt tattgctatt taccgcggct ttttattgag cttgaaagat aaataaaata   7380
gataggtttt atttgaagct aaatcttctt tatcgtaaaa aatgccctct tgggttatca   7440
agagggtcat tatatttcgc ggaataacat catttggtga cgaaataact aagcacttgt   7500
ctcctgttta ctcccctgag cttgaggggt taacatgaag gtcatcgata gcaggataat   7560
aatacagtaa aacgctaaac caataatcca aatccagcca tcccaaattg gtagtgaatg   7620
attataaata acagcaaaca gtaatgggcc aataacaccg gttgcattgg taaggctcac   7680
caataatccc tgtaaagcac cttgctgatg actctttgtt tggatagaca tcactccctg   7740
taatgcaggt aaagcgatcc caccaccagc caataaaatt aaaacaggga aaactaacca   7800
accttcagat ataaacgcta aaaaggcaaa tgcactacta tctgcaataa atccgagcag   7860
tactgccgtt ttttcgcccc atttagtggc tattcttcct gccacaaagg cttggaatac   7920
tgagtgtaaa agaccaagac ccgctaatga aaagccaacc atcatgctat tccatccaaa   7980
```

-continued

```
acgattttcg gtaaatagca cccacaccgt tgcgggaatt tggcctatca attgcgctga   8040
aaaataaata atcaacaaaa tggcatcgtt ttaaataaag tgatgtatac cgaattcagc   8100
ttttgttccc tttagtgagg gttaattgcg cgcttggcgt aatcatggtc atagctgttt   8160
cctgtgtgaa attgttatcc gctcacaatt ccacacaaca tacgagccgg aagcataaag   8220
tgtaaagcct ggggtgccta atgagtgagc taactcacat taattgcgtt gcgctcactg   8280
cccgctttcc agtcgggaaa cctgtcgtgc cagctgcatt aatgaatcgg ccaacgcgcg   8340
gggagaggcg gtttgcgtat tgggcgctct tccgcttcct cgctcactga ctcgctgcgc   8400
tcggtcgttc ggctgcggcg agcggtatca gctcactcaa aggcggtaat acggttatcc   8460
acagaatcag gggataacgc aggaaagaac atgtgagcaa aaggccagca aaaggccagg   8520
aaccgtaaaa aggccgcgtt gctggcgttt ttccataggc tccgcccccc tgacgagcat   8580
cacaaaaatc gacgctcaag tcagaggtgg cgaaacccga caggactata aagataccag   8640
gcgtttcccc ctggaagctc cctcgtgcgc tctcctgttc cgaccctgcc gcttaccgga   8700
tacctgtccg cctttctccc ttcgggaagc gtggcgcttt ctcatagctc acgctgtagg   8760
tatctcagtt cggtgtaggt cgttcgctcc aagctgggct gtgtgcacga accccccgtt   8820
cagcccgacc gctgcgcctt atccggtaac tatcgtcttg agtccaaccc ggtaagacac   8880
gacttatcgc cactggcagc agccactggt aacaggatta gcagagcgag gtatgtaggc   8940
ggtgctacag agttcttgaa gtggtggcct aactacggct acactagaag gacagtattt   9000
ggtatctgcg ctctgctgaa gccagttacc ttcggaaaaa gagttggtag ctcttgatcc   9060
ggcaaacaaa ccaccgctgg tagcggtggt ttttttgttt gcaagcagca gattacgcgc   9120
agaaaaaaag gatctcaaga agatcctttg atcttttcta cggggtctga cgctcagtgg   9180
aacgaaaact cacgttaagg gattttggtc atgagattat caaaaaggat cttcacctag   9240
atccttttaa attaaaaatg aagttttaaa tcaatctaaa gtatatatga gtaaacttgg   9300
tctgacagtt accaatgctt aatcagtgag gcacctatct cagcgatctg tctatttcgt   9360
tcatccatag ttgcctgact ccccgtcgtg tagataacta cgatacggga gggcttacca   9420
tctggcccca gtgctgcaat gataccgcga gacccacgct caccggctcc agatttatca   9480
gcaataaacc agccagccgg aagggccgag cgcagaagtg gtcctgcaac tttatccgcc   9540
tccatccagt ctattaattg ttgccgggaa gctagagtaa gtagttcgcc agttaatagt   9600
ttgcgcaacg ttgttgccat tgctacaggc atcgtggtgt cacgctcgtc gtttggtatg   9660
gcttcattca gctccggttc ccaacgatca aggcgagtta catgatcccc catgttgtgc   9720
aaaaaagcgg ttagctcctt cggtcctccg atcgttgtca gaagtaagtt ggccgcagtg   9780
ttatcactca tggttatggc agcactgcat aattctctta ctgtcatgcc atccgtaaga   9840
tgcttttctg tgactggtga gtactcaacc aagtcattct gagaatagtg tatgcggcga   9900
ccgagttgct cttgcccggc gtcaatacgg gataataccg cgccacatag cagaacttta   9960
aaagtgctca tcattggaaa acgttcttcg gggcgaaaac tctcaaggat cttaccgctg  10020
ttgagatcca gttcgatgta acccactcgt gcacccaact gatcttcagc atcttttact  10080
ttcaccagcg tttctgggtg agcaaaaaca ggaaggcaaa atgccgcaaa aaagggaata  10140
agggcgacac ggaaatgttg aatactcata ctcttccttt ttcaatatta ttgaagcatt  10200
tatcagggtt attgtctcat gagcggatac atatttgaat gtatttagaa aaataaacaa  10260
ataggggttc cgcgcacatt tccccgaaaa gtgccac                            10297
```

<210> SEQ ID NO 30
<211> LENGTH: 10272
<212> TYPE: DNA
<213> ORGANISM: Artificial Sequence
<220> FEATURE:
<223> OTHER INFORMATION: Synthetic

<400> SEQUENCE: 30

```
ctgacgcgcc ctgtagcggc gcattaagcg cggcgggtgt ggtggttacg cgcagcgtga     60
ccgctacact tgccagcgcc ctagcgcccg ctcctttcgc tttcttccct tcctttctcg    120
ccacgttcgc cggcatcaga ttggctattg gccattgcat acgttgtatc catatcataa    180
tatgtacatt tatattggct catgtccaac attaccgcca tgttgacatt gattattgac    240
tagttattaa tagtaatcaa ttacggggtc attagttcat agcccatata tggagttccg    300
cgttacataa cttacggtaa atggcccgcc tggctgaccg cccaacgacc cccgcccatt    360
gacgtcaata atgacgtatg ttcccatagt aacgccaata gggactttcc attgacgtca    420
atgggtggag tatttacggt aaactgccca cttggcagta catcaagtgt atcatatgcc    480
aagtacgccc cctattgacg tcaatgacgg taaatggccc gcctggcatt atgcccagta    540
catgacctta tgggactttc ctacttggca gtacatctac gtattagtca tcgctattac    600
catggtgatg cggttttggc agtacatcaa tgggcgtgga tagcggtttg actcacgggg    660
atttccaagt ctccacccca ttgacgtcaa tgggagtttg ttttggcacc aaaatcaacg    720
ggactttcca aaatgtcgta acaactccgc cccattgacg caaatgggcg gtaggcgtgt    780
acggtgggag gtctatataa gcagagctcg tttagtgaac cgtcagatcg cctggagacg    840
ccatccacgc tgttttgacc tccatagaag acaccgggac cgatccagcc tccgcggccg    900
ggaacggtgc attggaacgc ggattccccg tgccaagagt gacgtaagta ccgcctatag    960
actctatagg cacacccctt tggctcttat gcatgctata ctgtttttgg cttggggcct   1020
atacaccccc gcttccttat gctataggtg atggtatagc ttagcctata ggtgtgggtt   1080
attgaccatt attgaccact cccctattgg tgacgatact ttccattact aatccataac   1140
atggctcttt gccacaacta tctctattgg ctatatgcca atactctgtc cttcagagac   1200
tgacacggac tctgtatttt tacaggatgg ggtcccattt attatttaca aattcacata   1260
tacaacaacg ccgtcccccg tgcccgcagt ttttattaaa catagcgtgg gatctccacg   1320
cgaatctcgg gtacgtgttc cggacatggg ctcttctccg gtagcggcgg agcttccaca   1380
tccgagccct ggtcccatgc ctccagcggc tcatggtcgc tcggcagctc cttgctccta   1440
acagtggagg ccagacttag gcacagcaca atgcccacca ccaccagtgt gccgcacaag   1500
gccgtggcgg tagggtatgt gtctgaaaat gagcgtggag attgggctcg cacggctgac   1560
gcagatggaa gacttaaggc agcggcagaa gaagatgcag gcagctgagt tgttgtattc   1620
tgataagagt cagaggtaac tcccgttgcg gtgctgttaa cggtggaggg cagtgtagtc   1680
tgagcagtac tcgttgctgc cgcgcgcgcc accagacata atagctgaca gactaacaga   1740
ctgttccttt ccatgggtct tttctgcagt caccgtcgga ccatgtgtga acttgatatt   1800
ttacatgatt ctctttacca attctgcccc gaattacact taaaacgact caacagctta   1860
acgttggctt gccacgcatt acttgactgt aaaactctca ctcttaccga acttggccgt   1920
aacctgccaa ccaaagcgag aacaaaacat aacatcaaac gaatcgaccg attgttaggt   1980
aatcgtcacc tccacaaaga gcgactcgct gtataccgtt ggcatgctag ctttatctgt   2040
tcgggaatac gatgcccatt gtacttgttg actggtctga tattcgtgag caaaaacgac   2100
```

```
ttatggtatt gcgagcttca gtcgcactac acggtcgttc tgttactctt tatgagaaag   2160
cgttcccgct ttcagagcaa tgttcaaaga aagctcatga ccaatttcta gccgaccttg   2220
cgagcattct accgagtaac accacaccgc tcattgtcag tgatgctggc tttaaagtgc   2280
catggtataa atccgttgag aagctgggtt ggtactggtt aagtcgagta agaggaaaag   2340
tacaatatgc agacctagga gcggaaaact ggaaacctat cagcaactta catgatatgt   2400
catctagtca ctcaaagact ttaggctata agaggctgac taaaagcaat ccaatctcat   2460
gccaaattct attgtataaa tctcgctcta aaggccgaaa aaatcagcgc tcgacacgga   2520
ctcattgtca ccacccgtca cctaaaatct actcagcgtc ggcaaaggag ccatgggttc   2580
tagcaactaa cttacctgtt gaaattcgaa cacccaaaca acttgttaat atctattcga   2640
agcgaatgca gattgaagaa accttccgag acttgaaaag tcctgcctac ggactaggcc   2700
tacgccatag ccgaacgagc agctcagagc gttttgatat catgctgcta atcgccctga   2760
tgcttcaact aacatgttgg cttgcgggcg ttcatgctca gaaacaaggt tgggacaagc   2820
acttccaggc taacacagtc agaaatcgaa acgtactctc aacagttcgc ttaggcatgg   2880
aagttttgcg gcattctggc tacacaataa caagggaaga cttactcgtg gctgcaaccc   2940
tactagctca aaatttattc acacatggtt acgctttggg gaaattatga taatgatcca   3000
gatcacttct ggctaataaa agatcagagc tctagagatc tgtgtgttgg ttttttgtgg   3060
atctgctgtg ccttctagtt gccagccatc tgttgtttgc ccctcccccg tgccttcctt   3120
gaccctggaa ggtgccactc ccactgtcct ttcctaataa aatgaggaaa ttgcatcgca   3180
ttgtctgagt aggtgtcatt ctattctggg gggtggggtg gggcagcaca gcaaggggga   3240
ggattgggaa gacaatagca ggcatgctgg ggatgcggtg ggctctatgg gtacctctct   3300
ctctctctct ctctctctct ctctctctct ctctcggtac ctctctctct ctctctctct   3360
ctctctctct ctctctctct cggtaccagg tgctgaagaa ttgacccggt gaccaaaggt   3420
gccttttatc atcactttaa aaataaaaaa caattactca gtgcctgtta taagcagcaa   3480
ttaattatga ttgatgccta catcacaaca aaaactgatt taacaaatgg ttggtctgcc   3540
ttagaaagta tatttgaaca ttatcttgat tatattattg ataataataa aaaccttatc   3600
cctatccaag aagtgatgcc tatcattggt tggaatgaac ttgaaaaaaa ttagccttga   3660
atacattact ggtaaggtaa acgccattgt cagcaaattg atccaagaga accaacttaa   3720
agctttcctg acggaatgtt aattctcgtt gaccctgagc actgatgaat cccctaatga   3780
ttttggtaaa aatcattaag ttaaggtgga tacacatctt gtcatatgat cccggtaatg   3840
tgagttagct cactcattag gcaccccagg ctttacactt tatgcttccg gctcgtatgt   3900
tgtgtggaat tgtgagcgga taacaatttc acacaggaaa cagctatgac catgattacg   3960
ccaagcgcgc aattaaccct cactaaaggg aacaaaagct ggagctccac cgcggtggcg   4020
gccgctctag aactagtgga tcccccgggg aggtcagaat ggtttcttta ctgtttgtca   4080
attctattat ttcaatacag aacaaaagct tctataactg aaatatattt gctattgtat   4140
attatgattg tccctcgaac catgaacact cctccagctg aatttcacaa ttcctctgtc   4200
atctgccagg ctggaagatc atggaagatc tctgaggaac attgcaagtt cataccataa   4260
actcatttgg aattgagtat tattttgctt tgaatggagc tatgttttgc agttccctca   4320
gaagaaaagc ttgttataaa gcgtctacac ccatcaaaag atatatttaa atattccaac   4380
tacagaaaga ttttgtctgc tcttcactct gatctcagtt ggtttcttca cgtacatgct   4440
```

-continued

```
tctttatttg cctattttgt caagaaaata ataggtcaag tcctgttctc acttatctcc   4500
tgcctagcat ggcttagatg cacgttgtac attcaagaag gatcaaatga aacagacttc   4560
tggtctgtta caacaaccat agtaataaac agactaacta ataattgcta attatgtttt   4620
ccatctctaa ggttcccaca tttttctgtt ttaagatccc attatctggt tgtaactgaa   4680
gctcaatgga acatgaacag tatttctcag tcttttctcc agcaatcctg acggattaga   4740
agaactggca gaaaacactt tgttacccag aattaaaaac taatatttgc tctcccttca   4800
atccaaaatg gacctattga aactaaaatc tgacccaatc ccattaaatt atttctatgg   4860
cgtcaaaggt caaacttttg aagggaacct gtgggtgggt cccaattcag gctatatatt   4920
ccccagggct cagccagtgg atccatgggc tccatcggtg cagcaagcat ggaattttgt   4980
tttgatgtat tcaaggagct caaagtccac catgccaatg acaacatgct ctactccccc   5040
tttgccatct tgtcaactct ggccatggtc ttcctaggtg caaaagacag caccaggacc   5100
cagataaata aggttgttca ctttgataaa cttccaggat tcggagacag tattgaagct   5160
cagtgtggca catctgtaaa tgttcactct tcacttagag acatactcaa ccaaatcacc   5220
aaacaaaatg atgcttattc gttcagcctt gccagtagac tttatgctca agagacatac   5280
acagtcgtgc cggaatactt gcaatgtgtg aaggaactgt atagaggagg cttagaatcc   5340
gtcaactttc aaacagctgc agatcaagcc agaggcctca tcaatgcctg ggtagaaagt   5400
cagacaaacg gaattatcag aaacatcctt cagccaagct ccgtggattc tcaaactgca   5460
atggtcctgg ttaatgccat tgccttcaag ggactgtggg agaaagcatt taaggctgaa   5520
gacacgcaaa caataccttt cagagtgact gagcaagaaa gcaaacctgt gcagatgatg   5580
taccagattg gttcatttaa agtggcatca atggcttctg agaaaatgaa gatcctggag   5640
cttccatttg ccagtggaac aatgagcatg ttggtgctgt tgcctgatga tgtctcaggc   5700
cttgagcagc ttgagagtat aatcagcttt gaaaaactga ctgaatggac cagttctagt   5760
attatggaag agaggaaggt caaagtgtac ttacctcgca tgaagatgga ggagaaatac   5820
aacctcacat ctctcttaat ggctatggga attactgacc tgttcagctc ttcagccaat   5880
ctgtctggca tctcctcagt agggagcctg aagatatctc aagctgtcca tgcagcacat   5940
gcagaaatca atgaagcggg cagagatgtg gtaggctcag cagaggctgg agtggatgct   6000
actgaagaat ttagggctga ccatccattc ctcttctgtg tcaagcacat cgaaaccaac   6060
gccattctcc tctttggcag atgtgtttct ccgcggccag cagatgacgc accagcagat   6120
gacgcaccag cagatgacgc accagcagat gacgcaccag cagatgacgc accagcagat   6180
gacgcaacaa catgtatcct gaaaggctct tgtggctgga tcggcctgct ggatgacgat   6240
gacaaaaaat acaaaaaagc actgaaaaaa ctggcaaaac tgctgtaatg agggcgcctg   6300
gatccagatc acttctggct aataaaagat cagagctcta gagatctgtg tgttggtttt   6360
ttgtggatct gctgtgcctt ctagttgcca gccatctgtt gtttgcccct cccccgtgcc   6420
ttccttgacc ctggaaggtg ccactcccac tgtcctttcc taataaaatg aggaaattgc   6480
atcgcattgt ctgagtaggt gtcattctat tctggggggt ggggtggggc agcacagcaa   6540
gggggaggat tgggaagaca atagcaggca tgctggggat gcggtgggct ctatgggtac   6600
ctctctctct ctctctctct ctctctctct ctctctctct cggtacctct ctcgaggggg   6660
ggcccggtac ccaattcgcc ctatagtgag tcgtattacg cgcgctcact ggccgtcgtt   6720
ttacaacgtc gtgactggga aaaccctggc gttacccaac ttaatcgcct tgcagcacat   6780
ccccctttcg ccagctggcg taatagcgaa gaggcccgca ccgatcgccc ttcccaacag   6840
```

```
ttgcgcagcc tgaatggcga atggaaattg taagcgttaa tattttgtta aaattcgcgt   6900
taaatttttg ttaaatcagc tcatttttta accaataggc cgaaatcggc aaaatccctt   6960
ataaatcaaa agaatagacc gagatagggt tgagtgttgt tccagtttgg aacaagagtc   7020
cactattaaa gaacgtggac tccaacgtca aagggcgaaa aaccgtctat cagggcgatg   7080
gcccactact ccgggatcat atgacaagat gtgtatccac cttaacttaa tgatttttac   7140
caaaatcatt aggggattca tcagtgctca gggtcaacga gaattaacat tccgtcagga   7200
aagcttatga tgatgatgtg cttaaaaact tactcaatgg ctggttatgc atatcgcaat   7260
acatgcgaaa aacctaaaag agcttgccga taaaaaaggc caatttattg ctatttaccg   7320
cggcttttta ttgagcttga aagataaata aaatagatag gttttatttg aagctaaatc   7380
ttctttatcg taaaaaatgc cctcttgggt tatcaagagg gtcattatat ttcgcggaat   7440
aacatcattt ggtgacgaaa taactaagca cttgtctcct gtttactccc ctgagcttga   7500
ggggttaaca tgaaggtcat cgatagcagg ataataatac agtaaaacgc taaaccaata   7560
atccaaatcc agccatccca aattggtagt gaatgattat aaataacagc aaacagtaat   7620
gggccaataa caccggttgc attggtaagg ctcaccaata atccctgtaa agcaccttgc   7680
tgatgactct ttgtttggat agacatcact ccctgtaatg caggtaaagc gatcccacca   7740
ccagccaata aaattaaaac agggaaaact aaccaacctt cagatataaa cgctaaaaag   7800
gcaaatgcac tactatctgc aataaatccg agcagtactg ccgttttttc gccccattta   7860
gtggctattc ttcctgccac aaaggcttgg aatactgagt gtaaaagacc aagacccgct   7920
aatgaaaagc caaccatcat gctattccat ccaaaacgat ttcggtaaa tagcacccac   7980
accgttgcgg gaatttggcc tatcaattgc gctgaaaaat aaataatcaa caaaatggca   8040
tcgttttaaa taaagtgatg tataccgaat tcagcttttg ttccctttag tgagggttaa   8100
ttgcgcgctt ggcgtaatca tggtcatagc tgtttcctgt gtgaaattgt tatccgctca   8160
caattccaca caacatacga gccggaagca taaagtgtaa agcctggggt gcctaatgag   8220
tgagctaact cacattaatt gcgttgcgct cactgcccgc tttccagtcg ggaaacctgt   8280
cgtgccagct gcattaatga atcggccaac gcgcggggag aggcggtttg cgtattgggc   8340
gctcttccgc ttcctcgctc actgactcgc tgcgctcggt cgttcggctg cggcgagcgg   8400
tatcagctca ctcaaaggcg gtaatacggt tatccacaga atcaggggat aacgcaggaa   8460
agaacatgtg agcaaaaggc cagcaaaagg ccaggaaccg taaaaaggcc gcgttgctgg   8520
cgtttttcca taggctccgc ccccctgacg agcatcacaa aaatcgacgc tcaagtcaga   8580
ggtggcgaaa cccgacagga ctataaagat accaggcgtt tccccctgga agctccctcg   8640
tgcgctctcc tgttccgacc ctgccgctta ccggatacct gtccgccttt ctcccttcgg   8700
gaagcgtggc gctttctcat agctcacgct gtaggtatct cagttcggtg taggtcgttc   8760
gctccaagct gggctgtgtg cacgaacccc ccgttcagcc cgaccgctgc gccttatccg   8820
gtaactatcg tcttgagtcc aacccggtaa gacacgactt atcgccactg gcagcagcca   8880
ctggtaacag gattagcaga gcgaggtatg taggcggtgc tacagagttc ttgaagtggt   8940
ggcctaacta cggctacact agaaggacag tatttggtat ctgcgctctg ctgaagccag   9000
ttaccttcgg aaaaagagtt ggtagctctt gatccggcaa acaaaccacc gctggtagcg   9060
gtggtttttt tgtttgcaag cagcagatta cgcgcagaaa aaaaggatct caagaagatc   9120
ctttgatctt ttctacgggg tctgacgctc agtggaacga aaactcacgt taagggattt   9180
```

-continued

```
tggtcatgag attatcaaaa aggatcttca cctagatcct tttaaattaa aaatgaagtt   9240
ttaaatcaat ctaaagtata tatgagtaaa cttggtctga cagttaccaa tgcttaatca   9300
gtgaggcacc tatctcagcg atctgtctat ttcgttcatc catagttgcc tgactccccg   9360
tcgtgtagat aactacgata cgggagggct taccatctgg ccccagtgct gcaatgatac   9420
cgcgagaccc acgctcaccg gctccagatt tatcagcaat aaaccagcca gccggaaggg   9480
ccgagcgcag aagtggtcct gcaactttat ccgcctccat ccagtctatt aattgttgcc   9540
gggaagctag agtaagtagt tcgccagtta atagtttgcg caacgttgtt gccattgcta   9600
caggcatcgt ggtgtcacgc tcgtcgtttg gtatggcttc attcagctcc ggttcccaac   9660
gatcaaggcg agttacatga tcccccatgt tgtgcaaaaa agcggttagc tccttcggtc   9720
ctccgatcgt tgtcagaagt aagttggccg cagtgttatc actcatggtt atggcagcac   9780
tgcataattc tcttactgtc atgccatccg taagatgctt ttctgtgact ggtgagtact   9840
caaccaagtc attctgagaa tagtgtatgc ggcgaccgag ttgctcttgc ccggcgtcaa   9900
tacgggataa taccgcgcca catagcagaa ctttaaaagt gctcatcatt ggaaaacgtt   9960
cttcggggcg aaaactctca aggatcttac cgctgttgag atccagttcg atgtaaccca  10020
ctcgtgcacc caactgatct tcagcatctt ttactttcac cagcgtttct gggtgagcaa  10080
aaacaggaag gcaaaatgcc gcaaaaaagg gaataagggc gacacggaaa tgttgaatac  10140
tcatactctt cctttttcaa tattattgaa gcatttatca gggttattgt ctcatgagcg  10200
gatacatatt tgaatgtatt tagaaaaata aacaaatagg ggttccgcgc acatttcccc  10260
gaaaagtgcc ac                                                      10272
```

<210> SEQ ID NO 31
<211> LENGTH: 10512
<212> TYPE: DNA
<213> ORGANISM: Artificial Sequence
<220> FEATURE:
<223> OTHER INFORMATION: Synthetic

<400> SEQUENCE: 31

```
ctgacgcgcc ctgtagcggc gcattaagcg cggcgggtgt ggtggttacg cgcagcgtga     60
ccgctacact tgccagcgcc ctagcgcccg ctcctttcgc tttcttccct tcctttctcg    120
ccacgttcgc cggcatcaga ttggctattg gccattgcat acgttgtatc catatcataa    180
tatgtacatt tatattggct catgtccaac attaccgcca tgttgacatt gattattgac    240
tagttattaa tagtaatcaa ttacggggtc attagttcat agcccatata tggagttccg    300
cgttacataa cttacggtaa atggcccgcc tggctgaccg cccaacgacc cccgcccatt    360
gacgtcaata atgacgtatg ttcccatagt aacgccaata gggactttcc attgacgtca    420
atgggtggag tatttacggt aaactgccca cttggcagta catcaagtgt atcatatgcc    480
aagtacgccc cctattgacg tcaatgacgg taaatggccc gcctggcatt atgcccagta    540
catgacctta tgggactttc ctacttggca gtacatctac gtattagtca tcgctattac    600
catggtgatg cggttttggc agtacatcaa tgggcgtgga tagcggtttg actcacgggg    660
atttccaagt ctccacccca ttgacgtcaa tgggagtttg ttttggcacc aaaatcaacg    720
ggactttcca aaatgtcgta acaactccgc cccattgacg caaatgggcg gtaggcgtgt    780
acggtgggag gtctatataa gcagagctcg tttagtgaac cgtcagatcg cctggagacg    840
ccatccacgc tgttttgacc tccatagaag acaccgggac cgatccagcc tccgcggccg    900
ggaacggtgc attggaacgc ggattccccg tgccaagagt gacgtaagta ccgcctatag    960
```

-continued

```
actctatagg cacacccctt tggctcttat gcatgctata ctgtttttgg cttggggcct   1020
atacaccccc gcttccttat gctataggtg atggtatagc ttagcctata ggtgtgggtt   1080
attgaccatt attgaccact cccctattgg tgacgatact ttccattact aatccataac   1140
atggctcttt gccacaacta tctctattgg ctatatgcca atactctgtc cttcagagac   1200
tgacacggac tctgtatttt tacaggatgg ggtcccattt attatttaca aattcacata   1260
tacaacaacg ccgtcccccg tgcccgcagt ttttattaaa catagcgtgg gatctccacg   1320
cgaatctcgg gtacgtgttc cggacatggg ctcttctccg gtagcggcgg agcttccaca   1380
tccgagccct ggtcccatgc ctccagcggc tcatggtcgc tcggcagctc cttgctccta   1440
acagtggagg ccagacttag gcacagcaca atgcccacca ccaccagtgt gccgcacaag   1500
gccgtggcgg tagggtatgt gtctgaaaat gagcgtggag attgggctcg cacggctgac   1560
gcagatggaa gacttaaggc agcggcagaa gaagatgcag gcagctgagt tgttgtattc   1620
tgataagagt cagaggtaac tcccgttgcg gtgctgttaa cggtggaggg cagtgtagtc   1680
tgagcagtac tcgttgctgc cgcgcgcgcc accagacata atagctgaca gactaacaga   1740
ctgttccttt ccatgggtct tttctgcagt caccgtcgga ccatgtgtga acttgatatt   1800
ttacatgatt ctctttacca attctgcccc gaattacact taaaacgact caacagctta   1860
acgttggctt gccacgcatt acttgactgt aaaactctca ctcttaccga acttggccgt   1920
aacctgccaa ccaaagcgag aacaaaacat aacatcaaac gaatcgaccg attgttaggt   1980
aatcgtcacc tccacaaaga gcgactcgct gtataccgtt ggcatgctag ctttatctgt   2040
tcgggaatac gatgcccatt gtacttgttg actggtctga tattcgtgag caaaaacgac   2100
ttatggtatt gcgagcttca gtcgcactac acggtcgttc tgttactctt tatgagaaag   2160
cgttcccgct ttcagagcaa tgttcaaaga aagctcatga ccaatttcta gccgaccttg   2220
cgagcattct accgagtaac accacaccgc tcattgtcag tgatgctggc tttaaagtgc   2280
catggtataa atccgttgag aagctgggtt ggtactggtt aagtcgagta agaggaaaag   2340
tacaatatgc agacctagga gcggaaaact ggaaacctat cagcaactta catgatatgt   2400
catctagtca ctcaaagact ttaggctata agaggctgac taaaagcaat ccaatctcat   2460
gccaaattct attgtataaa tctcgctcta aaggccgaaa aaatcagcgc tcgacacgga   2520
ctcattgtca ccacccgtca cctaaaatct actcagcgtc ggcaaaggag ccatgggttc   2580
tagcaactaa cttacctgtt gaaattcgaa cacccaaaca acttgttaat atctattcga   2640
agcgaatgca gattgaagaa accttccgag acttgaaaag tcctgcctac ggactaggcc   2700
tacgccatag ccgaacgagc agctcagagc gttttgatat catgctgcta atcgccctga   2760
tgcttcaact aacatgttgg cttgcgggcg ttcatgctca gaaacaaggt tgggacaagc   2820
acttccaggc taacacagtc agaaatcgaa acgtactctc aacagttcgc ttaggcatgg   2880
aagttttgcg gcattctggc tacacaataa caagggaaga cttactcgtg gctgcaaccc   2940
tactagctca aaatttattc acacatggtt acgctttggg gaaattatga taatgatcca   3000
gatcacttct ggctaataaa agatcagagc tctagagatc tgtgtgttgg tttttttgtgg   3060
atctgctgtg ccttctagtt gccagccatc tgttgtttgc ccctcccccg tgccttcctt   3120
gaccctggaa ggtgccactc ccactgtcct ttcctaataa aatgaggaaa ttgcatcgca   3180
ttgtctgagt aggtgtcatt ctattctggg gggtggggtg gggcagcaca gcaaggggga   3240
ggattgggaa gacaatagca ggcatgctgg ggatgcggtg ggctctatgg gtacctctct   3300
```

-continued

```
ctctctctct ctctctctct ctctctctct ctctcggtac ctctctctct ctctctctct   3360
ctctctctct ctctctctct cggtaccagg tgctgaagaa ttgacccggt gaccaaaggt   3420
gccttttatc atcactttaa aaataaaaaa caattactca gtgcctgtta taagcagcaa   3480
ttaattatga ttgatgccta catcacaaca aaaactgatt taacaaatgg ttggtctgcc   3540
ttagaaagta tatttgaaca ttatcttgat tatattattg ataataataa aaaccttatc   3600
cctatccaag aagtgatgcc tatcattggt tggaatgaac ttgaaaaaaa ttagccttga   3660
atacattact ggtaaggtaa acgccattgt cagcaaattg atccaagaga accaacttaa   3720
agctttcctg acggaatgtt aattctcgtt gaccctgagc actgatgaat cccctaatga   3780
ttttggtaaa aatcattaag ttaaggtgga tacacatctt gtcatatgat cccggtaatg   3840
tgagttagct cactcattag gcaccccagg ctttacactt tatgcttccg gctcgtatgt   3900
tgtgtggaat tgtgagcgga taacaatttc acacaggaaa cagctatgac catgattacg   3960
ccaagcgcgc aattaaccct cactaaaggg aacaaaagct ggagctccac cgcggtggcg   4020
gccgctctag aactagtgga tcccccgggg aggtcagaat ggtttcttta ctgtttgtca   4080
attctattat ttcaatacag aacaatagct tctataactg aaatatattt gctattgtat   4140
attatgattg tccctcgaac catgaacact cctccagctg aatttcacaa ttcctctgtc   4200
atctgccagg ccattaagtt attcatggaa gatctttgag gaacactgca agttcatatc   4260
ataaacacat ttgaaattga gtattgtttt gcattgtatg gagctatgtt ttgctgtatc   4320
ctcagaaaaa aagtttgtta taaagcattc acacccataa aaagatagat ttaaatattc   4380
cagctatagg aaagaaagtg cgtctgctct tcactctagt ctcagttggc tccttcacat   4440
gcatgcttct ttatttctcc tattttgtca agaaaataat aggtcacgtc ttgttctcac   4500
ttatgtcctg cctagcatgg ctcagatgca cgttgtagat acaagaagga tcaaatgaaa   4560
cagacttctg gtctgttact acaaccatag taataagcac actaactaat aattgctaat   4620
tatgttttcc atctctaagg ttcccacatt tttctgtttt cttaaagatc ccattatctg   4680
gttgtaactg aagctcaatg gaacatgagc aatatttccc agtcttctct cccatccaac   4740
agtcctgatg gattagcaga acaggcagaa aacacattgt tacccagaat taaaaactaa   4800
tatttgctct ccattcaatc caaaatggac ctattgaaac taaaatctaa cccaatccca   4860
ttaaatgatt tctatggcgt caaaggtcaa acttctgaag ggaacctgtg ggtgggtcac   4920
aattcaggct atatattccc cagggctcag cggatccatg ggctccatcg gcgcagcaag   4980
catggaattt tgttttgatg tattcaagga gctcaaagtc caccatgcca atgagaacat   5040
cttctactgc cccattgcca tcatgtcagc tctagccatg gtatacctgg gtgcaaaaga   5100
cagcaccagg acacagataa ataaggttgt tcgctttgat aaacttccag gattcggaga   5160
cagtattgaa gctcagtgtg gcacatctgt aaacgttcac tcttcactta gagacatcct   5220
caaccaaatc accaaaccaa atgatgttta ttcgttcagc cttgccagta gactttatgc   5280
tgaagagaga tacccaatcc tgccagaata cttgcagtgt gtgaaggaac tgtatagagg   5340
aggcttggaa cctatcaact ttcaaacagc tgcagatcaa gccagagagc tcatcaattc   5400
ctgggtagaa agtcagacaa atggaattat cagaaatgtc cttcagccaa gctccgtgga   5460
ttctcaaact gcaatggttc tggttaatgc cattgtcttc aaaggactgt gggagaaaac   5520
atttaaggat gaagacacac aagcaatgcc tttcagagtg actgagcaag aaagcaaacc   5580
tgtgcagatg atgtaccaga ttggtttatt tagagtggca tcaatggctt ctgagaaaat   5640
gaagatcctg gagcttccat ttgccagtgg gacaatgagc atgttggtgc tgttgcctga   5700
```

-continued

```
tgaagtctca ggccttgagc agcttgagag tataatcaac tttgaaaaac tgactgaatg   5760
gaccagttct aatgttatgg aagagaggaa gatcaaagtg tacttacctc gcatgaagat   5820
ggaggaaaaa tacaacctca catctgtctt aatggctatg ggcattactg acgtgtttag   5880
ctcttcagcc aatctgtctg gcatctcctc agcagagagc ctgaagatat ctcaagctgt   5940
ccatgcagca catgcagaaa tcaatgaagc aggcagagag gtggtagggt cagcagaggc   6000
tggagtggat gctgcaagcg tctctgaaga atttagggct gaccatccat tcctcttctg   6060
tatcaagcac atcgcaacca acgccgttct cttctttggc agatgtgttt cccctccgcg   6120
gccagcagat gacgcaccag cagatgacgc accagcagat gacgcaccag cagatgacgc   6180
accagcagat gacgcaccag cagatgacgc aacaacatgt atcctgaaag gctcttgtgg   6240
ctggatcggc ctgctggatg acgatgacaa atttgtgaac caacacctgt gcggctcaca   6300
cctggtggaa gctctctacc tagtgtgcgg ggaacgaggc ttcttctaca cacccaagac   6360
ccgccgggag gcagaggacc tgcaggtggg gcaggtggag ctgggcgggg gccctggtgc   6420
aggcagcctg cagcccttgg ccctggaggg gtccctgcag aagcgtggca ttgtggaaca   6480
atgctgtacc agcatctgct ccctctacca gctggagaac tactgcaact agggcgcctg   6540
gatccagatc acttctggct aataaaagat cagagctcta gagatctgtg tgttggtttt   6600
ttgtggatct gctgtgcctt ctagttgcca gccatctgtt gtttgcccct cccccgtgcc   6660
ttccttgacc ctggaaggtg ccactcccac tgtcctttcc taataaaatg aggaaattgc   6720
atcgcattgt ctgagtaggt gtcattctat tctggggggt ggggtggggc agcacagcaa   6780
gggggaggat tgggaagaca atagcaggca tgctggggat gcggtgggct ctatgggtac   6840
ctctctctct ctctctctct ctctctctct ctctctctct cggtacctct ctcgaggggg   6900
ggcccggtac ccaattcgcc ctatagtgag tcgtattacg cgcgctcact ggccgtcgtt   6960
ttacaacgtc gtgactggga aaaccctggc gttacccaac ttaatcgcct tgcagcacat   7020
ccccctttcg ccagctggcg taatagcgaa gaggcccgca ccgatcgccc ttcccaacag   7080
ttgcgcagcc tgaatggcga atggaaattg taagcgttaa tattttgtta aaattcgcgt   7140
taaatttttg ttaaatcagc tcatttttta accaataggc cgaaatcggc aaaatccctt   7200
ataaatcaaa agaatagacc gagatagggt tgagtgttgt tccagtttgg aacaagagtc   7260
cactattaaa gaacgtggac tccaacgtca aagggcgaaa aaccgtctat cagggcgatg   7320
gcccactact ccgggatcat atgacaagat gtgtatccac cttaacttaa tgatttttac   7380
caaaatcatt aggggattca tcagtgctca gggtcaacga gaattaacat tccgtcagga   7440
aagcttatga tgatgatgtg cttaaaaact tactcaatgg ctggttatgc atatcgcaat   7500
acatgcgaaa aacctaaaag agcttgccga taaaaaaggc caatttattg ctatttaccg   7560
cggcttttta ttgagcttga aagataaata aaatagatag gttttatttg aagctaaatc   7620
ttctttatcg taaaaaatgc cctcttgggt tatcaagagg gtcattatat ttcgcggaat   7680
aacatcattt ggtgacgaaa taactaagca cttgtctcct gtttactccc ctgagcttga   7740
ggggttaaca tgaaggtcat cgatagcagg ataataatac agtaaaacgc taaaccaata   7800
atccaaatcc agccatccca aattggtagt gaatgattat aaataacagc aaacagtaat   7860
gggccaataa caccggttgc attggtaagg ctcaccaata atccctgtaa agcaccttgc   7920
tgatgactct ttgtttggat agacatcact ccctgtaatg caggtaaagc gatcccacca   7980
ccagccaata aaattaaaac agggaaaact aaccaacctt cagatataaa cgctaaaaag   8040
```

-continued

```
gcaaatgcac tactatctgc aataaatccg agcagtactg ccgtttttttc gccccattta   8100
gtggctattc ttcctgccac aaaggcttgg aatactgagt gtaaaagacc aagacccgct   8160
aatgaaaagc caaccatcat gctattccat ccaaaacgat tttcggtaaa tagcacccac   8220
accgttgcgg gaatttggcc tatcaattgc gctgaaaaat aaataatcaa caaaatggca   8280
tcgttttaaa taaagtgatg tataccgaat tcagcttttg ttccctttag tgagggttaa   8340
ttgcgcgctt ggcgtaatca tggtcatagc tgtttcctgt gtgaaattgt tatccgctca   8400
caattccaca caacatacga gccggaagca taaagtgtaa agcctggggt gcctaatgag   8460
tgagctaact cacattaatt gcgttgcgct cactgcccgc tttccagtcg ggaaacctgt   8520
cgtgccagct gcattaatga atcggccaac gcgcggggag aggcggtttg cgtattgggc   8580
gctcttccgc ttcctcgctc actgactcgc tgcgctcggt cgttcggctg cggcgagcgg   8640
tatcagctca ctcaaaggcg gtaatacggt tatccacaga atcaggggat aacgcaggaa   8700
agaacatgtg agcaaaaggc cagcaaaagg ccaggaaccg taaaaaggcc gcgttgctgg   8760
cgtttttcca taggctccgc ccccctgacg agcatcacaa aaatcgacgc tcaagtcaga   8820
ggtggcgaaa cccgacagga ctataaagat accaggcgtt tccccctgga agctccctcg   8880
tgcgctctcc tgttccgacc ctgccgctta ccggatacct gtccgccttt ctcccttcgg   8940
gaagcgtggc gctttctcat agctcacgct gtaggtatct cagttcggtg taggtcgttc   9000
gctccaagct gggctgtgtg cacgaacccc ccgttcagcc cgaccgctgc gccttatccg   9060
gtaactatcg tcttgagtcc aacccggtaa gacacgactt atcgccactg gcagcagcca   9120
ctggtaacag gattagcaga gcgaggtatg taggcggtgc tacagagttc ttgaagtggt   9180
ggcctaacta cggctacact agaaggacag tatttggtat ctgcgctctg ctgaagccag   9240
ttaccttcgg aaaaagagtt ggtagctctt gatccggcaa acaaaccacc gctggtagcg   9300
gtggtttttt tgtttgcaag cagcagatta cgcgcagaaa aaaaggatct caagaagatc   9360
ctttgatctt ttctacgggg tctgacgctc agtggaacga aaactcacgt taagggattt   9420
tggtcatgag attatcaaaa aggatcttca cctagatcct tttaaattaa aaatgaagtt   9480
ttaaatcaat ctaaagtata tatgagtaaa cttggtctga cagttaccaa tgcttaatca   9540
gtgaggcacc tatctcagcg atctgtctat ttcgttcatc catagttgcc tgactccccg   9600
tcgtgtagat aactacgata cgggagggct taccatctgg ccccagtgct gcaatgatac   9660
cgcgagaccc acgctcaccg gctccagatt tatcagcaat aaaccagcca gccggaaggg   9720
ccgagcgcag aagtggtcct gcaactttat ccgcctccat ccagtctatt aattgttgcc   9780
gggaagctag agtaagtagt tcgccagtta atagtttgcg caacgttgtt gccattgcta   9840
caggcatcgt ggtgtcacgc tcgtcgtttg gtatggcttc attcagctcc ggttcccaac   9900
gatcaaggcg agttacatga tcccccatgt tgtgcaaaaa agcggttagc tccttcggtc   9960
ctccgatcgt tgtcagaagt aagttggccg cagtgttatc actcatggtt atggcagcac   10020
tgcataattc tcttactgtc atgccatccg taagatgctt ttctgtgact ggtgagtact   10080
caaccaagtc attctgagaa tagtgtatgc ggcgaccgag ttgctcttgc ccggcgtcaa   10140
tacgggataa taccgcgcca catagcagaa ctttaaaagt gctcatcatt ggaaaacgtt   10200
cttcggggcg aaaactctca aggatcttac cgctgttgag atccagttcg atgtaaccca   10260
ctcgtgcacc caactgatct tcagcatctt ttactttcac cagcgtttct gggtgagcaa   10320
aaacaggaag gcaaaatgcc gcaaaaaagg gaataagggc gacacggaaa tgttgaatac   10380
tcatactctt cctttttcaa tattattgaa gcatttatca gggttattgt ctcatgagcg   10440
```

-continued

```
gatacatatt tgaatgtatt tagaaaaata aacaaatagg ggttccgcgc acatttcccc  10500

gaaaagtgcc ac                                                      10512
```

```
<210> SEQ ID NO 32
<211> LENGTH: 10487
<212> TYPE: DNA
<213> ORGANISM: Artificial Sequence
<220> FEATURE:
<223> OTHER INFORMATION: Synthetic

<400> SEQUENCE: 32

ctgacgcgcc ctgtagcggc gcattaagcg cggcgggtgt ggtggttacg cgcagcgtga     60

ccgctacact tgccagcgcc ctagcgcccg ctcctttcgc tttcttccct tcctttctcg    120

ccacgttcgc cggcatcaga ttggctattg gccattgcat acgttgtatc catatcataa    180

tatgtacatt tatattggct catgtccaac attaccgcca tgttgacatt gattattgac    240

tagttattaa tagtaatcaa ttacggggtc attagttcat agcccatata tggagttccg    300

cgttacataa cttacggtaa atggcccgcc tggctgaccg cccaacgacc cccgcccatt    360

gacgtcaata atgacgtatg ttcccatagt aacgccaata gggactttcc attgacgtca    420

atgggtggag tatttacggt aaactgccca cttggcagta catcaagtgt atcatatgcc    480

aagtacgccc cctattgacg tcaatgacgg taaatggccc gcctggcatt atgcccagta    540

catgacctta tgggactttc ctacttggca gtacatctac gtattagtca tcgctattac    600

catggtgatg cggttttggc agtacatcaa tgggcgtgga tagcggtttg actcacgggg    660

atttccaagt ctccacccca ttgacgtcaa tgggagtttg ttttggcacc aaaatcaacg    720

ggactttcca aaatgtcgta acaactccgc cccattgacg caaatgggcg gtaggcgtgt    780

acggtgggag gtctatataa gcagagctcg tttagtgaac cgtcagatcg cctggagacg    840

ccatccacgc tgttttgacc tccatagaag acaccgggac cgatccagcc tccgcggccg    900

ggaacggtgc attggaacgc ggattccccg tgccaagagt gacgtaagta ccgcctatag    960

actctatagg cacacccctt tggctcttat gcatgctata ctgtttttgg cttggggcct   1020

atacaccccc gcttccttat gctataggtg atggtatagc ttagcctata ggtgtgggtt   1080

attgaccatt attgaccact cccctattgg tgacgatact ttccattact aatccataac   1140

atggctcttt gccacaacta tctctattgg ctatatgcca atactctgtc cttcagagac   1200

tgacacggac tctgtatttt tacaggatgg ggtcccattt attatttaca aattcacata   1260

tacaacaacg ccgtcccccg tgcccgcagt ttttattaaa catagcgtgg gatctccacg   1320

cgaatctcgg gtacgtgttc cggacatggg ctcttctccg gtagcggcgg agcttccaca   1380

tccgagccct ggtcccatgc ctccagcggc tcatggtcgc tcggcagctc cttgctccta   1440

acagtggagg ccagacttag gcacagcaca atgcccacca ccaccagtgt gccgcacaag   1500

gccgtggcgg tagggtatgt gtctgaaaat gagcgtggag attgggctcg cacggctgac   1560

gcagatggaa gacttaaggc agcggcagaa gaagatgcag gcagctgagt tgttgtattc   1620

tgataagagt cagaggtaac tcccgttgcg gtgctgttaa cggtggaggg cagtgtagtc   1680

tgagcagtac tcgttgctgc cgcgcgcgcc accagacata atagctgaca gactaacaga   1740

ctgttccttt ccatgggtct tttctgcagt caccgtcgga ccatgtgtga acttgatatt   1800

ttacatgatt ctctttacca attctgcccc gaattacact taaaacgact caacagctta   1860

acgttggctt gccacgcatt acttgactgt aaaactctca ctcttaccga acttggccgt   1920
```

-continued

```
aacctgccaa ccaaagcgag aacaaaacat aacatcaaac gaatcgaccg attgttaggt   1980
aatcgtcacc tccacaaaga gcgactcgct gtataccgtt ggcatgctag ctttatctgt   2040
tcgggaatac gatgcccatt gtacttgttg actggtctga tattcgtgag caaaaacgac   2100
ttatggtatt gcgagcttca gtcgcactac acggtcgttc tgttactctt tatgagaaag   2160
cgttcccgct ttcagagcaa tgttcaaaga aagctcatga ccaatttcta gccgaccttg   2220
cgagcattct accgagtaac accacaccgc tcattgtcag tgatgctggc tttaaagtgc   2280
catggtataa atccgttgag aagctgggtt ggtactggtt aagtcgagta agaggaaaag   2340
tacaatatgc agacctagga gcggaaaact ggaaacctat cagcaactta catgatatgt   2400
catctagtca ctcaaagact ttaggctata agaggctgac taaaagcaat ccaatctcat   2460
gccaaattct attgtataaa tctcgctcta aaggccgaaa aaatcagcgc tcgacacgga   2520
ctcattgtca ccacccgtca cctaaaatct actcagcgtc ggcaaaggag ccatgggttc   2580
tagcaactaa cttacctgtt gaaattcgaa cacccaaaca acttgttaat atctattcga   2640
agcgaatgca gattgaagaa accttccgag acttgaaaag tcctgcctac ggactaggcc   2700
tacgccatag ccgaacgagc agctcagagc gttttgatat catgctgcta atcgccctga   2760
tgcttcaact aacatgttgg cttgcgggcg ttcatgctca gaaacaaggt tgggacaagc   2820
acttccaggc taacacagtc agaaatcgaa acgtactctc aacagttcgc ttaggcatgg   2880
aagttttgcg gcattctggc tacacaataa caagggaaga cttactcgtg gctgcaaccc   2940
tactagctca aaatttattc acacatggtt acgctttggg gaaattatga taatgatcca   3000
gatcacttct ggctaataaa agatcagagc tctagagatc tgtgtgttgg tttttttgtgg   3060
atctgctgtg ccttctagtt gccagccatc tgttgtttgc ccctcccccg tgccttcctt   3120
gaccctggaa ggtgccactc ccactgtcct ttcctaataa aatgaggaaa ttgcatcgca   3180
ttgtctgagt aggtgtcatt ctattctggg gggtggggtg gggcagcaca gcaaggggga   3240
ggattgggaa gacaatagca ggcatgctgg ggatgcggtg ggctctatgg gtacctctct   3300
ctctctctct ctctctctct ctctctctct ctctcggtac ctctctctct ctctctctct   3360
ctctctctct ctctctctct cggtaccagg tgctgaagaa ttgacccggt gaccaaaggt   3420
gccttttatc atcactttaa aaataaaaaa caattactca gtgcctgtta taagcagcaa   3480
ttaattatga ttgatgccta catcacaaca aaaactgatt taacaaatgg ttggtctgcc   3540
ttagaaagta tatttgaaca ttatcttgat tatattattg ataataataa aaaccttatc   3600
cctatccaag aagtgatgcc tatcattggt tggaatgaac ttgaaaaaaa ttagccttga   3660
atacattact ggtaaggtaa acgccattgt cagcaaattg atccaagaga accaacttaa   3720
agctttcctg acggaatgtt aattctcgtt gaccctgagc actgatgaat cccctaatga   3780
ttttggtaaa aatcattaag ttaaggtgga tacacatctt gtcatatgat cccggtaatg   3840
tgagttagct cactcattag gcaccccagg ctttacactt tatgcttccg gctcgtatgt   3900
tgtgtggaat tgtgagcgga taacaatttc acacaggaaa cagctatgac catgattacg   3960
ccaagcgcgc aattaaccct cactaaaggg aacaaaagct ggagctccac cgcggtggcg   4020
gccgctctag aactagtgga tcccccgggg aggtcagaat ggtttcttta ctgtttgtca   4080
attctattat ttcaatacag aacaaaagct tctataactg aaatatattt gctattgtat   4140
attatgattg tccctcgaac catgaacact cctccagctg aatttcacaa ttcctctgtc   4200
atctgccagg ctggaagatc atggaagatc tctgaggaac attgcaagtt cataccataa   4260
actcatttgg aattgagtat tattttgctt tgaatggagc tatgttttgc agttccctca   4320
```

```
gaagaaaagc ttgttataaa gcgtctacac ccatcaaaag atatatttaa atattccaac   4380
tacagaaaga ttttgtctgc tcttcactct gatctcagtt ggtttcttca cgtacatgct   4440
tctttatttg cctattttgt caagaaaata ataggtcaag tcctgttctc acttatctcc   4500
tgcctagcat ggcttagatg cacgttgtac attcaagaag gatcaaatga aacagacttc   4560
tggtctgtta caacaaccat agtaataaac agactaacta ataattgcta attatgtttt   4620
ccatctctaa ggttcccaca tttttctgtt ttaagatccc attatctggt tgtaactgaa   4680
gctcaatgga acatgaacag tatttctcag tcttttctcc agcaatcctg acggattaga   4740
agaactggca gaaaacactt tgttacccag aattaaaaac taatatttgc tctcccttca   4800
atccaaaatg gacctattga aactaaaatc tgacccaatc ccattaaatt atttctatgg   4860
cgtcaaaggt caaactttg aagggaacct gtgggtgggt cccaattcag gctatatatt   4920
ccccagggct cagccagtgg atccatgggc tccatcggtg cagcaagcat ggaattttgt   4980
tttgatgtat tcaaggagct caaagtccac catgccaatg acaacatgct ctactccccc   5040
tttgccatct tgtcaactct ggccatggtc ttcctaggtg caaaagacag caccaggacc   5100
cagataaata aggttgttca ctttgataaa cttccaggat tcggagacag tattgaagct   5160
cagtgtggca catctgtaaa tgttcactct tcacttagag acatactcaa ccaaatcacc   5220
aaacaaaatg atgcttattc gttcagcctt gccagtagac tttatgctca agagacatac   5280
acagtcgtgc cggaatactt gcaatgtgtg aaggaactgt atagaggagg cttagaatcc   5340
gtcaactttc aaacagctgc agatcaagcc agaggcctca tcaatgcctg ggtagaaagt   5400
cagacaaacg gaattatcag aaacatcctt cagccaagct ccgtggattc tcaaactgca   5460
atggtcctgg ttaatgccat tgccttcaag ggactgtggg agaaagcatt taaggctgaa   5520
gacacgcaaa caataccttt cagagtgact gagcaagaaa gcaaacctgt gcagatgatg   5580
taccagattg gttcatttaa agtggcatca atggcttctg agaaaatgaa gatcctggag   5640
cttccatttg ccagtggaac aatgagcatg ttggtgctgt tgcctgatga tgtctcaggc   5700
cttgagcagc ttgagagtat aatcagcttt gaaaaactga ctgaatggac cagttctagt   5760
attatggaag agaggaaggt caaagtgtac ttacctcgca tgaagatgga ggagaaatac   5820
aacctcacat ctctcttaat ggctatggga attactgacc tgttcagctc ttcagccaat   5880
ctgtctggca tctcctcagt agggagcctg aagatatctc aagctgtcca tgcagcacat   5940
gcagaaatca atgaagcggg cagagatgtg gtaggctcag cagaggctgg agtggatgct   6000
actgaagaat ttagggctga ccatccattc ctcttctgtg tcaagcacat cgaaaccaac   6060
gccattctcc tctttggcag atgtgtttct ccgcggccag cagatgacgc accagcagat   6120
gacgcaccag cagatgacgc accagcagat gacgcaccag cagatgacgc accagcagat   6180
gacgcaacaa catgtatcct gaaaggctct tgtggctgga tcggcctgct ggatgacgat   6240
gacaaatttg tgaaccaaca cctgtgcggc tcacacctgg tggaagctct ctacctagtg   6300
tgcggggaac gaggcttctt ctacacaccc aagacccgcc gggaggcaga ggacctgcag   6360
gtggggcagg tggagctggg cgggggccct ggtgcaggca gcctgcagcc cttggccctg   6420
gaggggtccc tgcagaagcg tggcattgtg gaacaatgct gtaccagcat ctgctccctc   6480
taccagctgg agaactactg caactagggc gcctggatcc agatcacttc tggctaataa   6540
aagatcagag ctctagagat ctgtgtgttg gttttttgtg gatctgctgt gccttctagt   6600
tgccagccat ctgttgtttg cccctccccc gtgccttcct tgaccctgga aggtgccact   6660
```

-continued

```
cccactgtcc tttcctaata aaatgaggaa attgcatcgc attgtctgag taggtgtcat   6720
tctattctgg ggggtggggt ggggcagcac agcaaggggg aggattggga agacaatagc   6780
aggcatgctg gggatgcggt gggctctatg ggtacctctc tctctctctc tctctctctc   6840
tctctctctc tctctcggta cctctctcga ggggggggcc ggtacccaat tcgccctata   6900
gtgagtcgta ttacgcgcgc tcactggccg tcgttttaca acgtcgtgac tgggaaaacc   6960
ctggcgttac ccaacttaat cgccttgcag cacatccccc tttcgccagc tggcgtaata   7020
gcgaagaggc ccgcaccgat cgcccttccc aacagttgcg cagcctgaat ggcgaatgga   7080
aattgtaagc gttaatattt tgttaaaatt cgcgttaaat ttttgttaaa tcagctcatt   7140
ttttaaccaa taggccgaaa tcggcaaaat cccttataaa tcaaaagaat agaccgagat   7200
agggttgagt gttgttccag tttggaacaa gagtccacta ttaaagaacg tggactccaa   7260
cgtcaaaggg cgaaaaaccg tctatcaggg cgatggccca ctactccggg atcatatgac   7320
aagatgtgta tccaccttaa cttaatgatt tttaccaaaa tcattagggg attcatcagt   7380
gctcagggtc aacgagaatt aacattccgt caggaaagct tatgatgatg atgtgcttaa   7440
aaacttactc aatggctggt tatgcatatc gcaatacatg cgaaaaacct aaaagagctt   7500
gccgataaaa aaggccaatt tattgctatt taccgcggct ttttattgag cttgaaagat   7560
aaataaaata gataggtttt atttgaagct aaatcttctt tatcgtaaaa aatgccctct   7620
tgggttatca agagggtcat tatatttcgc ggaataacat catttggtga cgaaataact   7680
aagcacttgt ctcctgttta ctcccctgag cttgaggggt taacatgaag gtcatcgata   7740
gcaggataat aatacagtaa aacgctaaac caataatcca aatccagcca tcccaaattg   7800
gtagtgaatg attataaata acagcaaaca gtaatgggcc aataacaccg gttgcattgg   7860
taaggctcac caataatccc tgtaaagcac cttgctgatg actctttgtt tggatagaca   7920
tcactccctg taatgcaggt aaagcgatcc caccaccagc caataaaatt aaaacaggga   7980
aaactaacca accttcagat ataaacgcta aaaaggcaaa tgcactacta tctgcaataa   8040
atccgagcag tactgccgtt ttttcgcccc atttagtggc tattcttcct gccacaaagg   8100
cttggaatac tgagtgtaaa agaccaagac ccgctaatga aaagccaacc atcatgctat   8160
tccatccaaa acgattttcg gtaaatagca cccacaccgt tgcgggaatt tggcctatca   8220
attgcgctga aaaataaata atcaacaaaa tggcatcgtt ttaaataaag tgatgtatac   8280
cgaattcagc ttttgttccc tttagtgagg gttaattgcg cgcttggcgt aatcatggtc   8340
atagctgttt cctgtgtgaa attgttatcc gctcacaatt ccacacaaca tacgagccgg   8400
aagcataaag tgtaaagcct ggggtgccta atgagtgagc taactcacat taattgcgtt   8460
gcgctcactg cccgctttcc agtcgggaaa cctgtcgtgc cagctgcatt aatgaatcgg   8520
ccaacgcgcg gggagaggcg gtttgcgtat tgggcgctct tccgcttcct cgctcactga   8580
ctcgctgcgc tcggtcgttc ggctgcggcg agcggtatca gctcactcaa aggcggtaat   8640
acggttatcc acagaatcag gggataacgc aggaaagaac atgtgagcaa aaggccagca   8700
aaaggccagg aaccgtaaaa aggccgcgtt gctggcgttt ttccataggc tccgcccccc   8760
tgacgagcat cacaaaaatc gacgctcaag tcagaggtgg cgaaacccga caggactata   8820
aagataccag gcgtttcccc ctggaagctc cctcgtgcgc tctcctgttc cgaccctgcc   8880
gcttaccgga tacctgtccg cctttctccc ttcgggaagc gtggcgcttt ctcatagctc   8940
acgctgtagg tatctcagtt cggtgtaggt cgttcgctcc aagctgggct gtgtgcacga   9000
accccccgtt cagcccgacc gctgcgcctt atccggtaac tatcgtcttg agtccaaccc   9060
```

-continued

```
ggtaagacac gacttatcgc cactggcagc agccactggt aacaggatta gcagagcgag   9120
gtatgtaggc ggtgctacag agttcttgaa gtggtggcct aactacggct acactagaag   9180
gacagtattt ggtatctgcg ctctgctgaa gccagttacc ttcggaaaaa gagttggtag   9240
ctcttgatcc ggcaaacaaa ccaccgctgg tagcggtggt ttttttgttt gcaagcagca   9300
gattacgcgc agaaaaaaag gatctcaaga agatcctttg atcttttcta cggggtctga   9360
cgctcagtgg aacgaaaact cacgttaagg gattttggtc atgagattat caaaaaggat   9420
cttcacctag atccttttaa attaaaaatg aagttttaaa tcaatctaaa gtatatatga   9480
gtaaacttgg tctgacagtt accaatgctt aatcagtgag gcacctatct cagcgatctg   9540
tctatttcgt tcatccatag ttgcctgact ccccgtcgtg tagataacta cgatacggga   9600
gggcttacca tctggcccca gtgctgcaat gataccgcga gacccacgct caccggctcc   9660
agatttatca gcaataaacc agccagccgg aagggccgag cgcagaagtg gtcctgcaac   9720
tttatccgcc tccatccagt ctattaattg ttgccgggaa gctagagtaa gtagttcgcc   9780
agttaatagt ttgcgcaacg ttgttgccat tgctacaggc atcgtggtgt cacgctcgtc   9840
gtttggtatg gcttcattca gctccggttc ccaacgatca aggcgagtta catgatcccc   9900
catgttgtgc aaaaaagcgg ttagctcctt cggtcctccg atcgttgtca gaagtaagtt   9960
ggccgcagtg ttatcactca tggttatggc agcactgcat aattctctta ctgtcatgcc  10020
atccgtaaga tgcttttctg tgactggtga gtactcaacc aagtcattct gagaatagtg  10080
tatgcggcga ccgagttgct cttgcccggc gtcaatacgg gataataccg cgccacatag  10140
cagaacttta aaagtgctca tcattggaaa acgttcttcg gggcgaaaac tctcaaggat  10200
cttaccgctg ttgagatcca gttcgatgta acccactcgt gcacccaact gatcttcagc  10260
atcttttact ttcaccagcg tttctgggtg agcaaaaaca ggaaggcaaa atgccgcaaa  10320
aaagggaata agggcgacac ggaaatgttg aatactcata ctcttccttt ttcaatatta  10380
ttgaagcatt tatcagggtt attgtctcat gagcggatac atatttgaat gtatttagaa  10440
aaataaacaa ataggggttc cgcgcacatt tccccgaaaa gtgccac                10487
```

<210> SEQ ID NO 33
<211> LENGTH: 315
<212> TYPE: DNA
<213> ORGANISM: Artificial Sequence
<220> FEATURE:
<223> OTHER INFORMATION: Synthetic

<400> SEQUENCE: 33

```
tctgccattg ctgcttcctc tgcccttcct cgtcactctg aatgtggctt cttcgctact     60
gccacagcaa gaaataaaat ctcaacatct aaatgggttt cctgaggttt ttcaagagtc    120
gttaagcaca ttccttcccc agcacccctt gctgcaggcc agtgccaggc accaacttgg    180
ctactgctgc ccatgagaga aatccagttc aatattttcc aaagcaaaat ggattacata    240
tgccctagat cctgattaac aggcgtttgt attatctagt gctttcgctt cacccagatt    300
atcccattgc ctccc                                                     315
```

<210> SEQ ID NO 34
<211> LENGTH: 645
<212> TYPE: DNA
<213> ORGANISM: Artificial Sequence
<220> FEATURE:
<223> OTHER INFORMATION: Synthetic

<400> SEQUENCE: 34

```
gagctcgtga tgacccagac tccatcctcc ctgtctgcct ctctgggaga cagagtcacc     60
atcagttgca gggcaaatca ggacattagc aattatttaa actggtatca gcagaaacca    120
gatggaactg ttaaactcct gatctactac acatcaagat tacactcagg ggtcccatca    180
aggttcagtg gcagtgggtc tggaacagat tattctctca ccattagcaa cctggagcaa    240
gaagattttg ccacttactt ttgccaacag ggtaatacgc ttccgtggac gttcggtgga    300
ggcaccaacc tggaaatcaa acgggctgat gctgcaccaa ctgtatccat cttcccacca    360
tccagtgagc agttaacatc tggaggtgcc tcagtcgtgt gcttcttgaa caacttctac    420
cccaaagaca tcaatgtcaa gtggaagatt gatggcagtg aacgacaaaa tggcgtcctg    480
aacagttgga ctgatcagga cagcaaagac agcacctaca gcatgagcag caccctcacg    540
ttgaccaagg acgagtatga acgacataac agctatacct gtgaggccac tcacaagaca    600
tcaacttcac ccattgtcaa gagcttcaac aggaatgagt gttaa                    645
```

<210> SEQ ID NO 35
<211> LENGTH: 657
<212> TYPE: DNA
<213> ORGANISM: Artificial Sequence
<220> FEATURE:
<223> OTHER INFORMATION: Synthetic

<400> SEQUENCE: 35

```
ctcgagtcag gacctggcct ggtggcgccc tcacagaacc tgtccatcac ttgcactgtc     60
tctgggtttt cattaaccag ctatggtgta cactgggttc gccagcctcc aggaaagggt    120
ctggaatggc tgggagtaat atggactggt agaagcacaa cttataattc ggctctcatg    180
tccagactga gcatcagcaa agacaactcc aagagccaag ttttcttaaa aatgaacagt    240
ctgcaaactg atgacacagc catttactac tgtggcagag gggtctgat tacgtccttt     300
gctatggact actggggtca aggaacctca gtcaccgtct cctcagccaa aacgacaccc    360
ccatctgtct atccactggc ccctggatct gctgcccaaa ctaactccat ggtgaccctg    420
ggatgcctgg tcaagggcta tttccctgag ccagtgacag tgacctggaa ctctggatcc    480
ctgtccagcg gtgtgcacac cttcccagct gtcctgcagt ctgacctcta cactctgagc    540
agctcagtga ctgtcccctc cagcacctgg cccagcgaga ccgtcacctg caacgttgcc    600
cacccggcca gcagcaccaa ggtggacaag aaaattgtgc ccagggattg tactagt       657
```

<210> SEQ ID NO 36
<211> LENGTH: 7315
<212> TYPE: DNA
<213> ORGANISM: Artificial Sequence
<220> FEATURE:
<223> OTHER INFORMATION: Synthetic

<400> SEQUENCE: 36

```
ctgacgcgcc ctgtagcggc gcattaagcg cggcgggtgt ggtggttacg cgcagcgtga     60
ccgctacact tgccagcgcc ctagcgcccg ctcctttcgc tttcttccct tcctttctcg    120
ccacgttcgc cggcatcaga ttggctattg gccattgcat acgttgtatc catatcataa    180
tatgtacatt tatattggct catgtccaac attaccgcca tgttgacatt gattattgac    240
tagttattaa tagtaatcaa ttacggggtc attagttcat agcccatata tggagttccg    300
cgttacataa cttacggtaa atggcccgcc tggctgaccg cccaacgacc cccgcccatt    360
gacgtcaata atgacgtatg ttcccatagt aacgccaata gggactttcc attgacgtca    420
```

```
atgggtggag tatttacggt aaactgccca cttggcagta catcaagtgt atcatatgcc    480
aagtacgccc cctattgacg tcaatgacgg taaatggccc gcctggcatt atgcccagta    540
catgacctta tgggactttc ctacttggca gtacatctac gtattagtca tcgctattac    600
catggtgatg cggttttggc agtacatcaa tgggcgtgga tagcggtttg actcacgggg    660
atttccaagt ctccacccca ttgacgtcaa tgggagtttg ttttggcacc aaaatcaacg    720
ggactttcca aaatgtcgta acaactccgc cccattgacg caaatgggcg gtaggcgtgt    780
acggtgggag gtctatataa gcagagctcg tttagtgaac cgtcagatcg cctggagacg    840
ccatccacgc tgttttgacc tccatagaag acaccgggac cgatccagcc tccgcggccg    900
ggaacggtgc attggaacgc ggattccccg tgccaagagt gacgtaagta ccgcctatag    960
actctatagg cacacccctt tggctcttat gcatgctata ctgtttttgg cttggggcct   1020
atacaccccc gcttccttat gctataggtg atggtatagc ttagcctata ggtgtgggtt   1080
attgaccatt attgaccact cccctattgg tgacgatact ttccattact aatccataac   1140
atggctcttt gccacaacta tctctattgg ctatatgcca atactctgtc cttcagagac   1200
tgacacggac tctgtatttt tacaggatgg ggtcccattt attatttaca aattcacata   1260
tacaacaacg ccgtcccccg tgcccgcagt ttttattaaa catagcgtgg gatctccacg   1320
cgaatctcgg gtacgtgttc cggacatggg ctcttctccg gtagcggcgg agcttccaca   1380
tccgagccct ggtcccatgc ctccagcggc tcatggtcgc tcggcagctc cttgctccta   1440
acagtggagg ccagacttag gcacagcaca atgcccacca ccaccagtgt gccgcacaag   1500
gccgtggcgg tagggtatgt gtctgaaaat gagcgtggag attgggctcg cacggctgac   1560
gcagatggaa gacttaaggc agcggcagaa gaagatgcag gcagctgagt tgttgtattc   1620
tgataagagt cagaggtaac tcccgttgcg gtgctgttaa cggtggaggg cagtgtagtc   1680
tgagcagtac tcgttgctgc cgcgcgcgcc accagacata atagctgaca gactaacaga   1740
ctgttccttt ccatgggtct tttctgcagt caccgtcgga ccatgtgcga actcgatatt   1800
ttacacgact ctctttacca attctgcccc gaattacact taaaacgact caacagctta   1860
acgttggctt gccacgcatt acttgactgt aaaactctca ctcttaccga acttggccgt   1920
aacctgccaa ccaaagcgag aacaaaacat aacatcaaac gaatcgaccg attgttaggt   1980
aatcgtcacc tccacaaaga gcgactcgct gtataccgtt ggcatgctag ctttatctgt   2040
tcgggcaata cgatgcccat tgtacttgtt gactggtctg atattcgtga gcaaaaacga   2100
cttatggtat tgcgagcttc agtcgcacta cacggtcgtt ctgttactct ttatgagaaa   2160
gcgttcccgc tttcagagca atgttcaaag aaagctcatg accaatttct agccgacctt   2220
gcgagcattc taccgagtaa caccacaccg ctcattgtca gtgatgctgg ctttaaagtg   2280
ccatggtata aatccgttga gaagctgggt tggtactggt taagtcgagt aagaggaaaa   2340
gtacaatatg cagacctagg agcggaaaac tggaaaccta tcagcaactt acatgatatg   2400
tcatctagtc actcaaagac tttaggctat aagaggctga ctaaaagcaa tccaatctca   2460
tgccaaattc tattgtataa atctcgctct aaaggccgaa aaaatcagcg ctcgacacgg   2520
actcattgtc accacccgtc acctaaaatc tactcagcgt cggcaaagga gccatgggtt   2580
ctagcaacta acttacctgt tgaaattcga acacccaaac aacttgttaa tatctattcg   2640
aagcgaatgc agattgaaga aaccttccga gacttgaaaa gtcctgccta cggactaggc   2700
ctacgccata gccgaacgag cagctcagag cgttttgata tcatgctgct aatcgccctg   2760
```

-continued

```
atgcttcaac taacatgttg gcttgcgggc gttcatgctc agaaacaagg ttgggacaag   2820
cacttccagg ctaacacagt cagaaatcga aacgtactct caacagttcg cttaggcatg   2880
gaagttttgc ggcattctgg ctacacaata acaagggaag acttactcgt ggctgcaacc   2940
ctactagctc aaaatttatt cacacatggt tacgctttgg ggaaattatg aggggatcgc   3000
tctagagcga tccgggatct cgggaaaagc gttggtgacc aaaggtgcct tttatcatca   3060
ctttaaaaat aaaaaacaat tactcagtgc ctgttataag cagcaattaa ttatgattga   3120
tgcctacatc acaacaaaaa ctgatttaac aaatggttgg tctgccttag aaagtatatt   3180
tgaacattat cttgattata ttattgataa taataaaaac cttatcccta tccaagaagt   3240
gatgcctatc attggttgga atgaacttga aaaaaattag ccttgaatac attactggta   3300
aggtaaacgc cattgtcagc aaattgatcc aagagaacca acttaaagct ttcctgacgg   3360
aatgttaatt ctcgttgacc ctgagcactg atgaatcccc taatgatttt ggtaaaaatc   3420
attaagttaa ggtggataca catcttgtca tatgatcccg gtaatgtgag ttagctcact   3480
cattaggcac cccaggcttt acactttatg cttccggctc gtatgttgtg tggaattgtg   3540
agcggataac aatttcacac aggaaacagc tatgaccatg attacgccaa gcgcgcaatt   3600
aaccctcact aaagggaaca aaagctggag ctccaccgcg gtggcggccg ctctagaact   3660
agtggatccc ccgggctgca ggaattcgat atcaagctta tcgataccgc tgacctcgag   3720
ggggggcccg gtacccaatt cgccctatag tgagtcgtat tacgcgcgct cactggccgt   3780
cgttttacaa cgtcgtgact gggaaaaccc tggcgttacc caacttaatc gccttgcagc   3840
acatccccct ttcgccagct ggcgtaatag cgaagaggcc cgcaccgatc gcccttccca   3900
acagttgcgc agcctgaatg gcgaatggaa attgtaagcg ttaatatttt gttaaaattc   3960
gcgttaaatt tttgttaaat cagctcattt tttaaccaat aggccgaaat cggcaaaatc   4020
ccttataaat caaaagaata gaccgagata gggttgagtg ttgttccagt ttggaacaag   4080
agtccactat taaagaacgt ggactccaac gtcaaagggc gaaaaaccgt ctatcagggc   4140
gatggcccac tactccggga tcatatgaca agatgtgtat ccaccttaac ttaatgattt   4200
ttaccaaaat cattagggga ttcatcagtg ctcagggtca acgagaatta acattccgtc   4260
aggaaagctt atgatgatga tgtgcttaaa aacttactca atggctggtt atgcatatcg   4320
caatacatgc gaaaaaccta aaagagcttg ccgataaaaa aggccaattt attgctattt   4380
accgcggctt tttattgagc ttgaaagata aataaaatag ataggtttta tttgaagcta   4440
aatcttcttt atcgtaaaaa atgccctctt gggttatcaa gagggtcatt atatttcgcg   4500
gaataacatc atttggtgac gaaataacta agcacttgtc tcctgtttac tcccctgagc   4560
ttgaggggtt aacatgaagg tcatcgatag caggataata atacagtaaa acgctaaacc   4620
aataatccaa atccagccat cccaaattgg tagtgaatga ttataaataa cagcaaacag   4680
taatgggcca ataacaccgg ttgcattggt aaggctcacc aataatccct gtaaagcacc   4740
ttgctgatga ctctttgttt ggatagacat cactccctgt aatgcaggta aagcgatccc   4800
accaccagcc aataaaatta aaacagggaa aactaaccaa ccttcagata taaacgctaa   4860
aaaggcaaat gcactactat ctgcaataaa tccgagcagt actgccgttt tttcgcccat   4920
ttagtggcta ttcttcctgc cacaaaggct tggaatactg agtgtaaaag accaagaccc   4980
gtaatgaaaa gccaaccatc atgctattca tcatcacgat ttctgtaata gcaccacacc   5040
gtgctggatt ggctatcaat gcgctgaaat aataatcaac aaatggcatc gttaaataag   5100
tgatgtatac cgatcagctt ttgttccctt tagtgagggt taattgcgcg cttggcgtaa   5160
```

-continued

```
tcatggtcat agctgtttcc tgtgtgaaat tgttatccgc tcacaattcc acacaacata   5220

cgagccggaa gcataaagtg taaagcctgg ggtgcctaat gagtgagcta actcacatta   5280

attgcgttgc gctcactgcc cgctttccag tcgggaaacc tgtcgtgcca gctgcattaa   5340

tgaatcggcc aacgcgcggg gagaggcggt ttgcgtattg ggcgctcttc cgcttcctcg   5400

ctcactgact cgctgcgctc ggtcgttcgg ctgcggcgag cggtatcagc tcactcaaag   5460

gcggtaatac ggttatccac agaatcaggg gataacgcag gaaagaacat gtgagcaaaa   5520

ggccagcaaa aggccaggaa ccgtaaaaag gccgcgttgc tggcgttttt ccataggctc   5580

cgcccccctg acgagcatca caaaaatcga cgctcaagtc agaggtggcg aaacccgaca   5640

ggactataaa gataccaggc gtttccccct ggaagctccc tcgtgcgctc tcctgttccg   5700

accctgccgc ttaccggata cctgtccgcc tttctccctt cgggaagcgt ggcgctttct   5760

catagctcac gctgtaggta tctcagttcg gtgtaggtcg ttcgctccaa gctgggctgt   5820

gtgcacgaac cccccgttca gcccgaccgc tgcgccttat ccggtaacta tcgtcttgag   5880

tccaacccgg taagacacga cttatcgcca ctggcagcag ccactggtaa caggattagc   5940

agagcgaggt atgtaggcgg tgctacagag ttcttgaagt ggtggcctaa ctacggctac   6000

actagaagga cagtatttgg tatctgcgct ctgctgaagc cagttacctt cggaaaaaga   6060

gttggtagct cttgatccgg caaacaaacc accgctggta gcggtggttt ttttgtttgc   6120

aagcagcaga ttacgcgcag aaaaaaagga tctcaagaag atcctttgat cttttctacg   6180

gggtctgacg ctcagtggaa cgaaaactca cgttaaggga ttttggtcat gagattatca   6240

aaaaggatct tcacctagat ccttttaaat taaaaatgaa gttttaaatc aatctaaagt   6300

atatatgagt aaacttggtc tgacagttac caatgcttaa tcagtgaggc acctatctca   6360

gcgatctgtc tatttcgttc atccatagtt gcctgactcc ccgtcgtgta gataactacg   6420

atacgggagg gcttaccatc tggccccagt gctgcaatga taccgcgaga cccacgctca   6480

ccggctccag atttatcagc aataaaccag ccagccggaa gggccgagcg cagaagtggt   6540

cctgcaactt tatccgcctc catccagtct attaattgtt gccgggaagc tagagtaagt   6600

agttcgccag ttaatagttt gcgcaacgtt gttgccattg ctacaggcat cgtggtgtca   6660

cgctcgtcgt ttggtatggc ttcattcagc tccggttccc aacgatcaag gcgagttaca   6720

tgatccccca tgttgtgcaa aaaagcggtt agctccttcg gtcctccgat cgttgtcaga   6780

agtaagttgg ccgcagtgtt atcactcatg gttatggcag cactgcataa ttctcttact   6840

gtcatgccat ccgtaagatg cttttctgtg actggtgagt actcaaccaa gtcattctga   6900

gaatagtgta tgcggcgacc gagttgctct tgcccggcgt caatacggga taataccgcg   6960

ccacatagca gaactttaaa agtgctcatc attggaaaac gttcttcggg gcgaaaactc   7020

tcaaggatct taccgctgtt gagatccagt tcgatgtaac ccactcgtgc acccaactga   7080

tcttcagcat cttttacttt caccagcgtt tctgggtgag caaaaacagg aaggcaaaat   7140

gccgcaaaaa agggaataag ggcgacacgg aaatgttgaa tactcatact cttccttttt   7200

caatattatt gaagcattta tcagggttat tgtctcatga gcggatacat atttgaatgt   7260

atttagaaaa ataaacaaat aggggttccg cgcacatttc cccgaaaagt gccac        7315
```

<210> SEQ ID NO 37
<211> LENGTH: 680
<212> TYPE: DNA
<213> ORGANISM: Artificial Sequence
<220> FEATURE:

-continued

<223> OTHER INFORMATION: Synthetic

<400> SEQUENCE: 37

```
ccgggctgca gaaaaatgcc aggtggacta tgaactcaca tccaaaggag cttgacctga     60
tacctgattt tcttcaaact ggggaaacaa cacaatccca caaaacagct cagagagaaa    120
ccatcactga tggctacagc accaaggtat gcaatggcaa tccattcgac attcatctgt    180
gacctgagca aaatgattta tctctccatg aatggttgct tctttccctc atgaaaaggc    240
aatttccaca ctcacaatat gcaacaaaga caaacagaga acaattaatg tgctccttcc    300
taatgtcaaa attgtagtgg caaagaggag aacaaaatct caagttctga gtaggtttta    360
gtgattggat aagaggcttt gacctgtgag ctcacctgga cttcatatcc ttttggataa    420
aaagtgcttt tataactttc aggtctccga gtctttattc atgagactgt tggtttaggg    480
acagacccac aatgaaatgc ctggcatagg aaagggcagc agagccttag ctgacctttt    540
cttgggacaa gcattgtcaa acaatgtgtg acaaaactat ttgtactgct ttgcacagct    600
gtgctgggca gggcaatcca ttgccaccta tcccaggtaa ccttccaact gcaagaagat    660
tgttgcttac tctctctaga                                                680
```

<210> SEQ ID NO 38
<211> LENGTH: 72
<212> TYPE: DNA
<213> ORGANISM: Artificial Sequence
<220> FEATURE:
<223> OTHER INFORMATION: Synthetic

<400> SEQUENCE: 38

```
gtggatcaac atacagctag aaagctgtat tgcctttagc actcaagctc aaaagacaac     60
tcagagttca cc                                                         72
```

<210> SEQ ID NO 39
<211> LENGTH: 62
<212> TYPE: DNA
<213> ORGANISM: Artificial Sequence
<220> FEATURE:
<223> OTHER INFORMATION: Synthetic

<400> SEQUENCE: 39

```
acatacagct agaaagctgt attgccttta gcactcaagc tcaaaagaca actcagagtt     60
ca                                                                    62
```

<210> SEQ ID NO 40
<211> LENGTH: 902
<212> TYPE: DNA
<213> ORGANISM: Artificial Sequence
<220> FEATURE:
<223> OTHER INFORMATION: Synthetic

<400> SEQUENCE: 40

```
gaggtcagaa tggtttcttt actgtttgtc aattctatta tttcaataca gaacaatagc     60
ttctataact gaaatatatt tgctattgta tattatgatt gtccctcgaa ccatgaacac    120
tcctccagct gaatttcaca attcctctgt catctgccag gccattaagt tattcatgga    180
agatctttga ggaacactgc aagttcatat cataaacaca tttgaaattg agtattgttt    240
tgcattgtat ggagctatgt tttgctgtat cctcagaaaa aaagtttgtt ataaagcatt    300
cacacccata aaaagataga tttaaatatt ccagctatag gaaagaaagt gcgtctgctc    360
ttcactctag tctcagttgg ctccttcaca tgcatgcttc tttatttctc ctattttgtc    420
```

```
aagaaaataa taggtcacgt cttgttctca cttatgtcct gcctagcatg gctcagatgc    480

acgttgtaga tacaagaagg atcaaatgaa acagacttct ggtctgttac tacaaccata    540

gtaataagca cactaactaa taattgctaa ttatgttttc catctctaag gttcccacat    600

ttttctgttt tcttaaagat cccattatct ggttgtaact gaagctcaat ggaacatgag    660

caatatttcc cagtcttctc tcccatccaa cagtcctgat ggattagcag aacaggcaga    720

aaacacattg ttacccagaa ttaaaaacta atatttgctc tccattcaat ccaaaatgga    780

cctattgaaa ctaaaatcta acccaatccc attaaatgat ttctatggcg tcaaaggtca    840

aacttctgaa gggaacctgt gggtgggtca caattcaggc tatatattcc ccagggctca    900

gc                                                                   902
```

```
<210> SEQ ID NO 41
<211> LENGTH: 10895
<212> TYPE: DNA
<213> ORGANISM: Artificial Sequence
<220> FEATURE:
<223> OTHER INFORMATION: Synthetic

<400> SEQUENCE: 41

ctgacgcgcc ctgtagcggc gcattaagcg cggcgggtgt ggtggttacg cgcagcgtga     60

ccgctacact tgccagcgcc ctagcgcccg ctcctttcgc tttcttccct tcctttctcg    120

ccacgttcgc cggcatcaga ttggctattg gccattgcat acgttgtatc catatcataa    180

tatgtacatt tatattggct catgtccaac attaccgcca tgttgacatt gattattgac    240

tagttattaa tagtaatcaa ttacggggtc attagttcat agcccatata tggagttccg    300

cgttacataa cttacggtaa atggcccgcc tggctgaccg cccaacgacc cccgcccatt    360

gacgtcaata atgacgtatg ttcccatagt aacgccaata gggactttcc attgacgtca    420

atgggtggag tatttacggt aaactgccca cttggcagta catcaagtgt atcatatgcc    480

aagtacgccc cctattgacg tcaatgacgg taaatggccc gcctggcatt atgcccagta    540

catgacctta tgggactttc ctacttggca gtacatctac gtattagtca tcgctattac    600

catggtgatg cggttttggc agtacatcaa tgggcgtgga tagcggtttg actcacgggg    660

atttccaagt ctccacccca ttgacgtcaa tgggagtttg ttttggcacc aaaatcaacg    720

ggactttcca aaatgtcgta acaactccgc cccattgacg caaatgggcg gtaggcgtgt    780

acggtgggag gtctatataa gcagagctcg tttagtgaac cgtcagatcg cctggagacg    840

ccatccacgc tgttttgacc tccatagaag acaccgggac cgatccagcc tccgcggccg    900

ggaacggtgc attggaacgc ggattccccg tgccaagagt gacgtaagta ccgcctatag    960

actctatagg cacacccctt tggctcttat gcatgctata ctgtttttgg cttggggcct   1020

atacaccccc gcttccttat gctataggtg atggtatagc ttagcctata ggtgtgggtt   1080

attgaccatt attgaccact cccctattgg tgacgatact ttccattact aatccataac   1140

atggctcttt gccacaacta tctctattgg ctatatgcca atactctgtc cttcagagac   1200

tgacacggac tctgtatttt tacaggatgg ggtcccattt attatttaca aattcacata   1260

tacaacaacg ccgtcccccg tgcccgcagt ttttattaaa catagcgtgg gatctccacg   1320

cgaatctcgg gtacgtgttc cggacatggg ctcttctccg gtagcggcgg agcttccaca   1380

tccgagccct ggtcccatgc ctccagcggc tcatggtcgc tcggcagctc cttgctccta   1440

acagtggagg ccagacttag gcacagcaca atgcccacca ccaccagtgt gccgcacaag   1500
```

-continued

```
gccgtggcgg tagggtatgt gtctgaaaat gagcgtggag attgggctcg cacggctgac   1560
gcagatggaa gacttaaggc agcggcagaa gaagatgcag gcagctgagt tgttgtattc   1620
tgataagagt cagaggtaac tcccgttgcg gtgctgttaa cggtggaggg cagtgtagtc   1680
tgagcagtac tcgttgctgc cgcgcgcgcc accagacata atagctgaca gactaacaga   1740
ctgttccttt ccatgggtct tttctgcagt caccgtcgga ccatgtgcga actcgatatt   1800
ttacacgact ctctttacca attctgcccc gaattacact taaaacgact caacagctta   1860
acgttggctt gccacgcatt acttgactgt aaaactctca ctcttaccga acttggccgt   1920
aacctgccaa ccaaagcgag aacaaaacat aacatcaaac gaatcgaccg attgttaggt   1980
aatcgtcacc tccacaaaga gcgactcgct gtataccgtt ggcatgctag ctttatctgt   2040
tcgggcaata cgatgcccat tgtacttgtt gactggtctg atattcgtga gcaaaaacga   2100
cttatggtat tgcgagcttc agtcgcacta cacggtcgtt ctgttactct ttatgagaaa   2160
gcgttcccgc tttcagagca atgttcaaag aaagctcatg accaatttct agccgacctt   2220
gcgagcattc taccgagtaa caccacaccg ctcattgtca gtgatgctgg ctttaaagtg   2280
ccatggtata aatccgttga gaagctgggt tggtactggt taagtcgagt aagaggaaaa   2340
gtacaatatg cagacctagg agcggaaaac tggaaaccta tcagcaactt acatgatatg   2400
tcatctagtc actcaaagac tttaggctat aagaggctga ctaaaagcaa tccaatctca   2460
tgccaaattc tattgtataa atctcgctct aaaggccgaa aaaatcagcg ctcgacacgg   2520
actcattgtc accacccgtc acctaaaatc tactcagcgt cggcaaagga gccatgggtt   2580
ctagcaacta acttacctgt tgaaattcga acacccaaac aacttgttaa tatctattcg   2640
aagcgaatgc agattgaaga aaccttccga gacttgaaaa gtcctgccta cggactaggc   2700
ctacgccata gccgaacgag cagctcagag cgttttgata tcatgctgct aatcgccctg   2760
atgcttcaac taacatgttg gcttgcgggc gttcatgctc agaaacaagg ttgggacaag   2820
cacttccagg ctaacacagt cagaaatcga aacgtactct caacagttcg cttaggcatg   2880
gaagttttgc ggcattctgg ctacacaata acaagggaag acttactcgt ggctgcaacc   2940
ctactagctc aaaatttatt cacacatggt tacgctttgg ggaaattatg aggggatcgc   3000
tctagagcga tccgggatct cgggaaaagc gttggtgacc aaaggtgcct tttatcatca   3060
ctttaaaaat aaaaaacaat tactcagtgc ctgttataag cagcaattaa ttatgattga   3120
tgcctacatc acaacaaaaa ctgatttaac aaatggttgg tctgccttag aaagtatatt   3180
tgaacattat cttgattata ttattgataa taataaaaac cttatcccta tccaagaagt   3240
gatgcctatc attggttgga atgaacttga aaaaaattag ccttgaatac attactggta   3300
aggtaaacgc cattgtcagc aaattgatcc aagagaacca acttaaagct ttcctgacgg   3360
aatgttaatt ctcgttgacc ctgagcactg atgaatcccc taatgatttt ggtaaaaatc   3420
attaagttaa ggtggataca catcttgtca tatgatcccg gtaatgtgag ttagctcact   3480
cattaggcac cccaggcttt acactttatg cttccggctc gtatgttgtg tggaattgtg   3540
agcggataac aatttcacac aggaaacagc tatgaccatg attacgccaa gcgcgcaatt   3600
aaccctcact aaagggaaca aaagctggag ctccaccgcg gtggcggccg ctctagaact   3660
agtggatccc ccgggcatca gattggctat tggccattgc atacgttgta tccatatcat   3720
aatatgtaca tttatattgg ctcatgtcca acattaccgc catgttgaca ttgattattg   3780
actagttatt aatagtaatc aattacgggg tcattagttc atagcccata tatggagttc   3840
cgcgttacat aacttacggt aaatggcccg cctggctgac cgcccaacga cccccgccca   3900
```

-continued

```
ttgacgtcaa taatgacgta tgttcccata gtaacgccaa tagggacttt ccattgacgt   3960
caatgggtgg agtatttacg gtaaactgcc cacttggcag tacatcaagt gtatcatatg   4020
ccaagtacgc cccctattga cgtcaatgac ggtaaatggc ccgcctggca ttatgcccag   4080
tacatgacct tatgggactt tcctacttgg cagtacatct acgtattagt catcgctatt   4140
accatggtga tgcggttttg gcagtacatc aatgggcgtg gatagcggtt tgactcacgg   4200
ggatttccaa gtctccaccc cattgacgtc aatgggagtt tgttttggca ccaaaatcaa   4260
cgggactttc caaaatgtcg taacaactcc gccccattga cgcaaatggg cggtaggcgt   4320
gtacggtggg aggtctatat aagcagagct cgtttagtga accgtcagat cgcctggaga   4380
cgccatccac gctgttttga cctccataga agacaccggg accgatccag cctccgcggc   4440
cgggaacggt gcattggaac gcggattccc cgtgccaaga gtgacgtaag taccgcctat   4500
agactctata ggcacacccc tttggctctt atgcatgcta tactgttttt ggcttggggc   4560
ctatacaccc ccgcttcctt atgctatagg tgatggtata gcttagccta taggtgtggg   4620
ttattgacca ttattgacca ctcccctatt ggtgacgata ctttccatta ctaatccata   4680
acatggctct ttgccacaac tatctctatt ggctatatgc caatactctg tccttcagag   4740
actgacacgg actctgtatt tttacaggat ggggtcccat ttattattta caaattcaca   4800
tatacaacaa cgccgtcccc cgtgcccgca gtttttatta aacatagcgt gggatctcca   4860
cgcgaatctc gggtacgtgt tccggacatg ggctcttctc cggtagcggc ggagcttcca   4920
catccgagcc ctggtcccat gcctccagcg gctcatggtc gctcggcagc tccttgctcc   4980
taacagtgga ggccagactt aggcacagca caatgcccac caccaccagt gtgccgcaca   5040
aggccgtggc ggtagggtat gtgtctgaaa atgagcgtgg agattgggct cgcacggctg   5100
acgcagatgg aagacttaag gcagcggcag aagaagatgc aggcagctga gttgttgtat   5160
tctgataaga gtcagaggta actcccgttg cggtgctgtt aacggtggag ggcagtgtag   5220
tctgagcagt actcgttgct gccgcgcgcg ccaccagaca taatagctga cagactaaca   5280
gactgttcct ttccatgggt cttttctgca gtcaccgtcg ggatccatgg gctccatcgg   5340
cgcagcaagc atggaatttt gttttgatgt attcaaggag ctcaaagtcc accatgccaa   5400
tgagaacatc ttctactgcc ccattgccat catgtcagct ctagccatgg tatacctggg   5460
tgcaaaagac agcaccagga cacagataaa taaggttgtt cgctttgata aacttccagg   5520
attcggagac agtattgaag ctcagtgtgg cacatctgta aacgttcact cttcacttag   5580
agacatcctc aaccaaatca ccaaaccaaa tgatgtttat tcgttcagcc ttgccagtag   5640
actttatgct gaagagagat acccaatcct gccagaatac ttgcagtgtg tgaaggaact   5700
gtatagagga ggcttggaac ctatcaactt tcaaacagct gcagatcaag ccagagagct   5760
catcaattcc tgggtagaaa gtcagacaaa tggaattatc agaaatgtcc ttcagccaag   5820
ctccgtggat tctcaaactg caatggttct ggttaatgcc attgtcttca aaggactgtg   5880
ggagaaaaca tttaaggatg aagacacaca agcaatgcct ttcagagtga ctgagcaaga   5940
aagcaaacct gtgcagatga tgtaccagat tggtttattt agagtggcat caatggcttc   6000
tgagaaaatg aagatcctgg agcttccatt tgccagtggg acaatgagca tgttggtgct   6060
gttgcctgat gaagtctcag gccttgagca gcttgagagt ataatcaact ttgaaaaact   6120
gactgaatgg accagttcta atgttatgga agagaggaag atcaaagtgt acttacctcg   6180
catgaagatg gaggaaaaat acaacctcac atctgtctta atggctatgg gcattactga   6240
```

-continued

```
cgtgtttagc tcttcagcca atctgtctgg catctcctca gcagagagcc tgaagatatc   6300
tcaagctgtc catgcagcac atgcagaaat caatgaagca ggcagagagg tggtagggtc   6360
agcagaggct ggagtggatg ctgcaagcgt ctctgaagaa tttagggctg accatccatt   6420
cctcttctgt atcaagcaca tcgcaaccaa cgccgttctc ttctttggca gatgtgtttc   6480
ccgcggccag cagatgacgc accagcagat gacgcaccag cagatgacgc accagcagat   6540
gacgcaccag cagatgacgc accagcagat gacgcaacaa catgtatcct gaaaggctct   6600
tgtggctgga tcggcctgct ggatgacgat gacaaatttg tgaaccaaca cctgtgcggc   6660
tcacacctgg tggaagctct ctacctagtg tgcggggaac gaggcttctt ctacacaccc   6720
aagacccgcc gggaggcaga ggacctgcag gtggggcagg tggagctggg cgggggccct   6780
ggtgcaggca gcctgcagcc cttggccctg gaggggtccc tgcagaagcg tggcattgtg   6840
gaacaatgct gtaccagcat ctgctccctc taccagctgg agaactactg caactagggc   6900
gcctaaaggg cgaattatcg cggccgctct agaccaggcg cctggatcca gatcacttct   6960
ggctaataaa agatcagagc tctagagatc tgtgtgttgg tttttttgtgg atctgctgtg   7020
ccttctagtt gccagccatc tgttgtttgc ccctcccccg tgccttcctt gaccctggaa   7080
ggtgccactc ccactgtcct ttcctaataa aatgaggaaa ttgcatcgca ttgtctgagt   7140
aggtgtcatt ctattctggg gggtggggtg gggcagcaca gcaaggggga ggattgggaa   7200
gacaatagca ggcatgctgg ggatgcggtg ggctctatgg gtacctctct ctctctctct   7260
ctctctctct ctctctctct ctctcggtac ctctctcgag ggggggcccg gtacccaatt   7320
cgccctatag tgagtcgtat tacgcgcgct cactggccgt cgttttacaa cgtcgtgact   7380
gggaaaaccc tggcgttacc caacttaatc gccttgcagc acatccccct ttcgccagct   7440
ggcgtaatag cgaagaggcc cgcaccgatc gcccttccca acagttgcgc agcctgaatg   7500
gcgaatggaa attgtaagcg ttaatatttt gttaaaattc gcgttaaatt tttgttaaat   7560
cagctcattt tttaaccaat aggccgaaat cggcaaaatc ccttataaat caaaagaata   7620
gaccgagata gggttgagtg ttgttccagt ttggaacaag agtccactat taaagaacgt   7680
ggactccaac gtcaaagggc gaaaaaccgt ctatcagggc gatggcccac tactccggga   7740
tcatatgaca agatgtgtat ccaccttaac ttaatgattt ttaccaaaat cattagggga   7800
ttcatcagtg ctcagggtca acgagaatta acattccgtc aggaaagctt atgatgatga   7860
tgtgcttaaa aacttactca atggctggtt atgcatatcg caatacatgc gaaaaaccta   7920
aaagagcttg ccgataaaaa aggccaattt attgctattt accgcggctt tttattgagc   7980
ttgaaagata aataaaatag ataggtttta tttgaagcta aatcttcttt atcgtaaaaa   8040
atgccctctt gggttatcaa gagggtcatt atatttcgcg gaataacatc atttggtgac   8100
gaaataacta agcacttgtc tcctgtttac tcccctgagc ttgaggggtt aacatgaagg   8160
tcatcgatag caggataata atacagtaaa acgctaaacc aataatccaa atccagccat   8220
cccaaattgg tagtgaatga ttataaataa cagcaaacag taatgggcca ataacaccgg   8280
ttgcattggt aaggctcacc aataatccct gtaaagcacc ttgctgatga ctctttgttt   8340
ggatagacat cactccctgt aatgcaggta aagcgatccc accaccagcc aataaaatta   8400
aaacagggaa aactaaccaa ccttcagata taaacgctaa aaaggcaaat gcactactat   8460
ctgcaataaa tccgagcagt actgccgttt tttcgcccat ttagtggcta ttcttcctgc   8520
cacaaaggct tggaatactg agtgtaaaag accaagaccc gtaatgaaaa gccaaccatc   8580
atgctattca tcatcacgat ttctgtaata gcaccacacc gtgctggatt ggctatcaat   8640
```

-continued

```
gcgctgaaat aataatcaac aaatggcatc gttaaataag tgatgtatac cgatcagctt   8700
ttgttccctt tagtgagggt taattgcgcg cttggcgtaa tcatggtcat agctgtttcc   8760
tgtgtgaaat tgttatccgc tcacaattcc acacaacata cgagccggaa gcataaagtg   8820
taaagcctgg ggtgcctaat gagtgagcta actcacatta attgcgttgc gctcactgcc   8880
cgctttccag tcgggaaacc tgtcgtgcca gctgcattaa tgaatcggcc aacgcgcggg   8940
gagaggcggt ttgcgtattg ggcgctcttc cgcttcctcg ctcactgact cgctgcgctc   9000
ggtcgttcgg ctgcggcgag cggtatcagc tcactcaaag gcggtaatac ggttatccac   9060
agaatcaggg gataacgcag gaaagaacat gtgagcaaaa ggccagcaaa aggccaggaa   9120
ccgtaaaaag gccgcgttgc tggcgttttt ccataggctc cgcccccctg acgagcatca   9180
caaaaatcga cgctcaagtc agaggtggcg aaacccgaca ggactataaa gataccaggc   9240
gtttccccct ggaagctccc tcgtgcgctc tcctgttccg accctgccgc ttaccggata   9300
cctgtccgcc tttctccctt cgggaagcgt ggcgctttct catagctcac gctgtaggta   9360
tctcagttcg gtgtaggtcg ttcgctccaa gctgggctgt gtgcacgaac cccccgttca   9420
gcccgaccgc tgcgccttat ccggtaacta tcgtcttgag tccaacccgg taagacacga   9480
cttatcgcca ctggcagcag ccactggtaa caggattagc agagcgaggt atgtaggcgg   9540
tgctacagag ttcttgaagt ggtggcctaa ctacggctac actagaagga cagtatttgg   9600
tatctgcgct ctgctgaagc cagttacctt cggaaaaaga gttggtagct cttgatccgg   9660
caaacaaacc accgctggta gcggtggttt ttttgtttgc aagcagcaga ttacgcgcag   9720
aaaaaaagga tctcaagaag atcctttgat cttttctacg gggtctgacg ctcagtggaa   9780
cgaaaactca cgttaaggga ttttggtcat gagattatca aaaaggatct tcacctagat   9840
ccttttaaat taaaaatgaa gttttaaatc aatctaaagt atatatgagt aaacttggtc   9900
tgacagttac caatgcttaa tcagtgaggc acctatctca gcgatctgtc tatttcgttc   9960
atccatagtt gcctgactcc ccgtcgtgta gataactacg atacgggagg gcttaccatc  10020
tggccccagt gctgcaatga taccgcgaga cccacgctca ccggctccag atttatcagc  10080
aataaaccag ccagccggaa gggccgagcg cagaagtggt cctgcaactt tatccgcctc  10140
catccagtct attaattgtt gccgggaagc tagagtaagt agttcgccag ttaatagttt  10200
gcgcaacgtt gttgccattg ctacaggcat cgtggtgtca cgctcgtcgt ttggtatggc  10260
ttcattcagc tccggttccc aacgatcaag gcgagttaca tgatccccca tgttgtgcaa  10320
aaaagcggtt agctccttcg gtcctccgat cgttgtcaga agtaagttgg ccgcagtgtt  10380
atcactcatg gttatggcag cactgcataa ttctcttact gtcatgccat ccgtaagatg  10440
cttttctgtg actggtgagt actcaaccaa gtcattctga gaatagtgta tgcggcgacc  10500
gagttgctct tgcccggcgt caatacggga taataccgcg ccacatagca gaactttaaa  10560
agtgctcatc attggaaaac gttcttcggg gcgaaaactc tcaaggatct taccgctgtt  10620
gagatccagt tcgatgtaac ccactcgtgc acccaactga tcttcagcat cttttacttt  10680
caccagcgtt tctgggtgag caaaaacagg aaggcaaaat gccgcaaaaa agggaataag  10740
ggcgacacgg aaatgttgaa tactcatact cttccttttt caatattatt gaagcattta  10800
tcagggttat tgtctcatga gcggatacat atttgaatgt atttagaaaa ataaacaaat  10860
aggggttccg cgcacatttc cccgaaaagt gccac                             10895
```

<210> SEQ ID NO 42

-continued

<211> LENGTH: 11271
<212> TYPE: DNA
<213> ORGANISM: Artificial Sequence
<220> FEATURE:
<223> OTHER INFORMATION: Synthetic

<400> SEQUENCE: 42

```
ctgacgcgcc ctgtagcggc gcattaagcg cggcgggtgt ggtggttacg cgcagcgtga     60
ccgctacact tgccagcgcc ctagcgcccg ctcctttcgc tttcttccct tcctttctcg    120
ccacgttcgc cggcatcaga ttggctattg gccattgcat acgttgtatc catatcataa    180
tatgtacatt tatattggct catgtccaac attaccgcca tgttgacatt gattattgac    240
tagttattaa tagtaatcaa ttacggggtc attagttcat agcccatata tggagttccg    300
cgttacataa cttacggtaa atggcccgcc tggctgaccg cccaacgacc cccgcccatt    360
gacgtcaata atgacgtatg ttcccatagt aacgccaata gggactttcc attgacgtca    420
atgggtggag tatttacggt aaactgccca cttggcagta catcaagtgt atcatatgcc    480
aagtacgccc cctattgacg tcaatgacgg taaatggccc gcctggcatt atgcccagta    540
catgacctta tgggactttc ctacttggca gtacatctac gtattagtca tcgctattac    600
catggtgatg cggttttggc agtacatcaa tgggcgtgga tagcggtttg actcacgggg    660
atttccaagt ctccacccca ttgacgtcaa tgggagtttg ttttggcacc aaaatcaacg    720
ggactttcca aaatgtcgta acaactccgc cccattgacg caaatgggcg gtaggcgtgt    780
acggtgggag gtctatataa gcagagctcg tttagtgaac cgtcagatcg cctggagacg    840
ccatccacgc tgttttgacc tccatagaag acaccgggac cgatccagcc tccgcggccg    900
ggaacggtgc attggaacgc ggattccccg tgccaagagt gacgtaagta ccgcctatag    960
actctatagg cacacccctt tggctcttat gcatgctata ctgtttttgg cttggggcct   1020
atacaccccc gcttccttat gctataggtg atggtatagc ttagcctata ggtgtgggtt   1080
attgaccatt attgaccact cccctattgg tgacgatact ttccattact aatccataac   1140
atggctcttt gccacaacta tctctattgg ctatatgcca atactctgtc cttcagagac   1200
tgacacggac tctgtatttt tacaggatgg ggtcccattt attatttaca aattcacata   1260
tacaacaacg ccgtcccccg tgcccgcagt ttttattaaa catagcgtgg gatctccacg   1320
cgaatctcgg gtacgtgttc cggacatggg ctcttctccg gtagcggcgg agcttccaca   1380
tccgagccct ggtcccatgc ctccagcggc tcatggtcgc tcggcagctc cttgctccta   1440
acagtggagg ccagacttag gcacagcaca atgcccacca ccaccagtgt gccgcacaag   1500
gccgtggcgg tagggtatgt gtctgaaaat gagcgtggag attgggctcg cacggctgac   1560
gcagatggaa gacttaaggc agcggcagaa gaagatgcag gcagctgagt tgttgtattc   1620
tgataagagt cagaggtaac tcccgttgcg gtgctgttaa cggtggaggg cagtgtagtc   1680
tgagcagtac tcgttgctgc cgcgcgcgcc accagacata atagctgaca gactaacaga   1740
ctgttccttt ccatgggtct tttctgcagt caccgtcgga ccatgtgtga acttgatatt   1800
ttacatgatt ctctttacca attctgcccc gaattacact taaaacgact caacagctta   1860
acgttggctt gccacgcatt acttgactgt aaaactctca ctcttaccga acttggccgt   1920
aacctgccaa ccaaagcgag aacaaaacat aacatcaaac gaatcgaccg attgttaggt   1980
aatcgtcacc tccacaaaga gcgactcgct gtataccgtt ggcatgctag ctttatctgt   2040
tcgggcaata cgatgcccat tgtacttgtt gactggtctg atattcgtga gcaaaaacga   2100
cttatggtat tgcgagcttc agtcgcacta cacggtcgtt ctgttactct ttatgagaaa   2160
```

-continued

```
gcgttcccgc tttcagagca atgttcaaag aaagctcatg accaatttct agccgacctt   2220
gcgagcattc taccgagtaa caccacaccg ctcattgtca gtgatgctgg ctttaaagtg   2280
ccatggtata aatccgttga gaagctgggt tggtactggt taagtcgagt aagaggaaaa   2340
gtacaatatg cagacctagg agcggaaaac tggaaaccta tcagcaactt acatgatatg   2400
tcatctagtc actcaaagac tttaggctat aagaggctga ctaaaagcaa tccaatctca   2460
tgccaaattc tattgtataa atctcgctct aaaggccgaa aaaatcagcg ctcgacacgg   2520
actcattgtc accacccgtc acctaaaatc tactcagcgt cggcaaagga gccatgggtt   2580
ctagcaacta acttacctgt tgaaattcga acacccaaac aacttgttaa tatctattcg   2640
aagcgaatgc agattgaaga aaccttccga gacttgaaaa gtcctgccta cggactaggc   2700
ctacgccata gccgaacgag cagctcagag cgttttgata tcatgctgct aatcgccctg   2760
atgcttcaac taacatgttg gcttgcgggc gttcatgctc agaaacaagg ttgggacaag   2820
cacttccagg ctaacacagt cagaaatcga aacgtactct caacagttcg cttaggcatg   2880
gaagttttgc ggcattctgg ctacacaata acaagggaag acttactcgt ggctgcaacc   2940
ctactagctc aaaatttatt cacacatggt tacgctttgg ggaaattatg ataatgatcc   3000
agatcacttc tggctaataa aagatcagag ctctagagat ctgtgtgttg gttttttgtg   3060
gatctgctgt gccttctagt tgccagccat ctgttgtttg cccctccccc gtgccttcct   3120
tgaccctgga aggtgccact cccactgtcc tttcctaata aaatgaggaa attgcatcgc   3180
attgtctgag taggtgtcat tctattctgg ggggtggggt ggggcagcac agcaaggggg   3240
aggattggga agacaatagc aggcatgctg gggatgcggt gggctctatg ggtacctctc   3300
tctctctctc tctctctctc tctctctctc tctctcggta cctctctctc tctctctctc   3360
tctctctctc tctctctctc tcggtaccag gtgctgaaga attgacccgg tgaccaaagg   3420
tgccttttat catcacttta aaaataaaaa acaattactc agtgcctgtt ataagcagca   3480
attaattatg attgatgcct acatcacaac aaaaactgat ttaacaaatg gttggtctgc   3540
cttagaaagt atatttgaac attatcttga ttatattatt gataataata aaaaccttat   3600
ccctatccaa gaagtgatgc ctatcattgg ttggaatgaa cttgaaaaaa attagccttg   3660
aatacattac tggtaaggta aacgccattg tcagcaaatt gatccaagag aaccaactta   3720
aagctttcct gacggaatgt taattctcgt tgaccctgag cactgatgaa tcccctaatg   3780
attttggtaa aaatcattaa gttaaggtgg atacacatct tgtcatatga tcccggtaat   3840
gtgagttagc tcactcatta ggcaccccag gctttacact ttatgcttcc ggctcgtatg   3900
ttgtgtggaa ttgtgagcgg ataacaattt cacacaggaa acagctatga ccatgattac   3960
gccaagcgcg caattaaccc tcactaaagg gaacaaaagc tggagctcca ccgcggtggc   4020
ggccgctcta gaactagtgg atcccccggg catcagattg gctattggcc attgcatacg   4080
ttgtatccat atcataatat gtacatttat attggctcat gtccaacatt accgccatgt   4140
tgacattgat tattgactag ttattaatag taatcaatta cggggtcatt agttcatagc   4200
ccatatatgg agttccgcgt tacataactt acggtaaatg gcccgcctgg ctgaccgccc   4260
aacgaccccc gcccattgac gtcaataatg acgtatgttc ccatagtaac gccaataggg   4320
actttccatt gacgtcaatg ggtggagtat ttacggtaaa ctgcccactt ggcagtacat   4380
caagtgtatc atatgccaag tacgccccct attgacgtca atgacggtaa atggcccgcc   4440
tggcattatg cccagtacat gaccttatgg gactttccta cttggcagta catctacgta   4500
```

-continued

```
ttagtcatcg ctattaccat ggtgatgcgg ttttggcagt acatcaatgg gcgtggatag   4560
cggtttgact cacggggatt tccaagtctc caccccattg acgtcaatgg gagtttgttt   4620
tggcaccaaa atcaacggga ctttccaaaa tgtcgtaaca actccgcccc attgacgcaa   4680
atgggcggta ggcgtgtacg gtgggaggtc tatataagca gagctcgttt agtgaaccgt   4740
cagatcgcct ggagacgcca tccacgctgt tttgacctcc atagaagaca ccgggaccga   4800
tccagcctcc gcggccggga acggtgcatt ggaacgcgga ttccccgtgc caagagtgac   4860
gtaagtaccg cctatagact ctataggcac acccctttgg ctcttatgca tgctatactg   4920
tttttggctt ggggcctata cacccccgct tccttatgct ataggtgatg gtatagctta   4980
gcctataggt gtgggttatt gaccattatt gaccactccc ctattggtga cgatactttc   5040
cattactaat ccataacatg gctctttgcc acaactatct ctattggcta tatgccaata   5100
ctctgtcctt cagagactga cacggactct gtatttttac aggatggggt cccatttatt   5160
atttacaaat tcacatatac aacaacgccg tcccccgtgc ccgcagtttt tattaaacat   5220
agcgtgggat ctccacgcga atctcgggta cgtgttccgg acatgggctc ttctccggta   5280
gcggcggagc ttccacatcc gagccctggt cccatgcctc cagcggctca tggtcgctcg   5340
gcagctcctt gctcctaaca gtggaggcca gacttaggca cagcacaatg cccaccacca   5400
ccagtgtgcc gcacaaggcc gtggcggtag ggtatgtgtc tgaaaatgag cgtggagatt   5460
gggctcgcac ggctgacgca gatggaagac ttaaggcagc ggcagaagaa gatgcaggca   5520
gctgagttgt tgtattctga taagagtcag aggtaactcc cgttgcggtg ctgttaacgg   5580
tggagggcag tgtagtctga gcagtactcg ttgctgccgc gcgcgccacc agacataata   5640
gctgacagac taacagactg ttcctttcca tgggtctttt ctgcagtcac cgtcgggatc   5700
catgggctcc atcggcgcag caagcatgga attttgtttt gatgtattca aggagctcaa   5760
agtccaccat gccaatgaga acatcttcta ctgccccatt gccatcatgt cagctctagc   5820
catggtatac ctgggtgcaa aagacagcac caggacacag ataaataagg ttgttcgctt   5880
tgataaactt ccaggattcg gagacagtat tgaagctcag tgtggcacat ctgtaaacgt   5940
tcactcttca cttagagaca tcctcaacca aatcaccaaa ccaaatgatg tttattcgtt   6000
cagccttgcc agtagacttt atgctgaaga gagataccca atcctgccag aatacttgca   6060
gtgtgtgaag gaactgtata gaggaggctt ggaacctatc aactttcaaa cagctgcaga   6120
tcaagccaga gagctcatca attcctgggt agaaagtcag acaaatggaa ttatcagaaa   6180
tgtccttcag ccaagctccg tggattctca aactgcaatg gttctggtta atgccattgt   6240
cttcaaagga ctgtgggaga aaacatttaa ggatgaagac acacaagcaa tgcctttcag   6300
agtgactgag caagaaagca aacctgtgca gatgatgtac cagattggtt tatttagagt   6360
ggcatcaatg gcttctgaga aaatgaagat cctggagctt ccatttgcca gtgggacaat   6420
gagcatgttg gtgctgttgc ctgatgaagt ctcaggcctt gagcagcttg agagtataat   6480
caactttgaa aaactgactg aatggaccag ttctaatgtt atggaagaga ggaagatcaa   6540
agtgtactta cctcgcatga agatggagga aaaatacaac ctcacatctg tcttaatggc   6600
tatgggcatt actgacgtgt ttagctcttc agccaatctg tctggcatct cctcagcaga   6660
gagcctgaag atatctcaag ctgtccatgc agcacatgca gaaatcaatg aagcaggcag   6720
agaggtggta gggtcagcag aggctggagt ggatgctgca agcgtctctg aagaatttag   6780
ggctgaccat ccattcctct tctgtatcaa gcacatcgca accaacgccg ttctcttctt   6840
tggcagatgt gtttcccgcg gccagcagat gacgcaccag cagatgacgc accagcagat   6900
```

-continued

```
gacgcaccag cagatgacgc accagcagat gacgcaccag cagatgacgc aacaacatgt   6960
atcctgaaag gctcttgtgg ctggatcggc ctgctggatg acgatgacaa atttgtgaac   7020
caacacctgt gcggctcaca cctggtggaa gctctctacc tagtgtgcgg ggaacgaggc   7080
ttcttctaca cacccaagac ccgccgggag gcagaggacc tgcaggtggg gcaggtggag   7140
ctgggcgggg gccctggtgc aggcagcctg cagcccttgg ccctggaggg gtccctgcag   7200
aagcgtggca ttgtggaaca atgctgtacc agcatctgct ccctctacca gctggagaac   7260
tactgcaact agggcgccta aagggcgaat tatcgcggcc gctctagacc aggcgcctgg   7320
atccagatca cttctggcta ataaaagatc agagctctag agatctgtgt gttggttttt   7380
tgtggatctg ctgtgccttc tagttgccag ccatctgttg tttgcccctc ccccgtgcct   7440
tccttgaccc tggaaggtgc cactcccact gtcctttcct aataaaatga ggaaattgca   7500
tcgcattgtc tgagtaggtg tcattctatt ctggggggtg gggtggggca gcacagcaag   7560
ggggaggatt gggaagacaa tagcaggcat gctggggatg cggtgggctc tatgggtacc   7620
tctctctctc tctctctctc tctctctctc tctctctctc ggtacctctc ctcgaggggg   7680
ggcccggtac ccaattcgcc ctatagtgag tcgtattacg cgcgctcact ggccgtcgtt   7740
ttacaacgtc gtgactggga aaaccctggc gttacccaac ttaatcgcct tgcagcacat   7800
ccccctttcg ccagctggcg taatagcgaa gaggcccgca ccgatcgccc ttcccaacag   7860
ttgcgcagcc tgaatggcga atggaaattg taagcgttaa tattttgtta aaattcgcgt   7920
taaatttttg ttaaatcagc tcatttttta accaataggc cgaaatcggc aaaatccctt   7980
ataaatcaaa agaatagacc gagatagggt tgagtgttgt tccagtttgg aacaagagtc   8040
cactattaaa gaacgtggac tccaacgtca aagggcgaaa aaccgtctat cagggcgatg   8100
gcccactact ccgggatcat atgacaagat gtgtatccac cttaacttaa tgatttttac   8160
caaaatcatt aggggattca tcagtgctca gggtcaacga gaattaacat tccgtcagga   8220
aagcttatga tgatgatgtg cttaaaaact tactcaatgg ctggttatgc atatcgcaat   8280
acatgcgaaa aacctaaaag agcttgccga taaaaaaggc caatttattg ctatttaccg   8340
cggcttttta ttgagcttga aagataaata aaatagatag gttttatttg aagctaaatc   8400
ttctttatcg taaaaaatgc cctcttgggt tatcaagagg gtcattatat ttcgcggaat   8460
aacatcattt ggtgacgaaa taactaagca cttgtctcct gtttactccc ctgagcttga   8520
ggggttaaca tgaaggtcat cgatagcagg ataataatac agtaaaacgc taaaccaata   8580
atccaaatcc agccatccca aattggtagt gaatgattat aaataacagc aaacagtaat   8640
gggccaataa caccggttgc attggtaagg ctcaccaata atccctgtaa agcaccttgc   8700
tgatgactct ttgtttggat agacatcact ccctgtaatg caggtaaagc gatcccacca   8760
ccagccaata aaattaaaac agggaaaact aaccaacctt cagatataaa cgctaaaaag   8820
gcaaatgcac tactatctgc aataaatccg agcagtactg ccgttttttc gcccatttag   8880
tggctattct tcctgccaca aaggcttgga atactgagtg taaaagacca agacccgtaa   8940
tgaaaagcca accatcatgc tattcatcat cacgatttct gtaatagcac cacaccgtgc   9000
tggattggct atcaatgcgc tgaaataata atcaacaaat ggcatcgtta aataagtgat   9060
gtataccgat cagcttttgt tccctttagt gagggttaat tgcgcgcttg gcgtaatcat   9120
ggtcatagct gtttcctgtg tgaaattgtt atccgctcac aattccacac aacatacgag   9180
ccggaagcat aaagtgtaaa gcctggggtg cctaatgagt gagctaactc acattaattg   9240
```

-continued

```
cgttgcgctc actgcccgct ttccagtcgg gaaacctgtc gtgccagctg cattaatgaa   9300
tcggccaacg cgcggggaga ggcggtttgc gtattgggcg ctcttccgct tcctcgctca   9360
ctgactcgct gcgctcggtc gttcggctgc ggcgagcggt atcagctcac tcaaaggcgg   9420
taatacggtt atccacagaa tcaggggata acgcaggaaa gaacatgtga gcaaaaggcc   9480
agcaaaaggc caggaaccgt aaaaaggccg cgttgctggc gtttttccat aggctccgcc   9540
cccctgacga gcatcacaaa aatcgacgct caagtcagag gtggcgaaac ccgacaggac   9600
tataaagata ccaggcgttt ccccctggaa gctccctcgt gcgctctcct gttccgaccc   9660
tgccgcttac cggatacctg tccgcctttc tcccttcggg aagcgtggcg ctttctcata   9720
gctcacgctg taggtatctc agttcggtgt aggtcgttcg ctccaagctg ggctgtgtgc   9780
acgaaccccc cgttcagccc gaccgctgcg ccttatccgg taactatcgt cttgagtcca   9840
acccggtaag acacgactta tcgccactgg cagcagccac tggtaacagg attagcagag   9900
cgaggtatgt aggcggtgct acagagttct tgaagtggtg gcctaactac ggctacacta   9960
gaaggacagt atttggtatc tgcgctctgc tgaagccagt taccttcgga aaaagagttg  10020
gtagctcttg atccggcaaa caaaccaccg ctggtagcgg tggttttttt gtttgcaagc  10080
agcagattac gcgcagaaaa aaaggatctc aagaagatcc tttgatcttt tctacggggt  10140
ctgacgctca gtggaacgaa aactcacgtt aagggatttt ggtcatgaga ttatcaaaaa  10200
ggatcttcac ctagatcctt ttaaattaaa aatgaagttt taaatcaatc taaagtatat  10260
atgagtaaac ttggtctgac agttaccaat gcttaatcag tgaggcacct atctcagcga  10320
tctgtctatt tcgttcatcc atagttgcct gactccccgt cgtgtagata actacgatac  10380
gggagggctt accatctggc cccagtgctg caatgatacc gcgagaccca cgctcaccgg  10440
ctccagattt atcagcaata aaccagccag ccggaagggc cgagcgcaga agtggtcctg  10500
caactttatc cgcctccatc cagtctatta attgttgccg ggaagctaga gtaagtagtt  10560
cgccagttaa tagtttgcgc aacgttgttg ccattgctac aggcatcgtg gtgtcacgct  10620
cgtcgtttgg tatggcttca ttcagctccg gttcccaacg atcaaggcga gttacatgat  10680
cccccatgtt gtgcaaaaaa gcggttagct ccttcggtcc tccgatcgtt gtcagaagta  10740
agttggccgc agtgttatca ctcatggtta tggcagcact gcataattct cttactgtca  10800
tgccatccgt aagatgcttt tctgtgactg gtgagtactc aaccaagtca ttctgagaat  10860
agtgtatgcg gcgaccgagt tgctcttgcc cggcgtcaat acgggataat accgcgccac  10920
atagcagaac tttaaaagtg ctcatcattg gaaaacgttc ttcggggcga aaactctcaa  10980
ggatcttacc gctgttgaga tccagttcga tgtaacccac tcgtgcaccc aactgatctt  11040
cagcatcttt tactttcacc agcgtttctg ggtgagcaaa aacaggaagg caaaatgccg  11100
caaaaaaggg aataagggcg acacggaaat gttgaatact catactcttc ctttttcaat  11160
attattgaag catttatcag ggttattgtc tcatgagcgg atacatattt gaatgtattt  11220
agaaaaataa acaaataggg gttccgcgca catttccccg aaaagtgcca c            11271
```

<210> SEQ ID NO 43
<211> LENGTH: 11332
<212> TYPE: DNA
<213> ORGANISM: Artificial Sequence
<220> FEATURE:
<223> OTHER INFORMATION: Synthetic

<400> SEQUENCE: 43

```
ctgacgcgcc ctgtagcggc gcattaagcg cggcgggtgt ggtggttacg cgcagcgtga     60
```

-continued

```
ccgctacact tgccagcgcc ctagcgcccg ctcctttcgc tttcttccct tcctttctcg    120
ccacgttcgc cggcatcaga ttggctattg gccattgcat acgttgtatc catatcataa    180
tatgtacatt tatattggct catgtccaac attaccgcca tgttgacatt gattattgac    240
tagttattaa tagtaatcaa ttacggggtc attagttcat agcccatata tggagttccg    300
cgttacataa cttacggtaa atggcccgcc tggctgaccg cccaacgacc cccgcccatt    360
gacgtcaata atgacgtatg ttcccatagt aacgccaata gggactttcc attgacgtca    420
atgggtggag tatttacggt aaactgccca cttggcagta catcaagtgt atcatatgcc    480
aagtacgccc cctattgacg tcaatgacgg taaatggccc gcctggcatt atgcccagta    540
catgacctta tgggactttc ctacttggca gtacatctac gtattagtca tcgctattac    600
catggtgatg cggttttggc agtacatcaa tgggcgtgga tagcggtttg actcacgggg    660
atttccaagt ctccacccca ttgacgtcaa tgggagtttg ttttggcacc aaaatcaacg    720
ggactttcca aaatgtcgta acaactccgc cccattgacg caaatgggcg gtaggcgtgt    780
acggtgggag gtctatataa gcagagctcg tttagtgaac cgtcagatcg cctggagacg    840
ccatccacgc tgttttgacc tccatagaag acaccgggac cgatccagcc tccgcggccg    900
ggaacggtgc attggaacgc ggattccccg tgccaagagt gacgtaagta ccgcctatag    960
actctatagg cacacccctt tggctcttat gcatgctata ctgtttttgg cttggggcct   1020
atacaccccc gcttccttat gctataggtg atggtatagc ttagcctata ggtgtgggtt   1080
attgaccatt attgaccact cccctattgg tgacgatact ttccattact aatccataac   1140
atggctcttt gccacaacta tctctattgg ctatatgcca atactctgtc cttcagagac   1200
tgacacggac tctgtatttt tacaggatgg ggtcccattt attatttaca aattcacata   1260
tacaacaacg ccgtcccccg tgcccgcagt ttttattaaa catagcgtgg gatctccacg   1320
cgaatctcgg gtacgtgttc cggacatggg ctcttctccg gtagcggcgg agcttccaca   1380
tccgagccct ggtcccatgc ctccagcggc tcatggtcgc tcggcagctc cttgctccta   1440
acagtggagg ccagacttag gcacagcaca atgcccacca ccaccagtgt gccgcacaag   1500
gccgtggcgg tagggtatgt gtctgaaaat gagcgtggag attgggctcg cacggctgac   1560
gcagatggaa gacttaaggc agcggcagaa gaagatgcag gcagctgagt tgttgtattc   1620
tgataagagt cagaggtaac tcccgttgcg gtgctgttaa cggtggaggg cagtgtagtc   1680
tgagcagtac tcgttgctgc cgcgcgcgcc accagacata atagctgaca gactaacaga   1740
ctgttccttt ccatgggtct tttctgcagt caccgtcgga ccatgtgcga actcgatatt   1800
ttacacgact ctctttacca attctgcccc gaattacact taaaacgact caacagctta   1860
acgttggctt gccacgcatt acttgactgt aaaactctca ctcttaccga acttggccgt   1920
aacctgccaa ccaaagcgag aacaaaacat aacatcaaac gaatcgaccg attgttaggt   1980
aatcgtcacc tccacaaaga gcgactcgct gtataccgtt ggcatgctag ctttatctgt   2040
tcgggcaata cgatgcccat tgtacttgtt gactggtctg atattcgtga gcaaaaacga   2100
cttatggtat tgcgagcttc agtcgcacta cacggtcgtt ctgttactct ttatgagaaa   2160
gcgttcccgc tttcagagca atgttcaaag aaagctcatg accaatttct agccgacctt   2220
gcgagcattc taccgagtaa caccacaccg ctcattgtca gtgatgctgg ctttaaagtg   2280
ccatggtata aatccgttga gaagctgggt tggtactggt taagtcgagt aagaggaaaa   2340
gtacaatatg cagacctagg agcggaaaac tggaaaccta tcagcaactt acatgatatg   2400
```

-continued

```
tcatctagtc actcaaagac tttaggctat aagaggctga ctaaaagcaa tccaatctca   2460
tgccaaattc tattgtataa atctcgctct aaaggccgaa aaaatcagcg ctcgacacgg   2520
actcattgtc accacccgtc acctaaaatc tactcagcgt cggcaaagga gccatgggtt   2580
ctagcaacta acttacctgt tgaaattcga acacccaaac aacttgttaa tatctattcg   2640
aagcgaatgc agattgaaga aaccttccga gacttgaaaa gtcctgccta cggactaggc   2700
ctacgccata gccgaacgag cagctcagag cgttttgata tcatgctgct aatcgccctg   2760
atgcttcaac taacatgttg gcttgcgggc gttcatgctc agaaacaagg ttgggacaag   2820
cacttccagg ctaacacagt cagaaatcga aacgtactct caacagttcg cttaggcatg   2880
gaagttttgc ggcattctgg ctacacaata acaagggaag acttactcgt ggctgcaacc   2940
ctactagctc aaaatttatt cacacatggt tacgctttgg ggaaattatg aggggatcgc   3000
tctagagcga tccgggatct cgggaaaagc gttggtgacc aaaggtgcct tttatcatca   3060
ctttaaaaat aaaaaacaat tactcagtgc ctgttataag cagcaattaa ttatgattga   3120
tgcctacatc acaacaaaaa ctgatttaac aaatggttgg tctgccttag aaagtatatt   3180
tgaacattat cttgattata ttattgataa taataaaaac cttatcccta tccaagaagt   3240
gatgcctatc attggttgga atgaacttga aaaaaattag ccttgaatac attactggta   3300
aggtaaacgc cattgtcagc aaattgatcc aagagaacca acttaaagct ttcctgacgg   3360
aatgttaatt ctcgttgacc ctgagcactg atgaatcccc taatgatttt ggtaaaaatc   3420
attaagttaa ggtggataca catcttgtca tatgatcccg gtaatgtgag ttagctcact   3480
cattaggcac cccaggcttt acactttatg cttccggctc gtatgttgtg tggaattgtg   3540
agcggataac aatttcacac aggaaacagc tatgaccatg attacgccaa gcgcgcaatt   3600
aaccctcact aaagggaaca aaagctggag ctccaccgcg gtggcggccg ctctagaact   3660
agtggatccc ccgggctgca gaaaaatgcc aggtggacta tgaactcaca tccaaaggag   3720
cttgacctga tacctgattt tcttcaaact ggggaaacaa cacaatccca caaaacagct   3780
cagagagaaa ccatcactga tggctacagc accaaggtat gcaatggcaa tccattcgac   3840
attcatctgt gacctgagca aaatgattta tctctccatg aatggttgct tctttccctc   3900
atgaaaaggc aatttccaca ctcacaatat gcaacaaaga caaacagaga acaattaatg   3960
tgctccttcc taatgtcaaa attgtagtgg caaagaggag aacaaaatct caagttctga   4020
gtaggtttta gtgattggat aagaggcttt gacctgtgag ctcacctgga cttcatatcc   4080
ttttggataa aaagtgcttt tataactttc aggtctccga gtctttattc atgagactgt   4140
tggtttaggg acagacccac aatgaaatgc ctggcatagg aaagggcagc agagccttag   4200
ctgacctttt cttgggacaa gcattgtcaa acaatgtgtg acaaaactat ttgtactgct   4260
ttgcacagct gtgctgggca gggcaatcca ttgccaccta tcccaggtaa ccttccaact   4320
gcaagaagat tgttgcttac tctctctaga aagcttctgc agactgacat gcatttcata   4380
ggtagagata acatttactg ggaagcacat ctatcatcat aaaaagcagg caagattttc   4440
agactttctt agtggctgaa atagaagcaa aagacgtgat taaaaacaaa atgaaacaaa   4500
aaaaatcagt tgatacctgt ggtgtagaca tccagcaaaa aaatattatt tgcactacca   4560
tcttgtctta agtcctcaga cttggcaagg agaatgtaga tttctacagt atatatgttt   4620
tcacaaaagg aaggagagaa acaaaagaaa atggcactga ctaaacttca gctagtggta   4680
taggaaagta attctgctta acagagattg cagtgatctc tatgtatgtc ctgaagaatt   4740
atgttgtact tttttccccc atttttaaat caaacagtgc tttacagagg tcagaatggt   4800
```

```
ttctttactg tttgtcaatt ctattatttc aatacagaac aatagcttct ataactgaaa   4860
tatatttgct attgtatatt atgattgtcc ctcgaaccat gaacactcct ccagctgaat   4920
ttcacaattc ctctgtcatc tgccaggcca ttaagttatt catggaagat ctttgaggaa   4980
cactgcaagt tcatatcata aacacatttg aaattgagta ttgttttgca ttgtatggag   5040
ctatgttttg ctgtatcctc agaaaaaaag tttgttataa agcattcaca cccataaaaa   5100
gatagattta aatattccag ctataggaaa gaaagtgcgt ctgctcttca ctctagtctc   5160
agttggctcc ttcacatgca tgcttcttta tttctcctat tttgtcaaga aaataatagg   5220
tcacgtcttg ttctcactta tgtcctgcct agcatggctc agatgcacgt tgtagataca   5280
agaaggatca aatgaaacag acttctggtc tgttactaca accatagtaa taagcacact   5340
aactaataat tgctaattat gttttccatc tctaaggttc ccacattttt ctgttttctt   5400
aaagatccca ttatctggtt gtaactgaag ctcaatggaa catgagcaat atttcccagt   5460
cttctctccc atccaacagt cctgatggat tagcagaaca ggcagaaaac acattgttac   5520
ccagaattaa aaactaatat ttgctctcca ttcaatccaa aatggaccta ttgaaactaa   5580
aatctaaccc aatcccatta aatgatttct atggcgtcaa aggtcaaact tctgaaggga   5640
acctgtgggt gggtcacaat tcaggctata tattccccag ggctcagcca gtggatcaac   5700
atacagctag aaagctgtat tgcctttagc actcaagctc aaaagacaac tcagagttca   5760
ccatgggctc catcggcgca gcaagcatgg aattttgttt tgatgtattc aaggagctca   5820
aagtccacca tgccaatgag aacatcttct actgccccat tgccatcatg tcagctctag   5880
ccatggtata cctgggtgca aaagacagca ccaggacaca gataaataag gttgttcgct   5940
ttgataaact tccaggattc ggagacagta ttgaagctca gtgtggcaca tctgtaaacg   6000
ttcactcttc acttagagac atcctcaacc aaatcaccaa accaaatgat gtttattcgt   6060
tcagccttgc cagtagactt tatgctgaag agagataccc aatcctgcca gaatacttgc   6120
agtgtgtgaa ggaactgtat agaggaggct tggaacctat caactttcaa acagctgcag   6180
atcaagccag agagctcatc aattcctggg tagaaagtca gacaaatgga attatcagaa   6240
atgtccttca gccaagctcc gtggattctc aaactgcaat ggttctggtt aatgccattg   6300
tcttcaaagg actgtgggag aaaacattta aggatgaaga cacacaagca atgcctttca   6360
gagtgactga gcaagaaagc aaacctgtgc agatgatgta ccagattggt ttatttagag   6420
tggcatcaat ggcttctgag aaaatgaaga tcctggagct tccatttgcc agtgggacaa   6480
tgagcatgtt ggtgctgttg cctgatgaag tctcaggcct tgagcagctt gagagtataa   6540
tcaactttga aaaactgact gaatggacca gttctaatgt tatggaagag aggaagatca   6600
aagtgtactt acctcgcatg aagatggagg aaaaatacaa cctcacatct gtcttaatgg   6660
ctatgggcat tactgacgtg tttagctctt cagccaatct gtctggcatc tcctcagcag   6720
agagcctgaa gatatctcaa gctgtccatg cagcacatgc agaaatcaat gaagcaggca   6780
gagaggtggt agggtcagca gaggctggag tggatgctgc aagcgtctct gaagaattta   6840
gggctgacca tccattcctc ttctgtatca agcacatcgc aaccaacgcc gttctcttct   6900
ttggcagatg tgtttctccg cggccagcag atgacgcacc agcagatgac gcaccagcag   6960
atgacgcacc agcagatgac gcaccagcag atgacgcacc agcagatgac gcaacaacat   7020
gtatcctgaa aggctcttgt ggctggatcg gcctgctgga tgacgatgac aaatttgtga   7080
accaacacct gtgcggctca cacctggtgg aagctctcta cctagtgtgc ggggaacgag   7140
```

-continued

```
gcttcttcta cacacccaag acccgccggg aggcagagga cctgcaggtg gggcaggtgg   7200
agctgggcgg gggccctggt gcaggcagcc tgcagccctt ggccctggag gggtccctgc   7260
agaagcgtgg cattgtggaa caatgctgta ccagcatctg ctccctctac cagctggaga   7320
actactgcaa ctagggcgcc taaagggcga attatcgcgg ccgctctaga ccaggcgcct   7380
ggatccagat cacttctggc taataaaaga tcagagctct agagatctgt gtgttggttt   7440
tttgtggatc tgctgtgcct tctagttgcc agccatctgt tgtttgcccc tcccccgtgc   7500
cttccttgac cctggaaggt gccactccca ctgtcctttc ctaataaaat gaggaaattg   7560
catcgcattg tctgagtagg tgtcattcta ttctgggggg tggggtgggg cagcacagca   7620
agggggagga ttgggaagac aatagcaggc atgctgggga tgcggtgggc tctatgggta   7680
cctctctctc tctctctctc tctctctctc tctctctctc tcggtacctc tctcgagggg   7740
gggcccggta cccaattcgc cctatagtga gtcgtattac gcgcgctcac tggccgtcgt   7800
tttacaacgt cgtgactggg aaaaccctgg cgttacccaa cttaatcgcc ttgcagcaca   7860
tccccctttc gccagctggc gtaatagcga agaggcccgc accgatcgcc cttcccaaca   7920
gttgcgcagc ctgaatggcg aatggaaatt gtaagcgtta atattttgtt aaaattcgcg   7980
ttaaattttt gttaaatcag ctcatttttt aaccaatagg ccgaaatcgg caaaatccct   8040
tataaatcaa aagaatagac cgagataggg ttgagtgttg ttccagtttg gaacaagagt   8100
ccactattaa agaacgtgga ctccaacgtc aaagggcgaa aaaccgtcta tcagggcgat   8160
ggcccactac tccgggatca tatgacaaga tgtgtatcca ccttaactta atgattttta   8220
ccaaaatcat taggggattc atcagtgctc agggtcaacg agaattaaca ttccgtcagg   8280
aaagcttatg atgatgatgt gcttaaaaac ttactcaatg gctggttatg catatcgcaa   8340
tacatgcgaa aaacctaaaa gagcttgccg ataaaaaagg ccaatttatt gctatttacc   8400
gcggcttttt attgagcttg aaagataaat aaaatagata ggttttattt gaagctaaat   8460
cttctttatc gtaaaaaatg ccctcttggg ttatcaagag ggtcattata tttcgcggaa   8520
taacatcatt tggtgacgaa ataactaagc acttgtctcc tgtttactcc cctgagcttg   8580
aggggttaac atgaaggtca tcgatagcag gataataata cagtaaaacg ctaaaccaat   8640
aatccaaatc cagccatccc aaattggtag tgaatgatta taaataacag caaacagtaa   8700
tgggccaata acaccggttg cattggtaag gctcaccaat aatccctgta aagcaccttg   8760
ctgatgactc tttgtttgga tagacatcac tccctgtaat gcaggtaaag cgatcccacc   8820
accagccaat aaaattaaaa cagggaaaac taaccaacct tcagatataa acgctaaaaa   8880
ggcaaatgca ctactatctg caataaatcc gagcagtact gccgtttttt cgcccattta   8940
gtggctattc ttcctgccac aaaggcttgg aatactgagt gtaaaagacc aagacccgta   9000
atgaaaagcc aaccatcatg ctattcatca tcacgatttc tgtaatagca ccacaccgtg   9060
ctggattggc tatcaatgcg ctgaaataat aatcaacaaa tggcatcgtt aaataagtga   9120
tgtataccga tcagcttttg ttccctttag tgagggttaa ttgcgcgctt ggcgtaatca   9180
tggtcatagc tgtttcctgt gtgaaattgt tatccgctca caattccaca caacatacga   9240
gccggaagca taaagtgtaa agcctggggt gcctaatgag tgagctaact cacattaatt   9300
gcgttgcgct cactgcccgc tttccagtcg ggaaacctgt cgtgccagct gcattaatga   9360
atcggccaac gcgcggggag aggcggtttg cgtattgggc gctcttccgc ttcctcgctc   9420
actgactcgc tgcgctcggt cgttcggctg cggcgagcgg tatcagctca ctcaaaggcg   9480
gtaatacggt tatccacaga atcaggggat aacgcaggaa agaacatgtg agcaaaaggc   9540
```

-continued

```
cagcaaaagg ccaggaaccg taaaaaggcc gcgttgctgg cgtttttcca taggctccgc   9600

ccccctgacg agcatcacaa aaatcgacgc tcaagtcaga ggtggcgaaa cccgacagga   9660

ctataaagat accaggcgtt tccccctgga agctccctcg tgcgctctcc tgttccgacc   9720

ctgccgctta ccggatacct gtccgccttt ctcccttcgg gaagcgtggc gctttctcat   9780

agctcacgct gtaggtatct cagttcggtg taggtcgttc gctccaagct gggctgtgtg   9840

cacgaacccc ccgttcagcc cgaccgctgc gccttatccg gtaactatcg tcttgagtcc   9900

aacccggtaa gacacgactt atcgccactg gcagcagcca ctggtaacag gattagcaga   9960

gcgaggtatg taggcggtgc tacagagttc ttgaagtggt ggcctaacta cggctacact  10020

agaaggacag tatttggtat ctgcgctctg ctgaagccag ttaccttcgg aaaaagagtt  10080

ggtagctctt gatccggcaa acaaaccacc gctggtagcg gtggtttttt tgtttgcaag  10140

cagcagatta cgcgcagaaa aaaaggatct caagaagatc ctttgatctt ttctacgggg  10200

tctgacgctc agtggaacga aaactcacgt taagggattt tggtcatgag attatcaaaa  10260

aggatcttca cctagatcct tttaaattaa aaatgaagtt ttaaatcaat ctaaagtata  10320

tatgagtaaa cttggtctga cagttaccaa tgcttaatca gtgaggcacc tatctcagcg  10380

atctgtctat ttcgttcatc catagttgcc tgactccccg tcgtgtagat aactacgata  10440

cgggagggct taccatctgg ccccagtgct gcaatgatac cgcgagaccc acgctcaccg  10500

gctccagatt tatcagcaat aaaccagcca gccggaaggg ccgagcgcag aagtggtcct  10560

gcaactttat ccgcctccat ccagtctatt aattgttgcc gggaagctag agtaagtagt  10620

tcgccagtta atagtttgcg caacgttgtt gccattgcta caggcatcgt ggtgtcacgc  10680

tcgtcgtttg gtatggcttc attcagctcc ggttcccaac gatcaaggcg agttacatga  10740

tcccccatgt tgtgcaaaaa agcggttagc tccttcggtc ctccgatcgt tgtcagaagt  10800

aagttggccg cagtgttatc actcatggtt atggcagcac tgcataattc tcttactgtc  10860

atgccatccg taagatgctt ttctgtgact ggtgagtact caaccaagtc attctgagaa  10920

tagtgtatgc ggcgaccgag ttgctcttgc ccggcgtcaa tacgggataa taccgcgcca  10980

catagcagaa ctttaaaagt gctcatcatt ggaaaacgtt cttcggggcg aaaactctca  11040

aggatcttac cgctgttgag atccagttcg atgtaaccca ctcgtgcacc caactgatct  11100

tcagcatctt ttactttcac cagcgtttct gggtgagcaa aaacaggaag gcaaaatgcc  11160

gcaaaaaagg gaataagggc gacacggaaa tgttgaatac tcatactctt cctttttcaa  11220

tattattgaa gcatttatca gggttattgt ctcatgagcg gatacatatt tgaatgtatt  11280

tagaaaaata aacaaatagg ggttccgcgc acatttcccc gaaaagtgcc ac          11332
```